US008236950B2

(12) United States Patent
Betebenner et al.

(10) Patent No.: US 8,236,950 B2
(45) Date of Patent: Aug. 7, 2012

(54) ANTI-VIRAL COMPOUNDS

(75) Inventors: David A. Betebenner, Libertyville, IL (US); Clarence J. Maring, Palatine, IL (US); Todd W. Rockway, Grayslake, IL (US); Curt S. Cooper, Vernon Hills, IL (US); David D. Anderson, Groton, CT (US); Rolf Wagner, Antioch, IL (US); Rong Zhang, Niskayuna, NY (US); Akhteruzzaman Molla, Gurnee, IL (US); Hongmei Mo, Foster City, CA (US); Tami J. Pilot-Matias, Green Oaks, IL (US); Sherie V L. Masse, Kenosha, WI (US); Robert J. Carrick, Pleasant Prairie, WI (US); Wenping He, Libertyville, IL (US); Liangjun Lu, Kildeer, IL (US)

(73) Assignee: Abbott Laboratories, Abbott Park, IL (US)

( * ) Notice: Subject to any disclaimer, the term of this patent is extended or adjusted under 35 U.S.C. 154(b) by 1215 days.

(21) Appl. No.: 11/960,298

(22) Filed: Dec. 19, 2007

(65) Prior Publication Data
US 2011/0160233 A1    Jun. 30, 2011

Related U.S. Application Data

(60) Provisional application No. 60/871,054, filed on Dec. 20, 2006.

(51) Int. Cl.
*C07D 491/02* (2006.01)
(52) U.S. Cl. ........ 544/251; 544/250; 544/249; 544/245; 544/242; 544/224; 514/267; 514/257; 514/256; 514/247; 514/183
(58) Field of Classification Search .................. None
See application file for complete search history.

(56) References Cited

U.S. PATENT DOCUMENTS

| | | | |
|---|---|---|---|
| 3,021,332 A | 2/1962 | Hitchings et al. |
| 4,066,643 A | 1/1978 | Denzel et al. |
| 4,871,851 A | 10/1989 | Beck |
| 5,034,393 A | 7/1991 | Hackler et al. |
| 5,350,749 A | 9/1994 | Hackler et al. |
| 5,654,307 A | 8/1997 | Bridges et al. |
| 5,925,644 A | 7/1999 | Jakobi et al. |
| 5,965,563 A | 10/1999 | Buzzetti et al. |
| 6,130,217 A | 10/2000 | Arnold et al. |
| 6,169,091 B1 | 1/2001 | Cockerill et al. |
| 6,174,889 B1 | 1/2001 | Cockerill et al. |
| 6,184,226 B1 | 2/2001 | Chakravarty et al. |
| 6,277,989 B1 | 8/2001 | Chakravarty et al. |
| 6,284,764 B1 | 9/2001 | Kath et al. |
| 6,323,180 B1 | 11/2001 | Llinas-Brunet et al. |
| 6,348,587 B1 | 2/2002 | Schinazi et al. |
| 6,395,733 B1 | 5/2002 | Arnold et al. |
| 6,413,971 B1 | 7/2002 | Arnold et al. |
| 6,476,031 B1 | 11/2002 | Chakravarty et al. |
| 6,541,481 B2 | 4/2003 | Kath et al. |
| 6,610,677 B2 | 8/2003 | Davies et al. |
| 6,703,421 B1 | 3/2004 | Nunokawa et al. |
| 6,723,726 B1 | 4/2004 | Cockerill et al. |
| 6,784,174 B1 | 8/2004 | Cumming |
| 6,903,096 B2 | 6/2005 | Chakravarty et al. |
| 7,037,913 B2 | 5/2006 | Wang et al. |
| 7,183,302 B2 | 2/2007 | Romine et al. |
| 7,763,731 B2 * | 7/2010 | Rockway et al. ............. 546/122 |
| 7,910,595 B2 * | 3/2011 | Betebenner et al. ...... 514/264.11 |
| 7,915,411 B2 * | 3/2011 | Betebenner et al. .......... 544/279 |
| 2003/0125343 A1 | 7/2003 | Gambacorti-Passerini et al. |
| 2004/0242604 A1 | 12/2004 | Bhattacharya et al. |
| 2004/0265792 A1 | 12/2004 | Glenn et al. |
| 2005/0075331 A1 | 4/2005 | Pratt et al. |
| 2005/0090522 A1 | 4/2005 | Wang et al. |
| 2005/0107364 A1 | 5/2005 | Hutchinson et al. |
| 2005/0215575 A1 | 9/2005 | Bakthavatchalam et al. |
| 2006/0014764 A1 | 1/2006 | Feng et al. |
| 2006/0035965 A1 | 2/2006 | Dalton et al. |
| 2007/0232627 A1 | 10/2007 | Betebenner et al. |
| 2007/0232645 A1 | 10/2007 | Rockway et al. |

FOREIGN PATENT DOCUMENTS

| | | |
|---|---|---|
| EP | 0 404 355 | 12/1990 |
| EP | 0 414 386 | 2/1991 |
| EP | 0 912 570 | 5/1999 |
| EP | 1 162 196 | 12/2001 |
| ES | 2 009 217 | 9/1989 |
| GB | 774 094 | 5/1957 |
| JP | 47 25076 | 7/1972 |
| WO | 93/13097 | 7/1993 |
| WO | 95/00511 | 1/1995 |
| WO | 95/19774 | 7/1995 |

(Continued)

OTHER PUBLICATIONS

"Synthesis and SAR of novel 1,1,-dialky1-2(1H)-naphthalenones as potent HCV polymerase inhibitors" by Bosse et al., Bioorg. Med. Chem. Lett. 18, 568-70 (2008).*
"Side Reactions in Organic Synthesis: A Guide to Successful Synthesis Design" by Dorwald, Wiley (Germany), p. IX (2005).*
"Role of the Development Scientist in Compound Lead Selection and Optimization" by Venkatesh et al., J. Pharm. Sci. 89, 145-54 (2000).*
Ahmed, et al., *Journal of Heterocyclic Chemistry* (2002), 39(2), 309-314.
Blight, K.J., et al., "Efficient Initiation of HCV RNA Replication in Cell Culture", *Science*, 290:1972-1974 (2000).
Bundgaard, H., "Design of prodrugs", pp. 7-9 & 21-24 (1985).
Chen, et al., *Yaoxue Xuebao* (1982), 17(2), 112-17.
Cortese, F. & Bauman, L., "A Synthesis of Conjugatred Bile Acids. I. Glycocholic Acid", *JACS*, 57:1393-1395 (1935).
Cross, L.C. & Klyne, W., "Rules for the Nomenclature of Organic Chemistry—Section E: Stereochemistry", *Pure Appl. Chem.*, 45:11-30 (1976).

(Continued)

*Primary Examiner* — Anish Gupta
*Assistant Examiner* — Theodore R West
(74) *Attorney, Agent, or Firm* — Bradley E. Davis

(57) ABSTRACT

Compounds effective in inhibiting replication of Hepatitis C virus ("HCV") or other viruses are disclosed. This invention is also directed to compositions comprising such compounds, co-formulation or co-administration of such compounds with other anti-viral or therapeutic agents, processes and intermediates for the syntheses of such compounds, and methods of using such compounds for the treatment of HCV or other viral infections.

19 Claims, No Drawings

FOREIGN PATENT DOCUMENTS

| | | |
|---|---|---|
| WO | 96/09294 | 3/1996 |
| WO | 96/40142 | 12/1996 |
| WO | 97/13771 | 4/1997 |
| WO | 98/02428 | 1/1998 |
| WO | 98/02437 | 1/1998 |
| WO | 98/02438 | 1/1998 |
| WO | 98/05661 | 2/1998 |
| WO | 98/08846 | 3/1998 |
| WO | 98/13350 | 4/1998 |
| WO | 98/22444 | 5/1998 |
| WO | 98/23613 | 6/1998 |
| WO | 98/46605 | 10/1998 |
| WO | 99/59587 | 11/1999 |
| WO | 00/12497 | 3/2000 |
| WO | 00/44728 | 8/2000 |
| WO | 00/56738 | 9/2000 |
| WO | 01/32153 | 5/2001 |
| WO | 01/32632 | 5/2001 |
| WO | 01/57040 | 8/2001 |
| WO | 01/60315 | 8/2001 |
| WO | 01/90121 | 11/2001 |
| WO | 02/04425 | 1/2002 |
| WO | 03051366 | 6/2003 |
| WO | 03059913 | 7/2003 |
| WO | 03062209 | 7/2003 |
| WO | 03097615 | 11/2003 |
| WO | WO03099274 A1 | 12/2003 |
| WO | 2004/055004 | 1/2004 |
| WO | 2004/014313 | 2/2004 |
| WO | 2004/014852 | 2/2004 |
| WO | 2004/024693 | 3/2004 |
| WO | 2004/047818 | 6/2004 |
| WO | 2004055003 | 7/2004 |
| WO | 2004/065392 | 8/2004 |
| WO | 2004071460 | 8/2004 |
| WO | WO2004081008 A1 | 9/2004 |
| WO | 2004/087056 | 10/2004 |
| WO | 2005/007652 | 1/2005 |
| WO | 2005003100 | 1/2005 |
| WO | 2005023807 | 3/2005 |
| WO | 2005032481 | 4/2005 |
| WO | 2005/047288 | 5/2005 |
| WO | 2005042498 | 5/2005 |
| WO | 2005049033 | 9/2005 |
| WO | 2005082865 | 9/2005 |
| WO | 2005087227 | 9/2005 |
| WO | 2005/105761 | 11/2005 |
| WO | 2006/012333 | 2/2006 |
| WO | 2006/035061 | 4/2006 |
| WO | 2006/038039 | 4/2006 |
| WO | 2006067614 | 6/2006 |
| WO | 2006071875 | 7/2006 |
| WO | 2006100310 | 9/2006 |
| WO | 2006105063 | 10/2006 |
| WO | 2006/120251 | 11/2006 |
| WO | 2006/120252 | 11/2006 |
| WO | 2006120252 | 11/2006 |
| WO | 2007/035010 | 3/2007 |
| WO | 2007/060404 | 5/2007 |

OTHER PUBLICATIONS

International Search Report for PCT/US2006/049079 dated Aug. 17, 2007.
International Search Report for PCT/US2006/048685 dated Oct. 30, 2007.
International Search Report for PCT/uS2006/049080 dated Aug. 23, 2007.
Das, S., et al., "A Small yeast RNA Blocks Hepatitis C Virus Internal Ribosome Entry Site (HCV IRES)-Mediated Translation and Inhibits Replication of a Chimeric Poliovirus under Translational control of the HCV IRES Element", *J of Virology*, 72(7):5638-5647 (1998).
Deeb, A., et al., "Pyridazine Derivatives and Related Comp9unds Part 5. Pyrazolo[3,4-c]Pyridazine: Synthesis and Some Reactoins", *Heterocycles*, 32(5):895-900 (1991).
Elneairy, et al. *Journal of Sulfur Chemistry* (2005), 26(4-5), 381-391.
Fieser, L.F., "Choline", *Reagents for Organic Synthesis*, vol. 1:142-144 (1967).
Godefroy, et al., *Comptes Rendus des Seances de l'Academie des Sciences, Serie B: Sciences Physiques* (1973), 277(16), 703-6.
Godefroy, et al., *Journal of Heterocyclic Chemistry* (1973), 10(6), 1077-8.
Gomtsyan, A., et al., "Design, Synthesis, and Structure-Activity Relationship of 6-Alkynylpyrimidines as Potent Adenosine Kinase Inhibitors", *J. Med. Chem.*, 45:3639-3648 (2002).
Greene & Wuts, *Protective Groups in Organic Synthesis*, 3$^{rd}$ Ed.:Tbl of Cont., (1999).
Hayashi, et al., *Yakugaku Zasshi* (1977), 97(9), 1022-33.
Hoover, J.E., *Remington's Pharmaceutical Sciences*, Tbl of Cont., (1975).
Ikeda, M., et al., "Selectable Subgenomic and Genome-Length Dicistronic RNAs Derived from an Infectious Molecular Clone of the HCV-N. Strain of Hepatitis C Virus Replicate Efficiently in Clutured Huh7 Cells", *J. of Virology*, 76(6):2997-3006 (2002).
Iwamura, et al., *Phytochemistry* (Elsevier) (1979), 18(8), 1265-8.
Iwamura, et al., *Journal of Medicinal Chemistry* (1985), 28(5), 577-83.
Jacques, et al., *Enantiomers, Racemates, and Resolutions*, Tble of Cont., (1981).
Janout, V., et al., "Design and Synthesis of Molecular Umbrellas", *J. Am. Chem. Soc.*, 119:640-647 (1997).
Lieberman, H.A. & Lachman, L., *Pharmaceutical Dosage Forms*, vol. 1:Tbl of Cont., (1980).
McKenzie, A. & Clough, G.W., "XLVIII.-Experiments on the Ealden Inversion. Part VIII. α-Amino-a-phenylpropionic Acids", *J. Chem. Soc.*, 101:390-397 (1912).
Miranda, E.I., et al., "Thiols, Unsymmetrical Sulfides and Thioacetals From the New Reagent: Trisopropysilanethiol", *Tetrahedron Ltrs.*, 35(20):3221-3224 (1994).
Monge, et al., *Arzneimittel-Forschung* (1990), 40(11), 1230-3.
Nakamura, S., "Studies on Growth Inhibition of hiochi-bacteria, Specific Saprophytes of Sake", *Agr. Biol. Chem.*, 25(8):665-670 (1961).
Nishikawa, et al., *Chem. & Pharm. Bulletin* (1976), 24(9), 2057-77.
Nishikawa, et al., *Bioscience, Biotech., and Biochem.* (1994), 58(9(, 1709-10).
Prakash, G.K.Su., et al., "Facile preparation of di- and monofluoromethyl ketones form trifluoromethyl ketones via fluorinated enol silyl ethers", *J. of Fluorine Chem.*, 112:357-362 (2001).
Refai, M., et al., "New Synthesis of Some 1,8- Naphthoyridines of Possible Lantimicrobial Lactivity", *Egypt. J. Pharm. Sci.*, 37(1-6):241-249 (1996).
Rewcastle, et al., *Journal of Medicinal Chemistry* (1996), 39(9), 1823-35.
Shuman, R.T., et al., "Structure-Activity Study of Tripeptide Thrombin Inhibitors Using α-Alkyl Amino Lacids and Other Conformationally Constrained Amino Acid Substitutions", *J. Med. Chem.*,38:4446-4453 (1995).
Soloducho, *Archiv der Pharmazie* (Weinheim, Germany), (1990), 323(8), 513-15.
Yi, M., et al., "Subjenomic Hepatitis C Virus Replicaons Inducting Expression of a Secreted Enzymatic Reporter Protein", *Virology*, 304:197-210 (2002).
International Search Report for PCT/US2007/088027 dated Oct. 28, 2008.
Supplementary European Search Report for Application No. EP07874373, mailed on Dec. 7, 2010, 2 pages.

\* cited by examiner

ANTI-VIRAL COMPOUNDS

This application claims the benefit of U.S. Provisional Application No. 60/871,054, filed Dec. 20, 2006.

FIELD

The present invention relates to compounds effective in inhibiting replication of Hepatitis C virus ("HCV"). The present invention also relates to methods of making such compounds, compositions comprising such compounds, intermediates for the syntheses of such compounds, and methods of using such compounds/compositions for the treatment of HCV infection or conditions/symptoms associated therewith. In addition, the present invention relates to use of such compounds for the manufacture of medicaments for the treatment of HCV infection.

BACKGROUND

HCV, a human pathogen, is an RNA virus belonging to the Hepacivirus genus in the Flaviviridae family. As is characteristic with all other members of the Flaviviridae family, HCV has enveloped virions that contain a positive stranded RNA genome encoding all known virus-specific proteins in one single, uninterrupted, open reading frame. The open reading frame comprises approximately 9500 nucleotides encoding a single large polyprotein of about 3000 amino acids. The polyprotein comprises a core protein, envelope proteins E1 and E2, a membrane bound protein p7, and the non-structural proteins NS2, NS3, NS4A, NS4B, NS5A and NS5B. A cellular protease cleaves the viral protein at the NS2-NS3 junction allowing a viral protease (NS3 protease) to mediate subsequent cleavages. The NS3 protein also exhibits nucleoside triphosphatase and RNA helicase activities. NS2 and NS4A may, too, be involved in proteolytic activity. NS5A is a phosphoprotein involved in replication. NS5B is a RNA-dependent RNA polymerase. U.S. Patent Pub. No. 2004/0265792, published 30 Dec. 2004, mentions that inhibition of the aforementioned non-structural proteins may inhibit HCV replication.

HCV infection is associated with progressive liver pathology, including cirrhosis and hepatocellular carcinoma. HCV-associated end-stage liver disease is the most frequent indication for liver transplantation among adults. Chronic hepatitis C may be treated with a once-weekly injection of peginterferon-alpha in combination with daily ribavarin. Peginterferon-alpha is interferon-alpha attached to polyethylene glycol to slow elimination of the drug from the body. This results in enhanced compliance and clinically superior anti-viral activity when compared to treatments of interferon-alpha daily injections. Substantial limitations to efficacy and tolerability remain as many users suffer from side effects and viral elimination from the body is often inadequate.

Attempts have been made to design drugs that specifically inhibit functions of the hepatitis C virus. Boehringer Ingelheim U.S. Pat. No. 6,323,180 mentions tri-peptide compounds as HCV serine protease inhibitors proposed for treatment of HCV infection.

Another approach is ISIS-14803 (Isis Pharmaceuticals), an antisense inhibitor complementary to a conserved sequence of the hepatitis C virus RNA. This molecule binds to the viral RNA and inhibits the expression of proteins required for replication.

Inhibition of HCV translation, by a yeast RNA that binds to cellular polypeptides and prevents their interaction with the viral internal ribosome entry site (IRES), is described in Das et al, J. VIROLOGY, 72(7):5638-5647 (1998).

Fused-bicyclic heterocyclic compounds have been proposed for diverse life-science-related uses. Examples of such heterocyclic compounds include naphthyridine, pyridopyrimidine, pyrimidopyrimidine, pyrazolopyrimidine and thiazolo/thienopyrimidine compounds.

Naphthyridine-type fused-bicyclic compounds have been investigated for disease-treatment uses. For example, Boots WO 93/13097, published 8 Jul. 1993, mentions [1,8]naphthyridine compounds, such as ethyl 4-(4-methoxyanilino)-6-ethoxy-7-methyl-1,8-naphthyridine-3-carboxylate hydrochloride, proposed for use as anti-rheumatic agents. Boots WO 95/00511, published 5 Jan. 1995, mentions substituted ring-fused 4-aminopyridines, such as 3-ethoxy-5-(2-ethoxy-5-pyridylamino)-2-methyl-1,8-naphthyridine, proposed for use as anti-rheumatic agents. Zeneca WO 98/13350, published 2 Apr. 1998, mentions [1,8]naphthyridine compounds, such as 2-acetamido-5-(2-fluoro-5-hydroxy-4-methylanilino)-1,8-naphthyridine hydrochloride, proposed as anti-angiogenic agents. Neurogen WO 2004/055004, published 1 Jul. 2004, mentions naphthyridine compounds as capsaicin-receptor modulators, specific compounds being 5-(4-trifluoromethyl-phenylamino)-2-(3-trifluoromethyl-pyridin-2-yl)-[1,6] naphthyridine-7-carboxylic acid, and 2-methoxymethyl-4-(4-trifluoromethyl-phenylamino)-7-(3-trifluoromethyl-pyridin-2-yl)[1,8] naphthyridine-3-carboxylic acid.

Pyridopyrimidine-type fused-bicyclic compounds have been investigated for various disease-treatment uses. For example, Pfizer WO 98/05661, published 12 Feb. 1998, mentions substituted pyridopyrimidine compounds, such as [8-(1-ethyl-propyl)-2-methyl-5,6,7,8-tetrahydro-pyrido(2,3-d) pyrimidin-4-yl]-(2,4,6-trimethyl-phenyl)-amine, as corticotrophin releasing factor (hormone) CRF (CRH) antagonists proposed for treatment of Alzheimer's Disease and obesity. Pfizer WO 98/23613, published 4 Jun. 1998, mentions fused-bicyclic pyrimidine compounds, including pyridopyrimidinyl-aminophenyl compounds, such as (3-ethynyl-phenyl)-pyrido[3,4-d]pyrimidin-4-yl-amine, proposed for treatment of hyperproliferative diseases such as cancer. Glaxo Wellcome U.S. Pat. No. 6,169,091, issued 2 Jan. 2001, mentions bicyclic heteroaromatic compounds, such as 4-(4-benzyloxyanilino)pyrido[2,3-d]-pyrimidine, as tyrosine kinase inhibitors proposed for treatment of fibrosis, inflammation, nervous system diseases and cancer. Eli Lilly WO 01/32632, published 10 May 2001, mentions 4-substituted pyrimidine compounds, including 2-trifluoromethyl-4-[2-(2-(2-chlorophenyl)ethylamino]pyrido-[2,3-d]pyrimidine hydrochloride, as mGluR1 antagonists proposed for treatment of neurological disorders associated with glutamate dysfunction such as convulsions, migraine, psychosis, anxiety and pain. Abbott Laboratories WO 01/57040 published 9 Aug. 2001, mentions 6,7-disubstituted-4-aminopyrido [2,3-d]pyrimidine compounds, such as 4-amino-6-(4-methylphenyl)-7-(4-bromophenyl)pyrido[2,3-d]pyrimidine, as adenosine kinase inhibitors proposed for treatment of pain and inflammation. Neurogen WO 2004/055004, published 1 Jul. 2004, mentions pyridopyrimidinyl-aminophenyl compounds, such as 2-methyl-2-{4-[2-methyl-7-(3-methyl-pyridin-2-yl)-pyrido[2,3-d]pyrimidin-4-ylamino]-phenyl}-propionic acid, as capsaicin-receptor modulators. Pfizer U.S. Pat. No. 6,395,733, issued 28 May 2002, mentions heterocyclic ring-fused pyrimidine compounds, such as 3-chloro-phenyl-pyrido[2,3-d]pyrimidin-4-yl-amine, proposed for treatment of hyper-proliferative disease, such as cancer.

Pyrimidopyrimidine-type fused bicyclic compounds have been investigated for both pest-control and disease-treatment uses. For example, Dow Elanco U.S. Pat. No. 5,350,749, issued 27 Sep. 1994, mentions 4-substituted-pyrimido [2,3-d]pyrimidine compounds proposed for use as fungicides, insecticides and miticides. Warner-Lambert WO 95/19774, published 27 Jul. 1995, mentions pyrimidopyrimidine compounds, such as 4-benzylamino-7-methylaminopyrimido[4,5-d]pyrimidine, as tyrosine kinase inhibitors proposed for treatment of cancer, vascular restenosis and psoriasis.

Thienopyrimidine-type fused-bicyclic compounds have been investigated for various disease-treatment uses. For example, Warner-Lambert WO 95/19774, published 27 Jul. 1995, mentions fused heterocyclic pyrimidine compounds, including 4-(3-bromoanilino)thieno[2,3-d]pyrimidine, as tyrosine kinase inhibitors proposed for treatment of cancer, vascular restenosis and psoriasis. Glaxo Wellcome U.S. Pat. No. 6,169,091, issued 2 Jan. 2001, mentions bicyclic heteroaromatic compounds, such as 5-methyl-4-(4-phenoxyanilino)thieno[2,3-d]pyrimidine hydrochloride as tyrosine kinase inhibitors, proposed for treatment of fibrosis, inflammation, nervous system diseases and cancer. Eli Lilly WO 01/32632, published 10 May 2001, mentions 4-substituted-pyrimidine compounds, such as 6-methyl-4-[2,6-dichlorobenzylthio)ethylamino]thieno[2,3-d]pyrimidine hydrochloride, as mGluR1 antagonists proposed for treatment of neurological disorders associated with glutamate dysfunction such as convulsions, migraine, psychosis, anxiety and pain.

Bristol-Myers Squibb WO 2004/014852, published 19 Feb. 2004, mentions iminothiazolidinones, including fused-bicyclic derivatives of 2-(4-aminophenyl)-5H-thiazolo[2,3-6]quinazolin-3-one, as NS5A-protein-inhibitors proposed to prevent HCV replication.

Bristol-Myers Squibb WO 2004/014313, published 19 Feb. 2004, mentions combination therapies for treatment of viral diseases, including iminothiazolidinone NS5A-protein-inhibiting anti-HCV compounds in combination with other agents capable of interfering with HCV function.

SUMMARY

The present invention features compounds having Formulae I, I(a) or I(b), tautomers of these compounds, and pharmaceutically acceptable salts of these compounds or tautomers. These compounds, tautomers or salts can be used, either individually or in combination with other drugs or agents, to inhibit the replication of HCV or other viruses. These compounds, tautomers or salts can also be used, either individually or in combination with other drugs or agents, to disrupt functions of HCV or other viruses.

The present invention also features compositions that comprise the compounds, tautomers or salts of the present invention. A composition of the present invention can include one or more compounds, tautomers or salts of the present invention. A composition of the present invention can also include one or more other antiviral or therapeutic agents.

In addition, the present invention features methods of using the compounds, tautomers or salts of the present invention, or compositions comprising the same, to inhibit the replication of HCV or other viruses. These methods comprise contacting HCV or another virus, or cells infected with HCV or said another virus, with an effective amount of a compound, tautomer or salt of the present invention, thereby inhibiting the replication of HCV or said another virus.

The present invention further features methods of using the compounds, tautomers or salts of the present invention, or compositions comprising the same, to inhibit the proliferation or transmission of HCV or other viruses. These methods comprise contacting HCV or another virus, or contacting cells infected with HCV or another virus, with an effective amount of a compound, tautomer or salt of the present invention, thereby inhibiting the proliferation or transmission of HCV or said another virus.

Moreover, the present invention features methods of using the compounds, tautomers or salts of the present invention, or compositions comprising the same, to treat HCV or other viral infections. These methods comprise administering to a patient in need of such treatment an effective amount of a compound, tautomer or salt of the present invention, thereby reducing the blood or tissue level of HCV or other viruses in the patient.

The present invention also features use of the compounds, tautomers or salts of the present invention for the manufacture of medicaments for the treatment of HCV or other viral infections.

Furthermore, the present invention features processes of making the compounds, tautomers or salts of the present invention, and intermediates employed in these processes.

Other features, objects, and advantages of the present invention are apparent in the detailed description that follows. It should be understood, however, that the detailed description, while indicating preferred embodiments of the invention, are given by way of illustration only, not limitation. Various changes and modifications within the scope of the invention will become apparent to those skilled in the art from the detailed description.

DETAILED DESCRIPTION

The following description is exemplary in nature and is not intended to limit the present disclosure, application, or uses.

Compounds

The present invention features compounds having Formula I, tautomers thereof, and pharmaceutically acceptable salts of the compounds or tautomers,

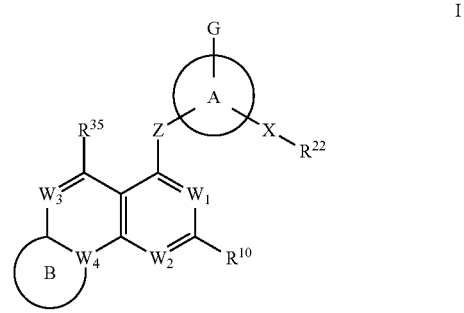

wherein:
A and B are each independently selected from carbocyclyl or heterocyclyl, and are each independently optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, carbocyclyl, heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=NR$_S$)N(R$_S$R$_{S''}$), -$L_S$-N(R$_{S'}$)C(=NR$_S$)R$_{S'''}$, -$L_S$-N(R$_S$)C(O)N(R$_S$R$_{S''}$), -$L_S$-N(R$_S$)SO$_2$R$_{S'}$, -$L_S$-SO$_2$N(R$_S$R$_{S'}$), and -$L_S$-N(R$_S$)SO$_2$N(R$_S$R$_{S''}$);

W$_1$, W$_2$, W$_3$ and W$_4$ are each independently selected from N or C(R$^{33}$);

Z is a bond, —CR$^{41}$R$^{41'}$— or —NR$^{41}$—, wherein R$^{41}$ and R$^{41'}$ are each independently selected from the group consisting of hydrogen, alkyl, alkenyl and alkynyl;

R$^{10}$, R$^{33}$ and R$^{35}$ are each independently selected at each occurrence from the group consisting of hydrogen, halogen, oxo, thioxo, hydroxy, mercapto, nitro, cyano, amino, carboxy, formyl, phosphate, azido, alkyl, alkenyl, alkynyl, carbocyclyl, heterocyclyl, -$L_S$-O—R$_S$, -$L_S$-S—R$_S$, -$L_S$-C(O)R$_S$, -$L_S$-OC(O)R$_S$, -$L_S$-C(O)OR$_S$, -$L_S$-N(R$_S$R$_{S'}$), -$L_S$-C(=NR$_S$)R$_{S'}$, -$L_S$-S(O)R$_S$, -$L_S$-SO$_2$R$_S$, -$L_S$-C(O)N(R$_S$R$_{S'}$), -$L_S$-N(R$_S$)C(O)R$_{S'}$, -$L_S$-C(=NR$_S$)N(R$_S$R$_{S''}$), -$L_S$-N(R$_{S'}$)C(=NR$_S$)R$_{S'''}$, -$L_S$-N(R$_S$)C(O)N(R$_S$R$_{S''}$), -$L_S$-N(R$_S$)SO$_2$R$_{S'}$, -$L_S$-SO$_2$N(R$_S$R$_{S'}$), and -$L_S$-N(R$_S$)SO$_2$N(R$_S$R$_{S''}$);

X is selected from the group consisting of a bond, alkylene, alkenylene, alkynylene, -$L_S$-O—, -$L_S$-S—, -$L_S$-C(O)—, -$L_S$-N(R$_S$)—, -$L_S$-N(R$_S$)C(O)—, -$L_S$-C(O)N(R$_S$)—, -$L_S$-N(R$_S$)C(O)O—, -$L_S$-OC(O)N(R$_S$)—, -$L_S$-N(R$_S$)C(O)N(R$_{S'}$)—, -$L_S$-C(=NR$_S$)N(R$_{S'}$)—, -$L_S$-N(R$_{S'}$)C(=NR$_S$)—, -$L_S$-S(O)—, -$L_S$-SO$_2$—, -$L_S$-C(O)O— and -$L_S$-OC(O)—;

R$^{22}$ is carbocyclyl or heterocyclyl, and is optionally substituted with one or more R$^{26}$, wherein R$^{26}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—R$_S$, -$L_S$-S—R$_S$, -$L_S$-C(O)R$_S$, -$L_S$-OC(O)R$_S$, -$L_S$-C(O)OR$_S$, -$L_S$-N(R$_S$R$_{S'}$), -$L_S$-C(=NR$_S$)R$_{S'}$, -$L_S$-S(O)R$_S$, -$L_S$-SO$_2$R$_S$, -$L_S$-C(O)N(R$_S$R$_{S'}$), -$L_S$-N(R$_S$)C(O)R$_{S'}$, -$L_S$-C(=NR$_S$)N(R$_S$R$_{S''}$), -$L_S$-N(R$_{S'}$)C(=NR$_S$)R$_{S'''}$, -$L_S$-N(R$_S$)C(O)N(R$_S$R$_{S''}$), -$L_S$-N=C(NR$_S$R$_{S'}$)(NR$_S$R$_{S'}$), -$L_S$-N(R$_S$)SO$_2$R$_{S'}$, -$L_S$-SO$_2$N(R$_S$R$_{S'}$), -$L_S$-N(R$_S$)SO$_2$N(R$_S$R$_{S''}$), -$L_E$-Q-$L_{E'}$-(C$_3$-C$_{18}$carbocyclyl) and -$L_E$-Q-$L_{E'}$-(M$_3$-M$_{18}$heterocyclyl); or R$^{22}$ is alkyl, alkenyl or alkynyl, and is optionally substituted with one or more R$^{26}$; or R$^{22}$ is hydrogen;

G is selected from the group consisting of hydrogen, halogen, oxo, thioxo, hydroxy, mercapto, nitro, cyano, amino, carboxy, formyl, phosphate, azido, alkyl, alkenyl, alkynyl, -$L_S$-O—R$_S$, -$L_S$-S—R$_S$, -$L_S$-C(O)R$_S$, -$L_S$-OC(O)R$_S$, -$L_S$-C(O)OR$_S$, -$L_S$-N(R$_S$R$_{S'}$), -$L_S$-C(=NR$_S$)R$_{S'}$, -$L_S$-S(O)R$_S$, -$L_S$-SO$_2$R$_S$, -$L_S$-C(O)N(R$_S$R$_{S'}$), -$L_S$-N(R$_S$)C(O)R$_{S'}$, -$L_S$-C(=NR$_S$)N(R$_S$R$_{S''}$), -$L_S$-N(R$_{S'}$)C(=NR$_S$)R$_{S'''}$, -$L_S$-N(R$_S$)C(O)N(R$_S$R$_{S''}$), -$L_S$-N(R$_S$)SO$_2$R$_{S'}$, -$L_S$-SO$_2$N(R$_S$R$_{S'}$), -$L_S$-N(R$_S$)SO$_2$N(R$_S$R$_{S''}$), and —Y—R$^{50}$, wherein G is optionally substituted with one or more R$^{18}$;

Y is selected from the group consisting of a bond, —O—, —C(O)—, —S(O)—, —S(O)$_2$—, —N(R$^{15}$)—, —C(O)O—, —OC(O)—, —C(O)N(R$^{15}$)—, —N(R$^{15}$)C(O)—, —C(O)N(R$^{15}$)O—, —N(R$^{15}$)C(O)O—, —OC(O)N(R$^{15}$)—, —N(R$^{15}$)C(O)N(R$^{15'}$)—, —C(O)N(R$^{15}$)N(R$^{15'}$)—, —S—, —C(S)—, —C(S)O—, —OC(S)—, —C(S)N(R$^{15}$)—, —N(R$^{15}$)C(S)—, —OS(O)$_2$—, —OS(O)—, —OC(O)O—, —N(R$^{15}$)—, —N(R$^{15}$)S(O)—, —N(R$^{15}$)S(O)$_2$—, —S(O)N(R$^{15}$)—, —S(O)$_2$N(R$^{15}$)—, —C(S)N(R$^{15}$)O—, —N(R$^{15}$)C(S)O—, —OC(S)N(R$^{15}$)—, —N(R$^{15}$)C(S)N(R$^{15'}$)—, and —C(S)N(R$^{15}$)N(R$^{15'}$)—, wherein R$^{15}$ and R$^{15'}$ are each independently selected at each occurrence from the group consisting of hydrogen, alkyl, alkenyl and alkynyl;

R$^{50}$ is -L$^1$-A$^1$, wherein A$^1$ is selected from the group consisting of carbocyclyl, heterocyclyl, alkyl, alkenyl and alkynyl, and L$^1$ is selected from the group consisting of a bond, alkylene, alkenylene and alkynylene, wherein A$^1$ is optionally substituted with one or more R$^{30}$, and R$^{30}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—R$_S$, -$L_S$-S—R$_S$, -$L_S$-C(O)R$_S$, -$L_S$-OC(O)R$_S$, -$L_S$-C(O)OR$_S$, -$L_S$-N(R$_S$R$_{S'}$), -$L_S$-C(=NR$_S$)R$_{S'}$, -$L_S$-S(O)R$_S$, -$L_S$-SO$_2$R$_S$, -$L_S$-C(O)N(R$_S$R$_{S'}$), -$L_S$-N(R$_S$)C(O)R$_{S'}$, -$L_S$-C(=NR$_S$)N(R$_S$R$_{S''}$), -$L_S$-N(R$_{S'}$)C(=NR$_S$)R$_{S'''}$, -$L_S$-N(R$_S$)C(O)N(R$_S$R$_{S''}$), -$L_S$-N(R$_S$)SO$_2$R$_{S'}$, -$L_S$-SO$_2$N(R$_S$R$_{S'}$), -$L_S$-N(R$_S$)SO$_2$N(R$_S$R$_{S''}$), -$L_E$-Q-$L_{E'}$-(C$_3$-C$_{18}$carbocyclyl) and -$L_E$-Q-$L_{E'}$-(M$_3$-M$_{18}$heterocyclyl), and wherein L$^1$ is optionally substituted with one or more R$^{38}$, and R$^{38}$ is independently selected at each occurrence from the group consisting of halogen, oxo, thioxo, hydroxy, mercapto, nitro, cyano, amino, carboxy, formyl, phosphate, azido, alkoxy, thioalkoxy, alkylcarbonyl, alkoxycarbonyl, alkylcarbonyloxy, alkylamino, alkoxycarbonylamino, -$L_S$-O—R$_S$, -$L_S$-S—R$_S$, -$L_S$-C(O)R$_S$, -$L_S$-OC(O)R$_S$, -$L_S$-C(O)OR$_S$, -$L_S$-N(R$_S$R$_{S'}$), -$L_S$-C(=NR$_S$)R$_{S'}$, -$L_S$-S(O)R$_S$, -$L_S$-SO$_2$R$_S$, -$L_S$-C(O)N(R$_S$R$_{S'}$), -$L_S$-N(R$_S$)C(O)R$_{S'}$, -$L_S$-C(=NR$_S$)N(R$_S$R$_{S''}$), -$L_S$-N(R$_{S'}$)C(=NR$_S$)R$_{S'''}$, -$L_S$-N(R$_S$)C(O)N(R$_S$R$_{S''}$), -$L_S$-N(R$_S$)SO$_2$R$_{S'}$, -$L_S$-SO$_2$N(R$_S$R$_{S'}$), -$L_S$-N(R$_S$)SO$_2$N(R$_S$R$_{S''}$), carbocyclyl, heterocyclyl, carbocyclylalkyl, heterocyclylalkyl, -$L_E$-Q-$L_{E'}$-(C$_3$-C$_{18}$carbocyclyl) and -$L_E$-Q-$L_{E'}$-(M$_3$-M$_{18}$heterocyclyl);

L$_S$ is independently selected at each occurrence from the group consisting of a bond, alkylene, alkenylene and alkynylene;

R$_S$, R$_{S'}$ and R$_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

L$_E$ and L$_{E'}$ are each independently selected at each occurrence from the group consisting of a bond, alkylene, alkenylene and alkynylene;

Q is independently selected at each occurrence from the group consisting of a bond, alkylene, alkenylene, alkynylene, —S—, —O—, —C(O)—, —N(R$_S$)—, —N(R$_S$)C(O)—, —C(O)N(R$_S$)—, —N(R$_S$)C(O)O—, —OC(O)N(R$_S$)—, —N(R$_S$)C(O)N(R$_{S'}$)—, —C(=NR$_S$)N(R$_{S'}$)—, —N(R$_{S'}$)C(=NR$_S$)—, —S(O)—, —SO$_2$—, —O—SO$_2$—, —SO$_2$—O—, —O—S(O)—, —S(O)—O—, —C(O)O— and —OC(O)—;

R$^{10}$, R$^{15}$, R$^{15'}$, R$^{18}$, R$^{26}$, R$^{30}$, R$^{33}$, R$^{35}$, R$^{38}$, R$^{41}$, and R$^{41'}$ are each independently optionally substituted at each occurrence with at least one substituent selected from the group consisting of halogen, oxo, thioxo, hydroxy, mercapto, nitro, cyano, amino, carboxy, formyl, phosphate and azido; and each C$_3$-C$_{18}$carbocyclyl and M$_3$-M$_{18}$heterocyclyl moiety in -$L_E$-Q-$L_{E'}$-(C$_3$-C$_{18}$carbocyclyl) and -$L_E$-Q-$L_{E'}$-(M$_3$-M$_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl.

In one embodiment, the present invention features compounds having Formula I, tautomers thereof, and pharmaceutically acceptable salts of the compounds or tautomers, wherein:

A and B are each independently selected from $C_3$-$C_{18}$carbocyclyl or $M_3$-$M_{18}$heterocyclyl, and are each independently optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), and -$L_S$-N($R_S$)SO$_2$N($R_{S'} R_{S''}$);

$W_1$, $W_2$, $W_3$ and $W_4$ are each independently selected from N or C($R^{33}$);

Z is a bond, —C$R^{41}R^{41'}$— or —N$R^{41}$—, wherein $R^{41}$ and $R^{41'}$ are each independently selected from the group consisting of hydrogen, $C_1$-$C_6$alkyl, $C_2$-$C_6$alkenyl and $C_2$-$C_6$alkynyl;

$R^{10}$, $R^{33}$ and $R^{35}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$--O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), and -$L_S$-N($R_S$)SO$_2$N($R_{S'} R_{S''}$);

X is selected from the group consisting of a bond, $C_1$-$C_6$alkylene, $C_2$-$C_6$alkenylene, $C_2$-$C_6$alkynylene, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is $C_3$-$C_{18}$carbocyclyl or $M_3$-$M_{18}$heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N=C(N$R_S R_{S'}$)N$R_S R_{S'}$), -$L_S$-N($R_S$)SO$_2 R_{S'}$, -$L_S$-SO$_2$N($R_S R_{S'}$), -$L_S$-N($R_S$)SO$_2$N($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl); or $R^{22}$ is $C_1$-$C_6$alkyl, $C_2$-$C_6$alkenyl or $C_2$-$C_6$alkynyl, and is optionally substituted with one or more $R^{26}$; or $R^{22}$ is hydrogen;

G is selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$) N($R_{S'} R_{S''}$), -$L_S$-N($R_{S'}$)C(=N$R_S$)$R_{S''}$, -$L_S$-N($R_S$)C(O)N ($R_{S'} R_{S''}$), -$L_S$-N($R_S$)SO$_2 R_{S'}$, -$L_S$-SO$_2$N($R_S R_{S'}$), -$L_S$-N ($R_S$)SO$_2$N($R_{S'} R_{S''}$), and —Y—$R^{50}$, wherein G is optionally substituted with one or more $R^{18}$;

Y is selected from the group consisting of a bond, —O—, —C(O)—, —S(O)—, —S(O)$_2$—, —N($R^{15}$)—, —C(O) O—, —OC(O)—, —C(O)N($R^{15}$)—, —N($R^{15}$)C(O)—, —C(O)N($R^{15}$)O—, —N($R^{15}$)C(O)O—, —OC(O)N ($R^{15}$)—, —N($R^{15}$)C(O)N($R^{15'}$)—, —C(O)N($R^{15}$)N ($R^{15'}$)—, —S—, —C(S)—, —C(S)O—, —OC(S)—, —C(S)N($R^{15}$)—, —N($R^{15}$)C(S)—, —OS(O)$_2$—, —OS (O)—, —OC(O)O—, —N($R^{15}$)—, —N($R^{15}$)S(O)—, —N($R^{15}$)S(O)$_2$—, —S(O)N($R^{15}$)—, —S(O)$_2$N ($R^{15}$)—, —C(S)N($R^{15}$)O—, —N($R^{15}$)C(S)O—, —OC (S)N($R^{15}$)—, —N($R^{15}$)C(S)N($R^{15'}$)—, and —C(S)N ($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl, and $C_2$-$C_6$alkynyl;

$R^{50}$ is -$L^1$-$A^1$, wherein $A^1$ is selected from the group consisting of $C_3$-$C_{18}$carbocyclyl, $M_3$-$M_{18}$heterocyclyl, $C_1$-$C_6$alkyl, $C_2$-$C_6$alkenyl and $C_2$-$C_6$alkynyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$--O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C (=N$R_S$)$R_{S'}$, -$L_S$-S(O)$R_S$, -$L_S$-SO$_2 R_S$, -$L_S$-C(O)N ($R_S R_{S'}$), -$L_S$-N($R_S$)C(O)$R_{S'}$, -$L_S$- C(=N$R_S$)N($R_{S'} R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N($R_S R_{S'}$), -$L_S$-N($R_S$)SO$_2$N ($R_{S'} R_{S''}$), -$L_E$-Q-$L_{E'}$-($C_3$-$C_{18}$carbocyclyl) and -$L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C (O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_{S'} R_{S''}$), -$L_S$-N($R_S$)SO$_2 R_{S'}$, -$L_S$-SO$_2$N ($R_S R_{S'}$), -$L_S$-N($R_S$)SO$_2$N($R_{S'} R_{S''}$), $C_3$-$C_{18}$carbocyclyl, $M_3$-$M_{18}$heterocyclyl, $C_3$-$C_{18}$carbocyclyl$C_1$-$C_6$alkyl, $M_3$-$M_{18}$heterocyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$ alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkyl, $C_2$-$C_6$alkenyl and $C_2$-$C_6$alkynyl;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{18}$, $R^{26}$, $R^{30}$, $R^{33}$, $R^{35}$, $R^{38}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_1$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl.

In one example of this embodiment, $W_1$, $W_2$, $W_3$ and $W_4$ are N.

In another example of this embodiment, A is $C_5$-$C_6$carbocyclyl optionally substituted with one or more $R^{18}$, and B is $M_5$-$M_6$heterocyclyl optionally substituted with one or more $R^{18}$.

In yet another example of this embodiment, A is $M_5$-$M_6$heterocyclyl optionally substituted with one or more $R^{18}$, and B is $M_5$-$M_6$heterocyclyl optionally substituted with one or more $R^{18}$.

In still another example of this embodiment, G is —Y—$R^{50}$, wherein $R^{50}$ is -$L^1$-$A^1$, and $A^1$ is $C_5$-$C_{12}$carbocyclyl or $M_5$-$M_{12}$heterocyclyl and is optionally substituted with one or more $R^{30}$.

In still yet another example of this embodiment, G is —Y—$R^{50}$, Y is —O—, —S—, —C(O)N($R^{15}$)— or —N($R^{15}$)C(O)—, $R^{15}$ is hydrogen, $C_1$-$C_6$alkyl, $C_2$-$C_6$alkenyl or $C_2$-$C_6$alkynyl, and $R^{50}$ is -$L^1$-$A^1$, wherein $L^1$ is $C_1$-$C_6$alkylene optionally substituted with one or more $R^{38}$, and $A^1$ is a $C_4$-$C_7$carbocyclyl or $M_4$-$M_7$heterocyclyl and is optionally substituted with one or more $R^{30}$.

In a further example of this embodiment, G is —Y—$R^{50}$, Y is —O—, —S—, —C(O)N($R^{15}$)— or —N($R^{15}$)C(O)—, $R^{15}$ is hydrogen, $C_1$-$C_6$alkyl, $C_2$-$C_6$alkenyl or $C_2$-$C_6$alkynyl, and $R^{50}$ is -$L^1$-$A^1$, wherein $L^1$ is a bond (i.e., $R^{50}$ is -$A^1$) or $C_1$-$C_6$alkylene optionally substituted with one or more $R^{38}$, and $A^1$ is a bicyclic ring (e.g., a fused bicyclic ring or a bridged bicyclic ring) which has from 6 to 11 ring atoms and is optionally substituted with one or more $R^{30}$.

In another example of this embodiment, X is —O— or —S—, and $R^{22}$ is $C_5$-$C_6$carbocyclyl or $M_5$-$M_6$heterocyclyl and is optionally substituted with one or more $R^{26}$.

In still another example of this embodiment, $R^{10}$, $R^{33}$, $R^{35}$, $K^{41}$ and $R^{41'}$ are each independently selected at each occurrence from hydrogen, halogen or $C_1$-$C_6$alkyl.

In yet another example of this embodiment, $R^{10}$ is hydrogen.

In still another example of this embodiment, $W_1$, $W_2$, $W_3$ and $W_4$ are N, and Z is —N$R^{41}$—, wherein:

$R^{35}$ is selected from hydrogen, halogen or $C_1$-$C_6$alkyl;

$R^{41}$ is selected from hydrogen or $C_1$-$C_6$alkyl;

$R^{10}$ is hydrogen;

A is a $C_5$-$C_6$carbocyclyl or $M_5$-$M_6$heterocyclyl and is optionally substituted with one or more $R^{18}$;

B is $M_5$-$M_6$heterocyclyl optionally substituted with one or more $R^{18}$.

X is —S— or —O—;

$R^{22}$ is

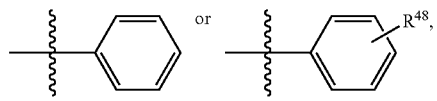

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ (e.g., $R^{48}$ or the phenyl ring in $R^{22}$) is optionally substituted with one or more $R^{26}$;

G is —Y—$R^{50}$;

Y is —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)S(O)—, —N($R^{15}$)S(O)$_2$—, —S(O)N($R^{15}$)—, —S(O)$_2$N($R^{15}$)—, —C(S)N($R^{15}$)O—, —N($R^{15}$)C(S)O—, —OC(S)N($R^{15}$)—, —N($R^{15}$)C(S)N($R^{15'}$)—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl and $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl (e.g., $C_5$-$C_7$carbocyclyl) or $M_4$-$M_{12}$heterocyclyl (e.g., $M_5$-$M_7$heterocyclyl) and is optionally substituted with one or more $R^{30}$; or $L^1$ is a bond (i.e., $R^{50}$ is -$A^1$), and $A^1$ is a $C_4$-$C_{12}$carbocyclyl (e.g., $C_5$-$C_7$carbocyclyl) or $M_4$-$M_{12}$heterocyclyl (e.g., $M_5$-$M_7$heterocyclyl) and is optionally substituted with one or more $R^{30}$; or $L^1$ is a bond (i.e., $R^{50}$ is -$A^1$), and $A^1$ is a bicyclic ring (e.g., a fused bicyclic ring or a bridged bicyclic ring) having from 6 to 12, preferably from 7 to 10, ring atoms and is optionally substituted with one or more $R^{30}$.

The ring member(s) in the moiety

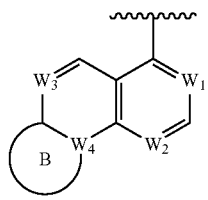

may be substituted with S or other heteroatoms.

In another embodiment, the present invention features compounds of Formula I(a), tautomers thereof, and pharmaceutically acceptable salts of the compounds or tautomers,

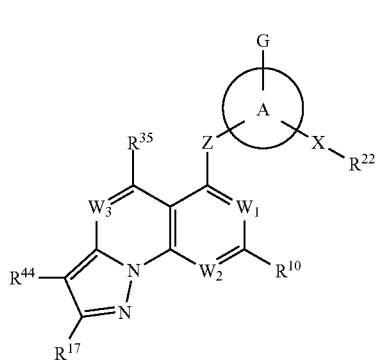

I(a)

wherein:

A is a carbocyclyl or heterocyclyl, and is optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $-L_S$-S—$R_S$, $-L_S$-C(O)$R_S$, $-L_S$-OC(O)$R_S$, $-L_S$-C(O)O$R_S$, $-L_S$-N($R_S R_{S'}$), $-L_S$-C(=N$R_S$)$R_{S'}$, $-L_S$-S(O)$R_S$, $-L_S$-SO$_2$$R_S$, $-L_S$-C(O)N($R_S R_{S'}$), $-L_S$-N($R_S$)C(O)$R_{S'}$, $-L_S$-C(=N$R_S$)N($R_S R_{S''}$), $-L_S$-N($R_{S'}$)C(=N$R_S$)$R_{S'''}$, $-L_S$-N($R_S$)C(O)N($R_S R_{S''}$), $-L_S$-N($R_S$)SO$_2$$R_{S'}$, $-L_S$-SO$_2$N($R_S R_{S'}$), and $-L_S$-N($R_S$)SO$_2$N($R_S R_{S''}$);

$W_1$, $W_2$ and $W_3$ are each independently selected from N or C($R_{33}$);

$R^{10}$, $R^{17}$, $R^{33}$, $R^{35}$ and $R^{44}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, $-L_S$-O—$R_S$, $-L_S$-S—$R_S$, $-L_S$-C(O)$R_S$, $-L_S$-OC(O)$R_S$, $-L_S$-C(O)O$R_S$, $-L_S$-N($R_S R_{S'}$), $-L_S$-C(=N$R_S$)$R_{S'}$, $-L_S$-S(O)$R_S$, $-L_S$-SO$_2$$R_S$, $-L_S$-C(O)N($R_S R_{S'}$), $-L_S$-N($R_S$)C(O)$R_{S'}$, $-L_S$-C(=N$R_S$)N($R_S$—$R_{S'}$), $-L_S$-N(ROC(=N$R_S$)$R_{S'''}$, $-L_S$-N($R_S$)C(O)N($R_S R_{S''}$), $-L_S$-N($R_S$)SO$_2$$R_{S'}$, $-L_S$-SO$_2$N($R_S R_{S'}$), and $-L_S$-N($R_S$)SO$_2$N($R_S R_{S''}$);

Z is a bond, $-CR^{41}R^{41'}$— or $-NR^{41}$—, wherein $R^{41}$ and $R^{41'}$ are each independently selected from the group consisting of hydrogen, $C_1$-$C_6$alkyl, $C_2$-$C_6$alkenyl and $C_2$-$C_6$alkynyl;

X is selected from the group consisting of a bond, $C_1$-$C_6$alkylene, $C_2$-$C_6$alkenylene, $C_2$-$C_6$alkynylene, $-L_S$-S—, $-L_S$-C(O)—, $-L_S$-N($R_S$)—, $-L_S$-N($R_S$)C(O)—, $-L_S$-C(O)N($R_S$)—, $-L_S$-N($R_S$)C(O)O—, $-L_S$-OC(O)N($R_S$)—, $-L_S$-N($R_S$)C(O)N($R_{S'}$)—, C(=N$R_S$)N($R_{S'}$)—, $-L_S$-N($R_{S'}$)C(=N$R_S$)—, $-L_S$-S(O)—, $-L_S$-SO$_2$—, $-L_S$-C(O)O— and $-L_S$-OC(O)—;

$R^{22}$ is $C_3$-$C_{18}$carbocyclyl or $M_3$-$M_{18}$heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $-L_S$-O—$R_S$, $-L_S$-S—$R_S$, $-L_S$-C(O)$R_S$, $-L_S$-OC(O)$R_S$, $-L_S$-C(O)O$R_S$, $-L_S$-N($R_S R_{S'}$), $-L_S$-C(=N$R_S$)$R_{S'}$, $-L_S$-S(O)$R_S$, $-L_S$-SO$_2$$R_S$, $-L_S$-C(O)N($R_S R_{S'}$), $-L_S$-N($R_S$)C(O)$R_{S'}$, $-L_S$-C(=N$R_S$)N($R_S R_{S''}$), $-L_S$-N($R_{S'}$)C(=N$R_S$)$R_{S'''}$, $-L_S$-N($R_S$)C(O)N($R_S R_{S''}$), $-L_S$-N=C(N$R_S R_{S'}$)(N$R_S R_{S'}$), $-L_S$-N($R_S$)SO$_2$$R_{S'}$, $-L_S$-SO$_2$N($R_S R_{S'}$), $-L_S$-N($R_S$)SO$_2$N($R_S R_{S''}$), $-L_E$-Q-$L_{E'}$-($C_3$-$C_{18}$carbocyclyl) and $-L_E$-Q-$L_{E'}$-($M_3$-$M_{18}$heterocyclyl); or $R^{22}$ is $C_1$-$C_6$alkyl, $C_2$-$C_6$alkenyl or $C_2$-$C_6$alkynyl, and is optionally substituted with one or more $R^{26}$; or $R^{22}$ is hydrogen;

G is selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_1$-$C_6$alkynyl, $-L_S$-O—$R_S$, $-L_S$-S—$R_S$, $-L_S$-C(O)$R_S$, $-L_S$-OC(O)$R_S$, $-L_S$-C(O)O$R_S$, $-L_S$-N($R_S R_{S'}$), $-L_S$-C(=N$R_S$)$R_{S'}$, $-L_S$-S(O)$R_S$, $-L_S$-SO$_2$$R_S$, $-L_S$-C(O)N($R_S R_{S'}$), $-L_S$-N($R_S$)C(O)$R_{S'}$, $-L_S$-C(=N$R_S$)N($R_S R_{S''}$), $-L_S$-N($R_{S'}$)C(=N$R_S$)$R_{S'''}$, $-L_S$-N($R_S$)C(O)N($R_S R_{S''}$), $-L_S$-N($R_S$)SO$_2$$R_{S'}$, $-L_S$-SO$_2$N($R_S R_{S'}$), $-L_S$-N($R_S$)SO$_2$N($R_S R_{S''}$), and $-Y-R^{50}$, wherein G is optionally substituted with one or more $R^{18}$;

Y is selected from the group consisting of a bond, $-O-$, $-C(O)-$, $-S(O)-$, $-S(O)_2-$, $-N(R^{15})-$, $-C(O)O-$, $-OC(O)-$, $-C(O)N(R^{15})-$, $-N(R^{15})C(O)-$, $-C(O)N(R^{15})O-$, $-N(R^{15})C(O)O-$, $-OC(O)N(R^{15})-$, $-N(R^{15})C(O)N(R^{15'})-$, $-C(O)N(R^{15})N(R^{15'})-$, $-S-$, $-C(S)-$, $-C(S)O-$, $-OC(S)-$, $-C(S)N(R^{15})-$, $-N(R^{15})C(S)-$, $-OS(O)_2-$, $-OS(O)-$, $-OC(O)O-$, $-N(R^{15})-$, $-N(R^{15})S(O)-$, $-N(R^{15})S(O)_2-$, $-S(O)N(R^{15})-$, $-S(O)_2N(R^{15})-$, $-C(S)N(R^{15})O-$, $-N(R^{15})C(S)O-$, $-OC(S)N(R^{15})-$, $-N(R^{15})C(S)N(R^{15'})-$, and $-C(S)N(R^{15})N(R^{15'})-$, wherein $R^{15}$ and $R^{15'}$ are each independently selected at each occurrence from the group consisting of hydrogen, $C_1$-$C_6$alkyl, $C_2$-$C_6$alkenyl, $C_2$-$C_6$alkynyl;

$R^{50}$ is $-L^1$-$A^1$, wherein $A^1$ is selected from the group consisting of $C_3$-$C_{18}$carbocyclyl, $M_3$-$M_{18}$heterocyclyl, $C_1$-$C_6$alkyl, $C_2$-$C_6$alkenyl and $C_2$-$C_6$alkynyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $-L_S$-O—$R_S$, $-L_S$-S—$R_S$, $-L_S$-C(O)$R_S$, $-L_S$-OC(O)$R_S$, $-L_S$-C(O)O$R_S$, $-L_S$-N($R_S R_{S'}$), $-L_S$-C(=N$R_S$)$R_{S'}$, $-L_S$-S(O)$R_S$, $-L_S$-SO$_2$$R_S$, $-L_S$-C(O)N($R_S R_{S'}$), $-L_S$-N($R_S$)C(O)$R_{S'}$, $-L_S$-C(=N$R_S$)N($R_S R_{S''}$), $-L_S$-N($R_{S'}$)C(=N$R_S$)$R_{S'''}$, $-L_S$-N($R_S$)C(O)N($R_S R_{S''}$), $-L_S$-N($R_S$)SO$_2$$R_{S'}$, $-L_S$-SO$_2$N($R_S R_{S'}$), $-L_S$-N($R_S$)SO$_2$N($R_S R_{S''}$), $-L_E$-Q-$L_{E'}$-($C_3$-$C_{18}$carbocyclyl) and $-L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, (O)$R_S$, -$L_S$-SO$_2R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_S$)C(=N$R_S$)$R_{S'}$, -$L_S$-N($R_S$)C(O)N($R_S R_{S''}$), -$L_S$-N($R_S$)SO$_2R_{S'}$, -$L_S$-SO$_2$N($R_S R_{S'}$), -$L_S$-N($R_S$)SO$_2$N($R_S R_{S''}$), $C_3$-$C_{18}$carbocyclyl, $M_3$-$M_{18}$heterocyclyl, $C_3$-$C_{18}$carbocyclyl$C_1$-$C_6$alkyl, $M_3$-$M_{18}$heterocyclyl$C_1$-$C_6$alkyl, -$L_E$-Q-$L_{E'}$-($C_3$-$C_8$carbocyclyl) and -$L_E$-Q-4-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkyl, $C_2$-$C_6$alkenyl and $C_2$-$C_6$alkynyl;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —SO$_2$—, —O—SO$_2$—, —O—S(O)—, —S(O)—O—, —C(O)O— and —OC(O)—;

$R^{10}$, $R^{15}$, $R^{15'}$, $R^{17}$, $R^{18}$, $R^{26}$, $R^{30}$, $R^{33}$, $R^{35}$, $R^{38}$, $R^{41}$, $R^{41'}$ and $R^{44}$ are each independently optionally substituted at each occurrence with at least one substituent selected from the group consisting of halogen, oxo, thioxo, hydroxy, mercapto, nitro, cyano, amino, carboxy, formyl, phosphate and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkyl carbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl.

In one example of this embodiment, $W_1$, $W_2$ and $W_3$ are N, and Z is —N$R^{41}$—.

In another example of this embodiment, A is a $C_5$-$C_6$carbocyclyl or $M_5$-$M_6$heterocyclyl and is optionally substituted with one or more $R^{18}$.

In still another example of this embodiment, G is —Y—$R^{50}$, and $R^{50}$ is -$L^1$-$A^1$, wherein $A^1$ is a $C_5$-$C_6$carbocyclyl or $M_5$-$M_6$heterocyclyl and is optionally substituted with one or more $R^{30}$.

In a further example of this embodiment, X is —O— or —S—, and $R^{22}$ is $C_5$-$C_6$carbocyclyl or $M_5$-$M_6$heterocyclyl and is optionally substituted with one or more $R^{26}$.

In yet another example of this embodiment, $R^{10}$, $R^{17}$, $R^{33}$, $R^{35}$, $R^{41}$, $R^{41'}$ and $R^{44}$ are each independently selected from hydrogen, halogen or $C_1$-$C_6$alkyl.

In still another embodiment, the present invention features compounds having Formula I(b), tautomers thereof, and pharmaceutically acceptable salts of the compounds or tautomers,

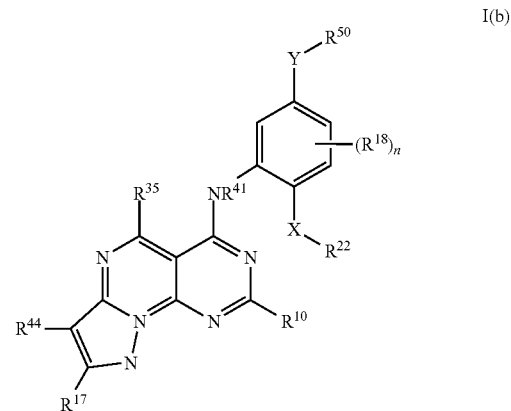

I(b)

wherein:
$R^{10}$, $R^{17}$, $R^{35}$, $R^{41}$ and $R^{44}$ are each independently selected from hydrogen, halogen, $C_1$-$C_6$alkyl or $C_3$-$C_6$cycloalkyl;
X is —S— or —O—;
$R^{22}$ is

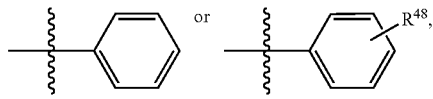

wherein $R^{48}$ is hydroxy, amino, $C_1$-$C_6$alkylamino or $C_1$-$C_6$alkoxy, and $R^{22}$ is optionally substituted with one or more $R^{26}$;
Y is selected from the group consisting of —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)—, —N($R^{15}$)S(O)—, —N($R^{15}$)S(O)$_2$—, —S(O)N($R^{15}$)—, —S(O)$_2$N($R^{15}$)—, —C(S)N($R^{15}$)O—, —N($R^{15}$)C(S)O—, —OC(S)N($R^{15}$)—, —N($R^{15}$)C(S)N($R^{15'}$)—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl, $C_2$-$C_6$alkynyl;
$R^{50}$ is -$L^1$-$A^1$, wherein $L^1$ a bond or $C_1$-$C_6$alkylene optionally substituted with one or more $R^{38}$, and $A^1$ is $C_5$-$C_{10}$carbocyclyl or $M_5$-$M_{10}$heterocyclyl and is optionally substituted with one or more $R^{30}$;

$R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N(ROC(=N$R_S$)$R_{S'}$, -$L_S$-N($R_S$)C(O)N($R_S R_{S''}$), -$L_S$-N($R_S$)SO$_2 R_{S'}$, and -$L_S$-N($R_S$)SO$_2$N($R_S R_{S''}$);

$R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S'}$), -$L_S$-N=C(N$R_S R_{S'}$)(N$R_S R_{S'}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

$R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

$R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), $C_3$-$C_{18}$carbocyclyl, $M_3$-$M_{18}$heterocyclyl, $C_3$-$C_{18}$carbocyclyl$C_1$-$C_6$alkyl, $M_3$-$M_{18}$heterooyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbony 1 amino$C_1$-$C_6$alkyl;

$L_E$ and $L_{E'}$ are each independently selected at each occurrence from the group consisting of a bond, $C_1$-$C_6$alkyl, $C_2$-$C_6$alkenyl and $C_2$-$C_6$alkynyl;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{17}$, $R^{18}$, $R^{26}$, $R^{30}$, $R^{35}$, $R^{38}$, $R^{41}$, and $R^{44}$ are each independently optionally substituted at each occurrence with at least one substituent selected from the group consisting of halogen, oxo, thioxo, hydroxy, mercapto, nitro, cyano, amino, carboxy, formyl, phosphate and azido;

each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, $C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkyl carbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl; and n is 0, 1, 2, or 3.

In one example of this embodiment, $R^{10}$ is hydrogen.

In another example of this embodiment, $R^{10}$, $R^{17}$, $R^{35}$, $R^{41}$ and $R^{44}$ are each independently selected from hydrogen, halogen or $C_1$-$C_6$alkyl.

In yet another example of this embodiment, X is —S—, and $R^{22}$ is

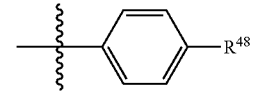

and is optionally substituted with one or more $R^{26}$, wherein $R^{48}$ is hydroxy or amino.

In still another example of this embodiment, $A^1$ is $C_5$-$C_{10}$carbocyclyl (e.g., phenyl) or $M_5$-$M_{10}$heterocyclyl, and is optionally substituted with one or more $R^{30}$.

In still yet another example of this embodiment, $R^{18}$, $R^{26}$, $R^{30}$, and $R^{38}$ are each independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, and $C_2$-$C_6$alkynyl.

Salts of the Compounds of this Invention

The compounds of the present invention, or tautomers thereof, can be used in the form of salts. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient, the salt preferably is pharmaceutically acceptable. Pharmaceutically acceptable salts include, but are not limited to, salts commonly used to form alkali metal salts and/or to form addition salts of free acids or free bases. In general, these salts typically may be prepared by conventional means with a compound of this invention by reacting, for example, the appropriate acid or base with the compound.

Pharmaceutically acceptable acid addition salts of the compounds of this invention may be prepared from an inorganic or organic acid. Examples of suitable inorganic acids include hydrochloric, hydrobromic acid, hydroionic, nitric, carbonic, sulfuric, and phosphoric acid. Suitable organic acids generally include, for example, aliphatic, cycloaliphatic, aromatic, araliphatic, heterocyclyl, carboxylc, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, b-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, hemisulfate, heptanoate, hexanoate, nicotinate, 2-naphthalesulfonate, oxalate, palmoate, pectinate, persulfate, 3-phenylpropionate, picrate, pivalate, thiocyanate, tosylate, and undecanoate.

Pharmaceutically acceptable base addition salts of the compounds of this invention include, for example, metallic salts and organic salts. Preferred metallic salts include, but are not limited to, alkali metal (group Ia) salts, alkaline earth metal (group IIa) salts, and other physiological acceptable metal salts. Such salts may be made from aluminum, calcium, lithium, magnesium, potassium, sodium, and zinc. Non-limiting examples of preferred organic salts can be made from tertiary amines and quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Solvates, Prodrugs, and Isomers

The compounds of the present invention, tautomers thereof, and their salts, may also exist in the form of solvates with water, for example hydrates, or with organic solvents such as methanol, ethanol or acetonitrile to form, respectively, a methanolate, ethanolate or acetonitrilate. The compounds of the present invention may exist in each form of solvate or mixtures thereof.

In one aspect, the compounds, tautomers or salts of the present invention may be in the form of prodrugs. Some are aliphatic or aromatic esters derived from acidic groups on compounds of this invention. Others are aliphatic or aromatic esters of hydroxyl or amino groups on compounds of this invention. The present invention also features phosphate prodrugs of hydroxyl groups on the compounds of this invention.

The compounds of the invention may comprise asymmetrically substituted carbon atoms known as chiral centers. These chiral centers are designated as "R" or "S" depending on the configuration of substituents around the chiral carbon atom. The terms "R" and "S" used herein are configurations as defined in Nomenclature of Organic Chemistry, Section E: Stereochemistry, Recommendations 1974, PURE APPL. CHEM., 45:11-30 (1976). The compounds of this invention may exist, without limitation, as single stereoisomers (e.g., single enantiomers or single diastereomer), mixtures of stereoisomers (e.g. any mixture of enantiomers or diastereomers), or racemic mixtures. All such single stereoisomers, mixtures and racemates are encompassed within the scope of the invention. Compounds identified herein as single stereoisomers are meant to describe compounds that are present in a form that is substantially free from other stereoisomers (e.g., other enantiomers or diastereomers). By "substantially free," it means that at least 80% of the compound in a composition is the desired stereoisomer; preferably, at least 90% of the compound in a composition is the desired stereoisomer; and more preferably, at least 95%, 96%, 97%, 98% or 99% of the compound in a composition is the desired stereoisomer. Where the stereochemistry of the chiral carbon(s) present in a chemical structure is not specified, the chemical structure is intended to encompass compounds containing either stereoisomer of each chiral center present in the chemical structure.

Individual stereoisomers of the compounds of this invention can be prepared using many methods known in the art. These methods include, but are not limited to, stereospecific synthesis, chromatographic separation of diastereomers, chromatographic resolution of enantiomers, conversion of enantiomers in an enantiomeric mixture to diastereomers followed by chromatographically separation of the diastereomers and regeneration of the individual enantiomers, and enzymatic resolution.

Stereospecific synthesis typically involves the use of appropriate optically pure (enantiomerically pure) or substantial optically pure materials and synthetic reactions that do not cause racemization or inversion of stereochemistry at the chiral centers. Mixtures of stereoisomers of compounds, including racemic mixtures, resulting from a synthetic reaction may be separated, for example, by chromatographic techniques as appreciated by those of ordinary skill in the art. Chromatographic resolution of enantiomers can be accomplished on chiral chromatography resins, many of which are commercially available. In a non-limiting example, racemate is placed in solution and loaded onto the column containing a chiral stationary phase. Enantiomers can then be separated by HPLC.

Resolution of enantiomers can also be accomplished by converting enantiomers in a mixture to diastereomers by reaction with chiral auxiliaries. The resulting diastereomers can be separated by column chromatography or crystallization/re-crystallization. This technique is useful when the compounds to be separated contain a carboxyl, amino or hydroxyl group that will form a salt or covalent bond with the chiral auxiliary. Non-limiting examples of suitable chiral auxiliaries include chirally pure amino acids, organic carboxylic acids or organosulfonic acids. Once the diastereomers are separated by chromatography, the individual enantiomers can be regenerated. Frequently, the chiral auxiliary can be recovered and used again.

Enzymes, such as esterases, phosphatases or lipases, can be useful for the resolution of derivatives of enantiomers in an enantiomeric mixture. For example, an ester derivative of a carboxyl group in the compounds to be separated can be treated with an enzyme which selectively hydrolyzes only one of the enantiomers in the mixture. The resulting enantiomerically pure acid can then be separated from the unhydrolyzed ester.

Alternatively, salts of enantiomers in a mixture can be prepared using any method known in the art, including treatment of the carboxylic acid with a suitable optically pure base such as alkaloids or phenethylamine, followed by precipitation or crystallization/re-crystallization of the enantiomerically pure salts. Methods suitable for the resolution/separation of a mixture of stereoisomers, including racemic mixtures, can be found in ENANTIOMERS, RACEMATES, AND RESOLUTIONS (Jacques et al., 1981, John Wiley and Sons, New York, N.Y.).

A compound of this invention may possess one or more unsaturated carbon-carbon double bonds. All double bond isomers, such as the cis (Z) and trans (E) isomers, and mixtures thereof are intended to be encompassed within the scope of a recited compound unless otherwise specified. In addition, where a compound exists in various tautomeric forms, a recited compound is not limited to any one specific tautomer, but rather is intended to encompass all tautomeric forms.

Certain compounds of the invention may exist in different stable conformational forms which may be separable. Torsional asymmetry due to restricted rotations about an asymmetric single bond, for example because of steric hindrance or ring strain, may permit separation of different conformers. The compounds of the invention includes each conformational isomer of these compounds and mixtures thereof.

Certain compounds of the invention may also exist in zwitterionic form and the invention includes each zwitterionic form of these compounds and mixtures thereof.

Defintions

The compounds of the present invention are generally described herein using standard nomenclature. For a recited compound having asymmetric center(s), it should be understood that all of the stereoisomers of the compound and mixtures thereof are encompassed in the present invention unless otherwise specified. Non-limiting examples of stereoisomers include enantiomers, diastereomers, and cis-transisomers. Where a recited compound exists in various tautomeric forms, the compound is intended to encompass all tautomeric forms. Certain compounds are described herein using general formulas that include variables (e.g., $A^1$, $L^1$, X, Y, $R^{17}$, or Z). Unless otherwise specified, each variable within such a formula is defined independently of any other variable, and any variable that occurs more than one time in a formula is defined independently at each occurrence. If substituents are described as being "independently selected" from a group, each substituent is selected independently from the other. Each substituent therefore can be identical to or different from the other substituent(s).

The number of carbon atoms in a hydrocarbyl substituent can be indicated by the prefix "$C_x$-$C_y$," where x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms. A prefix attached to a multiple-component substituent only applies to the first component that immediately follows the prefix. To illustrate, the term "alkylaryl" contains two components: alkyl and aryl. Thus, for example, $C_1$-$C_6$alkylaryl refers to a $C_1$-$C_6$alkyl appended to the parent molecular moiety through an aryl group. Likewise, alkyl$C_6$-$C_{10}$aryl refers to an alkyl group appended to the parent molecular moiety through a $C_6$-$C_{10}$aryl group. Similarly, the prefix "halo" on haloalkoxyalkyl indicates that the alkoxy component is substituted with one or more halogen radicals, while the prefix "halo" on alkoxyhaloalkyl indicates that the alkyl component is substituted with one or more halogen radicals.

When words are used to describe a linking element between two other elements of a depicted chemical structure, the leftmost-described component of the linking element is the component that is bound to the left element in the depicted structure. To illustrate, if the chemical structure is X-L-Y and L is described as methylarylethyl, then the chemical would be X-methyl-aryl-ethyl-Y.

If a linking element in a depicted structure is a bond, then the left element in the depicted structure is bound directly to the right element in the depicted structure. For example, if a chemical structure is depicted as X-L-Y and L is selected as a bond, then the chemical structure would be X—Y. For another example, if a chemical moiety is depicted as -L-X and L is selected as a bond, then the chemical moiety would be —X. For yet another example, if a chemical structure is depicted as X-$L_1$-$L_2$-Y, X-$L_1$-$L_2$-$L_3$-Y or X-$L_1$-$L_2$-...-$L_N$-Y, and $L_1$, $L_2$, $L_3$, ... $L_N$ are selected as bonds, then the chemical structure would be X—Y.

When a chemical formula is used to describe a substituent, the dash on the right (or left) side of the formula indicates the portion of the substituent that has the free valence(s).

If a substituent is described as being "substituted," a non-hydrogen radical is in the place of one or more hydrogen radials on a carbon, nitrogen or oxygen of the substituent. Thus, for example, a substituted alkyl substituent is an alkyl substituent wherein at least one non-hydrogen radical is in the place of a hydrogen radical(s) on the alkyl substituent. To illustrate, monofluoroalkyl is alkyl substituted with one fluoro radical, and difluoroalkyl is alkyl substituted with two fluoro radicals. It should be recognized that if there are two or more substitutions on a substituent, each of the non-hydrogen radicals may be identical or different unless otherwise stated.

A substituent is "substitutable" if it comprises at least one carbon, nitrogen or oxygen atom that is bonded to one or more hydrogen atoms.

If a substituent is described as being "optionally substituted", the substituent may be either substituted or not substituted. If a substituent is described as being optionally substituted with up to a particular number of non-hydrogen radicals, that substituent may be either not substituted, or substituted by up to that particular number of non-hydrogen radicals or by up to the maximum number of substitutable positions on the substituent, whichever is less. Thus, for example, if a substituent is described as a heteroaryl optionally substituted with up to three non-hydrogen radicals, then any heteroaryl with less than three substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to two non-hydrogen radicals, then a primary amino nitrogen will be optionally substituted with up to two non-hydrogen radicals, whereas a secondary amino nitrogen will be optionally substituted with up to only one non-hydrogen radical.

The term "alkenyl" (alone or in combination with another term(s)) means a straight- or branched-chain hydrocarbyl substituent containing one or more double bonds and typically from 2 to 20 carbon atoms, more typically from 2 to 8 carbon atoms, and even more typically from 2 to 6 carbon atoms. Each carbon-carbon double bond may have either cis or trans geometry within the alkenyl moiety, relative to groups substituted on the double bond carbons. Non-limiting examples of such substituents include ethenyl (vinyl), 2-propenyl, 3-propenyl, 1,4-pentadienyl, 1,4-butadienyl, 1-butenyl, 2-butenyl, and 3-butenyl.

The term "alkenylene" (alone or in combination with another term(s)) refers to a divalent unsaturated hydrocarbyl group which may be linear or branched and which has at least one carbon-carbon double bond. An alkenylene group typically contains 2 to 20 carbon atoms, more typically from 2 to 8 carbon atoms, and even more typically from 2 to 6 carbon atoms. Non-limiting examples of alkenylene groups include —C(H)=C(H)—, —C(H)=C(H)—CH$_2$—, —C(H)=C(H)—CH$_2$—CH$_2$—, —CH$_2$—C(H)=C(H)—CH$_2$—, —C(H)=C(H)—CH(CH$_3$)—, and —CH$_2$—C(H)=C(H)—CH(CH$_2$CH$_3$)—.

The term "alkoxy" (alone or in combination with another term(s)) refers to an alkyl group appended to the parent molecular moiety through an oxy moiety (i.e., —O-alkyl). Non-limiting examples of such a substituent include methoxy (—O—CH$_3$), ethoxy, n-propoxy, isopropoxy, n-butoxy, isobutoxy, sec-butoxy, and tert-butoxy.

The term "alkoxyalkyl" (alone or in combination with another term(s)) refers to an alkoxy group appended to the parent molecular moiety through an alkylene group. Non-limiting examples of alkoxyalkyl include tert-butoxymethyl, 2-ethoxyethyl, 2-methoxyethyl, and methoxymethyl.

The term "alkoxycarbonyl" (alone or in combination with another term(s)) refers to an alkoxy group appended to the parent molecular moiety through a carbonyl group (i.e., —C(O)—O-alkyl). Representative examples of alkoxycarbonyl include, but are not limited to, methoxycarbonyl, ethoxycarbonyl

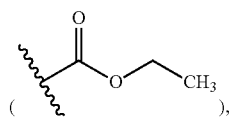

and tert-butoxycarbonyl.

The term "alkoxycarbonylamino" (alone or in combination with another term(s)) refers to N(R$_A$R$_B$)—, where R$_A$ is alkyl-OC(O)—, and R$_B$ is alkyl-O—C(O)— or hydrogen. R$_A$ and R$_B$ may be identical or different.

The term "alkoxycarbonylaminoalkyl" (alone or in combination with another term(s)) refers to N(R$_A$R$_B$)-alkylene-, where R$_A$ is alkyl-O—C(O)—, and R$_B$ is alkyl-O—C(O)— or hydrogen. R$_A$ and R$_B$ may be identical or different.

The term "alkoxycarbonylalkyl" (alone or in combination with another term(s)) refers to an alkoxycarbonyl group appended to the parent molecular moiety through an alkylene group. Representative examples of alkoxycarbonylalkyl include, but are not limited to, 2-methoxy-2-oxoethyl, 2-ethoxy-2-oxoethyl, 3-methoxy-3-oxopropyl, 3-ethoxy-3-oxopropyl, 4-ethoxy-2-(ethoxycarbonyl)-4-oxobutyl, 5-methoxy-5-oxopentyl, and 6-methoxy-6-oxohexyl.

The term "alkyl" (alone or in combination with another term(s)) means a straight- or branched-chain saturated hydrocarbyl substituent typically containing from 1 to 20 carbon atoms, more typically from 1 to 8 carbon atoms, and even more typically from 1 to 6 carbon atoms. Non-limiting examples of such substituents include methyl, ethyl, n-propyl, isopropyl, n-butyl, isobutyl, sec-butyl, t-butyl, pentyl, iso-amyl, hexyl, and octyl.

The term "alkylamino" (alone or in combination with another term(s)) refers to —NR$_A$R$_B$, wherein R$_A$ is alkyl, and R$_B$ is hydrogen or alkyl. R$_A$ and R$_B$ may be identical or different. For instance, C$_1$-C$_6$alkylamino refers to —NR$_A$R$_B$, wherein R$_A$ is C$_1$-C$_6$alkyl, and R$_B$ is hydrogen or C$_1$-C$_6$alkyl.

The term "alkylaminoalkyl" (alone or in combination with another term(s)) refers to N(R$_A$R$_B$)-alkylene-, wherein R$_A$ is alkyl, and R$_B$ is hydrogen or alkyl. R$_A$ and R$_B$ may be identical or different. Thus, C$_1$-C$_6$alkylaminoC$_1$-C$_6$alky refers to N(R$_A$R$_B$)—C$_1$-C$_6$alkylene-, wherein R$_A$ is C$_1$-C$_6$alkyl, and R$_B$ is hydrogen or C$_1$-C$_6$alkyl.

The term "alkylcarbonyl" (alone or in combination with another term(s)) refers to an alkyl group appended to the parent molecular moiety through a carbonyl group (i.e., —C(O)-alkyl). Representative examples of alkylcarbonyl include, but are not limited to, acetyl, ethylcarbonyl

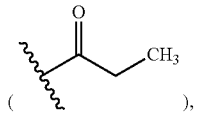

1-oxopropyl, 2,2-dimethyl-1-oxopropyl, 1-oxobutyl, and 1-oxopentyl.

The term "alkylcarbonylalkyl" (alone or in combination with another term(s)) refers to an alkylcarbonyl group appended to the parent molecular moiety through an alkylene group. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" (alone or in combination with another term(s)) refers to an alkylcarbonyl group appended to the parent molecular moiety through an oxy moiety. Representative examples of alkylcarbonyloxy include, but are not limited to, acetyloxy, ethylcarbonyloxy, and tert-butylcarbonyloxy.

The term "alkylcarbonyloxyalkyl" (alone or in combination with another term(s)) refers to an alkylcarbonyloxy group appended to the parent molecular moiety through an alkylene moiety. Representative examples of alkylcarbonyloxyalkyl include, but are not limited to, 2-(acetyloxy)ethyl, 3-(acetyloxy)propyl, and 3-(propionyloxy)propyl.

The terms "alkylene" or "alkylenyl" (alone or in combination with another term(s)) denote a divalent group derived from a straight or branched saturated hydrocarbyl chain typically containing from 1 to 20 carbon atoms, more typically from 1 to 8 carbon atoms, and even more typically from 1 to 6 carbon atoms. Representative examples of alkylene include, but are not limited to, —CH$_2$—, —CH$_2$CH$_2$—, —CH$_2$CH$_2$CH$_2$CH$_2$—, and —CH$_2$CH(CH$_3$)CH$_2$—.

The term "alkynyl" (alone or in combination with another term(s)) means a straight- or branched-chain hydrocarbyl substituent containing one or more triple bonds and typically from 2 to 20 carbon atoms, more typically from 2 to 8 carbon atoms, and even more typically from 2 to 6 carbon atoms. Non-limiting examples of such substituents include ethynyl, 1-propynyl, 2-propynyl, 3-propynyl, decynyl, 1-butynyl, 2-butynyl, and 3-butynyl.

The terms "alkynylene" (alone or in combination with another term(s)) refers to a divalent unsaturated hydrocarbon group which may be linear or branched and which has at least one carbon-carbon triple bonds. Representative alkynylene groups include, by way of example, —C≡C—, —C≡C—CH₂—, —C≡C—CH₂—CH₂—, —CH₂—C≡C—CH₂, —C≡C—CH(CH₃)—, and —CH₂—C≡C—CH(CH₂CH₃)—.

The term "amino" (alone or in combination with another term(s)) means —NH₂. The term "monosubstituted amino" (alone or in combination with another term(s)) means an amino substituent wherein one of the hydrogen radicals is replaced by a non-hydrogen substituent. The term "disubstituted amino" (alone or in combination with another term(s)) means an amino substituent wherein both of the hydrogen atoms are replaced by non-hydrogen substituents, which may be identical or different.

The term "aminocarbonyl" (alone or in combination with another term(s)) means —C(O)—NH₂, which also may be depicted as:

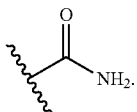

The term "aminoalkyl" (alone or in combination with another term(s)) means -alkylene-NH₂.

The term "aminoalkylcarbonyl" (alone or in combination with another term(s)) means —C(O)— alkylene-NH₂. For example, "aminomethylcarbonyl" may be depicted as:

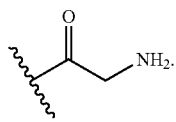

The term "aminosulfonyl" (alone or in combination with another term(s)) means —S(O)₂—NH₂, which also may be depicted as:

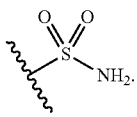

The term "aryl" (alone or in combination with another term(s)) refers to an aromatic carbocyclyl containing from 6 to 14 carbon ring atoms. Non-limiting examples of aryls include phenyl, naphthalenyl, anthracenyl, and indenyl. An aryl group can be connected to the parent molecular moiety through any substitutable carbon atom of the group.

The term "arylalkyl" (alone or in combination with another term(s)) refers to an aryl group appended to the parent molecular moiety through an alkylene group. Representative examples of substituted/unsubstituted arylalkyl include, but are not limited to, benzyl, 4-(benzyloxy)benzyl, 4-methoxybenzyl, 4-hydroxybenzyl, 3-(1,3-benzodioxol-5-yl)-2-methylpropyl, 3-(phenoxy)benzyl, 3-(1,3-benzodioxol-5-yl)propyl, 2-phenylethyl, 3-phenylpropyl, 2-naphthylmethyl, 3,5-ditert-butyl-2-hydroxybenzyl, 3-methoxybenzyl, 3,4-dimethoxybenzyl, 4-(dimethylamino)benzyl, 4-[3-(dimethylamino)propoxy]benzyl, (6-methoxy-2-naphthyl)methyl, and 2-naphth-2-ylethyl.

The term "arylalkylcarbonyl" (alone or in combination with another term(s)) refers to an arylalkyl group appended to the parent molecular moiety through a carbonyl group (i.e., arylalkyl-C(O)—). Representative examples of arylalkylcarbonyl include, but are not limited to, 2-naphthylacetyl and phenylacetyl.

The term "arylalkoxy" (alone or in combination with another term(s)) refers to an arylalkyl group appended to the parent molecular moiety through an oxy moiety (i.e., arylalkyl-O—). Representative examples of arylalkoxy include, but are not limited to, 2-phenylethoxy, 3-naphth-2-ylpropoxy, and 5-phenylpentyloxy.

The term "arylalkoxyalkyl" (alone or in combination with another term(s)) refers to an arylalkoxy group appended to the parent molecular moiety through an alkylene group. Representative examples of arylalkoxyalkyl include, but are not limited to, benzyloxymethyl, 2-(benzyloxy)ethyl, and (2-phenylethoxy)methyl.

The term "arylalkoxycarbonyl" (alone or in combination with another term(s)) refers to an arylalkoxy group appended to the parent molecular moiety through a carbonyl group. Representative examples of arylalkoxycarbonyl include, but are not limited to, benzyloxycarbonyl, and naphth-2-yl-methoxycarbonyl.

The term "arylcarbonyl" (alone or in combination with another term(s)) refers to an aryl group appended to the parent molecular moiety through a carbonyl group. Representative examples of arylcarbonyl include, but are not limited to, benzoyl and naphthoyl.

The term "aryloxy" (alone or in combination with another term(s)) refers to an aryl group appended to the parent molecular moiety through an oxy moiety. Representative examples of substituted/unsubstituted aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" (alone or in combination with another term(s)) refers to an aryloxy group appended to the parent molecular moiety through an alkylene group. Representative examples of aryloxyalkyl include, but are not limited to, 2-phenoxyethyl, 3-naphth-2-yloxypropyl, and phenoxymethyl.

The term "aryloxycarbonyl" (alone or in combination with another term(s)) refers to an aryloxy group appended to the parent molecular moiety through a carbonyl group.

The term "arylthio" (alone or in combination with another term(s)) refers to an aryl group appended to the parent molecular moiety through a sulfur atom (i.e., aryl-S—). Representative examples of arylthio include, but are not limited to, phenylthio, naphthalen-1-ylthio, and naphthalen-2-ylthio.

The term "arylthioalkyl" (alone or in combination with another term(s)) refers to aryl-S-alkylene-. Representative examples of arylthioalkyl include, but are not limited to, (phenylthio)methyl, 2-(phenylthio)ethyl, and 3-(phenylthio)propyl.

The term "arylthioalkoxy" (alone or in combination with another term(s)) refers to an arylthioalkyl group appended to the parent molecular moiety through an oxy group.

The term "arylthioalkoxyalkyl" (alone or in combination with another term(s)) refers to an arylthioalkoxy group appended to the parent molecular moiety through an alkylene group.

The terms "carbocycle" or "carbocyclic" or "carbocyclyl" (alone or in combination with another term(s)) refer to a saturated (e.g., "cycloalkyl"), partially saturated (e.g., "cycloalkenyl" or "cycloalkynyl") or completely unsaturated (e.g., "aryl") ring system containing zero heteroatom ring atom and typically from 3 to 18 carbon ring atoms. "Ring atoms" or "ring members" are the atoms bound together to form the ring or rings of a cyclic substituent. A carbocyclyl may be, without limitation, a single ring, or two or more fused rings, or bridged or spiro rings. A carbocyclyl may contain from 3 to 14 ring members (i.e., $C_3$-$C_{14}$carbocyclyl, such as $C_3$-$C_{14}$cycloalkyl), from 3 to 10 ring members (i.e., $C_3$-$C_{10}$carbocyclyl, such as $C_3$-$C_{10}$cycloalkyl), from 3 to 8 ring members (i.e., $C_3$-$C_8$carbocyclyl, such as $C_3$-$C_8$cycloalkyl), from 3 to 6 ring members (i.e., $C_3$-$C_6$carbocyclyl, such as $C_3$-$C_6$cycloalkyl), from 4 to 10 ring members (i.e., $C_4$-$C_{10}$carbocyclyl, such as $C_4$-$C_{10}$cycloalkyl and $C_4$-$C_{10}$cycloalkenyl), from 4 to 8 ring members (i.e., $C_4$-$C_8$carbocyclyl, such as $C_4$-$C_8$cycloalkyl and $C_4$-$C_8$cycloalkenyl), or from 5 to 7 ring members (i.e., $C_5$-$C_7$carbocyclyl, such as $C_5$-$C_7$cycloalkyl, $C_5$-$C_7$cycloalkenyl and phenyl). A substituted carbocyclyl may have either cis or trans geometry. Representative examples of carbocyclyl groups include, but are not limited to, cyclopropyl, cyclobutyl, cyclopentyl, cyclohexyl, cycloheptyl, cyclooctyl, cyclopentenyl, cyclopentadienyl, cyclohexadienyl, adamantyl, decahydro-naphthalenyl, octahydroindenyl, cyclohexenyl, phenyl, naphthyl, fluorenyl, indanyl, 1,2,3,4-tetrahydro-naphthyl, indenyl, isoindenyl, bicyclodecanyl, anthracenyl, phenanthrene, benzonaphthenyl (also known as "phenalenyl"), decalinyl, and norpinanyl. A carbocyclyl group can be attached to the parent molecular moiety through any substitutable carbon atom of the group.

The term "carbocyclylalkyl" (alone or in combination with another term(s)) refers to a carbocyclyl group appended to the parent molecular moiety through an alkylene group. For instance, $C_3$-$C_{10}$carbocyclyl$C_1$-$C_6$alkyl refers to a $C_3$-$C_{10}$carbocyclyl group appended to the parent molecular moiety through $C_1$-$C_6$alkylene. Likewise, $C_5$-$C_7$carbocyclyl$C_1$-$C_6$alkyl refers to a $C_5$-$C_7$carbocyclyl group appended to the parent molecular moiety through $C_1$-$C_6$alkylene.

The term "carbocyclylalkoxy" (alone or in combination with another term(s)) refers to a carbocyclylalkyl group appended to the parent molecular moiety through an oxy group (i.e., carbocyclyl-alkylene-O—). For instance, $C_3$-$C_{10}$carbocyclyl$C_1$-$C_6$alkoxy refers to a $C_3$-$C_{10}$carbocyclyl$C_1$-$C_6$alkyl group appended to the parent molecular moiety through an oxy group. Likewise, a $C_5$-$C_7$carbocyclyl$C_1$-$C_6$alkoxy group refers to a $C_5$-$C_7$carbocyclyl$C_1$-$C_6$alkyl group appended to the parent molecular moiety through an oxy group.

The term "carbocyclylalkoxyalkyl" (alone or in combination with another term(s)) refers to a carbocyclylalkoxy group appended to the parent molecular moiety through an alkylene group (i.e., carbocyclyl-alkylene-O-alkylene-). For instance, $C_3$-$C_{10}$carbocyclyl$C_1$-$C_6$alkoxy$C_1$-$C_6$alkyl refers to $C_3$-$C_{10}$carbocyclyl$C_1$-$C_6$alkoxy group appended to the parent molecular moiety through a $C_1$-$C_6$alkylene group.

The term "carbocyclylalkoxycarbonyl" (alone or in combination with another term(s)) refers to a carbocyclylalkoxy group appended to the parent molecular moiety through a carbonyl group (i.e., —C(O)—O-alkylene-carbocyclyl). For instance, $C_3$-$C_{10}$carbocyclyl$C_1$-$C_6$alkoxycarbonyl refers to a $C_3$-$C_{10}$carbocyclyl$C_1$-$C_6$alkoxy group appended to the parent molecular moiety through a carbonyl group. As a non-limiting example, "phenylethoxycarbonyl" may be depicted as:

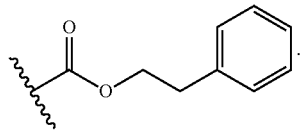

The term "carbocyclylalkylcarbonyl" (alone or in combination with another term(s)) refers to a carbocyclylalkyl group appended to the parent molecular moiety through a carbonyl group (i.e., —C(O)— alkylene-carbocyclyl). For example, "phenylethylcarbonyl" may be depicted as:

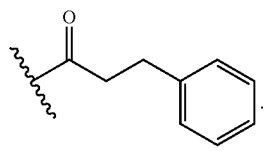

The term "carbocyclylcarbonyl" (alone or in combination with another term(s)) refers to a carbocyclyl group appended to the parent molecular moiety through a carbonyl group (i.e., carbocyclyl-C(O)—). For example, "phenylcarbonyl" may be depicted as:

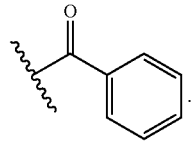

The term "carbocyclyloxy" (alone or in combination with another term(s)) refers to a carbocyclyl group appended to the parent molecular moiety through an oxy moiety (i.e., carbocyclyl-O—).

The term "carbocyclyloxyalkyl" (alone or in combination with another term(s)) refers to a carbocyclyloxy group appended to the parent molecular moiety through an alkylene group (i.e., carbocyclyl-O-alkylene-).

The term "carbocyclyloxycarbonyl" (alone or in combination with another term(s)) refers to a carbocyclyloxy group appended to the parent molecular moiety through a carbonyl group (i.e., —C(O)—O-carbocyclyl). For example, "phenyloxycarbonyl" may be depicted as:

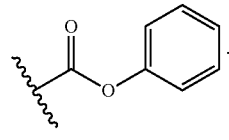

The term "carbocyclylthio" (alone or in combination with another term(s)) refers to a carbocyclyl group appended to the parent molecular moiety through a sulfur atom (i.e., carbocyclyl-S—).

The term "carbocyclylthioalkoxy" (alone or in combination with another term(s)) refers to carbocyclyl-alkylene-S—.

The term "carbocyclylthioalkoxyalkyl" (alone or in combination with another term(s)) refers to carbocyclyl-alkylene-S-alkylene-.

The term "carbocyclylthioalkyl" (alone or in combination with another term(s)) refers to a carbocyclylthio group appended to the parent molecular moiety through an alkylene group (i.e., carbocyclyl-S-alkylene-).

The term "carbocyclylcarbocyclyl" (alone or in combination with another term(s)) refers to a carbocyclyl group appended to the parent molecular moiety through another carbocyclyl group (i.e., carbocyclyl-carbocyclyl-). For instance, $C_3$-$C_{10}$carbocyclyl$C_5$-$C_7$carbocyclyl refers to a $C_3$-$C_{10}$carbocyclyl group appended to the parent molecular moiety through a $C_5$-$C_7$carbocyclyl group (i.e., $C_3$-$C_{10}$carbocyclyl-$C_5$-$C_7$carbocyclyl-).

The term "carbocyclylcarbocyclylalkyl" (alone or in combination with another term(s)) refers to a carbocyclylcarbocyclyl group appended to the parent molecular moiety through an alkylene group.

The term "carbocyclylalkoxycarbocyclylalkyl" (alone or in combination with another term(s)) refers to carbocyclyl-alkylene-O-carbocyclyl-alkylene-. For instance, $C_3$-$C_{10}$carbocyclyl$C_1$-$C_6$alkoxy$C_5$-$C_7$carbocyclyl$C_3$-$C_4$alkyl refers to $C_3$-$C_6$carbocyclyl-$C_1$-$C_6$alkylene-O—$C_5$-$C_7$carbocyclyl-$C_3$-$C_4$alkylene-.

The term "(carbocyclylalkyl)carbocyclylalkyl" (alone or in combination with another term(s)) refers to carbocyclyl-alkylene-carbocyclyl-alkylene-. For instance, $C_3$-$C_{10}$carbocyclyl$C_1$-$C_6$alkyl$C_5$-$C_7$carbocyclyl$C_3$-$C_4$alkyl refers to $C_3$-$C_6$carbocyclyl-$C_1$-$C_6$alkylene-$C_5$-$C_7$carbocyclyl-$C_3$-$C_4$alkylene-.

The term "carbocyclylalkoxyheterocycloalkyl" (alone or in combination with another term(s)) refers to carbocyclyl-alkylene-O-heterocyclyl-alkylene-.

The term "carbocyclylcarbonylheterocycloalkyl" (alone or in combination with another term(s)) refers to carbocyclyl-C(O)— heterocyclyl-alkylene-.

The term "carbocyclylheterocycloalkyl" (alone or in combination with another term(s)) refers to carbocyclyl-heterocyclyl-alkylene-.

The term "carbocyclylcarbonylcarbocyclylalkyl" (alone or in combination with another term(s)) refers to carbocyclyl-C(O)— carbocyclyl-alkylene-. For instance, $C_3$-$C_{10}$carbocyclylcarbonyl$C_4$-$C_8$carbocyclyl$C_1$-$C_6$alkyl refers to $C_3$-$C_{10}$carbocyclyl-C(O)—$C_4$-$C_8$carbocyclyl-$C_1$-$C_6$alkylene-.

The term "(carbocyclylalkyl)heterocycloalkyl" (alone or in combination with another term(s)) refers to carbocyclyl-alkylene-heterocyclyl-alkylene.

The term "carbonyl" (alone or in combination with another term(s)) refers to —C(O)—, which also may be depicted as:

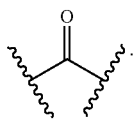

The term "carboxy" (alone or in combination with another term(s)) means —C(O)—OH, which also may be depicted as:

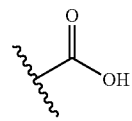

The term "carboxyalkyl" (alone or in combination with another term(s)) refers to a carboxy group appended to the parent molecular moiety through an alkylene group. Representative examples of carboxyalkyl include, but are not limited to, carboxymethyl, 2-carboxyethyl, and 3-carboxypropyl.

The term "cyclic amino" (alone or in combination with another term(s)) means a heterocyclyl moiety comprising at least one nitrogen ring atom, with the remaining ring atoms being carbon and optionally nitrogen or sulfur. Non-limiting examples of such moieties include piperidinyl, piperazinyl, and thiazine groups.

The term "cycloalkenyl" (alone or in combination with another term(s)) refers to a non-aromatic, partially unsaturated carbocyclyl substituent having zero heteroatom ring member and typically from 4 to 18 carbon ring members. Representative examples of cycloalkenyl groups include, but are not limited to, cyclobutenyl, cyclopentenyl, cyclohexenyl, and octahydronaphthalenyl.

The term "cycloalkyl" (alone or in combination with another term(s)) refers to a saturated carbocyclyl group containing zero heteroatom ring member and typically from 3 to 18 carbon ring members. Non-limiting examples of cycloalkyls include cyclopropyl, cyclobutyl, cyclopentyl, cyclohexyl, cycloheptyl, cyclooctyl, decalinyl and norpinanyl.

The term "cycloalkylcarbonyl" (alone or in combination with another term(s)) refers to a cycloalkyl group appended to the parent molecular moiety through a carbonyl group.

The term "cyano" (alone or in combination with another term(s)) means —CN, which also may be depicted as

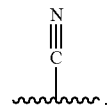

The term "dialkylamino" (alone or in combination with another term(s)) refers to —$NR_AR_B$, wherein $R_A$ and $R_B$ are independently selected from alkyl groups.

The term "dialkylaminocarbonyl" (alone or in combination with another term(s)) refers to a dialkylamino group appended to the parent molecular moiety through a carbonyl group (i.e., $N(R_AR_B)$—C(O)—, wherein $R_A$ and $R_B$ are independently selected from alkyl groups).

The term "formyl" (alone or in combination with another term(s)) refers to a —C(O)H group.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

The prefix "halo" indicates that the substituent to which the prefix is attached is substituted with one or more independently selected halogen radicals. For example, "haloalkyl" (alone or in combination with another term(s)) means an alkyl substituent wherein at least one hydrogen radical is replaced with a halogen radical. Non-limiting examples of haloalkyls include chloromethyl, 1-bromoethyl, fluoromethyl, difluoromethyl, trifluoromethyl, and 1,1,1-trifluoroethyl. Illustrating further, "haloalkoxy" (alone or in combination with another term(s)) means an alkoxy substituent wherein at least one hydrogen radical is replaced by a halogen radical. Non-limiting examples of haloalkoxy substituents include chloromethoxy, 1-bromoethoxy, fluoromethoxy, difluoromethoxy, trifluoromethoxy (also known as "perfluoromethyloxy"), and 1,1,1-trifluoroethoxy. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical. Non-limiting examples of perfluoroalkyl substituents include trifluoromethyl (—$CF_3$), perfluoroisopropyl, perfluorobutyl, perfluorodecyl, and perfluorododecyl. To illustrate further, the term "perfluoroalkoxy" means an alkoxy substituent wherein each hydrogen radical is replaced with a fluorine radical. Non-limiting examples of perfluoroalkoxy substituents include trifluoromethoxy (—O—$CF_3$), perfluoroisopropoxy, perfluorobutoxy, perfluorodecoxy, and perfluorododecoxy.

The terms "heterocycle" or "heterocyclo" or "heterocyclyl" (alone or in combination with another term(s)) refer to a saturated (e.g., "heterocycloalkyl"), partially unsaturated (e.g., "heterocycloalkenyl" or "heterocycloalkynyl") or completely unsaturated (e.g., "heteroaryl") ring system typically containing from 3 to 18 ring atoms, where at least one of the ring atoms is a heteroatom (i.e., nitrogen, oxygen or sulfur), with the remaining ring atoms being independently selected from the group consisting of carbon, nitrogen, oxygen and sulfur. A heterocyclyl group can be linked to the parent molecular moiety via any substitutable carbon or nitrogen atom in the group, provided that a stable molecule results.

A heterocyclyl may be, without limitation, a single ring, which typically contains from 3 to 14 ring atoms (i.e., $M_3$-$M_{14}$heterocyclyl), from 3 to 8 ring atoms (i.e., $M_3$-$M_{18}$heterocyclyl), from 3 to 6 ring atoms (i.e., $M_3$-$M_6$heterocyclyl), or from 5 to 6 ring atoms (i.e., $M_5$-$M_6$heterocyclyl). Non-limiting examples of single-ring heterocyclyls include furanyl, dihydrofuranyl, tetrahydrofuranyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl", oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl or 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl may also include, without limitation, two or more rings fused together, such as, for example, naphthyridinyl (including [1,8] naphthyridinyl, and [1,6] naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, and pyrido[4,3-b]-pyridinyl), pyridopyrimidine, and pteridinyl. Other non-limiting examples of fused-ring heterocyclyls include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzopyranyl (including "chromenyl" and "isochromenyl"), benzothiopyranyl (also known as "thiochromenyl"), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", and "benzothiofuranyl"), isobenzothienyl (also known as "isobenzothiophenyl", "isothionaphthenyl", and "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), tetrahydroisoquinolinyl, carbazolyl, xanthenyl, and acridinyl.

The term "two-fused-ring" heterocyclyl (alone or in combination with another term(s)) means a saturated, partially saturated, or aromatic heterocyclyl containing two fused rings. Non-limiting examples of two-fused-ring heterocyclyls include naphthyridinyl (including [1,8] naphthyridinyl, and [1,6] naphthyridinyl), thiazolpyrimidinyl, thienopyrimidinyl, pyrimidopyrimidinyl, pyridopyrimidinyl, pyrazolopyrimidinyl, indolizinyl, pyrindinyl, pyranopyrrolyl, 4H-quinolizinyl, purinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzoimidazolyl, benzotriazolyl, benzoxazinyl, benzoisoxazinyl, and tetrahydroisoquinolinyl.

A heterocyclyl may comprise one or more sulfur atoms as ring members; and in some cases, the sulfur atom(s) is oxidized to SO or $SO_2$. The nitrogen heteroatom(s) in a heterocyclyl may or may not be quaternized, and may or may not be oxidized to N-oxide. In addition, the nitrogen heteroatom(s) may or may not be N-protected.

As used herein, the number of ring atoms in a heterocyclyl moiety can be identified by the prefix "$M_x$-$M_y$," where x is the minimum and y is the maximum number of ring atoms in the heterocyclyl moiety.

The term "heterocycloalkoxy" (alone or in combination with another term(s)) refers to a heterocycloalkyl group appended to the parent molecular moiety through an oxy group.

The term "heterocycloalkoxyalkyl" (alone or in combination with another term(s)) refers to a heterocycloalkoxy group appended to the parent molecular moiety through an alkylene group (i.e., heterocyclyl-alkylene-O-alkylene-).

The term "heterocycloalkoxycarbonyl" (alone or in combination with another term(s)) refers to a heterocycloalkoxy group appended to the parent molecular moiety through a carbonyl group (i.e., heterocyclyl-alkylene-O—C(O)—).

The term "heterocycloalkyl" (alone or in combination with another term(s)) refers to a heterocyclyl appended to the parent molecular moiety through an alkylene group (e.g., heterocyclo$C_1$-$C_6$alkyl).

The term "heterocycloalkylcarbonyl" (alone or in combination with another term(s)) refers to a heterocycloalkyl group appended to the parent molecular moiety through a carbonyl group (i.e., —C(O)— alkylene-heterocyclyl).

The term "heterocyclocarbonyl" (alone or in combination with another term(s)) refers to a heterocyclyl appended to the parent molecular moiety through a carbonyl group (i.e., —C(O)-heterocyclyl).

The terms "heterocyclyloxy" or "(heterocyclo)oxy" (alone or in combination with another term(s)) refers to a heterocyclyl group appended to the parent molecular moiety through an oxy moiety.

The term "(heterocyclo)oxyalkyl" (alone or in combination with another term(s)) refers to a heterocyclyloxy group appended to the parent molecular moiety through an alkylene group (i.e., heterocyclyl-O-alkylene-).

The term "(heterocyclo)oxycarbonyl" (alone or in combination with another term(s)) refers to a (heterocyclo)oxy group appended to the parent molecular moiety through a carbonyl group (i.e., heterocyclyl-O—C(O)—).

The term "heterocyclothio" (alone or in combination with another term(s)) refers to a heterocyclyl appended to the parent molecular moiety through —S—.

The term "heterocyclothioalkoxy" (alone or in combination with another term(s)) refers to heterocyclyl-alkylene-S—.

The term "heterocyclothioalkoxyalkyl" (alone or in combination with another term(s)) refers to heterocyclyl-alkylene-S-alkylene-.

The term "heterocyclothioalkyl" (alone or in combination with another term(s)) refers to a heterocyclothio group appended to the parent molecular moiety through an alkylene group (i.e., heterocyclyl-S-alkylene-).

The term "heterocyclocarbocyclyl" (alone or in combination with another term(s)) refers to a heterocyclyl appended to the parent molecular moiety through a carbocyclyl group (i.e., heterocyclo-carbocyclyl-).

The term "heterocyclocarbocyclylalkyl" (alone or in combination with another term(s)) refers to a heterocyclocarbocyclyl group appended to the parent molecular moiety through an alkylene group (i.e., heterocyclyl-carbocyclyl-alkylene-).

The term "(heterocyclo)alkoxycarbocyclylalkyl" (alone or in combination with another term(s)) refers to heterocyclo-alkylene-O-carbocyclyl-alkylene-.

The term "(heterocyclo)carbonylcarbocyclylalkyl" (alone or in combination with another term(s)) refers to heterocyclo—C(O)-carbocyclyl-alkylene-.

The term "(heterocyclo)heterocycloalkyl" (alone or in combination with another term(s)) refers to heterocyclo-heterocyclo-alkylene-.

The term "(heterocyclo)alkoxyheterocycloalkyl" (alone or in combination with another term(s)) refers to heterocyclo-alkylene-O-heterocyclo-alkylene-.

The term "(heterocyclo)carbonylheterocycloalkyl" (alone or in combination with another term(s)) refers to heterocyclo—C(O)— heterocyclo-alkylene-.

The term "(heterocycloalkyl)carbocyclylalkyl" (alone or in combination with another term(s)) refers to heterocyclo-alkylene-carbocyclyl-alkylene-.

The term "(heterocycloalkyl)heterocycloalkyl" (alone or in combination with another term(s)) refers to heterocyclo-alkylene-heterocyclo-alkylene-. Thus, for example, ($M_3$-$M_{10}$heterocyclo$C_1$-$C_6$alkyl)$M_5$-$M_6$heterocyclo$C_1$-$C_3$alkyl means $M_3$-$M_{10}$heterocyclo-$C_1$-$C_6$alkylene-$M_5$-$M_6$ heterocyclo-$C_1$-$C_3$alkylene-.

The term "heteroaryl" (alone or in combination with another term(s)) means an aromatic heterocyclyl typically containing from 5 to 18 ring atoms. A heteroaryl may be a single ring, or two or more fused rings. Non-limiting examples of five-membered heteroaryls include imidazolyl; furanyl; thiophenyl (or thienyl or thiofuranyl); pyrazolyl; oxazolyl; isoxazolyl; thiazolyl; 1,2,3-, 1,2,4-, 1,2,5-, and 1,3,4-oxadiazolyl; and isothiazolyl. Non-limiting examples of six-membered heteroaryls include pyridinyl; pyrazinyl; pyrimidinyl; pyridazinyl; and 1,3,5-, 1,2,4-, and 1,2,3-triazinyl. Non-limiting examples of 6/5-membered fused ring heteroaryls include benzothiofuranyl, isobenzothiofuranyl, benzisoxazolyl, benzoxazolyl, purinyl, and anthranilyl. Non-limiting examples of 6/6-membered fused ring heteroaryls include quinolinyl; isoquinolinyl; and benzoxazinyl (including cinnolinyl and quinazolinyl).

The term "heteroarylalkoxy" (alone or in combination with another term(s)) refers to a heteroarylalkyl appended to the parent molecular moiety through an oxy group (i.e., heteroaryl-alkylene-O—). Representative examples of heteroarylalkoxy include, but are not limited to, 2-pyridin-3-ylethoxy, 1,3-thiazol-5-ylmethoxy, 3-quinolin-3-ylpropoxy, and 5-pyridin-4-ylpentyloxy.

The term "heteroarylalkoxyalkyl" (alone or in combination with another term(s)) refers to a heteroarylalkoxy group appended to the parent molecular moiety through an alkylene group (i.e., heteroaryl-alkylene-O-alkylene-). Representative examples of heteroarylalkoxyalkyl include, but are not limited to, (2-pyridin-3-ylethoxy)methyl, (3-quinolin-3-ylpropoxy)methyl, (1,3-thiazol-5-ylmethoxy)methyl, and 2-(5-pyridin-4-ylpentyloxy)ethyl.

The term "heteroarylalkoxycarbonyl" (alone or in combination with another term(s)) refers to a heteroarylalkoxy group appended to the parent molecular moiety through a carbonyl group (i.e., heteroaryl-alkylene-O—C(O)—). Representative examples of heteroarylalkoxycarbonyl include, but are not limited to, (2-pyridin-3-ylethoxy)carbonyl, (3-quinolin-3-ylpropoxy)carbonyl, 2-(1,3-thiazol-5-ylmethoxy)carbonyl, and (5-pyridin-4-ylpentyloxy)carbonyl.

The term "heteroarylalkyl" (alone or in combination with another term(s)) refers to a heteroaryl group appended to the parent molecular moiety through an alkylene group. Representative examples of heteroarylalkyl include, but are not limited to, 3-quinolinylmethyl, 3-pyridinylmethyl, 4-pyridinylmethyl, 1H-imidazol-4-ylmethyl, 1H-pyrrol-2-ylmethyl, pyridin-3-ylmethyl, and 2-pyrimidin-2-ylpropyl.

The term "heteroarylalkylcarbonyl" (alone or in combination with another term(s)) refers to a heteroarylalkyl group appended to the parent molecular moiety through a carbonyl group (i.e., heteroaryl-alkylene-C(O)—).

The term "heteroarylcarbonyl" (alone or in combination with another term(s)) refers to a heteroaryl group appended to the parent molecular moiety through a carbonyl group. Representative examples of heteroarylcarbonyl include, but are not limited to, pyridin-3-ylcarbonyl, (1,3-thiazol-5-yl)carbonyl, and quinolin-3-ylcarbonyl.

The term "heteroaryloxy" (alone or in combination with another term(s)) refers to a heteroaryl group appended to the parent molecular moiety through an oxy moiety. Representative examples of heteroaryloxy include, but are not limited to, pyridin-3-yloxy, and quinolin-3-yloxy.

The term "heteroaryloxyalkyl" (alone or in combination with another term(s)) refers to a heteroaryloxy group appended to the parent molecular moiety through an alkylene group (i.e., heteroaryl-O-alkylene-).

The term "heteroaryloxycarbonyl" (alone or in combination with another term(s)) refers to a heteroaryloxy group appended to the parent molecular moiety through a carbonyl group (i.e., heteroaryl-O—C(O)—).

The term "heteroarylthio" (alone or in combination with another term(s)) refers to a heteroaryl group appended to the parent molecular moiety through —S—.

The term "heteroarylthioalkoxy" (alone or in combination with another term(s)) refers to heteroaryl-alkylene-S—.

The term "heteroarylthioalkoxyalkyl" (alone or in combination with another term(s)) refers to heteroaryl-alkylene-S-alkylene-.

The term "heteroarylthioalkyl" (alone or in combination with another term(s)) refers to a heteroarylthio group appended to the parent molecular moiety through an alkylene group (i.e., heteroaryl-S-alkylene-).

The term "hydrogen" (alone or in combination with another term(s)) refers to a hydrogen radical, and may be depicted as —H.

The term "hydroxy" (alone or in combination with another term(s)) refers to —OH.

The term "hydroxyalkyl" (alone or in combination with another term(s)) refers to an alkyl substituent wherein one or more hydrogen radicals are replaced with —OH. Representative examples of hydroxyalkyl include, but are not limited to, hydroxymethyl, 2-hydroxyethyl, 3-hydroxypropyl, and 2-ethyl-4-hydroxyheptyl.

The term "keto" (alone or in combination with another term(s)) means an oxo radical, and may be depicted as =O.

The term "iminoalkyl" (alone or in combination with another term(s)) refers to a radical of the formula wherein the H may be optionally substituted with alkyl or hydroxy, in which case the substituent would be alkyliminoalkyl or hydroxyiminoalkyl respectively.

The term "nitro" (alone or in combination with another term(s)) means —NO$_2$.

The term "oxo" (alone or in combination with another term(s)) refers to a =O moiety The term "oxy" (alone or in combination with another term(s)) means —O—.

The term "propargyl" (alone or in combination with another term(s)) means the monovalent radical depicted as: —CH, —CH≡CH.

The term "sulfonyl" (alone or in combination with another term(s)) means —S(O)$_2$—, which also may be depicted as:

The term "sulfinyl" (alone or in combination with another term(s)) means —S(O)—, which also may be depicted as:

The term "thio" or "thia" (alone or in combination with another term(s)) means —S—.

The term "thiol," "mercapto" or "sulfhydryl" (alone or in combination with another term(s)) means a sulfhydryl substituent, (i.e., —SH). Thus, for example, thiolalkyl means an alkyl substituent wherein one or more hydrogen radicals are replaced with —SH, while alkylthio means alkyl-S—.

The term "thioalkoxy" (alone or in combination with another term(s)) refers to an alkyl group appended to the parent molecular moiety through —S—. Representative examples of thioalkoxy include, but are not limited to, methylthio, ethylthio, and butylthio.

The term "thioalkoxyalkyl" (alone or in combination with another term(s)) refers to a thioalkoxy group appended to the parent molecular moiety through an alkylene group (i.e., alkyl-S-alkylene-).

The term "thiocarbonyl" (alone or in combination with another term(s)) means a carbonyl wherein the oxygen atom has been replaced with a sulfur. Such a substituent may be depicted as —C(S)—, and also may be depicted as:

The term "pharmaceutically acceptable" is used adjectivally to mean that the modified noun is appropriate for use as a pharmaceutical product or as a part of a pharmaceutical product.

The term "therapeutically effective amount" refers to the total amount of each active substance that is sufficient to show a meaningful patient benefit, e.g. a reduction in viral load.

The term "prodrug" refers to derivatives of the compounds of the invention which have chemically or metabolically cleavable groups and become, by solvolysis or under physiological conditions, the compounds of the invention which are pharmaceutically active in vivo. A prodrug of a compound may be formed in a conventional manner by reaction of a functional group of the compound (such as an amino, hydroxy or carboxy group). The prodrug derivative form often offers advantages of solubility, tissue compatibility, or delayed release in a mammalian organism (see, Bungard, H., DESIGN OF PRODRUGS, pp. 7-9, 21-24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate or other acylated derivatives of alcohol or amine functional groups within the compounds of the invention.

The term "solvate" refers to the physical association of a compound of this invention with one or more solvent molecules, whether organic or inorganic. This physical association often includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include, but are not limited to, hydrates, ethanolates, and methanolates.

The term "chiral" refers to molecules that do not have a plane of symmetry and are therefore not superimposable on their mirror image. A chiral molecule may exists in two forms, one right-handed and one left-handed.

The term "stereoisomer" refers to isomers that have their atoms connected in the same order but have different three-dimensional arrangements. The term stereoisomer includes, for example, enantiomers and diastereomers.

The term "cis-trans isomer" refers to stereoisomers that differ in their stereochemistry about a double bond or ring. Cis-trans isomers are also called geometric isomers.

The term "enantiomer" refers to stereoisomers of a chiral substance that have a mirror-image relationship.

The term "diastereomer" refers to stereoisomers that are not enantiomers, or mirror images of each other.

The term "racemic mixture" refers to a mixture consisting of equal parts (+) and (−) enantiomers of a chiral substance. Even though the individual molecules are chiral, racemic mixtures are optically inactive.

The term "tautomer" refers to isomers that are interconvertible. For example, enols and ketones are tautomers because they are interconverted by treatment with either acid or base.

The term "position isomer" refers to any of two or more constitutional isomers that differ in the position of a particular substituent or group. Functional groups can be attached at structurally nonequivalent positions on a carbon skeleton. For example, [1,3] imidazole, depicted as

and [1,4] imidazole, depicted as

are position isomers.

The term "N-protecting group" or "N-protected" refers to those groups capable of protecting an amino group against undesirable reactions. Commonly used N-protecting groups are described in Greene and Wuts, PROTECTING GROUPS IN CHEMICAL SYNTHESIS (3$^{rd}$ ed., John Wiley & Sons, NY (1999), which is incorporate herein by reference in its entirety. Non-limiting examples of N-protecting groups include acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, benzoyl, 4-chlorobenzoyl, 4-bromobenzoyl, or 4-nitrobenzoyl; sulfonyl groups such as benzenesulfonyl or p-toluenesulfonyl; sulfenyl groups such as phenylsulfenyl (phenyl-S—) or triphenylmethylsulfenyl (trityl-S—); sulfonyl groups such as p-methylphenylsulfinyl (p-methylphenyl-S(O)—) or t-butylsulfinyl (t-Bu-S(O)—); carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, alkyloxycarbonyl, 2,2,2-trichloro-ethoxy-carbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, or phenylthiocarbonyl; alkyl groups such as benzyl, p-methoxybenzyl, triphenylmethyl, or benzyloxymethyl; p-methoxyphenyl; and silyl groups such as trimethylsilyl. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The following abbreviations are used in the General Synthetic Methods and Examples described below:
AcOH=acetic acid
atm=atmospheres
Boc=N-t-butoxycarbonyl (protecting group)
CDI=1,1'-carbonyldiimidazole
CH$_2$Cl$_2$=methylene chloride (dichloromethane)
CuI=cuprous iodide [copper (I) iodide]
DCE=1,2-dichloroethane
DEAD=diethyl azodicarboxylate
DMA=N—N-dimethylacetamide
DMAP=4-dimethylaminopyridine
DMF=N,N-dimethylformamide
DMSO=dimethylsulfoxide
EDCI=(N-ethyl-N'-(3-dimethylaminopropyl)carbodiimide hydrochloride
EMME=2-ethoxymethylene-malonic acid diethyl ester
Et$_3$N=triethylamine
Ether=diethyl ether
EU=ethyl iodide
EtOAc=ethyl acetate
EtOH=ethanol
Fe=iron
Fe(AcAc)3=Iron(III)-acetylacetonate
Fmoc chloride=9-fluorenylmethyl chloroformate
HOBt=N-Hydroxybenzotriazole
Hunig's base=N,N-diisopropylethylamine
IPA=isopropyl alcohol
K$_2$CO$_3$=potassium carbonate
KOH=potassium hydroxide
LDA=lithium diisopropylamine
MeOH=methanol
MsCl=methanesulfonyl chloride
NaH=sodium hydride
NH$_2$OH.HCl=hydroxylamine hydrochloride
NMP=1-methyl-2-pyrrolidinone
Mg$_2$SO$_4$=magnesium sulfate
Na$_2$SO$_4$=sodium sulfate
NH$_3$=ammonia NH₄Cl=ammonium chloride halogen. Likewise, compounds of Formulae I(a) or I(b) can be synthesized by reacting

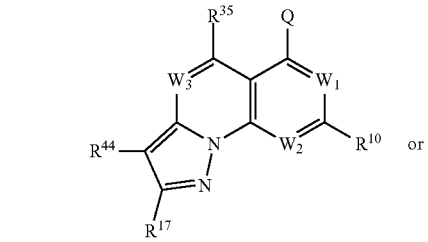 or

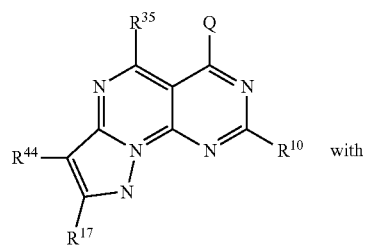 with

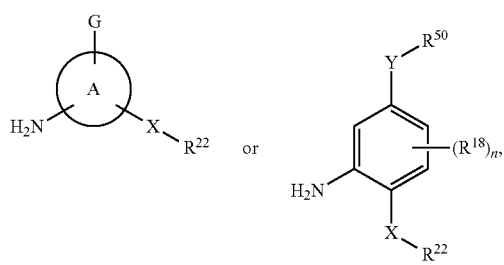

respectively, wherein W₁, W₂, W₃, W₄, A, G, X, R¹⁰, R¹⁷, R¹⁸, R²², R³⁵, R⁴⁴ and n have the meanings as set forth in the above embodiments or examples, and Q is Cl or another halogen.

The synthesis of compounds of Formulae I, I(a) or I(b) as described in the above embodiments or examples is exemplified in Schemes 1-3.

Representative compounds of Formulae I, I(a) or I(b) wherein W₁, W₂, W₃ and W₄ are N, and Z is NR⁴¹ can be prepared using the procedure as outlined in Scheme 1.

Scheme 1

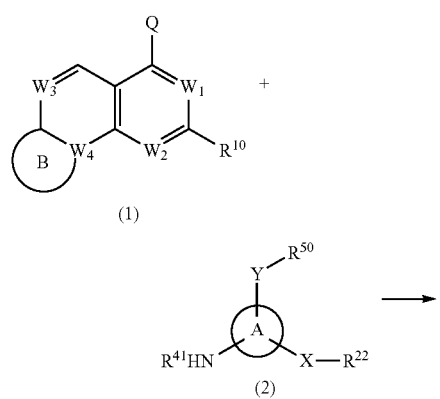

-continued

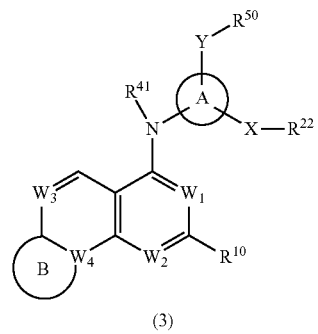

Amines of formula (2) wherein R⁴¹ is hydrogen can be reacted with compounds of formula (1) wherein Q is halogen (such as Cl or Br), thereby producing compounds of formula (3).

N alkylation of compounds of formula (2) wherein R⁴¹ is hydrogen provides formula (2) and (3) wherein R⁴¹ is alkyl. This process can be facilitated with an alkylating reagent of formula R⁴¹X¹, wherein X¹ is halogen, tosylate, triflate or mesylate, in the presence of a base such as, but not limited to, an organic base such as triethylamine or diisopropylamine, or an inorganic base such as sodium, cesium or potassium carbonate, in a suitable solvent, and at a temperature ranging from about room temperature to about 100° C.

NH₄OH=ammonium hydroxide
PG=protecting group such as Boc- or Troc-
POCl₃=phosphorous oxy chloride
R—MgCl=Grignard reagent
R—I=alkyl iodide or substituted alkyl iodide
SnCl2=Stannous chloride (Tin (H) chloride)
TFA=trifluoroacetic acid
THF=tetrahydrofuran
TLC=thin layer chromatography
Triflic Anhydride=trifluoromethanesulfonic anhydride
Troc=2,2,2-trichloroethoxycarbonyl- (protecting group)

General Synthetic Methods and Examples

The following synthetic methods and schemes illustrate the general methods by which the compounds of the present invention can be prepared. Starting materials can be obtained from commercial sources or prepared using methods well known to those of ordinary skill in the art. By way of example, synthetic routes similar to those shown hereinbelow may be used, together with synthetic methods known in the art of synthetic organic chemistry, or variations thereon, as appreciated by those skilled in the art.

The present invention is intended to encompass compounds prepared by either synthetic processes or metabolic processes. Metabolic processes include those occurring in the human or animal body (in vivo), or those occurring in vitro.

If a substituent described herein is not compatible with the synthetic methods of this invention, the substituent may be protected with a suitable protecting group that is stable to the reaction conditions used in these methods. The protecting group may be removed at a suitable point in the reaction sequence to provide a desired intermediate or target compound. Suitable protecting groups and methods for protecting or deprotecting substituents are well know in the art, examples of which can be found in Greene and Wuts, supra.

Preparation of Compounds of Formulae I, I(a) and I(b)

The synthesis of compounds of Formula I, generally involves reaction

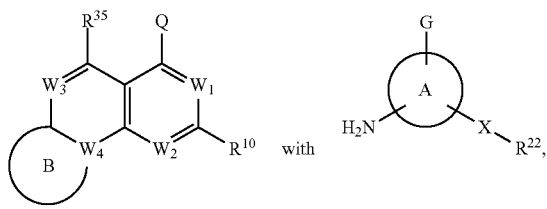

wherein $W_1$, $W_2$, $W_3$, $W_4$, A, B, G, X, $R^{10}$, $R^{22}$ and $R^{35}$ have the meanings as set forth in the above embodiments or examples, and Q is Cl or another Preparation of compounds of formula (1) can be accomplished as described in Example 1 or J. MED. CHEM. 45:3639 (2002), which is incorporated herein by reference in its entirety. Other suitable methods can also be used, as appreciated by those skilled in the art.

Compounds of formula (2) wherein $R^{41}$ is hydrogen and X is O or S, can be prepared from compounds of formula (10) according to Scheme 2, wherein $R_{101}$ is a leaving group such as, but not limited to, halogen, triflate or mesylate (the latter two can be prepared from the corresponding alcohol using methodologies known to one skilled in the art), via a two-step synthesis, namely, reduction of the nitro group followed by displacement of $R_{101}$, or displacement of $R_{101}$ followed by reduction of the nitro group.

$R_{101}$ is —X—H with compounds of formula $R^{22}X^3$ wherein $X^3$ is a leaving group such as, but not limited to, halogen, triflate or mesylate, using the aforementioned reaction conditions. The displacement reactions can also be effected in the presence of a metal catalyst such as, but not limited to, copper metal, CuI, or palladium acetate, optionally in the presence of a ligand such as, but not limited to, 2,2'-bis(diphenylphosphino)-1,1'-binaphthyl or tri-tert-butylphosphine, and optionally in the presence of a base such as, but not limited to, pyridine, triethylamine, sodium tert-butoxide, cesium carbonate, or sodium hydride. The reaction is generally performed at a temperature from about room temperature to about 180° C., in a solvent such as, but not limited to, toluene or N,N-dimethylformamide.

Reduction of the nitro group can be accomplished by treatment of nitro compound with a reducing agent such as, but not limited to, iron powder/ammonium chloride or tin(II) chloride, in a suitable solvent.

It is also appreciated that compounds of formula (10) can also be converted to compounds of formula (2) by first reducing the nitro functionality, followed by the displacement reaction, using reaction conditions as described hereinabove.

Scheme 2

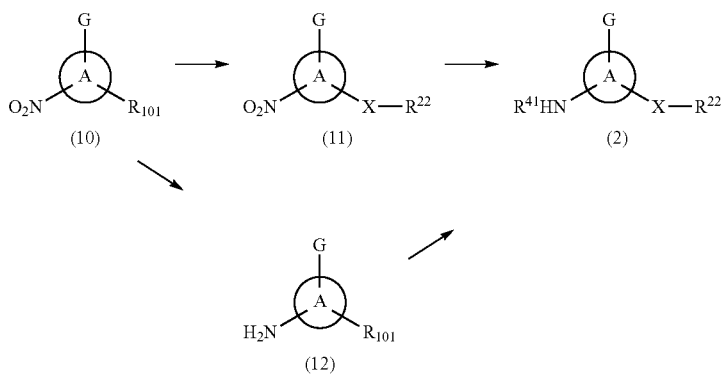

Displacement of $R_{101}$ with $R^{22}$XH wherein X is O or S can be facilitated in the presence of a suitable base such as, but not limited to, potassium, cesium or sodium carbonate or bicarbonate, or sodium or potassium hydride, and optionally in the presence of 18-crown-6, at elevated temperature. The reaction can generally be performed in a solvent such as, but not limited to, N,N-dimethylformamide or dimethylsulfoxide, at a temperature from about room temperature to about 180° C. The reaction can generally be performed in a solvent such as, but not limited to, N,N-dimethylformamide or dimethylsulfoxide, at a temperature from about room temperature to about 180° C. The reaction can also be conducted in a microwave oven. It is appreciated compounds of formula (11) can also be obtained from the reaction of formula (10) wherein Scheme 3

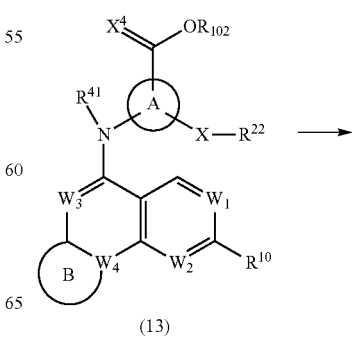

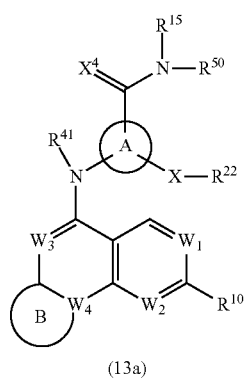

(13a)

Scheme 3 illustrates the preparation of compounds of Formula I wherein $W_1$, $W_2$, $W_3$ and $W_4$ may be N, Z is $NR^{41}$ and $X^4$ is O or S.

Acids of formula (13) wherein $X^4$ is oxygen and $R_{102}$ is hydrogen, obtained from hydrolysis or hydrogenation of the corresponding alkyl or benzyl esters, can be transformed to compounds of formula (13a). This can be accomplished by coupling with an appropriate amine. Standard coupling reaction conditions are known to one skilled in the art. One such conditions is to first convert the acid to an activated ester, for example, by treating the acid with N-hydroxyl succinamide, N-(3-dimethylaminopropyl)-N'-ethylcarbodiimide hydrochloride, or TBTU, and a base such as, but not limited to, N-methyl morpholine or diisopropylethyl amine, in a solvent such as, but not limited to, dichloromethane or dimethyl sulfoxide, and without isolation, followed by treatment of the activated ester with amines of formula $N(H)(R^{w'})(R^3)$ or of formula $NR^{15}R^{50}H$. Such procedures can also be made on compounds of formula (2) before reacting with compounds of formula (1) in Scheme 1.

Conversion of compounds of formulas (13) or (13a) wherein $X^4$ is O to formulas (13) or (13a) wherein $X^4$ is S can be achieved by treatment with Lawesson reagent.

A wide variety of aminophenyl coupling agents are possible. The agents in Scheme 4 are exemplary of this variety.

In a typical preparation, a substituted 2-chloro-nitrobenzene compound in dimethylformamide (DMF) is treated with a sodium thiophenolate at about 50° C. for about 2 hours, is cooled and diluted with methylene chloride, washed with water, dried over sodium sulfate, filtered and concentrated under vacuum to give the substituted-2-phenylsulfanyl-nitrobenzene compound. This nitrobenzene compound is then reduced with stannous chloride ($SnCl_2$) or iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenylsulfanyl-aminobenzene compound 10.

Similarly, the corresponding substituted-2-hydroxy-nitrobenzene compound is dissolved in dimethylformamide reacted with a sodium phenoxide solution, stirred and heated to 100° C. for about 5 days. The reaction mixture is cooled and diluted with methylene chloride, washed with water, dried over sodium sulfate, filtered and concentrated under vacuum to give the substituted-2-phenoxy-nitrobenzene compound. This nitrobenzene compound is then reduced with stannous chloride ($SnCl_2$) and iron (Fe) in ethanol. The reaction mixture is adjusted to pH 12 with 1 N sodium hydroxide, extracted with ethyl acetate, dried over sodium sulfate, filtered and concentrated under vacuum giving the substituted-2-phenoxy-aminobenzene compound 12.

Similarly, either compound 10 where $R^9$ is hydroxy- or protected hydroxyl- can be further modified by alkylating the hydroxy- group using a substituted benzyl bromide to give the corresponding 5-substituted-phenoxy-2-substituted-phenylsulfanyl-aminobenzene compound 11.

Scheme 4

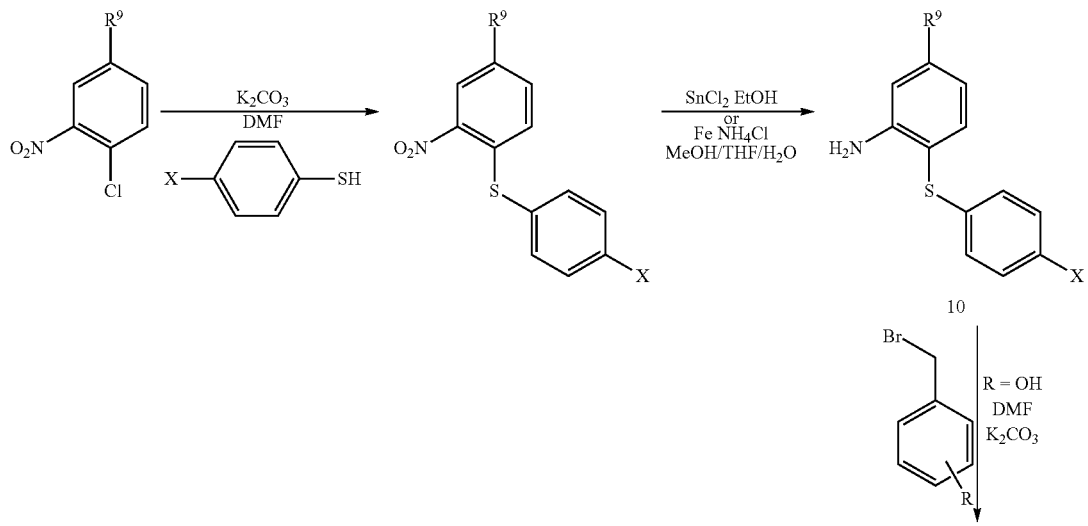

-continued

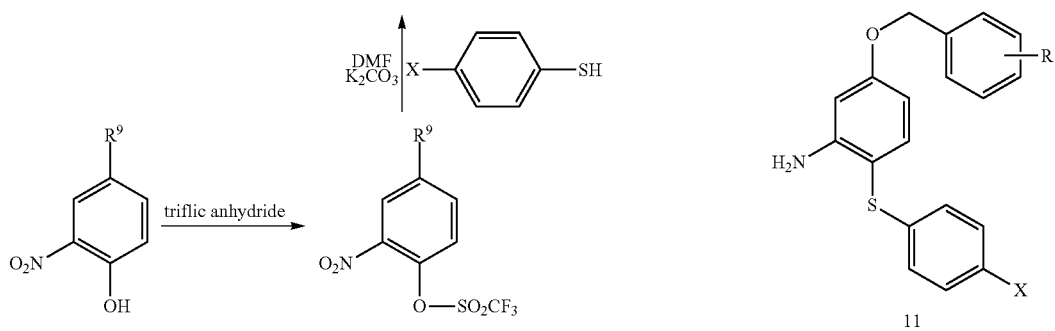

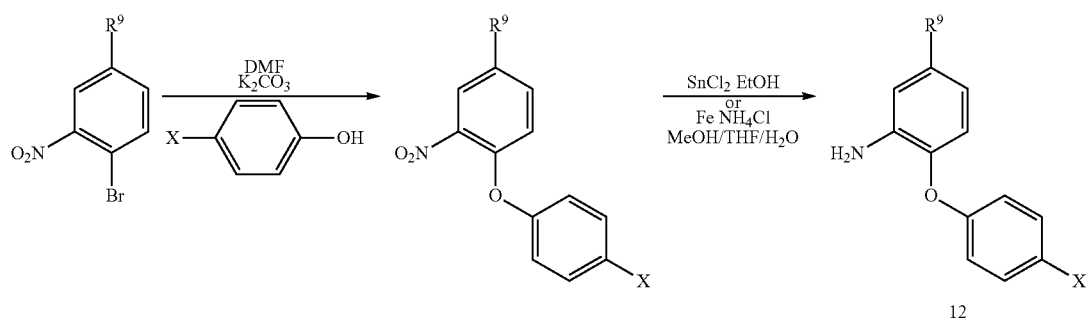

$R^9$ is defined above;
X is OH, NH₂, NHR, halo, alkyl, or alkoxy
R is alkyl, alkoxy, bromo, fluoro, chloro, or cyano As shown in Scheme 5, the coupling agent (compound 10, 11, 12 or the like) appropriate for the synthesis of the desired compound 13, 14, 15 or the like is dissolved in ethanol and reacted with compound 8 in ethanol at elevated temperatures for several hours. The solvent is removed, and the final reaction product is purified.

Scheme 5

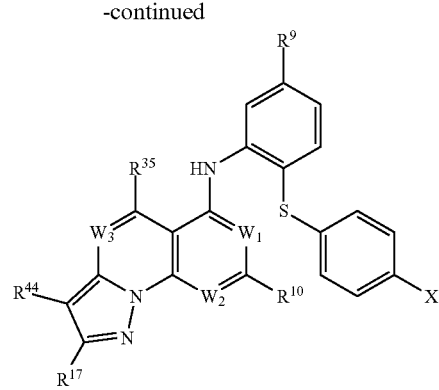

-continued

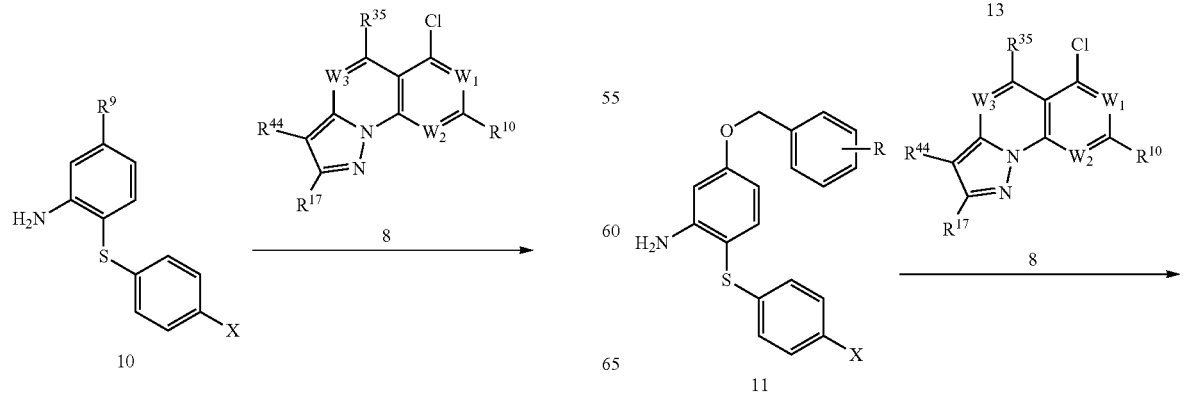

-continued

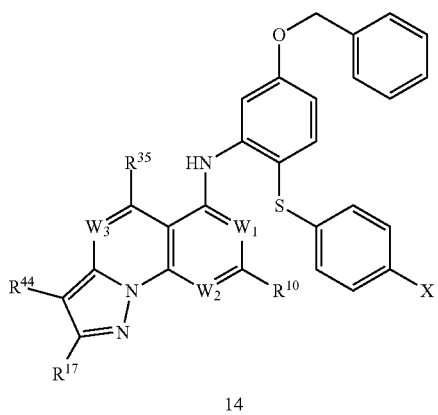

14

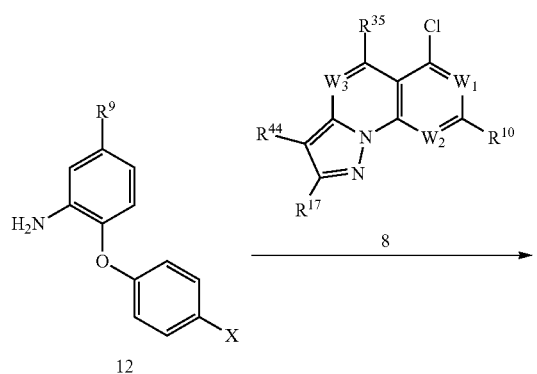

15

$R^9$ is defined above;
X is OH, NH$_2$, NHR, halo, alkyl, or alkoxy;
R is alkyl, alkoxy, bromo, fluoro, chloro, or cyano In Scheme 6, aminophenyl compounds with amide substitution in the 3-phenyl position are described.

A substituted aniline in methylene chloride is treated with 4-chloro-3-nitrobenzoyl chloride and N,N-diisopropylamine and stirred at room temperature for about 17 hours. The solvent is removed under vacuum, the residue dissolved in ethyl acetate, washed with water and brine, dried over sodium sulfate, filtered and concentrated under vacuum to give the N-substituted phenyl-4-chloro-3-nitrobenzamide 16.

Compound 16 can be further modified by displacement of the 4-chloro group to produce the 3-amino-4-substituted phenoxybenzamides 17 and the 3-amino-4-substituted phenylsufanylbenzamides 18.

Compounds 17 can typically be prepared by reacting the benzamide 16 in anhydrous N,N-dimethylformamide with 4-(N-t-butoxycarbonyl)aminophenol (N-Boc-4-hydroxyaniline) and potassium carbonate at room temperature, then heated to about 80° C. for about 5 hours. The reaction is cooled to room temperature, the solvent removed under vacuum, the residue taken up in ethyl acetate, washed with water and brine. The organic layer is dried over sodium sulfate, filtered and concentrated under vacuum to produce the 4-N-t-butoxycarbonylamino substituted compound 17. The Boc protecting group can be removed under a variety of methods to produce compounds of structure 17.

In a similar manner, compound 16 can be reacted with 4-aminothiophenol and anhydrous sodium acetate in anhydrous ethanol heating under reflux four about 19 hours. Upon cooling to room temperature the ethanol is removed under vacuum, the residue taken up in water and extracted with ethyl acetate. The organic extracts are washed with brine, dried over sodium sulfate, filtered and concentrated under vacuum. Trituration of the solid with ethylacetate-methylene chloride afforded compound 18.

Scheme 6

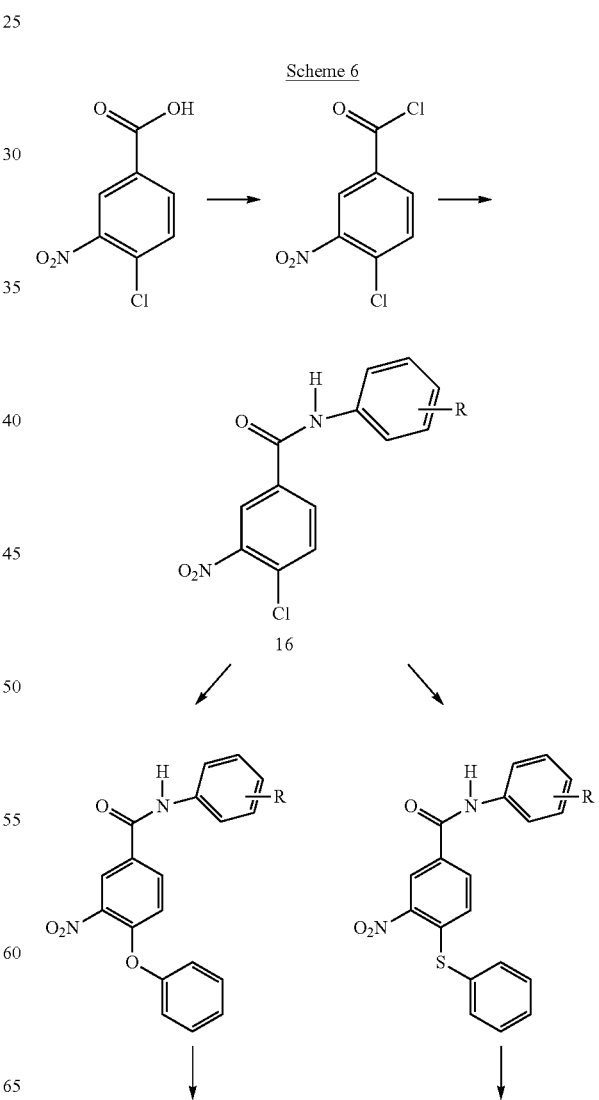

-continued

17

18

The amide phenyl ring, the phenyoxy ring and the phenylsuflanyl ring can be substituted as described above. Some examples will require the use of protecting groups followed by removal of the protecting group at the appropriate time.
R is as defined above.

The preparation of reverse amide agents for coupling is shown in Scheme 7. In a typical preparation 4-fluoro-3-nitroaniline is reacted with a substituted benzoyl chloride, Hunig's base (N,N-diisopropylethylamine) in tetrahydrofuran with stirring at room temperature for about 1 hour. Water is added to the solution and the resulting solid (compound 19) is collected by filtration and dried in a vacuum oven.

A solution of compound 19, 4-hydroxythiophenol and potassium carbonate in N,N-dimethylformamide is heated to about 80° C. for about 2 hours. After cooling to room temperature, the mixture is poured unto ice water, extracted with ethyl acetate, the extracts dried over magnesium sulfate, filtered and concentrated under vacuum to give the 4-hydroxyphenylsulfanyl intermediate. A solution of this intermediate, iron powder and ammonium chloride in tetrahydrofuran and water is heated to reflux for about 3 hours. The resulting mixture is cooled and diluted with methanol and filtered. The filtrate is diluted with water and extracted with methylene chloride. The methylene chloride extracts are dried over magnesium sulfate, filtered and concentrated under vacuum to give the 4-hydroxy analog of compound 23.

Similarly a compound 19 can be reacted with 4-aminothiophenol and cesium carbonate in N,N-dimethylformamide at about 90° C. for about 4 hours. After cooling to room temperature the mixture is poured into ice water and acidified to pH 5 with 1 N hydrochloric acid. The solution is extracted with ethyl acetate, the extracts dried over sodium sulfate, filtered and concentrated under vacuum to give the corresponding 4-aminophenylsulfanyl-3-nitroanilide. A methylene chloride solution of this anilide is then reacted with 2,2,2-trichloroethyl chloroformate and pyridine for about 16 hours. The solution is then washed with water, then brine and then the extracts are dried over sodium sulfate, filtered and concentrated under vacuum. The residue is triturated with hexane and ethyl acetate to give the corresponding Troc-amino-protected compound 22. This Troc-protected amino compound is then dissolved in ethanol and tetrahydrofuran and reacted with iron powder and ammonium chloride at reflux for about 6 hours. The resultant mixture is cooled diluted with ethanol and filtered. The filtrates are concentrated under vacuum to give the Troc-amino protected compound 23.

Similarly a solution of compound 19 in anhydrous N,N-dimethylformamide can also be reacted with the 4-t-butoxycarbonylaminophenol (N-Boc-4-hydroxyaniline) and potassium carbonate at room temperature, and then heated to about 80° C. for about 5 hours. The reaction is cooled to room temperature, the solvent removed under vacuum and the residue taken up in ethyl acetate, washed with water and brine dried over sodium sulfate, filtered and concentrated under vacuum to give the N-Boc protected compound 20. Compound 20 is then dissolved in ethanol, tetrahydrofuran and water and reacted with iron powder and ammonium chloride heating the mixture at about 90° C. for about 2 hours. After cooling to room temperature the mixture is diluted with ethyl acetate, filtered and the filtrate washed with water and brine. The organic phase is dried over sodium sulfate, filtered and concentrated under vacuum to give the coupling agent compound 22.

Compounds 17, 18, 22, and 23 can be reacted with compound 8, as depicted in Scheme 5, to produce the compounds of Formula I.

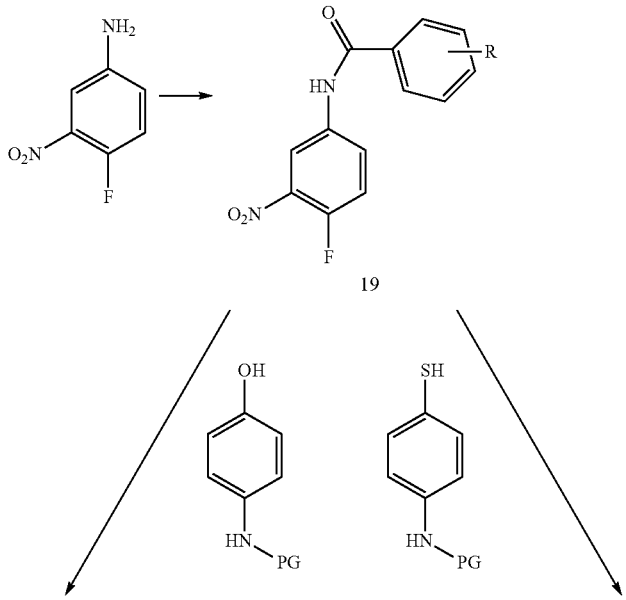

Scheme 7

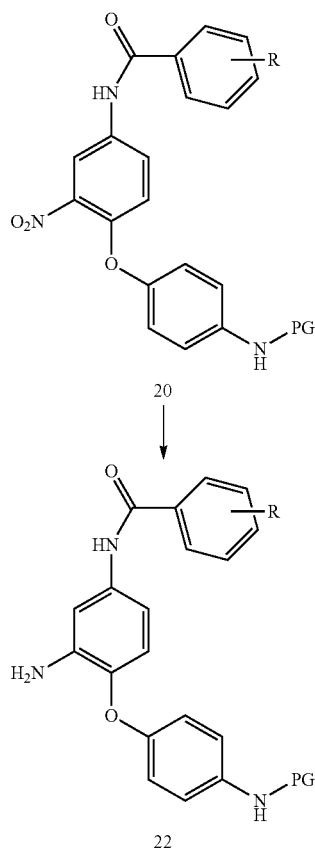

20

↓

22

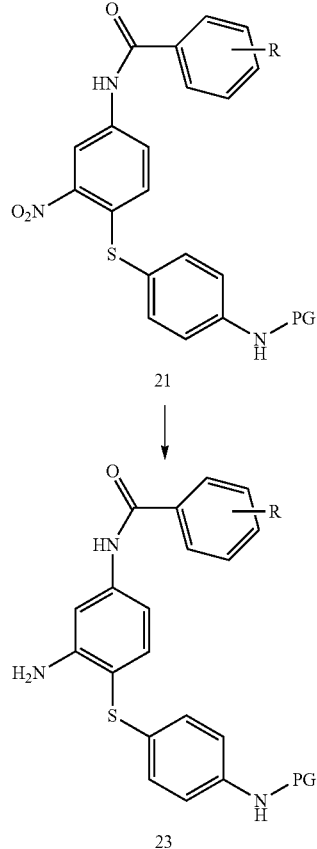

21

↓

23

PG = Protecting Group such as Boc-;
Troc- and the like;
R is defined as above

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Reactions may be worked up in the convention manner, e.g. by eliminating the solvent from the residue and further purified according to methodologies generally known in the art such as, but not limited to, crystallization, distillation, extraction, trituration and chromatography.

It should be understood that the above-described embodiments and schemes and the following examples are given by way of illustration, not limitation. Various changes and modifications within the scope of the present invention will become apparent to those skilled in the art from the present description.

Example 1

4-[4-Methyl-2-(1,4,7,9,9b-pentaaza-cyclopenta[a]naphthalen-6-ylamino)-phenylsulfanyl]-phenol

Example 1a 4,6-Dichloro-pyrimidine-5-carbaldehyde

The title compound was prepared following the procedure form J. MED. CHEM. 45:3639 (2002) to give the title compound as a solid (43.5 g, 55%).

Example 1b

6-Chloro-1,4,7,9,9b-pentaaza-cyclopenta[a]naphthalene

The product from Example 1a (1.24 g, 7.01 mmol) in 30 mL of THF was reacted with 5-aminopyrazole (0.58 g, 7.01 mmol) in 10 mL of THF under an argon atmosphere by dropwise addition. The mixture was stirred at room temperature for 1 hour and then added diisopropylethylamine (1.22 mL, 7.01 mmol) dropwise with stirring. The mixture was heated overnight at 60° C., and quenched with water and extracted with EtOAc, washed with brine, and dried over $Na_2SO_4$. The product was filtered and the solvent was removed under vacuum. The product was purified by silica gel chromatography eluting with EtOAc/hexane to give the title compound as a pale yellow solid (405 mg, 29%).

Example 1c

4-[4-Methyl-2-(1,4,7,9,9b-pentaaza-cyclopenta[a]naphthalen-6-ylamino)-phenylsulfanyl]-phenol A system under a positive $N_2$ atmosphere was charged with the product form 1b (82 mg, 0.40 mmol) and the product from Example 9c (92 mg, 0.40 mmol) in 5 mL of ethanol. The reaction mixture was heated at 70° C. with stirring for 18 hours. After cooling to room temperature the solvent was removed under vacuum. The crude product was purified by HPLC using ammonium acetate to give the title compound as a pale yellow powder (60 mg, 37%). $^1$H NMR (DMSO-$d_6$) δ ppm: 2.31 (s, 3H), 6.73 (d, J=11.18 Hz, 2H), 6.96 (m, 2H), 71.0 (m, J=9.79 Hz, 1H), 7.19 (m, J=9.79 Hz, 4H), 8.32 (d, J=4.19 Hz, 1H), 8.64 (d, J=2.80 Hz, 1H), 9.43 (d, J=2.80 Hz, 1H), 9.73 (brs 1H), 10.50 (m, 1H); (ESI+) m/z 401 (M+H)+.

Example 2

4-[4-(3-Fluoro-benzyloxy)-2-(1,4,9,9b-tetraaza-cyclopenta[a]naphthalen-6-ylamino)-phenylsulfanyl]-phenol A solution of 4-chloro-3-nitro-phenol was reacted with 1-bromomethyl-3-fluoro-benzene using the conditions described in Example 10C to provide 1-chloro-4-(3-fluoro-benzyloxy)-2-nitro-benzene which was treated sequentially using the procedures from Examples 10D and 10E to provide 4-[2-Amino-4-(3-fluoro-benzyloxy)-phenylsulfanyl]-phenol.

The product from Example 1b (82 mg, 0.40 mmol) was reacted with 4-[2-Amino-4-(3-fluoro-benzyloxy)-phenylsulfanyl]-phenol (148 mg, 0.40 mmol) in 5 mL of ethanol at 70° C. for 24 hours. After cooling to room temperature the solvent was removed under vacuum and the product was purified by HPLC with ammonium acetate to give the title compound as a pale yellow solid (18 mg, 8.5%). $^1$H NMR (DMSO-$d_6$) δ ppm: 5.15 (brs, 2H) 6.60 (d, J=8.86 Hz, 2H), 6.95 (d, J=2.75 Hz, 1H), 7.01 (dd, J=2.96 Hz, 2.75 Hz, 1H), 7.12 (d, J=8.46 Hz, 2h), 7.16-7.20 (m, 3H), 7.30 (m, 2H), 8.31 (d, J=2.32 Hz, 1H), 8.63 (brs, 1H), 9.40 (s, 1H) 10.51 (br s, 1H); (ESI+) m/z 511 (M+H)+.

Example 3

4-[4-(3-Bromo-benzyloxy)-2-(1,4,7,9,9b-pentaaza-cyclopenta[a]naphthalen-6-ylamino)-phenylsulfanyl]-phenol The product from Example 1b (82 mg, 0.40 mmol) was reacted with the product from Example 11A (160 mg, 0.40 mmol) in 5 mL of ethanol at 70° C. for 18 hours. After cooling to room temperature the solvent was removed under vacuum and the product was purified by HPLC using ammonium acetate to give the title compound as a white solid (20 mg, 9%). $^1$H NMR (300 MHz, DMSO-$d_6$) δ ppm: 5.10 (s, 1H), 6.66 (d, J=8.88 Hz, 2H), 6.93 (d, J=2.37 Hz, 1H), 7.00 (dd, J=2.81 Hz, J=8.73 Hz, 1H), 7.09-7.20 (m, 4H), 7.42 (d, J=8.13 Hz, 2H), 7.60 (d, J=8.58 Hz, 2H), 8.31 (d, J=2.22 Hz, 1H), 8.63 (s, 1H), 9.40 (s, 1H), 9.65 (br s, 1H), 10.50 (s, 1H); (ESI+) m/z 573 (M+H)+.

Example 4

4-[4-Methyl-2-(2-methyl-1,4,7,9,9b-pentaaza-cyclopenta[a]naphthalen-6-ylamino)-phenylsulfanyl]-phenol Example 4a 6-Chloro-2-methyl-1,4,7,9,9b-pentaaza-cyclopenta[a]naphthalene The product from Example 1a (1.24 g, 7.01 mmol) in 30 mL of THF was reacted with 5-amino-3-methylpyrazole (0.68 g, 7.01 mmol) in 10 mL of THF under an argon atmosphere by dropwise addition. Stirred at room temperature for 1 hour than added diisopropylethylamine (1.22 mL, 7.01 mmol) dropwise with stirring. Heated overnight at 60° C. Quenched with water and extracted with EtOAc washed with brine and dried over Na$_2$SO$_4$. Filtered and the solvent was removed under vacuum. The product was purified by silica gel chromatography eluting with EtOAc/hexane to give the title compound as a pale yellow solid (405 mg, 29%).

Example 4b

4-[4-Methyl-2-(2-methyl-1,4,7,9,9b-pentaaza-cyclopenta[a]naphthalen-6-ylamino)-phenylsulfanyl]-phenol The product from Example 4a (88 mg, 0.40 mmol) was reacted with the product from Example 9c (92 mg, 0.40 mmol) in 5 mL of ethanol at 70° C. with stirring for 3 hours. After cooling to room temperature the product was isolated by suction filtration followed by trituration with diethyl ether to give the title compound as a yellow solid (102 mg, 56%). $^1$H NMR (300 MHz, DMSO-$d_6$) δ ppm: 10.44 (s, 1H) 9.74 (s, 1H) 9.36 (s, 1H) 8.58 (s, 1H) 7.15-7.24 (m, 2H) 7.10 (dd, J=1.72 Hz, J=8.12 Hz, 1H) 6.91 (d, J=8.12 Hz, 1H0 6.69-6.74 (m, 3H) 4.35 S<1H) 2.48 (s, 3H) 2.30 (S, 3H); (ESI+) m/z 415 (M-Cl)+; (ESI−) m/z 413 (M−HCl)−.

Example 5

4-[4-(3-Fluoro-benzyloxy)-2-(2-methyl-1,4,7,9,9b-pentaaza-cyclopenta[a]naphthalen-6-ylamino)-phenylsulfanyl]-phenol The product from Example 4a (88 mg, 0.40 mmol) was reacted with 4-[2-Amino-4-(3-fluoro-benzyloxy)-phenylsulfanyl]-phenol (148 mg, 0.40 mmol) in 5 mL of ethanol at 70° C. with stirring for 6 hours. After cooling to room temperature the product was isolated by suction filtration and was triturated with diethyl ether to give the tile compound as a pale yellow solid (144 mg, 59%). $^1$H NMR (300 MHz, DMSO-$d_6$) δ ppm: 10.44 (s, 1H) 9.64 (S, 1H) 9.35 (s, 1H) 8.58 (s, 1H) 7.43 (m, 1H) 7.29 (m, 2H) 7.07-7.21 (m, 5H) 6.99 (dd, J=3.68 Hz, J=9.81 Hz, 2H) 6.72 (s, 1H) 6.65 (d, J=9.81 Hz, 2H) 5.14 (s, 2 h) 2.47 (s, 3H); (ESI+) m/z 525 (M+H−Cl)+.

Example 6

4-[2-(2-Methyl-1,4,7,9,9b-pentaaza-cyclopenta[a]naphthalen-6-ylamino)-4-(3-trifluoromethyl-benzyloxy)-phenylsulfanyl]-phenol A solution of 4-chloro-3-nitro-phenol was reacted with 1-chloromethyl-3-trifluoromethyl-benzene using the conditions described in Example 10C to provide 1-chloro-2-nitro-4-(3-trifluoromethyl-benzyloxy)-benzene which was treated sequentially using the procedures from Examples 10D and 10E to provide 4-[2-Amino-4-(3-trifluoromethyl-benzyloxy)-phenylsulfanyl]-phenol.

The product from Example 4a (88 mg, 0.40 mmol) was reacted with 4-[2-Amino-4-(3-trifluoromethyl-benzyloxy)-phenylsulfanyl]-phenol (151 mg, 0.40 mmol) in 5 mL of ethanol at 70° C. with stirring for 6 hours. After cooling to room temperature the product was isolated by suction filtration and was triturated with diethyl ether to give the title compound as a pale yellow solid (123 mg, 50%). $^1$H NMR (300 MHz, DMSO-$d_6$) δ ppm: 10.45 (s, 1H) 9.65 (s, 1H) 9.34 (s, 1H) 8.57 (s, 1H) 7.62-7.85 (m, 4H) 7.09-7.21 (m, 4H) 7.02 (dd, J=3.02 Hz, J=8.74 Hz, 1H) 6.74 (s, 1H) 6.65 (dd, J=2.19

Hz, J=8.74 Hz, 2H) 5.23 (s, 2H) 2.48 (s, 3H); (ESI+) m/z 575 (M+H−Cl)+; (ESI−) m/z 573 (m−H−Cl)−.

Although the compounds in Examples 7-96 do not include the moiety

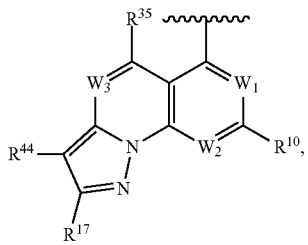

such a moiety

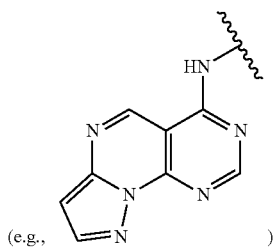

(e.g., )

can be readily substituted into these compounds according to the procedures depicted in Examples 1-6.

Example 7

(7-Methyl-[1,8]naphthyridin-4-yl)-(5-methyl-2-phenylsulfanyl-phenyl)-amine

Example 7a

2-[(6-Methyl-pyridin-2-ylamino)-methylene]-malonic acid diethyl ester

A mixture of 2-methyl-5-aminopyridine (12.48 g, 115 mmol) and 2-ethoxymethylene-malonic acid diethyl ester (7.46 mL, 89.2 mmol) was heated at 100° C. with stirring for 2.5 h. Cooled to room temperature and diluted with hexane. Filtered and dried under vacuum giving the title compound (21.05 g, 85%).

Example 7b

7-Methyl-4-oxo-1,4-dihydro-[1,8]naphthyridine-3-carboxylic acid ethyl ester

A solution of diphenyl ether was heated to 250° C. and the product of Example 7a (2.50 g, 9.0 mmol) was added in several small portions over a period of about 5 min then heated at 250° C. for 30 min. After cooling to room temperature diluted with hexane. The resulting solid was filtered and was dried under vacuum giving the title compound as a tan solid (1.47 g, 71%).

Example 7c

7-Methyl-[1,8]naphthyridin-4-ol

A solution of the product from Example 7b (1.30 g, 5.59 mmol) and NaOH (233 mg, 5.82 mmol) in 20 mL of water was heated in a sealed metal reactor at 180° C. for 16 h. Cooled to room temperature and adjusted to pH 6 with 1N HCl. The resulting precipitates was filtered and dried under vacuum giving the title compound as a black solid (743 mg, 82%).

Example 7d

5-Chloro-2-methyl-[1,8]naphthyridine

A mixture of the product from Example 7c (320 mg, 2.0 mmol) in 6 mL of POCl$_3$ was heated at 50° C. with stirring for 6 h. Cooled to room temperature and quenched by pouring into ice. Adjusted to pH 10 with NH$_4$OH and extracted with CH$_2$Cl$_2$. Dried over Na$_2$SO$_4$, filtered and concentrated under vacuum giving the title compound as a tan solid (322 mg, 90%).

Example 7e

4-Methyl-2-nitro-1-phenylsulfanyl-benzene

A solution of sodium thiophenolate (3.96 g, 30 mmol) in 60 mL of DMF was heated at 50° C. with 4-chloro-3-nitrotoluene (2.65 mL, 20 mmol) with stirring for 2 days. Cooled to room temperature and diluted with CH$_2$Cl$_2$. Washed with water and dried the organic layer over Na$_2$SO$_4$. Filtered and concentrated under vacuum giving the title compound (4.29 g, 87%) $^1$H NMR (300 MHz, CDCl$_3$) δ ppm: 2.36 (s, 3 H) 6.76 (d, J=8.09 Hz, 1 H) 7.16 (d, J=8.46 Hz, 1H) 7.45 (m, 3 H) 7.58 (m, 2 H) 8.03 (s, 1 H).

Example 7f

5-Methyl-2-phenylsulfanyl-phenylamine

A solution of the product from Example 7e (1.17 g, 7.0 mmol) in 25 mL of absolute EtOH and SnCl$_2$ (3.58 g, 29.8 mmol) was stirred at room temperature for 16 h. Adjusted to pH 12 with 1N NaOH and extracted with EtOAc. Dried over Na$_2$SO$_4$, filtered and concentrated under vacuum giving the title compound (835 mg, 82%) $^1$H NMR (300 MHz, CDCl$_3$) δ ppm: 2.30 (2, 3 H) 6.62 (d, J=8.83 Hz, 1 H) 6.69 (s, 1 H) 7.10 (m, 3 H) 7.21 (m, 2 H) 7.54 (d, J=7.72 Hz, 2 H).

Example 7g (7-Methyl-[1,8]naphthyridin-4-yl)-(5-methyl-2-phenylsulfanyl-phenyl)-amine A stirred solution of the product from Example 7d (65 mg, 0.36 mmol) and the product from Example 7f (77 mg, 0.36 mmol) in 3 mL of EtOH was heated at 80° C. for 7 h. Concentrated under vacuum. Recrystallized from THF with a few drops of MeOH. Filtration gave the title compound as the hydrochloride salt as a white solid (62 mg, 43%) $^1$H NMR (300 MHz, CDCl$_3$) δ ppm: 1.62 (brs, 1 H) 2.43 (s, 3 H) 2.52 (s, 3 H) 6.02 (d, J=7.0 Hz, 1 H) 7.05-7.35 (m, 8 H) 7.70 (brs, 1 H) 8.00 (d, J=7.0 Hz, 1 H) 8.85 (d, J=8.5 Hz, 1 H) 10.80 (brs, 1 H); MS (ESI+) m/z 358 (M-Cl)+; (ESI−) m/z 356 (M−HCl)−.

Example 8

(7-Ethyl-[1,8]naphthyridin-4-yl)-(5-methyl-2-phenylsulfanyl-phenyl)-amine

Example 8a 2-(2,5-Dimethyl-pyrrol-1-yl)-6-ethyl-pyridine

A solution of 2-methyl-5-aminopyridine (5.0 g, 46 mmol) and hexane-2,5-dione (5.4 mL, 46 mmol) in 60 mL benzene was treated with HOAc (0.5 mL, 7.9 mmol). The solution was heated under reflux with the azeotropic removal of water for 20 h. Cooled to room temperature and diluted with ether. Washed with dilute HCl and water. The organic layer was dried over MgSO$_4$, filtered and concentrated under vacuum giving 2-(2,5-Dimethyl-pyrrol-1-yl)-6-methyl-pyridine (4.7 g, 55%).

To a solution of 2-(2,5-Dimethyl-pyrrol-1-yl)-6-methyl-pyridine (6.82 g, 36.6 mmol) in 75 mL of dry THF cooled to −40° C. under a N$_2$ atmosphere was added dropwise n-BuLi as a 2.5M solution in hexanes (16 mL, 40 mmol). The resulting solution was stirred at low temperature for thirty minutes then treated with CH$_3$I (2.4 mL, 38.6 mmol). On completion of the addition the mixture was allowed to warm to −30° C. and after 20 min to room temperature. The reaction was subsequently quenched by pouring into brine solution, the product isolated by extraction with EtOAc. Dried over MgSO$_4$, filtered and concentration under vacuum. Purified by silica gel column chromatography eluting with EtOAc/hexane gave the title compound (4.42 g, 60%).

Example 8b

6-Ethyl-pyridin-2-ylamine

The product from Example 8a (4.93 g, 0.025 mol) was dissolved in a mixture of EtOH (80 mL) and water (30 mL). To this was added hydroxylamine hydrochloride (8.6 g, 0.123 mol) and the resulting mixture heated to 100° C. for 8 h. The reaction mixture was poured into dilute sodium hydroxide solution and the crude product isolated by extraction with CH$_2$Cl$_2$ and dried over MgSO$_4$ filtered and concentrated under vacuum giving the title compound. The material was used as isolated.

Example 8c

2-[(6-Ethyl-pyridin-2-ylamino)-methylene]-malonic acid diethyl ester

The crude product from Example 8b was combined with 2-ethoxymethylene-malonic acid diethyl ester (6.6 mL, 0.032 mol) and the mixture heated under a N$_2$ atmosphere in an oil bath at 100° C. for 2 h. Purified by flash chromatography on silica gel eluting with EtOAc/hexane giving the title compound (7.16 g, 98%).

Example 8d

7-Ethyl-4-oxo-1,4-dihydro-[1,8]naphthyridine-3-carboxylic acid ethyl ester

The product of Example 8c (7.16 g, 0.024 mol) was heated in diphenyl ether following the procedure in Example 7b giving the title compound (4.73 g, 79%) as a tan solid.

Example 8e

7-Ethyl-[1,8]naphthyridin-4-ol

The product from Example 8d (4.70 g, 19.1 mmol) was reacted with NaOH (0.808 g, 20.2 mmol) following the procedure of Example 7c giving the title compound as a light green solid (2.43 g, 73%).

Example 8f

5-Chloro-2-ethyl-[1,8]naphthyridine

The product from Example 8e (200 mg, 1.14 mmol) was treated with POCl$_3$ following the procedure from Example 7d giving the title compound as a brown solid (183 mg, 83%).

Example 8g (7-Ethyl-[1,8]naphthyridin-4-yl)-(5-methyl-2-phenylsulfanyl-phenyl)-amine The product from Example 8f (88 mg, 0.46 mmol) was reacted with the product from Example 7f (100 mg, 0.46 mmol) for 24 h following the procedure from Example 7f giving the title compound as a hydrochloride salt which was triturated with ether giving (134 mg, 70%). $^1$H NMR (300 MHz, DMSO-d$_6$) δ ppm: 1.34 (t, J=7.35 Hz, 3 H) 3.02 (q, J=7.35 Hz, 2 H) 6.69 (d, J=6.99 Hz, 1 H) 6.97 (d, J=8.82 Hz, 2 H) 7.10 (dd, J=7.35 Hz, 1 H) 7.15 (d, J=8.82 Hz, 2 H) 7.30 (dd, J=8.09 Hz, J=7.72 Hz, 2 H) 7.56 (dd, J=2.94 Hz, J=9.19 Hz, 1 H) 7.71 (d, J=2.57 Hz, 1 H) 7.88 (d, J=8.82 Hz, 1 H) 8.52 (d, J=6.99 Hz, 1 H) 9.02 (d, J=8.45 Hz, 1 H) 11.16 (br s, 1 H) 14.56 (br s, 1 H); MS (ESI+) m/z 376 (M-Cl)+; (ESI−) m/z 374 (M−HCl)−.

Example 9

4-[2-(7-Ethyl-[1,8]naphthyridin-4-ylamino)-4-methyl-phenylsulfanyl]-phenol

Example 9a

Trifluoro-methanesulfonic acid 4-methyl-2-nitro-phenyl ester

A solution of the 4-methyl-2-nitro phenol (6.0 g, 39.1 mmol) and Et$_3$N (16.38 mL, 117.5 mmol) in 100 mL of CH$_2$Cl$_2$ under a N$_2$ atmosphere was treated with trifluoromethanesulfonic anhydride (7.25 mL, 43.1 mmol) at 0° C. for 30 min. Quenched by addition of MeOH. Washed sequentially with 10% citric acid, 0.5 m KOH and water. Dried over MgSO$_4$, filtered and concentrated under vacuum giving the title compound which was purified by silica gel column chromatography eluting with CH$_2$Cl$_2$ giving an amber oil (11.22 g, 100%).

Example 9b 4-(4-Methyl-2-nitro-phenylsulfanyl)-phenol

The product from Example 9a (11.22 g, 39.3 mmol) and 4-mercaptophenol (4.96 g, 39.3 mmol) in 100 mL of EtOH was treated with Na$_2$CO$_3$ and heated overnight under efflux. Cooled to room temperature and quenched with water. Extracted with EtOAc. Dried over MgSO$_4$, filtered and concentrated under vacuum giving the title compound, which was purified by silica gel column chromatography eluting with 25% EtOAc/hexane giving a red oil (8.65 g, 85%).

Example 9c 4-(2-Amino-4-methyl-phenylsulfanyl)-phenol

The product from Example 9b (8.65 g, 31.3 mmol) was reduced with SnCl$_2$ following the procedure from Example 7f giving the title compound as a white solid (8.51 g, 100%).

Example 9d

4-[2-(7-Ethyl-[1,8]naphthyridin-4-ylamino)-4-methyl-phenylsulfanyl]-phenol

The product from Example 9c (131 mg, 0.530 mmol) was reacted with the product from Example 8f (97 mg, 0.503 mmol) for 21 h following the procedure from Example 7g giving the title compound as a hydrochloride salt which was triturated with 5:1 ether/THF giving (210 mg, 98%). $^1$H NMR (300 MHz, DMSO-$d_6$) δ ppm: 1.37 (t, J=7.35 Hz, 3 H) 2.33 (s, 3 H) 3.05 (q, J=7.35 Hz, 2 H) 6.29 (d, J=6.99 Hz, 1 H) 6.74 (d, J=8.46 Hz, 2 H) 7.00 (m, 1 H) 7.17-7.29 (m, 4 H) 7.84 (d, J=8.83 Hz, 1 H) 8.43 (d, J=6.98 Hz, 1 H) 9.09 (d, J=8.83 Hz, 1 H) 9.90 (s, 1 H) 11.12 (br s, 1 H) 14.38 (br s, 1 H); MS (ESI+) m/z 388 (M-Cl)+; (ESI-) m/z 386 (M-HCl)-.

Example 10

4-[4-(4-Methoxy-benzyloxy)-2-(7-methyl-pyrido[2,3-d]pyrimidin-4-ylamino)-phenylsulfanyl]-phenol

Example 10A

2-Amino-6-methyl-nicotinonitrile

2-Chloro-6-methyl-nicotinonitrile (25 g, 0.164 mol) and liquid ammonia (250 mL) in 500 mL of ethanol were reacted in a sealed high-pressure vessel at 130° C. for 20 hours. The reaction mixture was concentrated under vacuum and the residue washed with water (2×50 mL) then dried in a vacuum oven for 24 hours to provide the title compound as a light yellow solid (18 g, 82%). $^1$H NMR (300 MHz, DMSO-$d_6$) δ ppm: 2.30 (s, 3H), 6.52 (d, J=7.7 Hz, 1H), 6.78 (s, 2H), 7.73 (d, J=7.7 Hz, 1H).

Example 10B

N'-(3-Cyano-6-methyl-pyridin-2-yl)-N,N-dimethyl-formamidine

A solution of the product of Example 10A (10 g, 75.19 mmol) and N,N-Dimethylformamide dimethyl acetal (11 mL, 82.71 mmol) in toluene (100 mL) was heated at reflux for 6 hours. After cooling to room temperature, the solution was concentrated under vacuum to provide the title compound as a yellow solid (13.78 g, 98%). $^1$H NMR (300 MHz, DMSO-$d_6$) δ ppm: 2.41 (s, 3H), 3.06 (s, 3H), 3.14 (s, 3H), 6.87 (d, J=7.7 Hz, 1H), 7.89 (d, J=8.1 Hz, 1H), 8.59 (s, 1H).

Example 10C

1-Chloro-4-(4-methoxy-benzyloxy)-2-nitro-benzene

A solution of 4-chloro-3-nitro-phenol (0.5 g, 2.88 mmol), 1-chloromethyl-4-methoxy-benzene (0.496 g, 3.17 mmol), potassium carbonate (1.19 g, 8.64 mmol) and tetrabutylammonium iodide (0.005 g, 0.0135 mmol) in N,N-dimethylformamide (5 ml) was stirred at room temperature for 16 hours. Afterwards ice water (10 mL) was added to the solution and the resultant solid was collected by filtration and dried in a vacuum oven to provide the title compound (0.812 g, 96%).

Example 10D

4-[4-(4-Methoxy-benzyloxy)-2-nitro-phenylsulfanyl]-phenol

A solution of the product of Example 10C (0.812 g, 2.76 mmol), 4-hydroxythiophenol (0.419, 3.32 mmol) and cesium carbonate (2.16 g, 6.64 mmol) in N,N-dimethylformamide (5 mL) was heated to 100° C. for 16 hours. After cooling to room temperature the mixture was poured into ice water (20 mL) and the resultant solution acidified with 1N aqueous hydrochloric acid. The solution was then extracted with ethyl acetate (3×10 mL), the combined extracts dried over magnesium sulfate, filtered and concentrated under vacuum to provide the title compound (1.06 g, 100%).

Example 10E

4-[2-Amino-4-(4-methoxy-benzyloxy)-phenylsulfanyl]-phenol

A solution of the product of Example 10D (1.06 g, 2.76 mmol), iron powder (0.63 g, 11.04 mmol) and ammonium chloride (0.18 g, 3.31 mmol) in a methanol (18 mL), tetrahydrofuran (18 mL), and water (6 mL) solution was heated to reflux for 3 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over magnesium sulfate, filtered and concentrated under vacuum to provide the title compound (0.99 g, 100%).

Example 10F

4-[4-(4-Methoxy-benzyloxy)-2-(7-methyl-pyrido[2,3-d]pyrimidin-4-ylamino)-phenylsulfanyl]-phenol A solution of the product of Example 10B (28.4 mg, 0.151 mmol), and the product of Example 10E (53.3 mg, 0.151 mmol) in acetic acid (1 mL) was stirred in an oil bath preheated to 130° C. for 20 minutes. The mixture was then cooled to room temperature, the acetic acid removed under vacuum, and the resultant residue triturated with methanol to provide the title compound as a tan solid (26.5 mg, 35%). $^1$H NMR (300 MHz, DMSO-$d_6$) δ ppm: 9.92 (s, 1 H), 9.63 (s, 1 H), 8.70 (d, J=8.09 Hz, 1 H), 8.55 (s, 1 H), 7.52 (d, J=8.46 Hz, 1 H), 7.38 (d, J=8.82 Hz, 2 H), 7.27 (s, 1 H), 7.06-7.18 (m, 3 H), 6.94 (d, J=8.46 Hz, 3 H), 6.61-6.72 (m, 2 H), 5.02 (s, 2 H), 3.75 (s, 3 H), 2.66 (s, 3 H); MS (ESI+) m/z 497.2 (M+H)+, (ESI-) m/z 495.3 (M-H)-.

Example 11

4-[4-(3-Bromo-benzyloxy)-2-(7-methyl-pyrido[2,3-d]pyrimidin-4-ylamino)-phenylsulfanyl]-phenol

Example 11A

4-[2-Amino-4-(3-bromo-benzyloxy)-phenylsulfanyl]-phenol

A solution of 4-chloro-3-nitro-phenol was reacted with 1-Bromo-3-bromomethyl-benzene using the conditions described in Example 10C to provide 4-(3-Bromo-benzyloxy)-1-chloro-2-nitro-benzene which was treated sequentially using the procedures from Examples 10D and 10E to provide the title product.

Example 11B

4-[4-(3-Bromo-benzyloxy)-2-(7-methyl-pyrido[2,3-d]pyrimidin-4-ylamino)-phenylsulfanyl]-phenol The product of Example 11A was reacted with the product of Example 10B using the procedure of Example 10F substituting the product of Example 11A for the product of Example 10E to provide the crude title compound which was purified by HPLC with TFA to provide the title compound as a trifluoroacetic acid salt (25 mg, 23%). $^1$H NMR (300 MHz, DMSO-D6) δ ppm: 2.72 (s, 3 H) 5.13 (s, 2 H) 6.65 (m, 2 H) 7.11 (m, 5 H) 7.40 (m, 2 H) 7.54 (d, J=7.72 Hz, 1 H) 7.66 (s, 1 H) 7.72 (d, J=8.82 Hz, 1 H) 8.71 (s, 1 H) 8.84 (d, J=8.09 Hz, 1 H) 9.68 (s, 1 H), 11.04 (m, 1 H); MS (ESI+) m/z 545, 547 (M+H)+.

Example 12

3-[4-(4-Hydroxy-phenylsulfanyl)-3-(7-isopropyl-pyrido[2,3-d]pyrimidin-4-ylamino)-phenoxymethyl]-benzonitrile Example 12A 4-Methyl-3-oxo-pentanal, Sodium Salt A flame-dried 100-mL flask equipped with a 25-mL addition funnel was purged with nitrogen gas and charged with anhydrous diethyl ether (40 mL) followed by the addition of sodium slivers (1.65 g, 0.0725 mol). The reaction mixture was cooled to ice/water bath temperature and a solution of methyl isopropyl ketone (6.244 g, 0.0725 mol) and ethyl formate (5.481 g, 0.0725 mol) in anhydrous diethyl ether (5 mL) was added slowly dropwise over 1.5 hours, at 0° C. After the addition was complete the cooling bath was removed and the reaction mixture stirred at room temperature overnight. Additional ether (10 mL) was then added to break up the resulting precipitate, and the solid was isolated quickly by vacuum filtration. The solid was rinsed with small amounts of ether and then dried in a vacuum desiccator for one hour to provide the title product as an off-white solid (5.35 g, 54% yield). This material was used in the next step without further purification.

Example 12B

6-Isopropyl-2-oxo-1,2-dihydro-pyridine-3-carbonitrile

To a solution of the product of Example 12A (5.35 g, 0.0393 mol) and 2-cyanoacetamide (3.47 g, 0.0413 mol) in water (35 mL) was stirred at room temperature for 10 minutes. To this mixture was added 2.5 mL of a stock piperidine acetate solution (prepared from 9.8 mL of piperidine, 6 mL of acetic acid and 10 mL of water), and the solution was heated under reflux for 2 hours. The mixture was then cooled to room temperature and taken to pH 4 by the addition of glacial acetic acid. The resulting light yellow solid was isolated by vacuum filtration, rinsed with water (2×30 mL), and dried under vacuum to provide the title product (4.36 g, 68%).

Example 12C

2-Bromo-6-isopropyl-nicotinonitrile

To a solution of the product of Example 12B (4.35 g, 0.0269 mol), tertrabutylammonium bromide (10.4 g, 0.0323 mol) and phosphorous pentoxide (8.01 g, 1.05 mol) in toluene (80 mL) was heated under reflux for 5 hours. The reaction mixture was then cooled to room temperature, water (80 mL) was added, and the mixture was stirred for 2 h at room temperature. The reaction mixture was diluted with toluene (20 mL) and the organic layer separated. The aqueous layer was washed with toluene (50 mL) and the combined organic layers were washed with brine (50 mL), dried over anhydrous magnesium sulfate, filtered, and concentrated under vacuum to provide the title product as a yellow oil (5.64 g, 93%).

Example 12D

2-Amino-6-isopropyl-nicotinonitrile

To a solution of the product of Example 12C (21 g, 0.093 mol) and liquid ammonia (250 mL) in 500 mL of ethanol were reacted in a sealed high-pressure vessel at 130° C. for 20 hours. The reaction mixture was concentrated under vacuum and the residue ground to a fine powder then washed with water (2×50 mL) and dried in a vacuum oven for 24 hours to provide the title compound as a beige solid (14 g, 93%).

Example 12E

N'-(3-Cyano-6-isopropyl-pyridin-2-yl)-N—N-dimethyl-formamidine

To a solution of the product of Example 12D (7.1 g, 0.044 mol) and N,N-Dimethylformamide dimethyl acetal (6.44 mL, 0.0484 mol) in toluene (100 mL) was heated at reflux for 3 hours. The resulting solution was cooled to room temperature and concentrated under vacuum to provide the title compound (9.5 g, 100%) as a thick brown oil that solidified upon standing. Although this material appears to be pure by NMR, it contains small amounts of highly colored impurities. It can be chromatographed on silica gel (ethyl acetate/hexane gradient) to provide a slightly yellow oil that solidifies upon standing (about 70% recovery from chromatography).

Example 12F 3-(4-Chloro-3-nitro-phenoxymethyl)-benzonitrile

The title compound was prepared according to the procedure of Example 10C substituting 3-bromomethyl-benzonitrile for 1-chloromethyl-4-methoxy-benzene (0.813 g, 98%).

Example 12G

3-[4-(4-Hydroxy-phenylsulfanyl)-3-nitro-phenoxymethyl]-benzonitrile

The title compound was prepared according to the procedure of Example 10D substituting 3-(4-Chloro-3-nitro-phenoxymethyl)-benzonitrile for 1-Chloro-4-(4-methoxy-benzyloxy)-2-nitro-benzene (1.07 g, 100%).

Example 12H

3-[3-Amino-4-(4-hydroxy-phenylsulfanyl)-phenoxymethyl]-benzonitrile

The title compound was prepared according to the procedure of Example 10E substituting 3-[4-(4-Hydroxy-phenylsulfanyl)-3-nitro-phenoxymethyl]-benzonitrile for 4-[4-(4-Methoxy-benzyloxy)-2-nitro-phenylsulfanyl]-phenol (0.97 g, 98%).

Example 12I

3-[4-(4-Hydroxy-phenylsulfanyl)-3-(7-isopropyl-pyrido[2,3-d]pyrimidin-4-ylamino)-phenoxymethyl]-benzonitrile A solution of the product of Example 12E (47.4 mg, 0.219 mmol), and the product of Example 12H (76.3 mg, 0.219 mmol) in acetic acid (1 mL) was stirred in an oil bath preheated to 130° C. for 15 minutes. The mixture was then cooled to room temperature, the acetic acid removed under vacuum, and the resultant residue purified by reverse phase preparative HPLC on a Waters Symmetry C8 column (25 mm×100 mm, 7 μm particle size) using a gradient of 10% to 100% acetonitrile/0.1% trifluoroacetic acid in water over 8 minutes (10 minutes run time) at a flow rate of 40 mL/min to provide the title compound as a trifluoroacetic acid salt (14 mg, 10%). $^1$H NMR (300 MHz, DMSO-$d_6$) δ ppm: 10.94 (s, 1 H), 9.69 (s, 1 H), 8.88 (d, J=8.46 Hz, 1 H), 8.70 (s, 1 H), 7.92 (s, 1 H), 7.72-7.87 (m, 3 H), 7.62 (t, J=7.72 Hz, 1 H), 7.15-7.28 (m, J=8.82 Hz, 2 H), 7.08-7.15 (m, 2 H), 6.99-7.06 (m, 1 H), 6.61-6.72 (m, 2 H), 5.18 (s, 2 H), 3.19-3.30 (m, 1 H), 1.34 (d, J=6.99 Hz, 6H); MS (ESI) m/z 520.3 (M+H)+, (ESI−) m/z 518.3 (M−H)−.

Example 13

3-(7-Isopropyl-pyrido[2,3-d]pyrimidin-4-ylamino)-4-(4-methoxy-phenylsulfanyl)-benzoic acid methyl ester Example 13A 4-(4-Methoxy-phenylsulfanyl)-3-nitro-benzoic acid methyl ester To a solution of 4-methoxy thiophenol (5 mL, 40.7 mmol) and methyl-3-nitro-4-chlorobenzoate (10.52 g, 48.8 mmol) in DMF (40 mL) was added CsCO$_3$ (26.5 g, 81.4 mmol) and the reaction mixture heated at 80° C. for 3 hours. After cooling, the solution was poured into water and extracted with ethyl acetate (3×100 mL). The combined organic layers were dried over MgSO$_4$, filtered, and concentrated under vacuum to afford the title compound after chromatography on silica gel using ethyl acetate/hexanes as eluent (10.93 g, 80%).

Example 13B

3-Amino-4-(4-methoxy-phenylsulfanyl)-benzoic acid methyl ester

To a solution of the product from Example 13A, iron powder and ammonium chloride in a methanol, tetrahydrofuran, and water solution was heated to reflux. The resultant mixture was filtered, and the filtrate was concentrated. Then ethyl acetate was added, stirred, filtered and concentrated to provide the title compound (7.16 g, 90%).

Example 13C 3-(7-Isopropyl-pyrido[2,3-d]pyrimidin-4-ylamino)-4-(4-methoxy-phenylsulfanyl)-benzoic acid methyl ester The product from Example 13B (1.58 g, 5.5 mmol) and the product from Example 12E (1.18 g, 5.5 mmol) in acetic acid (10 mL) was heated at 140° C. for 1 hour. The reaction mixture was then cooled to room temperature and then concentrated under vacuum. The residue was then purified by silica gel chromatography using 4% methanol in dichloromethane as eluent to provide the title compound as a white solid (1.16 g, 46%). $^1$H NMR (300 MHz, DMSO-D6) δ ppm: 1.33 (d, J=6.99 Hz, 6H), 3.13-3.29 (m, 1H), 3.79 (s, 3H), 3.83 (s, 3H), 6.89-6.98 (m, 1H), 7.02 (d, J=8.46 Hz, 2H), 7.42 (d, J=8.82 Hz, 2H), 7.57-7.67 (m, 1H), 7.72-7.82 (m, 1H), 7.85-7.98 (m, 1H), 8.58 (s, 1H), 8.84 (s, 1H), 10.17 (s, 1H); MS (ESI)+ m/z 461 (M+H)+.

Example 14

N-(3-Hydroxy-4-methyl-phenyl)-3-(7-isopropyl-pyrido[2,3-d]pyrimidin-4-ylamino)-4-(4-methoxy-phenylsulfanyl)-benzamide Example 14A 3-(7-Isopropyl-pyrido[2,3-d]pyrimidin-4-ylamino)-4-(4-methoxy-phenylsulfanyl)-benzoic acid To the product from Example 13C (1.56 g, 3.4 mmol) in tetrahydrofuran (20 mL) was added 1N aqueous sodium hydroxide (10 mL, 10 mmol) and the reaction mixture heated at 50° C. for 3 hours. After cooling the reaction mixture to room temperature, the pH was adjusted to 6.5 with 1N aqueous hydrochloric acid and the resulting precipitate was removed by vacuum filtration. The product was dried under high vacuum overnight to provide the title compound as an off white solid (643 mg, 42%).

Example 14B 3-(7-Isopropyl-pyrido[2,3-d]pyrimidin-4-ylamino)-4-(4-methoxy-phenylsulfanyl)-benzoyl chloride The product from Example 14A (500 mg, 1.120 mmol) in dichloromethane (10 mL) was treated with oxalyl chloride (0.115 mL, 1.344 mmol) and 1 drop of DMF. The resulting reaction mixture was stirred at room temperature for 1 hour and then concentrated under vacuum to provide the title compound as a brown solid that was used without further manipulation.

Example 14C

N-(3-Hydroxy-4-methyl-phenyl)-3-(7-isopropyl-pyrido[2,3-d]pyrimidin-4-ylamino)-4-(4-methoxy-phenylsulfanyl)-benzamide A solution of 5-amino-o-cresol (20.4 mg, 0.1655 mmol) and the product from Example 14B (70 mg, 0.1655 mmol) in dichloromethane (4 mL) was treated with triethylamine (0.025 mL, 0.1806 mmol) at room temperature. The resulting solution was stirred for 18 hours. The reaction mixture was then washed with water and brine, and the combined organic layers were dried over MgSO$_4$, the concentrated under vacuum to give a residue which was purified by silica gel chromatography using methanol and dichloromethane as eluent to provide the title compound (55 mg, 65%). $^1$H NMR (300 MHz, DMSO-D6) δ ppm: 1.34 (d, J=6.99 Hz, 6H), 2.07 (s, 3H), 3.17-3.28 (m, 1H), 3.77 (s, 3H), 6.86-7.10 (m, 5H), 7.30-7.46 (m, 3H), 7.64 (d, J=7.35 Hz, 1H), 7.72-7.86 (m, 1H), 7.95 (s, 1H), 8.43-8.68 (m, 1H), 8.77-8.97 (m, 1H), 9.27-9.46 (m, 1H), 10.02 (s, 1H), 10.21-10.40 (m, 1H); MS (APCI) m/z 552 (M+H)+.

Example 15

4-[4-(3-Fluoro-benzyloxy)-2-(pyrido[2,3-d]pyrimidin-4-ylamino)-phenylsulfanyl]-phenol

Example 15A

N'-(3-Cyano-pyridin-2-yl)-N,N-dimethyl-formamidine

A solution of 2-Amino-nicotinonitrile (5 g, 42 mmol) and N,N-Dimethylformamide dimethyl acetal (6.13 mL, 46.2 mmol) in toluene (20 mL) was heated at reflux for 3 hours. After cooling to room temperature, the solution was concentrated under vacuum to provide the title compound (7.3 g, 100%).

Example 15B

1-Chloro-4-(3-fluoro-benzyloxy)-2-nitro-benzene

The title compound was prepared according to the procedure of Example 10C substituting 1-Bromomethyl-3-fluorobenzene for 1-chloromethyl-4-methoxy-benzene (0.56 g, 100%).

Example 15C

4-[4-(3-Fluoro-benzyloxy)-2-nitro-phenylsulfanyl]-phenol

The title compound was prepared according to the procedure of Example 10D substituting 1-Chloro-4-(3-fluoro-benzyloxy)-2-nitro-benzene for 1-Chloro-4-(4-methoxy-benzyloxy)-2-nitro-benzene (0.57 g, 77%).

Example 15D

4-[2-Amino-4-(3-fluoro-benzyloxy)-phenylsulfanyl]-phenol

The title compound was prepared according to the procedure of Example 10E substituting 4-[4-(3-Fluoro-benzyloxy)-2-nitro-phenylsulfanyl]-phenol for 4-[4-(4-Methoxy-benzyloxy)-2-nitro-phenylsulfanyl]-phenol (0.501 g, 96%).

Example 15E

4-[4-(3-Fluoro-benzyloxy)-2-(pyrido[2,3-d]pyrimidin-4-ylamino)-phenylsulfanyl]-phenol A solution of the product from Example 15A (35 mg, 0.2 mmol) and the product from Example 15D (68 mg, 0.2 mmol) in acetic acid (1 mL) was gradually heated form room temperature to 130° C. in an oil bath over a 15 minute time period, followed by heating at 130° C. for an additional 1.5 hours. The mixture was then cooled to room temperature, concentrated under vacuum to provide the crude title compound which was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title compound as the trifluoroacetic acid salt (28 mg, 30%). $^1$H NMR (300 MHz, DMSO-$d_6$) δ ppm: 5.14 (s, 2 H) 6.65 (m, 2 H) 7.14 (m, 8 H) 7.49 (m, 1 H) 7.66 (m, 1 H) 8.61 (s, 1 H) 8.88 (d, J=7.47 Hz, 1 H) 9.07 (s, 1 H) 9.65 (s, 1 H) 10.34 (s, 1 H); MS (ESI) m/z 471 (M+H)+.

Example 16

Carbonic acid 4-(4-tert-butoxycarbonyloxy-phenylsulfanyl)-3-(pyrido[2,3-d]pyrimidin-4-ylamino)-phenyl ester tert-butyl ester

Example 16A 4-(4-Hydroxy-phenylsulfanyl)-3-nitro-phenol

A solution of 4-Chloro-3-nitro-phenol (2.0 g, 11.52 mmol), 4-hydroxythiophenol (1.45 g, 11.52 mmol) and cesium carbonate (11.26 g, 34.56 mmol) in N,N-dimethylformamide (25 mL) was heated to 100° C. for 4 hours. After cooling to room temperature, 1N aqueous Hydrochloric acid (150 mL) was added and the resultant solution extracted with ethyl acetate (2×100 mL), the combined extracts dried over magnesium sulfate, filtered and concentrated under vacuum to provide the crude title compound which was purified by chromatography on silica gel using hexanes/ethyl acetate as eluent to obtain the title product as a bright orange solid (1.35 g, 45%).

Example 16B

3-Amino-4-(4-hydroxy-phenylsulfanyl)-phenol

The product from Example 16A (1.34 g, 5.09 mmol) was reacted with iron (1.42 g, 25.48 mmol) and ammonium chloride (409 mg, 1.5 mmol) in 20 mL EtOH/20 mL THF/6 mL water following the procedure from Example 10E to provide the title compound (1.168 g, 97%).

Example 16C 4-(4-Hydroxy-phenylsulfanyl)-3-(pyrido[2,3-d]pyrimidin-4-ylamino)-phenol The product of Example 16B (380 mg, 1.63 mmol) was reacted with the product of Example 15A (284 mg, 1.63 mmol) using the procedure of Example 15E substituting the product of Example 16B for the product of Example 15D to provide a solid which was triturated with methanol to provide the title compound (209 mg, 35%).

Example 16D

Carbonic acid 4-(4-tert-butoxycarbonyloxy-phenylsulfanyl)-3-(pyrido[2,3-d]pyrimidin-4-ylamino)-phenyl ester tert-butyl ester The product of Example 16C (195 mg, 0.539 mmol) was reacted with Di-tert-butyl dicarbonate (234 mg, 1.078 mmol), triethyl amine (0.165 mL, 1.19 mmol), and 4-dimethylaminopyridine (2 mg) in dichloromethane (5 mL), tetrahydrofuran (3 mL) and dimethyl formamide (1 mL) at room temperature for 16 hours. Afterwards, the mixture was poured into water (10 mL) and the resultant solution extracted with ethyl acetate (3×10 mL), the combined extracts dried over magnesium sulfate, filtered and concentrated under vacuum to provide the title compound (256 mg, 84%). $^1$H NMR (300 MHz, DMSO-$d_6$) δ ppm: 1.47 (s, 9H), 1.49 (s, 9H), 7.13 (d, J=8.8 Hz, 2H), 7.20 (m, 1H), 7.29 (d, J=8.8 Hz, 2H), 7.35 (m, 1H), 7.46 (m, 1H), 7.63 (m, 1H), 8.61 (m, 1H), 8.82 (m, 1H), 9.08 (m, 1H), 10.27 (s, 1H); MS (ESI+) m/z 563 (M+H)+.

Example 17

Benzenesulfonic acid 4-[4-phenylsulfonyloxy-2-(pyrido[2,3-d]pyrimidin-4-ylamino)-cyclohexa-1,3-dienylsulfanyl]-phenyl ester The product of Example 16C (65 mg, 0.180 mmol) was reacted with Benzene sulfonyl chloride (0.046 mL, 0.36 mmol), and triethylamine (0.066 mL, 0.468 mmol) in N,N-dimethylformamide (1 mL) at room temperature for 2 hours. Afterwards, the mixture was poured into water (10 mL) and the resultant solution extracted with ethyl acetate (3×10 mL), the combined extracts dried over magnesium sulfate, filtered and concentrated under vacuum the purified by HPLC with TFA to provide the title compound as a trifluoroacetic acid salt (19 mg, 14%). $^1$H NMR (300 MHz, DMSO-$d_6$) δ ppm: 6.92 (m, 4H), 7.19 (m, 4H), 7.62 (m, 6H), 7.81 (m, 5H), 7.92 (m, 2H), 9.01 (bs, 1H); MS (ESI+) m/z 643 (M+H)+.

Example 18

Furan-2-carboxylic acid [4-(4-hydroxy-phenylsulfanyl)-3-(7-isopropyl-pyrido[2,3-d]pyrimidin-4-ylamino)-phenyl]-amide

Example 18a

Furan-2-carboxylic acid (4-fluoro-3-nitro-phenyl)-amide

The title compound was synthesized from 4-fluoro-3-nitro-phenylamine (2.00 g, 12.81 mmol) dissolved in THF (25 ml) and Hunig's base (3.312 g, 25.62 mmol) to which was added furan-2-carbonyl chloride (1.672 g, 12.81 mmol) drop wise over 10 minutes. Reaction mixture was stirred at room temperature for 1 hr at which time water was added and the title compound was collected by filtration providing the title compound (2.90 g, 90%).

Example 18b

Furan-2-carboxylic acid [4-(4-hydroxy-phenylsulfanyl)-3-nitro-phenyl]-amide

The product of Example 18a (1.00 g, 2.89 mmol) was dissolved in DMF to which $K_2CO_3$ (801 mg, 5.79 mmol), and 4-mercapto-phenol (366 mg, 2.89 mmol) were added. The reaction mixture was then heated to 80° C. for 2 hrs. At this point the reaction mixture was cooled to room temperature and diluted with water which was then extracted with ethyl acetate to isolate the desired compound (1.00 g, 99%).

Example 18c

Furan-2-carboxylic acid [3-amino-4-(4-hydroxy-phenylsulfanyl)-phenyl]-amide

The product from Example 18b was reduced with Fe and $NH_4Cl$ following the procedure from Example 10E to provide the title compound (980 mg, 90%).

Example 18d

Furan-2-carboxylic acid [4-(4-hydroxy-phenylsulfanyl)-3-(7-isopropyl-pyrido[2,3-d]pyrimidin-4-ylamino)-phenyl]-amide The product of Example 12E (100 mg, 0.462 mmol) and of Example 18c (151 mg, 0.462 mmol) were dissolved in HOAc and placed in a preheated 120° C. oil bath for 10 minutes. Reaction mixture was then cooled to room temperature, the solvent removed under vacuum and the crude oil was purified by HPLC with TFA providing the product as a trifluoroacetic acid salt (93 mg, 45%). $^1$H NMR (300 MHz, DMSO-$d_6$) δ ppm: 1.36 (d, J=6.62 Hz, 6 H), 6.64-6.73 (m, 3 H), 7.09-7.20 (m, 3 H), 7.34 (d, J=3.31 Hz, 1 H), 7.63 (dd, J=8.64, 2.39 Hz, 1 H), 7.79-7.89 (m, 1 H), 7.93-8.00 (m, 2 H), 8.74-8.80 (m, 1 H), 8.95 (d, J=8.82 Hz, 1 H), 9.77 (s, 1 H), 10.40 (s, 1 H); MS (ESI+) m/z 498 (M+TFA+H)+; (ESI−) m/z 496 (M+TFA−H)−.

Example 19

4-[4-Methyl-2-(7-methyl-[1,8]naphthyridin-4-ylamino)-phenylsulfanyl]-phenol

The product from Example 7d (277 mg, 0.156 mmol) was reacted with the product from Example 9c (361 mg, 0.156 mmol) for 5 h by the procedure in Example 7g giving the title compound after purification of the crude product by HPLC with TFA as the trifluoroacetic acid salt (231 mg, 30%). $^1$H NMR (300 MHz, DMSO-$d_6$) δ ppm: 2.33 (s, 3 H) 2.77 (s, 3 H) 6.29 (d, J=6.99 Hz, 1 H) 6.73 (d, J=8.82 Hz, 2 H) 7.01 (d, J=7.72 Hz, 1 H) 7.19 (d, J=8.46 Hz, 2 H) 7.24 (s, 1 H) 7.27 (s, 1 H) 7.81 (d, J=8.82 Hz, 1 H) 8.44 (d, J=6.99 Hz, 1 H) 9.01 (d, J=8.82 Hz, 1 H) 9.91 (s, 1 H) 11.03 (s, 1 H) 14.38 (br. s, 1 H); MS (ESI+) m/z 374 (M+H)+.

Example 20

7-Methyl-4-(5-methyl-2-phenylsulfanyl-phenylamino)-[1,8]naphthyridine-3-carboxylic acid ethyl ester

Example 20a

4-Chloro-7-methyl-[1,8]naphthyridine-3-carboxylic acid ethyl ester

The product from Example 7b (1.0 g, 4.30 mmol) was reacted with 12 mL of $POCl_3$ for 4 h following the procedure from Example 7d giving the title compound as a brownish-pink solid (619 mg, 57%).

Example 20b

7-Methyl-4-(5-methyl-2-phenylsulfanyl-phenylamino)-[1,8]naphthyridine-3-carboxylic acid ethyl ester The product from Example 20a (438 mg, 2.03 mmol) was reacted with the product from Example 7f (510 mg, 2.03 mmol) for 10 min following the procedure from Example 7g giving the title compound which was purified by silica gel column chromatography eluting with 4% MeOH/$CH_2Cl_2$ as a solid (114 mg, 57%). $^1$H NMR (300 MHz, DMSO-$d_6$) δ ppm: 1.33 (t, J=6.99 Hz, 3 H) 2.16 (s, 3 H) 2.62 (s, 3 H) 4.29 (q, J=7.11 Hz, 2 H) 6.86 (s, 1 H) 7.04 (d, J=8.09 Hz, 1 H)

7.15-7.34 (m, 6 H) 7.39 (d, J=7.72 Hz, 1 H) 7.69 (d, J=8.82 Hz, 1 H) 9.17 (s, 1 H) 10.13 (s, 1 H); MS (ESI+) m/z 430 (M+H)+, (ESI−) m/z 428 (M−H)−.

Example 21

4-[2-(7-Ethoxy-[1,8]naphthyridin-4-ylamino)-4-methyl-phenylsulfanyl]-phenol

Example 21a 1-tert-Butyl-7-chloro-4-oxo-1,4-dihydro-[1,8]naphthyridine-3-carboxylic acid ethyl ester This compound was prepared from 2,6-dichloro-nicotinic acid as described in the U.S. Pat. No. 6,818,654 to give the title compound.

Example 21b

7-Chloro-4-oxo-1,4-dihydro-[1,8]naphthyridine-3-carboxylic acid ethyl ester

The product from Example 21a (0.282 gm, 0.91 mmol) was combined at room temperature with 2 mL of TFA containing 2 drops of sulfuric acid. The resulting mixture was heated at 70° C. for 16.5 h. The volatiles were removed under vacuum and the residue suspended in water. The product was collected by vacuum filtration, water washed and dried under vacuum to give the title compound as a cream colored solid (0.214 gm, 93%).

Example 21c

[1,8]Naphthyridine-2,5-diol

The product from Example 21b (0.208 gm, 0.82 mmol) was reacted as described in Example 7c to give the title compound as a dark brown solid (0.196 gm, 97%).

Example 21d 2,5-Dichloro-[1,8]naphthyridine

The product from Example 21c (0.111 gm, 0.68 mmol) was reacted as described in Example 7d to give the title compound as a pale yellow solid (0.124 gm, 91%).

Example 21e

4-[2-(7-Chloro-[1,8]naphthyridin-4-ylamino)-4-methyl-phenylsulfanyl]-phenol

The product from Example 21d (0.67 g, 3.36 mmol) and the product from Example 9c (0.78 g, 3.36 mmol) in 10 mL ethanol were heated under reflux for 5.5 hr. The reaction mixture was cooled to room temperature and the solvent was removed concentrated under vacuum leaving yellow solid that was used without further purification (1.43 g, 100%).

Example 21f

4-[2-(7-Ethoxy-[1,8]naphthyridin-4-ylamino)-4-methyl-phenylsulfanyl]-phenol

The product from Example 21e (0.025 g, 0.063 mmol) was treated with 2 mL 21% by weight NaOEt in EtOH. The resulting mixture was heated at reflux 4 h. The solvent was concentrated under vacuum leaving a brown oily residue. The crude oil was purified by HPLC with TFA. The title compound was isolated as a trifluoroacetic acid salt giving a light brown powder (20 mg, 78%). $^1$H NMR (300 MHz, DMSO-$d_6$) δ ppm: 1.44 (t, J=6.99 Hz, 3 H) 2.32 (s, 3 H) 4.56 (q, J=6.99 Hz, 2 H) 6.24 (d, J=6.99 Hz, 1 H) 6.68-6.81 (m, 2 H) 6.98 (d, J=8.09 Hz, 1 H) 7.05-7.34 (m, 3 H) 7.34 (d, J=9.19 Hz, 1 H) 8.30 (d, J=6.99 Hz, 1 H) 8.92 (d, J=9.19 Hz, 1 H) 10.81 (s, 1 H) 14.17 (s, 1 H); MS (ESI+) m/z 404 (M+H)+; (ESI−) m/z 402 (M+H)−.

Example 22

N-{4-[4-Methyl-2-(7-methyl-[1,8]naphthyridin-4-ylamino)-phenylsulfanyl]-phenyl}-acetamide

Example 22a

N-[4-(4-Methyl-2-nitro-phenylsulfanyl)-phenyl]-acetamide

The product from Example 9a (1 g, 3.51 mmol) was reacted with N-(4-mercapto-phenyl)-acetamide (0.65 g, 351 mmol) for 18 h following the procedure from Example 9b giving the title compound (1.04 g, 98%).

Example 22b

N-[4-(2-Amino-4-methyl-phenylsulfanyl)-phenyl]-acetamide

The product from Example 22a (0.30 gm, 1 mmol) was reacted with $SnCl_2$ as described in Example 7f to give the title compound (0.27 gm, 100%) as an amber oil which was used without further purification.

Example 22c

N-{4-[4-Methyl-2-(7-methyl-[1,8]naphthyridin-4-ylamino)-phenylsulfanyl]-phenyl}-acetamide The product from Example 22c (0.27 gm, 1 mmol) was combined with the product from Example 7d (0.178 gm, 1 mmole) and reacted according to the procedure described in Example 7g to give the crude product as a brown solid that purified by HPLC with TFA providing the trifluoroacetic acid salt which was converted to the hydrochloride salt by treatment with 4N HCl in dioxane at room temperature to give the title compound (40.0 mg, 7.5%). $^1$H NMR (300 MHz, DMSO-$d_6$) δ ppm: 2.04 (s, 3 H) 2.35 (s, 3 H) 2.76 (s, 3 H) 6.29 (d, J=6.99 Hz, 1 H) 7.24 (m, 5 H) 7.50 (d, J=8.82 Hz, 2 H) 7.78 (d, J=8.82 Hz, 1 H) 8.40 (d, J=6.99 Hz, 1 H) 9.02 (m, 1 H) 10.08 (s, 1 H) 11.09 (s, 1 H) 14.37 (s, 1 H); MS (ESI+) m/z 415.1 (M+H)+, (ESI−) m/z 413.1 (M−H)−.

Example 23

N-(4-{2-[7-(2-Hydroxy-ethyl)-[1,8]naphthyridin-4-ylamino]-4-methyl-phenylsulfanyl}-phenyl)-acetamide

Example 23a

N-{4-[2-(7-Chloro-[1,8]naphthyridin-4-ylamino)-4-methyl-phenylsulfanyl]-phenyl}-acetamide The product from Example 21d (200 mg, 1.0 mmol) and the product from Example 22b (215 mg, 1.0 mmol) were reacted following the procedure from Example 7g giving a crude solid that was purified by HPLC with TFA to give the title compound 200 mg, 48%).

Example 23b

2-{5-[2-(4-Acetylamino-phenylsulfanyl)-5-methyl-phenylamino]-[1,8]naphthyridin-2-yl}-malonic acid diethyl ester To a slurry of sodium hydride (95%, 0.045 g, 1.8 mmol) in 10 mL anhydrous THF at 0° C. under an atmosphere of $N_2$ was added diethyl malonate (0.32 g, 2.0 mmol) dropwise. The mixture was stirred for 30 minutes at ambient temperature, treated with the product from Example 23a (0.141 g, 0.3 mmol), heated at 110° C. for two hours, cooled and partitioned between EtOAc and water. The ethyl acetate layer was washed with saturated brine, dried over sodium sulfate, filtered and concentrated giving the title compound as a yellow glass, (0.14 g, 84% yield).

Example 23c

N-(4-{2-[7-(2-Hydroxy-ethyl)-[1,8]naphthyridin-4-ylamino]-4-methyl-phenylsulfanyl}-phenyl)-acetamide The product from Example 23b (56 mg, 0.10 mmol) was reacted with $NaBH_4$ (40 mg, 1.00 mmol) in 5 mL EtOH for 24 h. Quenched with aqueous $NH_4Cl$ and adjusted to pH 7 with dilute HCl. Extracted with EtOAc and dried over $Na_2SO_4$, filtered and concentrated under vacuum giving the crude title compound which was purified by HPLC with TFA giving the trifluoroacetic acid salt (15 mg, 25%). $^1$H NMR (300 MHz, DMSO-$d_6$) δ ppm: 2.04 (s, 3 H) 2.35 (s, 3 H) 3.16 (t, J=6.43 Hz, 2 H) 3.91 (t, J=6.25 Hz, 2 H) 6.31 (d, J=6.99 Hz, 1 H) 7.14 (d, J=8.09 Hz, 1 H) 7.22-7.33 (m, 4 H) 7.51 (d, J=8.82 Hz, 2 H) 7.83 (d, J=8.82 Hz, 1 H) 8.42 (d, J=6.99 Hz, 1 H) 8.94-9.05 (m, 1 H) 10.04 (s, 1 H) 11.03 (s, 1 H) 14.40 (s, 1 H); MS (ESI+) m/z 445 (M+H−TFA)+.

Example 24

[2-(4-Acetylamino-phenylsulfanyl)-5-methyl-phenyl]-[7-(2-hydroxy-ethyl)-[1,8]naphthyridin-4-yl]-carbamic acid tert-butyl ester The product from Example 23 (22 mg, 0.05 mmol) was reacted with the di-tert-butyl dicarbonate (16 mg, 0.07 mmol) in 2 mL of dry THF. Added Et3N (8.0 mg, 0.08 mmol) and a catalytic amount of N,N-4-dimethylaminopyridine and stirred for 2 h. Poured into water and neutralized with 1M HCl. Extracted with EtOAc, dried over $Na_2SO_4$ and filtered and concentrated under vacuum giving the crude title compound which was purified by silica gel column chromatography eluting with 1% MeOH/$CH_2Cl_2$ providing the product as a free base solid (7.0 mg, 26%). $^1$H NMR (300 MHz, DMSO-$d_6$) δ ppm: 1.59 (s, 9 H) 2.03 (s, 3 H) 2.25 (s, 3 H) 2.96 (t, J=6.62 Hz, 2 H) 3.81 (m, 2 H) 4.74 (t, J=5.33 Hz, 1 H) 5.76 (d, J=6.90 Hz, 1 H) 6.63 (s, 1 H) 6.85 (m, 2 H) 7.22 (d, J=8.82 Hz, 2 H) 7.36 (d, J=8.09 Hz, 1 H) 7.52 (d, J=8.82 Hz, 2 H) 7.70 (d, J=8.46 Hz, 1 H) 8.50 (d, J=8.09 Hz, 1 H) 10.00 (s, 1 H); MS (ESI−) m/z 545 (M+H)+.

Example 25

3-[4-Methyl-2-(7-methyl-[1,8]naphthyridin-4-ylamino)-phenylsulfanyl]-phenol

Example 25a 3-(4-Methyl-2-nitro-phenylsulfanyl)-phenol

The product from Example 9a (10.14 g, 35.6 mmol) was reacted with 3-(4-Methyl-2-nitro-phenylsulfanyl)-phenol (4.48 g, 35.6 mmol) for 18 h following the procedure from Example 9b giving the product as a solid (7.88 g, 85%).

Example 25b 3-(2-Amino-4-methyl-phenylsulfanyl)-phenol

The product from Example 25a was reduced with $SnCl_2$ following the procedure from Example 7f giving the title compound.

Example 25c

3-[4-Methyl-2-(7-methyl-[1,8]naphthyridin-4-ylamino)-phenylsulfanyl]-phenol

The product from Example 7d (277 mg, 1.56 mmol) was reacted with the product from Example 25b (245 mg, 1.56 mmol) for 5 h following the procedure from Example 7g giving the crude title compound which was purified by HPLC with TFA providing the trifluoroacetic acid salt (399 mg, 52%). $^1$H NMR (300 MHz, DMSO-$d_6$) δ ppm: 2.38 (s, 3 H) 2.75 (s, 3 H) 6.30 (d, J=6.99 Hz, 1 H) 6.53-6.58 (m, 2 H) 6.61 (d, J=8.09 Hz, 1 H) 6.90-7.08 (m, 1 H) 7.27-7.47 (m, 3 H) 7.77 (d, J=8.46 Hz, 1 H) 8.39 (d, J=6.99 Hz, 1 H) 8.94 (d, J=8.82 Hz, 1 H) 9.58 (s, 1 H) 10.96 (s, 1 H) 14.34 (s, 1 H); MS (ESI+) m/z 374 (M+H)+.

Example 26

N-(4-Bromo-phenyl)-4-(4-hydroxy-phenylsulfanyl)-3-(7-propyl-[1,8]naphthyridin-4-ylamino)-benzamide Example 26a N-(4-Bromo-phenyl)-4-chloro-3-nitro-benzamide A mixture of 4-bromoaniline (2.58 g 14.99 mmol) in dry $CH_2Cl_2$ (100 mL) was treated with 4-chloro-3-nitrobenzoyl chloride (3.60 g, 17.99 mmol) and N,N-diisopropyl-ethylamine (3.14 mL, 17.99 mmol), and the resulting mixture stirred at room temperature for 17 hours. The solvent was concentrated under vacuum giving the title compound and the residue taken up in ethyl acetate (100 mL) and washed with water and brine. The organic extract was dried over $Na_2SO_4$, filtered and concentrated under vacuum giving the title compound as a tan solid (5.132 g, 14.45 mmol, 96%).

Example 26b

N-(4-Bromo-phenyl)-4-(4-hydroxy-phenylsulfanyl)-3-nitro-benzamide

A solution of the product of Example 26a (553 mg, 1.557 mmol) in anhydrous DMF (15 mL) was treated with 4-mercaptophenol (196 mg, 1.557 mmol) and cesium carbonate (1.015 g, 3.114 mmol) at room temperature, then heated at 100° under a nitrogen atmosphere for 3 hours. The reaction was cooled to room temperature and the solvent concentrated under vacuum giving the title compound. The residue was taken up in $H_2O$ (30 mL) and the pH adjusted to 3 with 1N aqueous HCl. The aqueous was then extracted with ethyl acetate, and the combined organic extracts washed with brine (25 mL). The organic layer was dried over $Na_2SO_4$, filtered and concentrated under vacuum giving the title compound. The residue was triturated with methylene chloride and purified by silica gel flash chromatography with a gradient of 6% to 30% ethyl acetate/methylene chloride to afford the title product as a dark yellow solid (517 mg, 1.16 mmol, 75%).

Example 26c

3-Amino-N-(4-bromo-phenyl)-4-(4-hydroxy-phenyl-sulfanyl)-benzamide

The product from Example 26b was reduced with Fe and $NH_4Cl$ following the procedure form Example 10E to give the title compound.

Example 26d

N-(4-Bromo-phenyl)-4-(4-hydroxy-phenylsulfanyl)-3-(7-propyl-[1,8]naphthyridin-4-ylamino)-benzamide The product from Example 8g (138 mg, 0.154 mmol) was reacted with the product form Example 26C (64 mg, 0.154 mmol) for 40 h following the procedure from Example 7g giving the crude title compound which was purified by HPLC with TFA providing the trifluoroacetic acid salt (30 mg, 20%). $^1$H NMR (300 MHz, DMSO-$d_6$) δ ppm: 0.99 (t, J=7.35 Hz, 3 H) 1.69-1.96 (m, 2 H) 3.02 (t, J=7.35 Hz, 2 H) 6.42 (d, J=6.99 Hz, 1 H) 6.87 (d, J=8.46 Hz, 2 H) 7.02 (d, J=8.46 Hz, 1 H) 7.33 (d, J=8.46 Hz, 2 H) 7.54 (d, J=9.19 Hz, 2 H) 7.72 (d, J=8.82 Hz, 2 H) 7.87 (d, J=8.82 Hz, 1 H) 7.98 (dd, J=8.46, 1.84 Hz, 1 H) 8.02 (d, J=1.84 Hz, 1 H) 8.52 (d, J=6.62 Hz, 1 H) 9.09 (d, J=8.46 Hz, 1 H) 10.09 (s, 1 H) 10.37 (s, 1 H) 11.14 (s, 1 H) 14.54 (s, 1 H); MS (ESI+) m/z 585/587 (M+H)+.

Example 27

5-Dimethylamino-naphthalene-1-sulfonic acid 4-[4-methyl-2-(7-methyl-[1,8]naphthyridin-4-ylamino)-phenylsulfanyl]-phenyl ester The product from Example 19 (167 mg, 0.94 mmol) was reacted with 5-Dimethylamino-naphthalene-1-sulfonyl chloride (245 mg, 0.94 mmol) in 10 mL of $CH_2Cl_2$ with N,N-diisopropylethylamine (0.530 mL, 410 mmol) for 22 h. Washed with water and dried over $Na_2SO_4$, filtered and concentrated under vacuum giving the crude title compound which was purified by HPLC with TFA providing the trifluoroacetic acid salt (35 mg, 40%). $^1$H NMR (300 MHz, DMSO-$d_6$) δ ppm: 2.75 (s, 3 H) 2.86 (s, 6 H) 6.65 (d, J=6.99 Hz, 1 H) 6.76 (d, J=9.19 Hz, 2 H) 6.87 (d, 2 H) 7.16 (d, J=8.82 Hz, 1 H) 7.34 (d, J=7.72 Hz, 1 H) 7.53-7.62 (m, 2 H) 7.69-7.79 (m, 3 H) 7.97 (d, J=7.35 Hz, 1 H) 8.22 (d, J=8.82 Hz, 1 H) 8.50 (d, J=6.99 Hz, 1 H) 8.60 (d, J=8.46 Hz, 1 H) 8.82 (d, J=8.82 Hz, 1 H); MS 1 H) 8.50 (d, J=6.99 Hz, 1 H) 8.60 (d, J=8.46 Hz, 1 H) 8.82 (d, J=8.82 Hz, 1 H); MS (DCI NH3+) m/z 611 (M+H)+.

Example 28

N-{4-[4-Methyl-2-(7-methyl-[1,8]naphthyridin-4-ylamino)-phenyl sulfanyl]-phenyl}-2-phenyl-butyramide To a flask containing 3 equivalents of PS-DCC resin (polymer-bound 'N,N,'-dicyclohexylcarbodiimide) was added 2-Phenyl-butyric acid (27 mg, 0.16 mmol) dissolved in 3 mL of DMA, followed by HOBt (22 mg, 0.16 mmol), the product from Example 29 (50 mg, 0.134 mmol) and diethylisopropylamine (52 mg, 0.402 mmol). The reaction was heated to 55° C. overnight, filtered and transferred to a vial containing 3 equivalents of MP-Carbonate (macroporous carbonate) resin. The reaction vessel and PS-DCC resin were washed with MeOH and the combined filtrates were shaken over the MP-carbonate resin for 2 hours at room temperature. The MP-Carbonate resin was removed via filtration and the reactions were concentrated to dryness. Purified by HPLC with TFA providing the product as a trifluoroacetic acid (2 mg, 4%). $^1$H NMR (500 MHz, DMSO-$D_2O$) δ ppm: 0.83-0.89 (m, 3 H), 1.66-1.74 (m, J=7.17, 6.90, 6.90, 6.90, 6.90 Hz, 1 H), 2.00-2.08 (m, 1 H), 2.32-2.38 (m, 3 H), 2.72-2.75 (m, 3 H), 3.53-3.57 (m, 1 H), 6.37 (d, J=7.02 Hz, 1 H), 7.14-7.19 (m, 1 H), 7.21 (d, J=8.85 Hz, 2 H), 7.24-7.31 (m, 3 H), 7.32-7.39 (m, 4 H), 7.50 (dd, J=8.85, 1.53 Hz, 2 H), 7.69 (d, J=8.85 Hz, 1 H), 8.39 (d, J=7.02 Hz, 1 H), 8.84-8.88 (m, 1 H), 10.28 (s, 1 H); MS (ESI+) m/z 519; (ESI−) m/z 517, 631 (M+TFA−H)−.

Example 29

[2-(4-Amino-phenylsulfanyl)-5-methyl-phenyl]-(7-methyl-[1,8]naphthyridin-4-yl)-amine The product from Example 22 (200 mg, 0.48 mmol) was suspended in 6N HCl (10 mL) and heated in air to 100° C. for one hour. The solution was subsequently cooled in an ice bath and made basic with solid NaOH (2.64 gm). The crude product was isolated by extraction with dichloromethane and purified by HPLC with TFA providing the title compound as the trifluoroacetic acid salt (96.1 mg, 37%). $^1$H NMR (300 MHz, DMSO-$d_6$) δ ppm; 2.31 (s, 3 H) 2.77 (s, 3 H) 6.30 (d, J=6.99 Hz, 1 H) 6.57 (d, J=8.46 Hz, 2 H) 6.90 (d, J=7.72 Hz, 1 H) 7.07 (d, J=8.46 Hz, 2 H) 7.23 (m, J=7.72 Hz, 2 H) 7.81 (d, J=8.82 Hz, 1 H) 8.46 (d, J=7.35 Hz, 1 H) 9.04 (d, J=8.46 Hz, 1 H) 11.05 (s, 1 H). MS (ESI+) m/z 373.1 (M+H)+; (ESI−) m/z 371.1 (M−H)−.

Example 30

4-[4-Methyl-2-(7-methyl-[1,8]naphthyridin-4-ylamino)-phenylsulfanyl]-benzamide

Example 30a
4-(4-Methyl-2-nitro-phenylsulfanyl)-benzoic acid

The product from Example 9a (0.94 g, 3.31 mmol) was reacted with 4-mercapto-benzoic acid (0.51 g, 3.31 mmol) in aqueous ethanol at 80° C. under nitrogen. The reaction mixture was poured into water and acidified with glacial acetic acid. The solid product was collected by filtration, water washed and dried in vacuo to give the title compound (0.877 g, 91%) sufficiently pure for use as isolated.

Example 30b 4-(4-Methyl-2-nitro-phenylsulfanyl)-benzamide

The product from Example 30a (0.3 g, 1.04 mmol) was dissolved in THF (15 mL) and treated with N-methylmorpholine (0.131 mL, 1.19 mmol) followed by cooling in an ice bath and addition of isobutylchloroformate (0.148 mL, 1.14 mmol). The resulting mixture was allowed warm to room temperature with stirring for thirty minutes. Subsequent cooling in an ice bath was followed by addition of ammonia gas and warming to room temperature. The title compound was isolated by the addition of water and collection of the solid by vacuum filtration was used without further purification (0.289 g, 96%).

Example 30c

The product from Example 30c (0.289 g, 1.0 mmol) was reacted with stannous chloride (0.95 g, 5 mmol) as described in Example 7f to give the title compound as an off white solid (0.226 g, 88%).

Example 30d

4-[4-Methyl-2-(7-methyl-[1,8]naphthyridin-4-ylamino)-phenylsulfanyl]-benzamide

The product from Example 7d (0.156 g, 0.875 mmol) was reacted with the product from Example 30d (0.226 g, 0.875 mmol) for 24 hours following the procedure from Example 7g giving the crude title compound which was purified by HPLC with TFA providing the product as the trifluoroacetic acid salt (0.185 g, 38%). $^1$H NMR (300 MHz, DMSO-$d_6$) δ ppm: 2.37-2.46 (m, 3 H) 2.74 (s, 3 H) 6.36 (d, J=6.99 Hz, 1 H) 7.19 (d, J=8.46 Hz, 2 H) 7.31-7.46 (m, 3 H) 7.47-7.57 (m, 1 H) 7.68 (d, J=8.46 Hz, 2 H) 7.75 (d, J=8.46 Hz, 1 H) 7.90 (s, 1 H) 8.39 (d, J=7.35 Hz, 1 H) 8.90 (d, J=8.46 Hz, 1 H) 11.02 (s, 1 H); MS (ESI+) m/z 401.0 (M+H)+; (ESI−) m/z 399.0 (M−H—).

Example 31

[3-(7-Methyl-[1,8]naphthyridin-4-ylamino)-4-phenylsulfanyl-benzyl]-carbamic acid tert-butyl ester Example 31a 3-nitro-4-(phenylthio)benzonitrile A solution of sodium thiophenolate (16.29 g, 123.3 mmol) in 150 mL of DMF was heated at 100° C. with 4-chloro-3-nitrobenzonitrile (15.0 g, 82.2 mmol) with stirring for 24 hours. Cooled to room temperature and diluted with EtOAc. Washed with water and dried the organic layer over MgSO$_4$. Filtered and concentrated under vacuum giving the title compound, which was purified by silica gel column chromatography eluting with 5% EtOAc/hexane giving a yellow solid (4.0 g, 19%).

Example 31b tert-butyl 3-amino-4-(phenylthio)benzylcarbamate

A solution of the product from Example 31a (4.0 g, 15.6 mmol) and di-tert-butyl-dicarbonate (1.70 g, 7.79 mmol) was catalytically reduced using Ra—Ni in MeOH at 60 psi under an atmosphere of H$_2$. Removal of the catalyst and concentration under vacuum gave the title compound which was purified by silica gel column chromatography eluting with 10% EtOAc/hexane giving a mixture of the two examples as a clear oil (2.41 g, 46%).

Example 31d tert-butyl (3-(7-methyl-1,8-naphthyridin-4-ylamino)-4-(phenylthio)phenyl)methylcarbamate The product from Example 7d (557 mg, 3.12 mmol) was reacted with the product from Example 31b (1.032 mg, 3.12 mmol) for 18 h following the procedure from Example 7g giving the crude title compound which was purified by HPLC with TFA providing the product as a trifluoroacetic acid (310 mg, 17%). $^1$H NMR (300 MHz, DMSO-$d_6$) δ ppm: 1.37 (s, 9 H) 2.76 (s, 3 H) 4.19 (d, J=6.25 Hz, 2 H) 6.29 (d, J=6.99 Hz, 1 H) 7.25 (s, 5 H) 7.31 (s, 1 H) 7.37 (d, J=3.31 Hz, 2 H) 7.44-7.56 (m, 1 H) 7.79 (d, J=8.82 Hz, 1 H) 8.42 (d, J=6.99 Hz, 1 H) 8.94 (d, J=8.46 Hz, 1 H) 11.05 (s, 1 H) 14.43 (s, 1 H); MS (ESI+) m/z 473 (M+H)+.

Example 32

(4-{2-[Ethoxycarbonylmethyl-(7-methyl-[1,8]naphthyridin-4-yl)-amino]-4-methyl-phenylsulfanyl}-phenoxy)-acetic acid ethyl ester The product from Example 19 (200 mg, 0.536 mmol) was suspended in acetone to which K$_2$CO$_3$ (81 mg, 0.589 mmol), and bromoethyl acetate (89 mg, 0.536 mmol) were added. The reaction mixture was then heated to reflux for 4 h reaction mixture was cooled to room temperature and solvent removed under vacuum. Purified by HPLC with TFA providing the product as a trifluoroacetic acid (15 mg, 6%). $^1$H NMR (300 MHz, DMSO-$d_6$) δ ppm: 1.21 (td, J=7.08, 2.39 Hz, 6 H), 2.35 (s, 3 H), 2.73 (s, 3 H), 4.18 (ddd, J=14.16, 10.66, 7.17 Hz, 4 H), 4.76 (s, 2 H), 5.46 (s, 2 H), 6.47 (d, J=7.35 Hz, 1 H), 6.87 (d, J=8.82 Hz, 2 H), 7.14 (d, J=8.09 Hz, 1 H), 7.21-7.42 (m, 4 H), 7.86 (d, J=8.46 Hz, 1 H), 8.61 (d, J=7.72 Hz, 1 H), 9.03 (d, J=8.46 Hz, 1 H); MS (ESI+) m/z 546 (M+H−TFA)+.

Example 33

Propane-2-sulfonic acid 4-[2-(7-ethyl-[1,8]naphthyridin-4-ylamino)-4-methyl-phenylsulfanyl]-phenyl ester The product from Example 9 (100 mg, 0.233 mmol) was reacted with isopropyl sulfonyl chloride (40 mg, 0.280 mmol), N,N-diisopropylethylamine (90 mg, 0.70 mmol), and catalytic DMAP in dichloroethane for 18 h giving the crude title compound which was purified by HPLC with TFA providing the product as the trifluoroacetic acid (12 mg, 12%). $^1$H NMR (300 MHz, DMSO-$d_6$) δ ppm: 8.93 (d, J=8.46 Hz, 1H) 8.40 (d, J=7.35 Hz, 1H) 7.79 (d, J=8.82 Hz, 1 H) 7.46 (d, 1 H) 7.37 (s, 2 H) 7.27 (d, 2 H) 7.15 (d, J=8.82 Hz, 2 H) 6.35 (d, J=6.99 Hz, 1 H) 3.66 (m, J=7.72 Hz, 1 H) 3.03 (q, J=7.72 Hz, 2 H) 2.40 (s, 3 H) 1.40 (d, 6H) 1.36 (t, 3H); MS (ESI+) m/z 494 (M+H)+.

Example 34

4-[4-Chloro-2-(7-methyl-[1,8]naphthyridin-4-ylamino)-phenoxy]-N-(2-methoxy-ethyl)-benzamide Example 34a Methyl 4-(4-chloro-2-nitrophenoxy)benzoate A mixture of 1,4-dichloro-2-nitrobenzene (20.0 g, 104.2 mmol) and methyl 4-hydroxybenzoate (15.85 g, 104.2 mmol)

in 150 mL of EtOH was treated with Na₂CO₃ and heated overnight under reflux. Cooled to room temperature and quenched with water. Extracted with EtOAc. Dried over MgSO₄, filtered and concentrated under vacuum giving the title compound, which was purified by silica gel column chromatography eluting with 10% EtOAc/hexane giving the title compound as a yellow solid (29.6 g, 92%).

Example 34b 4-(4-chloro-2-nitrophenoxy)benzoic acid

The compound from Example 34a (29.6 g, 96.2 mmol) in 200 mL of MeOH was treated with aqueous LiOH (1 M) and heated under reflux for 1 hour. Cooled to room temperature and acidified with aqueous HCl (1 M). Precipitate was filtered, washed with H₂O and air-dried giving the title compound as a yellow solid (28.2 g, 100%).

Example 34c 4-(4-chloro-2-nitrophenoxy)benzoyl chloride

The product from Example 34b (4.0 g, 13.6 mmol) in 40 mL of CH₂Cl₂ was treated with oxalyl chloride (3.5 g, 27.2 mmol) and DMF (catalytic amount). Mixture was stirred for 12 hours. Mixture was concentrated under vacuum giving the title compound as a yellow oil (4.2 g, 100%).

Example 34d 4-(4-chloro-2-nitrophenoxy)-N-(2-methoxyethyl) benzamide

The compound from Example 34c (1.0 g, 3.2 mmol) in CH₂Cl, was added to a mixture of 2-methoxyethanamine (722 mg, 9.61 mmol) in CH₂Cl₂. Mixture was stirred for 12 hours. Mixture was concentrated under vacuum giving the title compound, which was purified by silica gel column chromatography eluting with 50% EtOAc/hexane giving the title compound as a yellow oil (1.1 g, 100%).

Example 34e 4-(2-Amino-4-chlorophenoxy)-N-(2-methoxyethyl) benzamide

The product from Example 34d (1.0 g, 2.85 mmol) was reduced with SnCl₂ following the procedure from Example 7f giving the title compound as a clear oil (900 mg, 100%).

Example 34f 4-(4-chloro-2-(7-methyl-1,8-naphthyridin-4-ylamino)phenoxy)-N-(2-methoxyethyl)benzamide The product from Example 7d (111 mg, 0.62 mmol) was reacted with the product from Example 34e (200 mg, 0.62 mmol) for 18 h following the procedure from Example 7g giving the crude title compound which was purified by HPLC with TFA providing the product as a trifluoroacetic acid (89.4 mg, 25%). ¹H NMR (300 MHz, DMSO-D₆) δ ppm: 2.73 (s, 3 H) 3.25 (s, 3 H) 3.32-3.50 (m, 4 H) 6.72 (d, J=6.99 Hz, 1 H) 6.97 (d, J=8.82 Hz, 2 H) 7.30 (d, J=8.82 Hz, 1 H) 7.61 (dd, J=8.82, 2.57 Hz, 1 H) 7.70-7.80 (m, 4 H) 8.42 (t, J=5.15 Hz, 1 H) 8.53 (d, J=6.99 Hz, 1 H) 8.82 (d, J=8.82 Hz, 1 H) 10.90 (s, 1 H) 14.54 (s, 1 H); MS (ESI+) m/z 463 (M+H−TFA)+.

Example 35

[5-Methyl-2-(1H-[1,2,4]triazol-3-ylsulfanyl)-phenyl]-(7-propyl-[1,8]naphthyridin-4-yl)-amine Example 35a 5-Methyl-2-(1H-[1,2,4]triazol-3-ylsulfanyl)-phenylamine The title compound was prepared from 1-Chloro-4-methyl-2-nitro-benzene (3.00 g, 17.5 mmol), 1H-[1,2,4]Triazole-3-thiol (1.94 g, 19.2 mmol), and K₂CO₃ (4.22 g, 30.6 mmol) heated in DMF at 100° C. for 16 hrs. Reaction mixture was then cooled to room temperature and diluted with water and extracted with ethyl acetate. Dried over Na₂SO₄, filtered and concentrated under vacuum giving the title compound (1.1 g, 26%).

Example 35b

5-Methyl-2-(1H-[1,2,4]triazol-3-ylsulfanyl)-phenylamine

The product form Example 35a was reduced with SnCl₂ following the procedure from Example 7f to give the title compound.

Example 35c

[5-Methyl-2-(1H-[1,2,4]triazol-3-ylsulfanyl)-phenyl]-(7-propyl-[1,8]naphthyridin-4-yl)-amine The product form Example 8g (60 mg, 0.290 mmol) was reacted with the product from Example 35b (60 mg, 0.290 mmol) for 18 h following the procedure from Example 7g giving the crude title compound which was purified by HPLC with TFA providing the product as a trifluoroacetic acid (17 mg, 16%). ¹H NMR (300 MHz, DMSO-d₆) δ ppm: 0.98 (t, J=7.35 Hz, 3 H), 1.78-1.91 (m, 2 H), 2.38 (s, 3 H), 2.99 (t, 2 H), 6.33 (d, J=6.99 Hz, 1 H), 7.29-7.39 (m, 2 H), 7.46 (d, J=8.09 Hz, 1 H), 7.83 (d, J=8.82 Hz, 1 H), 8.44 (d, J=6.99 Hz, 1 H), 9.00 (d, J=8.46 Hz, 1 H), 11.07 (s, 1 H), 14.16-14.55 (m, 2 H); MS (ESI+) m/z 377 (M+H−TFA)+; (ESI−) m/z 375 (M−H−TFA)−.

Example 36

(5-Chloro-2-phenoxy-phenyl)-[1,6]naphthyridin-5-yl-amine

Example 36a

2-Trimethylsilanylethynyl-nicotinonitrile

In a suitably sized pressure vessel, commercially available 2-chloro-nictinonitrile (1.5 g, 10.8 mmol) was combined with triphenylphosphine (0.228 g, 8 mole %) and palladium (II) acetate (0.083 g, 3.5 mol %) in triethylamine (20 mL). Nitrogen was bubbled through the resulting suspension at room temperature for five minutes then trimethylsilylacetylene (8.5 mL, 60.1 mmol) was added, the vessel sealed and immersed in an 80° C. oil bath. After 18.5 h the pressure tube was cooled to room temperature and the contents were filtered. The filtrate was concentrated under vacuum and the crude product purified by flash chromatography on silica gel eluting with EtOAc/hexanes to give the title compound (1.62 g, 75%) as a tan solid.

Example 36b 2-(2,2-Dimethoxy-ethyl)-nicotinonitrile

The product from Example 36a (1.62 g, 8.09 mmol) was reacted with sodium methoxide as a 25 wt % solution (8.74 g, 40.4 mmol) in methanol (5 mL) for two hours at 80° C. The crude product was isolated by extraction with ether, dried over MgSO$_4$, filtered and concentrated under vacuum to give the title compound (1.46 g, 94%) sufficiently pure for use as isolated.

Example 36c 2-(2,2-Dimethoxy-ethyl)-nicotinamide

The product from Example 36b (1.46 g, 7.6 mmol) was dissolved in methanol (20 mL) to which was added at room temperature sodium carbonate as a 3N solution (35 mL) followed by hydrogen peroxide as a 15% solution (35 mL). The reaction was allowed to stir for 4.5 hours then partitioned by the addition of ethyl acetate and solid sodium chloride. The aqueous phase was extracted several times with ethyl acetate and the combined organics stirred with solid sodium bisulfite followed by drying over MgSO$_4$, filtered and concentration under vacuum to give the title compound (1.36 g, 85%) sufficiently pure for use as isolated.

Example 36d

[1,6] Naphthyridin-5-ol

The product from Example 36c (1.36 g, 6.47 mmol) was dissolved in benzene (35 ml) and to this solution was added pyridinium-para-toluenesulfonate (0.20 g, 0.8 mmol). The mixture was heated to reflux for 23 h then concentrated under vacuum to give the title compound in quantitative yield sufficiently pure for use as isolated.

Example 36e

5-Chloro-[1,6]naphthyridine

The product from Example 36d (0.250 g, 1.71 mmol) was combined with phosphorous oxychloride (4 mL) and heated under a nitrogen atmosphere at 80° C. for 18.5 h followed by vacuum distillation to remove the volatiles. The residue was slurried with ice and made basic (pH 7-8) with concentrated ammonium hydroxide. The title compound was collected by vacuum filtration, water washed and dried under vacuum to give a gray solid (0.245 g, 87%) sufficiently pure for use as isolated.

Example 36f (5-Chloro-2-phenoxy-phenyl)-[1,6]naphthyridin-5-yl-amine

To a solution of DMF (50 mL) was added 1-bromo-2-nitro-4-chloro-benzene (5.0 g, 21.1 mmol), phenol (1.9 g, 21.1 mmol), and Na$_2$CO$_3$ (2.3 g, 21.1 mmol). The solution was heated to 85° C. and stirred overnight. The reaction was poured into water and extracted with EtOAc. Washed with water and dried over Na$_2$SO$_4$, filtered and concentrated under vacuum giving a yellow oil that was purified by silica gel column chromatography eluting with Hexanes:Ethyl Acetate (90:10) to give 4-chloro-2-nitro-1-phenoxy-benzene (3.8 g, 74%). 4-Chloro-2-nitro-1-phenoxy-benzene (13 g, 52.1 mmol) was reacted with SnCl$_2$ (49.3 g, 260 mmol) following the procedure from Example 7f giving 5-chloro-2-phenoxy-phenylamine as a white solid 9.0 g, 79%).

The product from Example 36e (0.040 g, 0.24 mmol) was reacted with 5-chloro-2-phenoxy-phenylamine as (0.048 g, 0.24 mmol) for 48 h at 100° C. following the procedure from Example 7g giving the crude title compound which was purified by HPLC with TFA providing the product as a trifluoroacetic acid salt (0.046 g, 40%). $^1$H NMR (300 MHz, DMSO-d$_6$) δ ppm: 6.96 (d, J=7.35 Hz, 2 H) 7.00-7.10 (m, 2 H) 7.22-7.39 (m, 4 H) 7.66 (dd, J=8.46, 4.41 Hz, 1 H) 7.91 (d, J=1.84 Hz, 1 H) 8.07 (d, J=6.25 Hz, 1 H) 8.76 (d, J=8.46 Hz, 1 H) 9.07 (d, J=3.31 Hz, 1 H); MS (ESI+) m/z 348.0 (M+H)+; (ESI−) m/z 346.1 (M−H)−.

Example 37

N-{4-[4-Methyl-2-([1,6]naphthyridin-5-ylamino)-phenylsulfanyl]-phenyl}-acetamide The product from Example 36e (0.040 g, 0.24 mmol) was reacted with the product from Example 22b as a 1.5M solution in ethanol (0.162 mL, 0.24 mmol) for 17.5 h at 100° C. following the procedure from Example 7g. Consumption of starting material required a second addition of the product from Example 36e (0.027 g, 0.16 mmol) and continued heating at 100° C. (24 h) giving the crude title compound which was purified by HPLC with TFA providing the product as a trifluoroacetic acid salt (0.038 g, 27%). $^1$H NMR (300 MHz, DMSO-d$_6$) δ ppm: 2.02 (s, 3 H) 2.36 (s, 3 H) 7.12-7.37 (m, 5 H) 7.38-7.53 (m, 3 H) 7.73-7.92 (m, J=8.64, 4.60 Hz, 2 H) 8.94 (d, J=8.46 Hz, 1 H) 9.18 (d, J=4.04 Hz, 1 H) 9.99 (s, 1 H); MS (ESI+) m/z 401.3 (M+H)+; (ESI−) m/z 399.0 (M−H)−.

Example 38

N-{4-[4-Cyanomethoxy-2-(7-methyl-[1,8]naphthyridin-4-ylamino)-phenylsulfanyl]-phenyl}-acetamide

Example 38a

N-[4-(4-Hydroxy-2-nitro-phenylsulfanyl)-phenyl]-acetamide

A mixture of 3-nitro-4-chloro phenol (1.59 g, 8.97 mmol), 4-acetamidothiophenol (2 g, 10.76 mmol) and cesium carbonate (7.0 g, 21.53 mmol) in DMF (20 mL) was heated 2.5 h at 100° C. The mixture was cooled, poured onto ice and the resulting solid is collected by filtration and dried under vacuum the title compound leaving a yellow solid (2.7 g, 100%).

Example 38b

N-[4-(2-Amino-4-hydroxy-phenylsulfanyl)-phenyl]-acetamide

A solution of the product of Example 38a (2.7 g, 8.97 mmol), iron powder (2.0 g, 35.9 mmol) and ammonium chloride (0.58 g, 10.76 mmol) in a methanol (6 mL), THF (6 mL), and water (2 mL) solution was heated to reflux for 1.5 hours.

The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (2.46 g, 77%).

Example 38c

N-[4-(2-Amino-4-cyanomethoxy-phenylsulfanyl)-phenyl]-acetamide

A mixture of the product from Example 38b (56 mg, 0.17 mmol), 2-Bromoacetonitrile (20 mg, 0.17 mmol) and potassium carbonate (26 mg, 0.19 mmol) in DMF (1 mL) was stirred at room temperature 15 hr. The next day, the reaction mixture was poured onto ice and the solid collected by filtration providing the title compound (53 mg, 100%).

Example 38d

N-{4-[4-Cyanomethoxy-2-(7-methyl-[1,8]naphthyridin-4-ylamino)-phenylsulfanyl]-phenyl}-acetamide The product from Example 7d (30 mg, 0.17 mmol) was reacted in ethanol (1 mL) with the product from Example 38c (53 mg, 0.17 mmol) for 18 h following the procedure from Example 7g giving the crude title compound which was purified by HPLC with TFA providing the product as a trifluoroacetic acid salt (9 mg, 19%). $^1$H NMR (300 MHz, DMSO-$d_6$) δ ppm: 2.03 (s, 3 H) 2.76 (s, 3 H), 5.23 (s, 2 H), 6.32 (d, J=6.99 Hz, 1 H), 7.18 (d, J=8.46 Hz, 2 H) 7.23 (dd, J=8.82, 2.57 Hz, 1 H), 7.31 (d, J=2.57 Hz, 1 H), 7.38 (d, J=8.82 Hz, 1 H) 7.45 (d, J=8.82 Hz, 2 H), 7.80 (d, J=8.46 Hz, 1 H), 8.41 (d, J=6.99 Hz, 1 H) 8.96 (d, J=8.46 Hz, 1 H), 10.01 (s, 1 H), 11.04 (s, 1 H), 14.42 (s, 1 H); MS (ESI+) m/z 456 (M+H)+.

Example 39

N-{4-[4-(3-Methyl-benzyloxy)-2-(7-propyl-[1,8]naphthyridin-4-ylamino)-phenylsulfanyl]-phenyl}-acetamide

Example 39a

N-{4-[2-Amino-4-(3-methyl-benzyloxy)-phenylsulfanyl]-phenyl}-acetamide

A mixture of the product from Example 38b (28 mg, 0.085 mmol), 3-methylbenzyl bromide (13 mg, 0.096 mmol) and potassium carbonate (13 mg, 0.09 mmol) in DMF (1 mL) was stirred at room temperature 15 hr. The next day, the reaction mixture was poured onto ice and the solid collected by filtration providing the tile compound (32 mg, 100%).

Example 39b

N-{4-[4-(3-Methyl-benzyloxy)-2-(7-methyl-[1,8]naphthyridin-4-ylamino)-phenylsulfanyl]-phenyl}-acetamide The product from Example 7d (18 mg, 0.085 mmol) was reacted in ethanol (1 mL) with the product from Example 39a (32 mg, 0.085 mmol) for 18 h following the procedure from Example 7g giving the crude title compound which was purified by HPLC with TFA providing the product as a trifluoroacetic acid salt (14 mg, 26%). $^1$H NMR (300 MHz, DMSO-$d_6$) δ ppm: 0.97 (t, J=7.35 Hz, 3 H) 1.62-1.93 (m, 2 H) 2.02 (s, 3 H) 2.31 (s, 3 H) 2.99 (t, J=7.35 Hz, 2 H) 5.11 (s, 2 H) 6.30 (d, J=6.99 Hz, 1 H) 6.97-7.33 (m, 8 H) 7.34-7.50 (m, 3 H) 7.80 (d, J=8.82 Hz, 1 H) 8.36 (d, J=6.99 Hz, 1 H) 8.97 (d, J=8.82 Hz, 1 H) 9.97 (s, 1 H) 11.01 (s, 1 H) 14.36 (s, 1 H); MS (ESI+) m/z 549 (M+H)+.

Example 40

[2-(3,4-Dimethyl-phenylsulfanyl)-5-methyl-phenyl]-(7-propyl-[1,8]naphthyridin-4-yl)-amine The product form Example 8g (70 mg, 0.338 mmol) was reacted with the product from Example 9c substituting 3,4-dimethylbenzenethiol for 4-mercaptophenol for 20 h following the procedure from Example 7g giving the crude title compound that was triturated with 4:1 ether/THF providing the title compound as a hydrochloride salt (135 mg, 88%). $^1$H NMR (300 MHz, DMSO-$d_6$) δ ppm: 0.99 (t, J=7.35 Hz, 3 H) 1.82 (m, J=7.35 HZ, 2 H) 1.93 (s, 3 H) 2.05 (s, 3 H) 2.36 (s, 3 H) 2.99 (q, J=7.35 Hz, 2 H) 6.20 (d, J=6.99 Hz, 1 H) 6.94 (m, 3 H) 7.32 (m, 2 H) 7.34 (s, 1 H) 7.80 (d, J=8.82 Hz, 1 H) 8.33 (d, J=7.35 Hz, 1 H) 8.97 (d, J=8.82 Hz, 1 H) 10.96 (br s, 1 H) 14.29 (br s, 1 H); MS (ESI+) m/z 414 (M−Cl)+; (ESI−) m/z 412 (M−HCl).

Example 41

3-(7-Isopropyl-pyrido[2,3-d]pyrimidin-4-ylamino)-4-(4-methoxy-phenylsulfanyl)-N-(3-trifluoromethyl-phenyl)-benzamide The product from Example 14B was reacted with 3-(trifluoromethyl)aniline according to the procedure from Example 14C substituting 3-(trifluoromethyl)aniline for 5-amino-o-cresol to provide the title compound as an off white solid after trituration of the reaction product from methanol (73 mg, 77%). 1 H NMR (300 MHz, DMSO-D6) δ ppm: 10.54 (s, 1 H), 8.93 (d, J=8.46 Hz, 1 H), 8.67 (s, 1 H), 8.22 (s, 1 H), 8.04 (d, J=8.09 Hz, 1 H), 7.99 (s, 1 H), 7.85 (d, J=7.72 Hz, 1 H), 7.74 (d, J=8.46 Hz, 1 H), 7.59 (t, J=8.09 Hz, 1 H), 7.45 (d, J=8.46 Hz, 1 H), 7.41 (d, J=8.82 Hz, 2 H), 6.92-7.11 (m, 4 H), 3.77 (s, 3 H), 3.20-3.31 (m, 1 H), 1.35 (d, J=6.62 Hz, 6 H); MS (ESI+) m/z 590.3 (M+H)$^+$, (ESI$^-$) m/z 588.1 (M−H)$^-$.

Example 42

4-[2-(7-Methyl-pyrido[2,3-d]pyrimidin-4-ylamino)-4-(pyridin-2-ylmethoxy)-phenylsulfanyl]-phenol

Example 42A

4-[2-Amino-4-(pyridin-2-ylmethoxy)-phenylsulfanyl]-phenol

A solution of 4-chloro-3-nitro-phenol was reacted with 2-Bromomethyl-pyridine hydrobromide salt using the conditions described in Example 10C to provide 2-(4-Chloro-3-nitro-phenoxymethyl)-pyridine which was treated sequentially using the procedures from Examples 10D and 10E to provide the title product.

Example 42B

4-[2-(7-Methyl-pyrido[2,3-d]pyrimidin-4-ylamino)-4-(pyridin-2-ylmethoxy)-phenylsulfanyl]-phenol The product of Example 42A was reacted with the product of Example 10B using the procedure of Example 10F substituting the product of Example 42A for the product of Example 10E to provide the crude title compound which was purified by HPLC with TFA to provide the title compound as a trifluoroacetic acid salt (15 mg, 17%). 1 H NMR (300 MHz, DMSO-D6) δ ppm 2.76 (s, 3 H) 5.19 (s, 2 H) 6.63 (d, J=8.82 Hz, 2 H) 6.98-7.17 (m, 3 H) 7.20 (d, J=2.57 Hz, 1 H) 7.22-7.30 (m, 1 H) 7.38 (dd, J=6.43, 4.96 Hz, 1 H) 7.53 (d, J=7.72 Hz, 1 H) 7.71-7.94 (m, 2 H) 8.58 (d, J=4.04 Hz, 1 H) 8.82 (s, 1 H) 8.93 (d, J=7.72 Hz, 1 H) 9.71 (br s, 1 H) 11.66 (br s, 1 H); MS (ESI+) m/z 468 (M+H)+.

Example 43

2-[4-(4-Hydroxy-phenylsulfanyl)-3-(7-methyl-pyrido[2,3-d]pyrimidin-4-ylamino)-phenoxymethyl]-benzonitrile

Example 43A

2-[3-Amino-4-(4-hydroxy-phenylsulfanyl)-phenoxymethyl]-benzonitrile

A solution of 4-chloro-3-nitro-phenol was reacted with 2-Bromomethyl-benzonitrile using the conditions described in Example 10C to provide 2-(4-Chloro-3-nitro-phenoxymethyl)-benzonitrile which was treated sequentially using the procedures from Examples 10D and 10E to provide the title product.

Example 43B

2-[4-(4-Hydroxy-phenylsulfanyl)-3-(7-methyl-pyrido[2,3-d]pyrimidin-4-ylamino)-phenoxymethyl]-benzonitrile The product of Example 43A was reacted with the product of Example 10B using the procedure of Example 10F substituting the product of Example 43A for the product of Example 10E to provide the crude title compound which was purified by HPLC with TFA to provide the title compound as a trifluoroacetic acid salt (21 mg, 16%). 1 H NMR (300 MHz, DMSO-D6) δ ppm: 9.93 (s, 1 H), 9.63 (s, 1 H), 8.75 (d, J=8.46 Hz, 1 H), 8.57 (s, 1 H), 7.60 (d, J=8.09 Hz, 1 H), 7.38 (d, J=8.46 Hz, 2 H), 7.27 (s, 1 H), 7.05-7.19 (m, 3 H), 6.85-7.00 (m, 3 H), 6.67 (d, J=8.82 Hz, 2 H), 5.02 (s, 2 H), 3.75 (s, 3 H), 3.14-3.28 (m, 1 H), 1.32 (d, J=6.62 Hz, 6 H); MS (ESI+) m/z 492.2 (M+H)+ (ESI−) m/z 490.2 (M−H)−.

Example 44

4-[4-[1-(4-Bromo-phenyl)-ethoxy]-2-(7-methyl-pyrido[2,3-d]pyrimidin-4-ylamino)-phenylsulfanyl]-phenol

Example 44A

1-Bromo-4-(1-bromo-ethyl)-benzene

A solution of 1-(4-bromo-phenyl)-ethanol (4.21 g, 20.9 mmol) in 15 mL of $CH_2Cl_2$ was reacted with 15 mL of 1.0M PBr$_3$ in $CH_2Cl_2$ at room temperature for 4 h. Quenched by pouring into ice and adjusted to pH 9 with 5% aqueous $NaHCO_3$. Extracted with $CH_2Cl_2$ and dried over $Na_2SO_4$, filtered and concentrated under vacuum giving the title compound (4.1 g, 75%).

Example 44B

4-[1-(4-Bromo-phenyl)-ethoxy]-1-chloro-2-nitrobenzene

The product from Example 44A (995 mg, 3.77 mmol) was reacted with 4-chloro-3-nitro-phenol (650 mg, 3.77 mmol) in 15 mL of DMF with $K_2CO_3$ (10.4 g, 3.77 mmol) at 80° C. for 3 h. Cooled to room temperature and diluted with water. Extracted with $CH_2Cl_2$, washed four times with water. Dried over $Na_2SO_4$, filtered and concentrated under vacuum giving the title compound (1.24 g, 92%).

Example 44C

4-{4-[1-(4-Bromo-phenyl)-ethoxy]-2-nitro-phenylsulfanyl}-phenol

The product from Example 44B (1.15 g, 3.22 mmol) was reacted with 4-mercapto-phenol (403 mg, 3.22 mmol) and $K_2CO_3$ (890 mg, 6.44 mmol) in 25 mL of DMF at 80° C. for 18 h. Cooled to room temperature and poured into water. Extracted with $CH_2Cl_2$ and washed several times with water. Dried over $Na_2SO_4$, filtered and concentrated under vacuum giving the title compound (980 mg, 68%).

Example 44D

4-[2-Amino-4-(1-phenyl-ethoxy)-phenylsulfanyl]-phenol

The product from Example 44C (560 mg, 1.25 mmol) was reacted with Fe (279 mg, 5.0 mmol) and $NH_4Cl$ (76 mg, 1.40 mmol) in 5 mL MeOH/5 mL THF/2.5 mL water following the procedure from Example 10E giving the title compound as a solid (439 mg, 84%).

Example 44E

4-[4-[1-(4-Bromo-phenyl)-ethoxy]-2-(7-methyl-pyrido[2,3-d]pyrimidin-4-ylamino)-phenylsulfanyl]-phenol The product from Example 44D (204 mg, 0.49 mmol) was reacted with the product from Example 10B (93 mg, 0.49 mmol) following the procedure from Example 10F to provide the crude title compound which was purified by HPLC with TFA to provide the title compound as a trifluoroacetic acid salt (38 mg, 12%). $^1$H NMR (300 MHz, DMSO-d$_6$) δ ppm: 11.24 (br s, 1H) 9.70 (s, 1H) 8.83 (d, J=8.09 Hz, 1H) 8.74 (s, 1H) 7.76 (d, J=8.45 Hz, 1H) 7.55 (d, J=8.46 Hz, 2H) 7.37 (d, J=8.46 Hz, 2H) 7.09 (m, 4H) 6.93 (dd, J=6.62 Hz, J=2.20 Hz, 1H) 6.63 (d, J=8.82 Hz, 2H) 5.51 (q, J=6.25 Hz, 2H) 2.73 (s, 3H), 1.53 (d, J=6.25 Hz, 3H); MS (ESI+) m/z, 559, 561 (M+H–TFA)+; (ESI–) m/z, 557, 559 (M–H–TFA)–.

Example 45

4-[2-(7-Methyl-pyrido[2,3-d]pyrimidin-4-ylamino)-4-(quinolin-2-ylmethoxy)-phenylsulfanyl]-phenol

Example 45A

4-[2-Amino-4-(quinolin-2-ylmethoxy)-phenylsulfanyl]-phenol

A solution of 4-chloro-3-nitro-phenol was reacted with 2-Chloromethyl-quinoline hydrochloride salt using the conditions described in Example 10C to provide 2-(4-Chloro-3-nitro-phenoxymethyl)-quinoline which was treated sequentially using the procedures from Examples 10D and 10E to provide the title product.

Example 45B

4-[2-(7-Methyl-pyrido[2,3-d]pyrimidin-4-ylamino)-4-(quinolin-2-ylmethoxy)-phenylsulfanyl]-phenol The product of Example 45A was reacted with the product of Example 10B using the procedure of Example 10F substituting the product of Example 45A for the product of Example 10E to provide the crude title compound which was purified by HPLC with TFA to provide the title compound as a trifluoroacetic acid salt (13 mg, 27%). 1H NMR (500 MHz, DMSO-D6) δ ppm: 2.75 (s, 3 H) 5.39 (s, 2 H) 6.62 (d, J=8.54 Hz, 2 H) 7.09 (d, J=8.54 Hz, 2 H) 7.14 (dd, J=8.54, 2.44 Hz, 1 H) 7.22-7.28 (m, 2 H) 7.63 (t, J=7.93 Hz, 1 H) 7.68 (d, J=8.54 Hz, 1 H) 7.74-7.81 (m, 1 H) 7.83 (d, J=8.54 Hz, 1 H) 8.00 (t, J=7.93 Hz, 2 H) 8.44 (d, J=8.54 Hz, 1 H) 8.76 (s, 1 H) 8.92 (d, J=8.54 Hz, 1 H) 9.68 (s, 1 H) 11.64 (br s, 1 H); MS (ESI+) 518 (M+H)+.

Example 46

3-[3-[7-(1-Hydroxy-1-methyl-ethyl)-pyrido[2,3-d]pyrimidin-4-ylamino]-4-(4-hydroxy-phenylsulfanyl)-phenoxymethyl]-benzonitrile The product from Example 12E (45.9 mg, 0.212 mmol) and the product from Example 12H (73.5 mg, 0.212 mmol) in acetic acid (1 mL) was gradually heated form room temperature to 130° C. in an oil bath over a 15 minute time period, followed by heating at 130° C. for an additional 1.5 hours. The mixture was then cooled to room temperature, concentrated under vacuum to provide the crude title compound which was purified by reverse phase preparative HPLC on a Waters Symmetry C8 column (25 mm×100 mm, 7 µm particle size) using a gradient of 10% to 100% acetonitrile/0.1% trifluoroacetic acid in water over 8 minutes (10 minutes run time) at a flow rate of 40 mL/min to provide the title compound as the trifluoroacetic acid salt (22 mg, 20%). ¹H NMR (300 MHz, DMSO-d₆) δ ppm: 11.76 (s, 1 H), 9.72 (s, 1 H), 9.06 (d, J=8.09 Hz, 1 H), 8.83 (s, 1 H), 8.20 (d, J=8.46 Hz, 1 H), 7.92 (s, 1 H), 7.75-7.88 (m, 2 H), 7.63 (t, J=7.72 Hz, 1 H), 7.21-7.26 (m, 1 H), 7.19 (d, J=2.57 Hz, 1 H), 7.07-7.15 (m, 3 H), 6.64 (d, J=8.46 Hz, 2 H), 5.18 (s, 2 H), 1.56 (s, 6 H); MS (ESI) m/z 536.2 (M+H)+, (ESI–) m/z 534.2 (M–H)–.

Example 47

(5-Benzyloxy-4-chloro-2-fluoro-phenyl)-(7-methyl-pyrido[2,3-d]pyrimidin-4-yl)-amine

Example 47A

Carbonic acid 2-chloro-4-fluoro-phenyl ester ethyl ester

To a solution of 2-chloro-4-fluoro-phenol (0.8 mL, 7.64 mmol) and triethylamine (1.3 mL, 9.16 mmol) in dichloromethane (10 mL) at 0° C. was added ethyl chloroformate (0.9 mL, 9.16 mmol) dropwise. The ice bath was removed and the solution was allowed to warm to room temperature and stirred for an additional 16 hours. Afterwards dichloromethane (20 mL) was added to the mixture, the organic solution was washed with brine (50 mL), dried over anhydrous magnesium sulfate, filtered, and concentrated under vacuum to provide the title product as an oil (1.65 g, 100%).

Example 47B

Carbonic acid 2-chloro-4-fluoro-5-nitro-phenyl ester ethyl ester

A solution of the product from Example 47A (0.88 g, 4.03 mmol) in concentrated sulfuric acid (2 mL) cooled in an ice bath was added fuming nitric acid (0.27 mL, 6.45 mmol) slowly to maintain the temperature at 0° C. The mixture was stirred for an additional 2 hours, then ice water (10 mL) was added to the solution and the resultant solid was collected by filtration washed with water and dried in a vacuum oven to provide the title compound (0.87 g, 82%).

Example 47C

2-Chloro-4-fluoro-5-nitro-phenol

To a solution of the product from Example 47B (0.87 g, 3.30 mmol) in methanol (20 mL) and water (1 mL) was added sodium bicarbonate (2.22 g, 26.4 mmol) and the mixture stirred at room temperature for 16 hours. The methanol was then removed under vacuum, dichloromethane (20 mL) was added to the mixture, the organic solution was washed with brine (50 mL), dried over anhydrous magnesium sulfate, filtered, and concentrated under vacuum to provide the title product (0.62 g, 98%).

Example 47D

1-Benzyloxy-2-chloro-4-fluoro-5-nitro-benzene

The title compound was prepared according to the procedure of Example 10C substituting benzyl bromide and the product from Example 47C for 1-chloromethyl-4-methoxy-benzene and 4-chloro-3-nitro-phenol (0.72 g, 79%).

Example 47E

5-Benzyloxy-4-chloro-2-fluoro-phenylamine

The title compound was prepared according to the procedure of Example 10D substituting the product from Example 47D for 1-Chloro-4-(4-methoxy-benzyloxy)-2-nitro-benzene (77 mg, 100%).

Example 47F (5-Benzyloxy-4-chloro-2-fluoro-phenyl)-(7-methyl-pyrido[2,3-d]pyrimidin-4-yl)-amine A solution of the product of Example 10B (17 mg, 0.0927 mmol), and the product of Example 47E (28 mg, 0.111 mmol) in acetic acid (1 mL) was stirred in an oil bath preheated to 130° C. for 15 minutes. The mixture was then cooled to room temperature, the acetic acid removed under vacuum, and the resultant residue was purified by HPLC with TFA to provide the title compound as a trifluoroacetic acid salt (8.1 mg, 17%). $^1$H NMR (300 MHz, DMSO-d$_6$) δ ppm: 2.72 (s, 3 H), 5.19 (s, 2 H), 7.28-7.53 (m, 6 H), 7.66 (d, J=9.56 Hz, 1 H), 7.70 (d, J=8.82 Hz, 1 H), 8.73 (s, 1 H), 8.84 (d, J=8.09 Hz, 1 H), 10.85 (s, 1 H); MS (ESI) m/z 395 (M+H)+.

Example 48

Carbonic acid 4-(4-tert-butoxycarbonyloxy-phenylsulfanyl)-3-(pyrido[2,3-d]pyrimidin-4-ylamino)-phenyl ester tert-butyl ester

Example 48A 4-(4-Hydroxy-phenylsulfanyl)-3-nitro-phenol

A solution of 4-Chloro-3-nitro-phenol (2.0 g, 11.52 mmol), 4-hydroxythiophenol (1.45 g, 11.52 mmol) and cesium carbonate (11.26 g, 34.56 mmol) in N,N-dimethylformamide (25 mL) was heated to 100° C. for 4 hours. After cooling to room temperature, 1N aqueous Hydrochloric acid (150 mL) was added and the resultant solution extracted with ethyl acetate (2×100 mL), the combined extracts dried over magnesium sulfate, filtered and concentrated under vacuum to provide the crude title compound which was purified by chromatography on silica gel using hexanes/ethyl acetate as eluent to obtain the title product as a bright orange solid (1.35 g, 45%).

Example 48B

3-Amino-4-(4-hydroxy-phenylsulfanyl)-phenol

The product from Example 48A (1.34 g, 5.09 mmol) was reacted with iron (1.42 g, 25.48 mmol) and ammonium chloride (409 mg, 1.5 mmol) in 20 mL EtOH/20 ml, THF/6 mL water following the procedure from Example 10E to provide the title compound (1.168 g, 97%).

Example 48C 4-(4-Hydroxy-phenylsulfanyl)-3-(pyrido[2,3-d]pyrimidin-4-ylamino)-phenol The product of Example 48B (380 mg, 1.63 mmol) was reacted with the product of Example 15A (284 mg, 1.63 mmol) using the procedure of Example 15E substituting the product of Example 48B for the product of Example 15D to provide a solid which was triturated with methanol to provide the title compound (209 mg, 35%).

Example 48D

Carbonic acid 4-(4-tert-butoxycarbonyloxy-phenylsulfanyl)-3-(pyrido[2,3-d]pyrimidin-4-ylamino)-phenyl ester tert-butyl ester The product of Example 48C (195 mg, 0.539 mmol) was reacted with Di-tert-butyl dicarbonate (234 mg, 1.078 mmol), triethyl amine (0.165 mL, 1.19 mmol), and 4-dimethylaminopryidine (2 mg) in dichloromethane (5 mL), tetrahydrofuran (3 mL) and dimethyl foramide (1 mL) at room temperature for 16 hours. Afterwards, the mixture was poured into water (10 mL) and the resultant solution extracted with ethyl acetate (3×10 mL), the combined extracts dried over magnesium sulfate, filtered and concentrated under vacuum to provide the title compound (256 mg, 84%). $^1$H NMR (300 MHz, DMSO-d$_6$) δ ppm: 1.47 (s, 9H), 1.49 (s, 9H), 7.13 (d, J=8.8 Hz, 2H), 7.20 (m, 1H), 7.29 (d, J=8.8 Hz, 2H), 7.35 (m, 1H), 7.46 (m, 1H), 7.63 (m, 1H), 8.61 (m, 1H), 8.82 (m, 1H), 9.08 (m, 1H), 10.27 (s, 1H); MS (ESI+) m/z 563 (M+H)+.

Example 49

4-(4-Amino-phenoxy)-N-(4-bromo-phenyl)-3-(7-isopropyl-pyrido[2,3-d]pyrimidin-4-ylamino)-benzamide

Example 49A

N-(4-Bromo-phenyl)-4-chloro-3-nitro-benzamide

A mixture of 4-bromoaniline (2.58 g 14.99 mmol) in dry methylene chloride (100 mL) was treated with 4-chloro-3-nitrobenzoyl chloride (3.60 g, 17.99 mmol) and N,N-diisopropylethylamine (3.14 mL, 17.99 mmol), and the resulting mixture stirred at room temperature for 17 hours. The solvent was removed by rotary evaporation in vacuo, the residue taken up in ethyl acetate (100 mL) and washed with water (2×50 mL) and brine. Dried the organic extract over anhydrous sodium sulfate, filtered, and concentrated in vacuo to give the product as a tan solid (5.132 g, 14.45 mmol, 96%)

Example 49B

{4-[4-(4-Bromo-phenylcarbamoyl)-2-nitro-phenoxy]phenyl}-carbamic acid tert-butyl ester A solution of the product of Example 49A (5.132 g, 14.45 mmol) in anhydrous N,N-dimethylformamide (50 mL) was treated with N-Boc-4-hydroxyaniline (3.024 g, 14.45 mmol) and potassium carbonate (3.994 g, 28.90 mmol) at room temperature, then heated at 80° under a nitrogen atmosphere for 4.5 hours. The reaction was cooled to room temperature and the solvent removed by rotary evaporation in vacuo. The residue was taken up in ethyl acetate (200 mL) and washed with water (4×50 mL) and brine (50 mL). The organic layer was dried over anhydrous sodium sulfate, filtered, and concentrated by rotary evaporation to give the product as a dark yellow solid (7.38 g, 13.97 mmol, 97%).

Example 49C

{4-[2-Amino-4-(4-bromo-phenylcarbamoyl)-phenoxy]-phenyl}-carbamic acid tert-butyl ester A solution of the product of Example 49B (7.383 g, 13.97 mmol), iron powder (4.80 g, 85.94 mmol) and ammonium chloride (4.896 g, 91.53 mmol) in ethanol (60 mL), tetrahydrofuran (60 mL), and water (30 mL) was heated at 80° for 1.5 hours. After cooling to room temperature, the mixture was diluted with ethyl acetate (300 mL) and washed with water (4×100 mL) and brine (50 mL). The organic phase was dried over sodium sulfate, filtered and concentrated under vacuum to provide the title compound as a light tan solid (6.658 g, 13.36 mmol, 96%).

Example 49D

{4-[4-(4-Bromo-phenylcarbamoyl)-2-(7-isopropyl-pyrido[2,3-d]pyrimidin-4-ylamino)-phenoxy]-phenyl}-carbamic acid tert-butyl ester A solution of the product of Example 12E (2.89 g, 13.36 mmol) and the product of Example 49C (6.658 g, 13.36 mmol) in acetic acid (50 mL) was stirred in an oil bath preheated to 140° C. for 20 minutes. The reaction was cooled to room temperature, diluted with hexanes (250 mL), concentrated by rotary evaporation, and co-evaporated with methylene chloride/hexanes (4×). The residue was dried on hi-vacuum overnight. The residue was purified by silica gel flash chromatography with 30% ethyl acetate/methylene chloride followed by methanol/methylene chloride to give the title compound as a brown solid (6.48 g, 72%).

Example 49E 4-(4-Amino-phenoxy)-N-(4-bromo-phenyl)-3-(7-isopropyl-pyrido[2,3-d]pyrimidin-4-ylamino)-benzamide The product of Example 49D (2.78 g, 4.152 mmol) was treated with trifluoroacetic acid (25 mL) in methylene chloride (25 mL) at room temperature for 30 minutes. The solvents were removed under vacuum by rotary evaporation and the residual oil taken up in ethyl acetate (400 mL) and washed with saturated aqueous sodium bicarbonate (2×100 mL), water (2×100 mL), and brine (100 mL). The organic phase was dried over anhydrous sodium sulfate, filtered, and concentrated in vacuo. The resulting solid was triturated with 3% methanol/methylene chloride and dried in vacuo to afford the title compound as a light beige solid (1.77 g, 75%). $^1$H NMR (300 MHz, DMSO-D6) δ ppm 1.32 (d, J=6.99 Hz, 6 H) 3.09-3.31 (m, 1 H) 5.03 (s, 2 H) 6.57 (d, J=8.82 Hz, 2 H) 6.78 (d, J=8.82 Hz, 2 H) 6.83 (d, J=8.82 Hz, 1 H) 7.53 (d, J=8.82 Hz, 2 H) 7.60 (d, J=8.82 Hz, 1 H) 7.75 (d, J=9.19 Hz, 2 H) 7.85 (dd, J=8.46, 2.21 Hz, 1 H) 8.16 (d, J=2.21 Hz, 1 H) 8.62 (s, 1 H) 8.84 (d, J=8.46 Hz, 1 H) 10.00 (s, 1 H) 10.29 (s, 1 H); MS (ESI+) m/z 569/571 (M+H)+, MS (ESI−) m/z 567/569 (M−H)−.

Example 50

4-(4-Amino-phenoxy)-N-(5-bromo-pyridin-2-yl)-3-(7-isopropyl-pyrido[2,3-d]pyrimidin-4-ylamino)-benzamide

Example 50A

{4-[2-Amino-4-(5-bromo-pyridin-2-ylcarbamoyl)-phenoxy]-phenyl}-carbamic acid tert-butyl ester A mixture of 4-chloro-3-nitrobenzoyl chloride was reacted with 5-Bromo-pyridin-2-ylamine to produce N-(4-Bromo-phenyl)-4-chloro-3-nitro-benzamide according to the procedure of Example 49A, which was treated sequentially using the procedures from Examples 49B and 49C to provide the title product.

Example 50B 4-(4-Amino-phenoxy)-N-(5-bromo-pyridin-2-yl)-3-(7-isopropyl-pyrido[2,3-d]pyrimidin-4-ylamino)-benzamide The product of Example 50A was reacted with the product of Example 12E using the procedure of Example 49D substituting the product of Example 50A for the product of Example 49C to provide {4-[4-(5-Bromo-pyridin-2-ylcarbamoyl)-2-(7-isopropyl-pyrido[2,3-d]pyrimidin-4-ylamino)-phenoxy]-phenyl}-carbamic acid tert-butyl ester which was reacted using the procedure of Example 49E to provide the crude title compound which was purified by column chromatography on silica gel using methanol/dichloromethane as eluent to provide the title compound (74 mg, 53%). $^1$H NMR (300 MHz, DMSO-D6) δ ppm 1.32 (d, J=6.99 Hz, 6 H) 3.13-3.30 (m, 1 H) 5.04 (s, 2 H) 6.57 (d, J=8.82 Hz, 2 H) 6.80 (d, J=8.83 Hz, 2 H) 6.78 (d, J=8.45 Hz, 1 H) 7.60 (d, J=8.46 Hz, 1 H) 7.95 (dd, J=8.64, 2.39 Hz, 1 H) 8.06 (dd, J=8.82, 2.57 Hz, 1 H) 8.18 (d, J=8.82 Hz, 1 H) 8.25 (d, J=1.84 Hz, 1 H) 8.50 (d, J=2.57 Hz, 1 H) 8.62 (s, 1 H) 8.85 (d, J=8.46 Hz, 1 H) 9.97 (s, 1 H) 10.90 (s, 1 H); MS (ESI+) m/z 570/572 (M+H)+, (ESI−) m/z 568/570 (M−H)−.

Example 51

4-(4-Amino-phenylsulfanyl)-N-(4-bromo-phenyl)-3-(7-isopropyl-pyrido[2,3-d]pyrimidin-4-ylamino)-benzamide

Example 51A 4-(4-Amino-phenylsulfanyl)-N-(4-bromo-phenyl)-3-nitro-benzamide

A mixture of the product of Example 49A (1.00 g, 2.816 mmol), 4-aminothiophenol (529 mg, 4.224 mmol) and anhydrous sodium acetate (1.155 g, 14.08 mmol) in anhydrous ethanol (30 mL) was heated at reflux under a nitrogen atmosphere for 19 hours. The reaction was cooled to room temperature and the ethanol removed by rotary evaporation. The residue was taken up in water (50 mL) and extracted with ethyl acetate (2×100 mL). The combined organic extracts were washed with brine (50 mL), dried over anhydrous sodium sulfate, filtered, and concentrated in vacuo. Trituration of the solid with 4% ethyl acetate/methylene chloride (25 mL) afforded the title compound as a yellow solid (1.091 g, 87%).

Example 51B

{4-[4-(4-Bromo-phenylcarbamoyl)-2-nitro-phenylsulfanyl]-phenyl}-carbamic acid tert-butyl ester A mixture of the product of Example 51A (1.091 g, 2.456 mmol) and di-tert-butyl dicarbonate (804 mg, 3.683 mmol) in 1,4-dioxane (16 mL) was heated at reflux under a nitrogen atmosphere for 5.5 hours, at which time additional Boc anhydride (750 mg) was added and the reaction allowed to reflux an additional 15 hours. The reaction was cooled to room temperature and the solvent removed by rotary evaporation in vacuo. The resulting solid was triturated with 2.5% ethyl acetate/methylene chloride to obtain the title compound as an orange solid (1.198 g, 90%).

Example 51C

{4-[2-Amino-4-(4-bromo-phenylcarbamoyl)-phenylsulfanyl]-phenyl}-carbamic acid tert-butyl ester A suspension of the product of Example 51B (1.198 g, 2.20 mmol), iron powder (756 mg, 13.53 mmol), and ammonium chloride (771 mg, 14.41 mmol) in water (15 mL) and ethanol (30 mL) was heated at 90° for 1 hour. The reaction was cooled to room temperature. The mixture was diluted with ethyl acetate (200 mL) and washed with water (2×50 mL) and brine (50 mL). The organic phase was dried over sodium sulfate, filtered, and concentrated under vacuum to provide the title compound as a light yellow solid (1.08 g, 95%).

Example 51D

{4-[4-(4-Bromo-phenylcarbamoyl)-2-(6-isopropyl-naphthalen-1-ylamino)-phenylsulfanyl]-phenyl}-carbamic acid tert-butyl ester A solution of the product of Example 12E (109 mg, 0.504 mmol) and the product of Example 51C (200 mg, 0.389 mmol) in acetic acid (10 mL) was stirred in an oil bath preheated to 140° C. for 15 minutes. The reaction was cooled to room temperature, diluted with hexanes (100 mL), concentrated by rotary evaporation, and co-evaporated with methylene chloride/hexanes (4×). The residue was dried on hi-vacuum. The residue was purified by silica gel flash chromatography with 20% ethyl acetate/methylene chloride followed by 4% methanol/methylene chloride to give the title compound (108 mg, 40%).

Example 51E 4-(4-Amino-phenylsulfanyl)-N-(4-bromo-phenyl)-3-(7-isopropyl-pyrido[2,3-d]pyrimidin-4-ylamino)-benzamide The product of Example 51D (106 mg, 0.1546 mmol) was treated with trifluoroacetic acid (3 mL) in methylene chloride (3 mL) at room temperature for 30 minutes. The solvents were removed by rotary evaporation and the residual oil taken up in ethyl acetate (75 mL) and washed with saturated aqueous sodium bicarbonate (50 mL), water, and brine. The organic phase was dried over anhydrous sodium sulfate, filtered, and concentrated in vacuo. Purification by silica gel flash chromatography with 5% methanol/methylene chloride provided the title compound as a light yellow solid (55 mg, 61%). $^1$H NMR (300 MHz, DMSO-D6) δ ppm: 1.34 (d, J=6.99 Hz, 6 H) 3.13-3.31 (m, 1 H) 5.60 (s, 2 H) 6.63 (d, J=8.82 Hz, 2 H) 6.88 (d, J=8.46 Hz, 1 H) 7.14 (d, J=8.46 Hz, 2 H) 7.52 (d, J=8.82 Hz, 2 H) 7.64 (d, J=8.46 Hz, 1 H) 7.73 (d, J=8.82 Hz, 2 H) 7.78 (dd, J=8.27, 1.65 Hz, 1 H) 7.94 (d, J=1.47 Hz, 1 H) 8.59 (s, 1 H) 8.88 (d, J=8.82 Hz, 1 H) 10.16 (s, 1 H) 10.28 (s, 1 H); MS (ESI+) m/z 585/587 (M+H)$^-$, MS (ESI−) m/z 583/585 (M−H)$^-$.

Example 52

4-(4-Amino-phenylsulfanyl)-N-(5-chloro-pyridin-2-yl)-3-(7-isopropyl-pyrido[2,3-d]pyrimidin-4-ylamino)-benzamide

Example 52A 4-(4-Amino-phenylsulfanyl)-3-nitro-benzoic acid

A solution of 4-chloro-3-nitrobenzoic acid (2.00 g, 10.0 mmol), 4-aminothiophenol (10.0 mmol), and cesium carbonate (6.52 g, 20.0 mmol) in anhydrous N,N-dimethylformamide (10 mL) was heated at 90° C. under a nitrogen atmosphere for 2 hours. The reaction was cooled to room temperature and poured into 50 mL of ice water and ethyl acetate (100 mL). The mixture was stirred while adjusting the pH to 2 with concentrated hydrochloric acid. The layers were separated and the organic phase washed with water (2×50 mL) and brine (50 mL), dried over anhydrous sodium sulfate, filtered, and concentrated by rotary evaporation in vacuo. The residue was co-evaporated with methylene chloride/hexanes and the residue triturated with methylene chloride to provide the title compound as a dark yellow solid (2.115 g, 73%).

Example 52B

4-[4-(9H-Fluoren-9-ylmethoxycarbonylamino)-phenylsulfanyl]-3-nitro-benzoic acid

A suspension of the product of Example 52A (1.00 g, 3.445 mmol) in anhydrous methylene chloride (40 mL) was treated with N,O-bis(trimethylsilyl)acetamide (1.77 mL, 7.234 mmol) dropwise, and the resulting orange-colored solution was stirred at room temperature for 30 minutes under a nitrogen atmosphere. Anhydrous pyridine (0.557 mL, 6.89 mmol) was then added, followed by solid 9-fluorenylmethoxycarbonyl chloride (1.114 g, 4.306 mmol) in three portions. The reaction was stirred for 30 minutes, then poured into water (75 mL) and adjusted the pH to 1 with 1N aqueous hydrochloric acid. After stirring for 15 minutes at room temperature, the mixture was transferred to a separatory funnel and extracted with ethyl acetate (500 mL, followed by 2×150 mL). The combined organic extracts were washed with water (2×50 mL) and brine (50 mL), dried over anhydrous sodium sulfate, filtered, and concentrated by rotary evaporation in vacuo. Trituration with methylene chloride provided the title compound as a yellow solid (1.29 g, 73%).

Example 52C

[4-(4-Chlorocarbonyl-2-nitro-phenylsulfanyl)-phenyl]-carbamic acid 9H-fluoren-9-ylmethyl ester A suspension of the product of Example 52B (500 mg, 0.976 mmol) in anhydrous methylene chloride (10 mL) and tetrahydrofuran (5 mL) was treated with oxalyl chloride (2M in methylene chloride, 0.976 mL, 1.951 mmol) and N,N-dimethylformamide (3 drops), and the resulting solution was stirred under a nitrogen atmosphere for 2 hours at room temperature. The solvent was removed by rotary evaporation in vacuo and the residue dried on hi-vacuum to give the title compound as a yellow solid (0.571 g).

Example 52D

{4-[4-(5-Chloro-pyridin-2-ylcarbamoyl)-2-nitro-phenylsulfanyl]-phenyl}-carbamic acid 9H-fluoren-9-ylmethyl ester A solution of the product of Example 52C (471 mg, 0.861 mmol) in anhydrous tetrahydrofuran (8 mL) was treated with 5-chloro-2-aminopyridine (125 mg, 0.972 mmol) and diisopropylethylamine (0.232 mL, 1.332 mmol), and stirred at room temperature under a nitrogen atmosphere for 18 hours. The solvent was removed by rotary evaporation in vacuo, the residue taken up in ethyl acetate (250 mL) and washed with saturated aqueous sodium bicarbonate (50 mL), water (2×50 mL), and brine (50 mL). The organic phase was dried over anhydrous sodium sulfate, filtered, and concentrated in vacuo. Trituration with methylene chloride provided the title compound as a yellow solid (373 mg, 61%).

Example 52E

{4-[2-Amino-4-(5-chloro-pyridin-2-ylcarbamoyl)-phenylsulfanyl]-phenyl}-carbamic acid 9H-fluoren-9-ylmethyl ester The product of Example 52D (371 mg, 0.5954 mmol), ammonium chloride (208.6 mg, 3.900 mmol), and iron powder (204.5 mg, 3.662 mmol) in a mixture of water (6 mL), ethanol (12 mL) and tetrahydrofuran (12 mL) was heated at 90° under a nitrogen atmosphere for 3 hours. The reaction was cooled to room temperature, diluted with ethyl acetate (200 mL), and washed with water (2×50 mL) and brine (50 mL). The organic was dried over anhydrous sodium sulfate, filtered, and concentrated by rotary evaporation in vacuo to give the product as an off-white solid (321 mg, 91%).

Example 52F

{4-[4-(5-Chloro-pyridin-2-ylcarbamoyl)-2-(7-isopropyl-pyrido[2,3-d]pyrimidin-4-ylamino)-phenylsulfanyl]-phenyl}-carbamic acid 9H-fluoren-9-ylmethyl ester A solution of the product of 276E (88 mg, 0.4063 mmol) and the product of Example 52E (241 mg, 0.4063 mmol) in acetic acid (10 mL) was stirred in an oil bath preheated to 140° C. for 1.5 hour. The reaction was cooled to room temperature, diluted with hexanes (100 mL), concentrated by rotary evaporation, and co-evaporated with methylene chloride/hexanes (4×). The residue was dried on hi-vacuum, then purified by silica gel flash chromatography with 2% methanol/methylene chloride to afford the title compound as a yellow solid (168 mg, 54%).

Example 52G 4-(4-Amino-phenylsulfanyl)-N-(5-chloro-pyridin-2-yl)-3-(7-isopropyl-pyrido[2,3-d]pyrimidin-4-ylamino)-benzamide A solution of the product of Example 52F (167 mg, 0.2185 mmol) in 1,4-dioxane (4 mL) was treated with a solution of lithium hydroxide monohydrate (18.3 mg, 0.437 mmol) in water (2 mL) at ambient temperature, then heated at 60° for 40 minutes. The reaction was cooled to room temperature, diluted with ethyl acetate (100 mL) and water (30 mL), adjusted the aqueous pH to 6 with 1N aqueous hydrochloric acid, and separated the layers. The organic phase was washed with water (2×25 mL) and brine (25 mL), dried over anhydrous sodium sulfate, filtered, and concentrated by rotary evaporation in vacuo. Purification of the residue by silica gel flash chromatography with 5% methanol/methylene chloride afforded the title compound as a yellow solid (84 mg, 71%). $^1$H NMR (300 MHz, DMSO-D6) δ ppm: 1.34 (d, J=6.99 Hz, 6 H) 3.15-3.30 (m, 1 H) 5.62 (s, 2 H) 6.65 (d, J=8.46 Hz, 2 H) 6.77-6.89 (m, 1 H) 7.15 (d, J=8.46 Hz, 2 H) 7.64 (d, J=8.09 Hz, 1 H) 7.87 (d, J=8.46 Hz, 1 H) 7.95 (dd, J=8.82, 2.57 Hz, 1 H) 8.04 (s, 1 H) 8.21 (d, J=9.19 Hz, 1 H) 8.42 (d, J=2.57 Hz, 1 H) 8.58 (s, 1 H) 8.89 (d, J=8.46 Hz, 1 H) 10.13 (s, 1 H) 10.92 (s, 1 H); MS (ESI+) m/z 542/544 (M+H)$^+$.

Example 53

N-(4-Bromo-phenyl)-4-(4-hydroxy-phenylsulfanyl)-3-(7-isopropyl-pyrido[2,3-d]pyrimidin-4-ylamino)-benzamide

Example 53A

N-(4-Bromo-phenyl)-4-(4-hydroxy-phenylsulfanyl)-3-nitro-benzamide

A solution of the product of Example 49A (553 mg, 1.557 mmol) in anhydrous N,N-dimethylformamide (15 mL) was treated with 4-mercaptophenol (196 mg, 1.557 mmol) and cesium carbonate (1.015 g, 3.114 mmol) at room temperature, then heated at 100° under a nitrogen atmosphere for 3 hours. The reaction was cooled to room temperature and the solvent removed by rotary evaporation in vacuo. The residue was taken up in H$_2$O (30 mL) and the pH adjusted to 3 with 1N aqueous HCl. The aqueous was extracted with ethyl acetate (2×50 mL), and the combined organic extracts washed with brine (25 mL). The organic layer was dried over anhydrous sodium sulfate, filtered, and concentrated by rotary evaporation. The residue was purified by trituration with methylene chloride and silica gel flash chromatography with a gradient of 6% to 30% ethyl acetate/methylene chloride to give the product as a dark yellow solid (517 mg, 75%).

Example 53B

3-Amino-N-(4-bromo-phenyl)-4-(4-hydroxy-phenylsulfanyl)-benzamide

A suspension of the product of Example 53A (409.9 mg, 0.9205 mmol) and iron powder (206 mg, 3.682 mmol) in acetic acid (7 mL) and ethanol (7 mL) was heated at reflux under a nitrogen atmosphere for 1 hour. The reaction was cooled to room temperature. The mixture was diluted with water (30 mL), the pH adjusted to 6 with solid sodium carbonate, and the aqueous extracted with ethyl acetate (2×50 mL). The combined organic extracts were washed with brine (25 mL), dried over sodium sulfate, filtered, and concentrated under vacuum to provide the title compound as a tan solid (290 mg, 0.6983 mmol, 76%).

Example 53C

N-(4-Bromo-phenyl)-4-(4-hydroxy-phenylsulfanyl)-3-(7-isopropyl-pyrido[2,3-d]pyrimidin-4-ylamino)-benzamide A solution of the product of Example 12E (21 mg, 0.0963 mmol) and the product of Example 53B (40 mg, 0.0963 mmol) in acetic acid (1 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4×). The residue was re-concentrated under hi-vacuum. The residue was purified by silica gel flash chromatography with 4% methanol/methylene chloride to provide the title compound as a yellow solid (29 mg, 0.0494 mmol, 51%). $^1$H NMR (300 MHz, DMSO-D6) δ ppm: 1.34 (d, J=6.99 Hz, 6 H) 3.18-3.29 (m, 1 H) 6.85 (d, J=8.82 Hz, 2 H) 6.89-6.97 (m, 1 H) 7.31 (d, J=8.46 Hz, 2 H) 7.52 (d, J=9.19 Hz, 2 H) 7.58-7.69 (m, 1 H) 7.73 (d, J=9.19 Hz, 2 H) 7.76-7.84 (m, 1 H) 7.86-8.07 (m, 1 H) 8.59 (s, 1 H) 8.76-9.01 (m, 1 H) 9.96 (s, 1 H) 10.20 (s, 1 H) 10.31 (s, 1 H); MS (ESI+) m/z 586/588 (M+H)+, MS (ESI−) m/z 584/586 (M+H)+.

Example 54

N-(4-Bromo-phenyl)-4-(4-hydroxy-phenoxy)-3-(7-isopropyl-pyrido[2,3-d]pyrimidin-4-ylamino)-benzamide

Example 54A 4-(4-Hydroxy-phenoxy)-3-nitro-benzoic acid

A solution of hydroquinone (3.00 g, 0.0272 mol) and potassium hydroxide (2.293 g, 0.0409 mol) in anhydrous dimethylsulfoxide (20 mL) was heated at 120° for 30 minutes under a nitrogen atmosphere. A solution of 4-chloro-3-nitrobenzoic acid (5.49 g, 0.0272 mol) in dimethylsulfoxide (25 mL) was added dropwise over a 30 minute period at 120°, then let the reaction stir an additional 2 hours at the same temperature. The reaction was then cooled in an ice bath and poured into 100 mL of ice-water. The mixture was acidified with concentrated HCl to pH 3 and extracted with ethyl ether (3×100 mL). The combined ethereal extracts were washed with water (3×150 mL), dried over anhydrous sodium sulfate, filtered, and concentrated by rotary evaporation in vacuo. Purification of the residue by silica gel flash chromatography with a gradient of 2% to 3% methanol/methylene chloride containing 0.5% acetic acid afforded the product as an orange solid after co-evaporation with methylene chloride/hexanes (2.432 g, 32%).

Example 54B

N-(4-Bromo-phenyl)-4-(4-hydroxy-phenoxy)-3-nitro-benzamide

A mixture of the product of Example 54A (200 mg, 0.7267 mmol) and 4-bromoaniline (193.3 mg, 1.090 mmol) in anhydrous toluene (6 mL) at 50° under a nitrogen atmosphere was treated with phosphorus trichloride (0.052 mL, 0.5814 mmol), then heated at reflux for 2 hours. The reaction was cooled to room temperature and water (30 mL) was added. Extracted the mixture with ethyl acetate (3×25 mL), then washed the combined organic extracts with brine, dried over anhydrous sodium sulfate, filtered, and concentrated by rotary evaporation in vacuo. Purification by silica gel flash chromatography with 10% ethyl acetate/methylene chloride afforded the product as a light orange solid (124 mg, 40%).

Example 54C

3-Amino-N-(4-bromo-phenyl)-4-(4-hydroxy-phenoxy)-benzamide

A solution of the product of Example 54B (116.6 mg, 0.2717 mmol) and iron powder (60.7 mg, 1.087 mmol) in acetic acid (2 mL) and ethanol (2 mL) was heated at reflux under a nitrogen atmosphere for 1 hour. The reaction was then cooled to room temperature. The mixture was diluted with water (20 mL), the pH adjusted to 6 with solid sodium carbonate, and the aqueous extracted with ethyl acetate (2×50 mL). The combined organic extracts were washed with brine (25 mL), dried over sodium sulfate, filtered, and concentrated under vacuum to provide the title compound as a beige solid (100 mg, 92%).

Example 54D

N-(4-Bromo-phenyl)-4-(4-hydroxy-phenoxy)-3-(7-isopropyl-pyrido[2,3-d]pyrimidin-4-ylamino)-benzamide A solution of the product of Example 12E (15.4 mg, 0.0714 mmol) and the product of Example 54C (28.5 mg, 0.0714 mmol) in acetic acid (1 mL) was stirred in an oil bath preheated to 140° C. for 1 hour. The reaction was cooled to room temperature, diluted with hexanes (100 mL), concentrated by rotary evaporation, and co-evaporated with methylene chloride/hexanes (4×). After drying on hi-vacuum, the residue was purified by silica gel flash chromatography with 5% methanol/methylene chloride to afford the title product (24 mg, 59%). $^1$H NMR (300 MHz, DMSO-D6) δ ppm: 1.32 (d, J=6.62 Hz, 6 H) 3.14-3.29 (m, 1 H) 6.75 (d, J=8.82 Hz, 2 H) 6.83-6.98 (m, 3 H) 7.53 (d, J=8.82 Hz, 2 H) 7.60 (d, J=8.46 Hz, 1 H) 7.76 (d, J=8.82 Hz, 2 H) 7.87 (dd, J=8.82, 1.84 Hz, 1 H) 8.17 (d, J=1.47 Hz, 1 H) 8.61 (s, 1 H) 8.82 (d, J=8.82 Hz, 1 H) 9.39 (s, 1 H) 10.02 (s, 1 H) 10.31 (s, 1 H); MS (ESI+) m/z 570/572 (M+H)+, MS (ESI−) m/z 568/570 (M−H)−.

Example 55

N-Benzyl-4-(4-hydroxy-phenoxy)-3-(7-isopropyl-pyrido[2,3-d]pyrimidin-4-ylamino)-N-methyl-benzamide

Example 55A

3-Amino-N-benzyl-4-(4-hydroxy-phenoxy)-N-methyl-benzamide

A mixture of 4-chloro-3-nitrobenzoic acid was reacted with hydroquinone to produce 4-(4-Hydroxy-phenoxy)-3-nitro-benzoic acid according to the procedure of Example 54A, which was treated sequentially with Benzyl-methyl-amine using the procedure from Example 54B and reduced using the procedure from Example 54C to provide the title product.

Example 55B

N-Benzyl-4-(4-hydroxy-phenoxy)-3-(7-isopropyl-pyrido[2,3-d]pyrimidin-4-ylamino)-N-methyl-benzamide The product of Example 55A was reacted with the product of Example 12E using the procedure of Example 54D substituting the product of Example 55A for the product of Example 54C to provide the crude title compound which was purified by column chromatography on silica gel using methanol/dichloromethane as eluent to provide the title product (37 mg, 45%).

Example 56

4-[4-(2-Amino-butyrylamino)-phenylsulfanyl]-N-(4-bromo-phenyl)-3-(7-isopropyl-pyrido[2,3-d]pyrimidin-4-ylamino)-benzamide To a solution of the product from Example 51E (59 mg, 0.1 mmol) and Boc-Abu-OH (22 mg, 0.11 mmol) in tetrahydrofuran (5 ml) was added 3-(diethoxyphosphoryloxy)-1,2,3-benzo-triazin-4(3H)-one (36 mg, 0.11 mmol) and triethylamine (0.07 ml, 0.5 mmol). The mixture was stirred at room temperature for 16 hours then poured into saturated sodium carbonate solution and extracted with ethyl acetate. The organic layer was dried with magnesium sulfate, filtered and evaporated. To the residue was added dichloromethane (2 ml) and trifluoroacetic acid (2 ml) then stirred at room temperature for 1 hour. The solvent was evaporated and the residue was purified by HPLC with NH4OH to provide the title compound. (62 mg, 85%). 1H NMR (300 MHz, DMSO-D6) δ ppm: 0.90 (t, J=7.54 Hz, 3 H) 1.33 (d, J=6.99 Hz, 6 H) 1.48 (m, 1 H) 1.66 (m, 1 H) 1.90 (s, 3 H) 3.22 (m, 2 H) 7.02 (m, 2 H) 7.40 (d, J=8.46 Hz, 2 H) 7.52 (d, J=8.46 Hz, 2 H) 7.61 (d, J=8.46 Hz, 1 H) 7.72 (m, 5 H) 7.94 (s, 1 H) 8.52 (s, 1 H) 8.79 (s, 1 H) 10.33 (s, 1 H); MS (ESI+) m/z 670, 672 (M+H)+.

Example 57

Pyrrolidine-2-carboxylic acid {4-[4-(4-bromo-phenylcarbamoyl)-2-(7-isopropyl-pyrido[2,3-d]pyrimidin-4-ylamino)-phenyl sulfanyl]-phenyl}-amide The product of Example 51E was reacted with (S)-Pyrrolidine-1,2-dicarboxylic acid 1-tert-butyl ester using the procedure of Example 56 substituting (S)-Pyrrolidine-1,2-dicarboxylic acid 1-tert-butyl for Boc-Abu-OH to provide the crude title compound which was purified by HPLC with TFA to provide the title compound as a trifluoroacetic acid salt (48 mg, 53%). 1H NMR (300 MHz, DMSO-D6) δ ppm: 1.35 (d, J=6.99 Hz, 6 H) 1.95 (m, 3 H) 2.37 (m, 1 H) 3.28 (m, 3 H) 4.32 (m, 1 H) 7.14 (s, 1 H) 7.45 (d, J=8.82 Hz, 2 H) 7.54 (d, J=8.82 Hz, 2 H) 7.63 (d, J=8.82 Hz, 2 H) 7.73 (d, J=8.82 Hz, 2 H) 7.85 (s, 2 H) 8.02 (s, 1 H) 8.70 (s, 2 H) 8.92 (s, 1 H) 9.23 (s, 1 H) 10.38 (s, 1 H) 10.67 (s, 1 H) 11.10 (s, 1 H); MS (ESI+) m/z 682/684 (M+H)+.

Example 58

4-(4-Hydroxy-phenylsulfanyl)-3-(7-isopropyl-pyrido[2,3-d]pyrimidin-4-ylamino)-N-thiazol-2-yl-benzamide

Example 58A

3-Amino-4-(4-hydroxy-phenylsulfanyl)-N-thiazol-2-yl-benzamide

A mixture of 4-chloro-3-nitrobenzoyl chloride was reacted with Thiazol-2-ylamine to produce 4-Chloro-3-nitro-N-thiazol-2-yl-benzamide according to the procedure of Example 49A, which was treated sequentially using the procedures from Examples 53A and 53B to provide the title product.

Example 58B 4-(4-Hydroxy-phenylsulfanyl)-3-(7-isopropyl-pyrido[2,3-d]pyrimidin-4-ylamino)-N-thiazol-2-yl-benzamide The product of Example 58A was reacted with the product of Example 12E using the procedure of Example 53C substituting the product of Example 58A for the product of Example 53B to provide the crude title compound which was purified by HPLC with TFA to provide the title compound as a trifluoroacetic acid salt (38 mg, 30%). 1H NMR (300 MHz, DMSO-D6) δ ppm: 1.37 (d, J=6.62 Hz, 6 H), 3.23-3.39 (m, 1 H), 6.87 (d, J=8.46 Hz, 2 H), 6.95 (d, J=8.46 Hz, 1 H), 7.28 (d, J=3.31 Hz, 1 H), 7.31-7.38 (m, 2 H), 7.55 (d, J=3.68 Hz, 1 H), 7.91 (d, J=8.46 Hz, 1 H), 8.02 (d, J=8.46 Hz, 1 H), 8.10 (d, J=1.84 Hz, 1 H), 8.85 (s, 1 H), 9.03 (d, J=8.46 Hz, 1 H), 10.07 (s, 1 H), 12.65 (s, 1 H); MS (ESI+) m/z 515 (M+H)+.

Example 59

N-(4-Bromo-phenyl)-4-(1H-indol-5-ylsulfanyl)-3-(7-isopropyl-pyrido[2,3-d]pyrimidin-4-ylamino)-benzamide

Example 59A

5-Iodo-indole-1-carboxylic acid tert-butyl ester

A solution of 5-iodoindole (2.00 g, 8.229 mmol) in dry methylene chloride (40 mL) was treated with di-tert-butyl dicarbonate (2.155 g, 9.875 mmol) and 4-dimethylaminopyridine (201 mg, 1.646 mmol) at room temperature and the solution was stirred at room temperature for 16 hours. The solvent was removed by rotary evaporation under vacuum and the residue purified by silica gel flash chromatography with 1:1 hexanes/methylene chloride to provide the title compound as a light pink oil (2.57 g, 91%).

Example 59B

5-Triisopropylsilanylsulfanyl-indole-1-carboxylic acid tert-butyl ester

A solution of the product of Example 59A (200 mg, 0.583 mmol) in anhydrous tetrahydrofuran (4 mL) under a nitrogen atmosphere was treated with [1,1'-bis(diphenylphosphino)ferrocene]dichloropalladium methylene chloride complex (5 mg) and the solution was sparged with nitrogen for several minutes. Potassium triisopropylsilanethiolate (146.5 mg, 0.6411 mmol), prepared according to *Tetrahedron Letters* 35 (20) 3221 1994, was added and the reaction was heated at reflux for 15 minutes. The reaction was cooled to room temperature and the solvent removed by rotary evaporation under vacuum to provide the title compound as a colorless oil (210 mg, 89%).

Example 59C

5-Mercapto-indole-1-carboxylic acid tert-butyl ester

A solution of the product of Example 59B (203.7 mg, 0.502 mmol) in anhydrous tetrahydrofuran (4 mL) at −20° under a nitrogen atmosphere was treated with a 1M solution of tetrabutylammonium fluoride in tetrahydrofuran (0.552 mL, 0.552 mmol) and the reaction stirred at −20° for 15 minutes. The reaction was diluted with ethyl acetate (50 mL) and washed with water (2×25 mL) and brine (25 mL). The organic was dried over anhydrous magnesium sulfate, filtered, and concentrated by rotary evaporation under vacuum to provide a yellow oil. Purification by silica gel flash chromatography using 5% ethyl acetate/hexanes as eluent afforded the title compound (42 mg, 33%).

Example 59D

5-[4-(4-Bromo-phenylcarbamoyl)-2-nitro-phenylsulfanyl]-indole-1-carboxylic acid tert-butyl ester A solution of the product of Example 59C (39.9 mg, 0.160 mmol) in anhydrous ethanol (2 mL) under a nitrogen atmosphere was treated with the product of Example 49A (56.8 mg, 0.160 mmol) and anhydrous sodium acetate (66 mg, 0.800 mmol) at room temperature, then heated at reflux for 2 hours. The reaction was cooled to room temperature and the solvent removed by rotary evaporation under vacuum. The residue was taken up in ethyl acetate (50 mL) and washed with water (2×25 mL) and brine (25 mL). The organic phase was dried over anhydrous sodium sulfate, filtered, and concentrated under vacuum. Purification by silica gel flash chromatography using methylene chloride as eluent afforded the title compound as a yellow solid (77 mg, 85%).

Example 59E

5-[2-Amino-4-(4-bromo-phenylcarbamoyl)-phenylsulfanyl]-indole-1-carboxylic acid tert-butyl ester A suspension of the product of Example 59D (75 mg, 0.132 mmol), iron powder (45.3 mg, 0.811 mmol), and ammonium chloride (46 mg, 0.864 mmol) in water (1 mL) and ethanol (2 mL) was heated at 95° for 30 minutes. The reaction was cooled to room temperature, diluted with ethyl acetate (50 mL), and washed with water (2×25 mL) and brine (25 mL). The organic phase was dried over anhydrous sodium sulfate, filtered, and concentrated by rotary evaporation under vacuum to afford the title compound as a yellow solid (65 mg, 92%).

Example 59F

N-(4-Bromo-phenyl)-4-(1H-indol-5-ylsulfanyl)-3-(7-isopropyl-pyrido[2,3-d]pyrimidin-4-ylamino)-benzamide A solution of the product of 276E (25 mg, 0.116 mmol) and the product of Example 59E (62.6 mg, 0.116 mmol) in acetic acid (2 mL) was stirred in an oil bath preheated to 140° C. for 1 hour. The reaction was cooled to room temperature, diluted with hexanes (50 mL), concentrated by rotary evaporation, and co-evaporated with methylene chloride/hexanes (4×). The residue was dried under vacuum, then purified by silica gel flash chromatography using 4% methanol/methylene chloride to provide the title compound (11 mg, 16%). $^1$H NMR (300 MHz, DMSO-D6) δ ppm: 1.35 (d, J=6.62 Hz, 6 H) 3.16-3.30 (m, 1 H) 6.44-6.53 (m, 1 H) 6.89 (d, J=8.46 Hz, 1 H) 7.15 (dd, J=8.46, 1.47 Hz, 1 H) 7.42-7.46 (m, 1 H) 7.46-7.55 (m, 3 H) 7.65 (d, J=8.46 Hz, 1 H) 7.69-7.78 (m, 4 H) 7.98 (d, J=1.47 Hz, 1 H) 8.61 (s, 1 H) 8.90 (d, J=8.82 Hz, 1 H) 10.22 (s, 1 H) 10.29 (s, 1 H) 11.38 (s, 1 H); MS (ESI+) m/z 609/611 (M+H)$^+$.

Example 60

{4-[4-(4-Bromo-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester Example 60A 4-(4-Amino-phenylsulfanyl)-N-(4-bromo-phenyl)-3-nitro-benzamide A solution of the product from Example 49A (3.0 g, 8.44 mmol), 4-aminothiophenol (1.06 g, 8.44 mmol) and cesium carbonate (5.5 g, 17.0 mmol) in N,N-dimethylformamide (15 mL) was heated to 90° C. for 4 hours. After cooling to room temperature the mixture was poured into ice water (100 mL) and the resultant solution acidified to pH 5 with 1N aqueous hydrochloric acid. The solution was then extracted with ethyl acetate (3×50 mL), the combined extracts dried over sodium sulfate, filtered and concentrated under vacuum to provide the title compound as an orange solid (3.6 g, 96%).

Example 60B

{4-[4-(4-Bromo-phenylcarbamoyl)-2-nitro-phenylsulfanyl]-phenyl}-carbamic acid 2,2,2-trichloro-ethyl ester To a slurry of the product of Example 60A (3.6 g, 8.1 mmol) in dichloromethane (100 mL) and pyridine (1.3 g, 16.2 mmol) was added 2,2,2-Trichloroethyl chloroformate (2.16 g, 10.2 mmol). The solution was stirred for 16 hours, washed with water, brine, dried over sodium sulfate and concentrated under vacuum. The resulting residue was triturated in 9:1 hexane/ethyl acetate to give the title compound as an orange powder (4.15 g, 83%).

Example 60C

{4-[2-Amino-4-(4-bromo-phenylcarbamoyl)-phenylsulfanyl]-phenyl}-carbamic acid 2,2,2-trichloro-ethyl ester A solution of the product of Example 60B (1.23 g, 2.0 mmol), iron powder (0.56 g, 10.0 mmol) and ammonium chloride (0.16 g, 3.0) in an ethanol (30 mL), tetrahydrofuran (30 mL), and water (10 mL) solution was heated to reflux for 6 hours. The resultant mixture was diluted with ethanol (50 mL) and filtered through a pad of celite. The filtrate was concentrated under vacuum to a volume of 10 mL, the solution diluted with water (50 mL) and extracted with ethyl acetate (2×50 mL). The combined extracts were dried over sodium sulfate, filtered and concentrated under vacuum to provide the title compound as a yellow powder (1.12 g, 95%).

Example 60D

{4-[4-(4-Bromo-phenylcarbamoyl)-2-(7-isopropyl-pyrido[2,3-d]pyrimidin-4-ylamino)-phenylsulfanyl]-phenyl}-carbamic acid 2,2,2-trichloro-ethyl ester A solution of the product of Example 60C (1.12 g, 1.9 mmol) and the product of Example 12E (0.41 mg, 1.9 mmol) in acetic acid (10 mL) was stirred in a preheated 140° C. oil bath for 40 minutes. The mixture was cooled and concentrated under vacuum. The resultant residue was triturated in a minimal volume of methanol and collected by filtration to give the title compound (0.98 g, 68%). 1H NMR (300 MHz, DMSO-D6) δ ppm: 1.34 (d, J=6.99 Hz, 6 H), 3.19-3.27 (m, 1 H), 4.96 (s, 2 H), 7.07 (d, J=8.46 Hz, 1 H), 7.41 (d, J=8.46 Hz, 2 H), 7.50-7.69 (m, 5 H), 7.74 (d, J=8.82 Hz, 2 H), 7.81 (d, J=8.46 Hz, 1 H), 8.00 (s, 1 H), 8.59 (s, 1 H), 8.85 (d, J=8.46 Hz, 1 H), 10.24 (s, 1 H), 10.35 (s, 1 H), 10.38 (s, 1 H); MS (ESI+) m/z 761 (M+H)+.

Example 61

N-(4-Bromo-phenyl)-3-(7-isopropyl-pyrido[2,3-d]pyrimidin-4-ylamino)-4-[4-(7-isopropyl-pyrido[2,3-d]pyrimidin-4-ylamino)-phenylsulfanyl]-benzamide A solution of the product of Example 51E (0.029 g, 0.05 mmol) and the product of Example 12E (0.011 mg, 0.05 mmol) in acetic acid (1.0 mL) was stirred in a preheated 140° C. oil bath for 20 minutes. The mixture was cooled and concentrated under vacuum. The resultant residue was purified by HPLC with TFA to provide the title compound as a trifluoroacetic acid salt (24 mg, 55%). 1H NMR (300 MHz, DMSO-D6) δ ppm: 1.33 (t, J=7.35 Hz, 12 H), 3.19-3.34 (m, 2 H), 7.30 (d, J=8.09 Hz, 1 H), 7.49 (d, J=8.82 Hz, 2 H), 7.54 (d, J=8.82 Hz, 2 H), 7.68-7.88 (m, 7 H), 7.91 (d, J=8.46 Hz, 1 H), 8.02 (s, 1 H), 8.74 (s, 1 H), 8.87 (s, 1 H), 8.93 (d, J=7.72 Hz, 1 H), 8.99 (d, J=8.82 Hz, 1 H), 10.42 (s, 1 H), 10.71 (s, 1 H); MS (ESI+) m/z 756/758 (M+H)+.

Example 62

4-[4-Benzylamino-2-(7-methyl-pyrido[2,3-d]pyrimidin-4-ylamino)-phenylsulfanyl]-phenol Example 62A 4-(4-Amino-2-nitro-phenylsulfanyl)-phenol A solution of 4-chloro-3-nitro aniline (1.0 g, 5.79 mmol), 4-hydroxythiophenol (0.75 g, 6.00 mmol), cesium carbonate (3.9 g, 12 mmol) in dimethylsulfoxide (10 ml) was heated at 100° C. for 16 hours. Afterwards ice water (50 mL) was added to the solution and the resultant slurry was treated with ethyl acetate (100 ml). The layers were separated and the organic layer was washed with 10% sodium bicarbonate and 10% sodium chloride, then dried over anhydrous sodium sulfate. The drying agent was filtered and solvent was removed under vacuum leaving a red solid as the title compound, (1.45 g, 92%).

Example 62B 4-(4-Benzylamino-2-nitro-phenylsulfanyl)-phenol

A solution of the product of Example 62A (0.63 g, 2.4 mmol), benzaldehyde (0.24 g, 2.3 mmol) and sodium cyanoborohydride (0.15 g, 2.4 mmol) in methanol (10 mL) containing 1% acetic acid was stirred at room temperature for 16 hours. The reaction mixture was quenched with water (20 mL) and the resultant solution was concentrated under vacuum to a yellow solid. The solid was dissolved in ethyl acetate (50 mL), and washed with water, 10% sodium bicarbonate and 10% sodium chloride. The organic layer was dried over anhydrous sodium sulfate, filtered and solvent removed under vacuum leaving a light yellow oil. The oil was purified by silica gel chromatography eluting with 1% methanol in methylene chloride to provide the title compound (0.63 g, 77%).

Example 62C 4-(2-Amino-4-benzylamino-phenylsulfanyl)-phenol

A solution of the product of Example 62B (0.5 g, 1.4 mmol), iron powder (0.49 g, 8.74 mmol) and ammonium chloride (0.50 g, 9.3 mmol) in a methanol (10 mL), tetrahydrofuran (10 mL), and water (5 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.30 g, 66%).

Example 62D

4-[4-Benzylamino-2-(7-methyl-pyrido[2,3-d]pyrimidin-4-ylamino)-phenylsulfanyl]-phenol A solution of the product from Example 10B (30 mg, 0.159 mmol), and the product from Example 62C (56.5 mg, 0.17 mmol) in acetic acid (2 mL) was stirred in an oil bath preheated to 130° C. for 20 minutes. The mixture was then cooled to room temperature, the acetic acid removed under vacuum, and the resultant residue purified by HPLC with TFA to provide the title compound as a trifluoroacetic acid salt (12 mg, 10%). 1H NMR (300 MHz, DMSO-D6) δ ppm: 2.71 (s, 3 H), 4.50 (s, 2 H), 6.60-6.69 (m, 2 H), 6.73-6.85 (m, 2 H), 7.04-7.29 (m, 6 H), 7.31-7.40 (m, 2 H), 7.46 (d, J=7.35 Hz, 2 H), 8.54 (s, 1 H), 8.75 (s, 1 H), 9.74 (s, 1 H); MS (ESI) m/z 466 (M+H)+, (ESI−) m/z 464 (M−H)−.

Example 63

N1-Benzyl-4-(4-benzyloxy-phenylsulfanyl)-N3-(7-methyl-pyrido[2,3-d]pyrimidin-4-yl)-benzene-1,3-diamine Example 63A 4-(2-Amino-4-nitro-phenylsulfanyl)-phenol A solution of 2-Chloro-5-nitroaniline (3 g, 17.4 mmole), 4-hydroxythiophenol (2.4 g, 19.0 mmol), cesium carbonate (12.35 g, 38 mmol) in dimethylformamide (35 ml) was heated at 100° C. for 16 hours. Afterwards ice water (200 mL) was added to the solution and to the resultant slurry was added ethyl acetate (200 ml). The layers were separated and the organic layer was washed with 10% sodium bicarbonate and 10% sodium chloride, dried over anhydrous sodium sulfate. The drying agent was filtered and solvent was removed under vacuum leaving a yellow oil. The oil was purified by silica gel chromatography eluting with methylene chloride/methanol (97:3), to provide a yellow solid as the title compound (2.1 g, 46%).

Example 63B 2-(4-Benzyloxy-phenylsulfanyl)-5-nitro-phenylamine

A slurry containing of the product from Example 63A (0.2 g, 0.763 mmole) and cesium carbonate (0.25 g, 0.763 mmole) in dimethylformamide (5 ml) was treated with benzyl bromide (0.091 ml, 0.763 mmole) and the resulting slurry was stirred 18 hours at room temperature. Afterwards ice water (50 mL) was added to the solution and to the resultant slurry was added ethyl acetate (50 ml). The layers were separated and the organic layer was washed with 10% sodium bicarbonate and 10% sodium chloride, dried over anhydrous sodium sulfate. The drying agent was filtered and solvent was removed under vacuum leaving a yellow solid as the title compound (0.24 g, 89%).

Example 63C

[2-(4-Benzyloxy-phenylsulfanyl)-5-nitro-phenyl]-(7-methyl-pyrido[2,3-d]pyrimidin-4-yl)-amine A solution of the product from Example 10B (62 mg, 0.331 mmol), and the product of Example 63B (120 mg, 0.331 mmol) in acetic acid (1 mL) was stirred in an oil bath preheated to 130° C. for 20 minutes. The mixture was then cooled to room temperature, the acetic acid removed under vacuum leaving a brown oil as the title compound (0.15 g, 92%). The compound was used without purification in the next step.

Example 63D 4-(4-Benzyloxy-phenylsulfanyl)-N3-(7-methyl-pyrido[2,3-d]pyrimidin-4-yl)-benzene-1,3-diamine A solution of the product from Example 63C (0.150 g, 0.303 mmole), iron powder (0.10 g, 1.86 mmol) and ammonium chloride (0.10 g, 1.98 mmol) in a methanol (2 mL), tetrahydrofuran (2 mL), and water (1 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.06 g, 42%).

Example 63E

N1-Benzyl-4-(4-benzyloxy-phenylsulfanyl)-N3-(7-methyl-pyrido[2,3-d]pyrimidin-4-yl)-benzene-1,3-diamine A mixture of the compound prepared in Example 63D (0.06 g, 0.130 mmole), benzaldehyde (0.013 g, 0.130 mmole) and sodium cyanoborohydride (0.0081 g, 0.13 mmole) in methanol (1 ml) containing 1 drop acetic acid was stirred 18 hr at room temperature. The solvent was removed under vacuum and the resultant residue purified by HPLC with TFA to provide the title compound as a trifluoroacetic acid salt (12 mg, 17%). 1H NMR (300 MHz, DMSO-D6) δ ppm: 2.69 (s, 3 H), 4.30 (s, 2 H), 4.96 (s, 2 H), 6.60 (dd, J=8.46, 2.57 Hz, 1 H), 6.72-6.89 (m, 3 H), 6.94-7.09 (m, 2 H), 7.19-7.29 (m, 1 H), 7.29-7.46 (m, 11 H), 7.63 (d, J=8.46 Hz, 1 H), 8.61 (s, 1 H), 8.71 (d, J=8.82 Hz, 1 H), 10.69 (s, 1 H).

Example 64

4-[4-[(Furan-3-ylmethyl)-amino]-2-(7-methyl-pyrido[2,3-d]pyrimidin-4-ylamino)-phenylsulfanyl]-phenol

Example 64A

4-[2-(7-Methyl-pyrido[2,3-d]pyrimidin-4-ylamino)-4-nitro-phenylsulfanyl]-phenol

A solution of the product from Example 10B (340 mg, 1.80 mmol), and the product of Example 63A (480 mg, 1.80 mmol) in acetic acid (10 mL) was stirred in an oil bath preheated to 130° C. for 30 minutes. The mixture was then cooled to room temperature, the acetic acid removed under vacuum leaving a brown oil as the title compound (0.65 g, 89%).

Example 64B

4-[4-Amino-2-(7-methyl-pyrido[2,3-d]pyrimidin-4-ylamino)-phenylsulfanyl]-phenol

A slurry of the product from Example 64A (0.19 g, 0.469 mmol) and 10% Pd/C (0.025 g) in acetic acid (3 ml) was placed under a hydrogen atmosphere with stirring for 2 hr at room temperature. The slurry was filtered and the solvent removed under vacuum leaving a brown solid as an acetate salt of the title compound (0.21 g, 91%).

Example 64C

4-[4-[(Furan-3-ylmethyl)-amino]-2-(7-methyl-pyrido[2,3-d]pyrimidin-4-ylamino)-phenylsulfanyl]-phenol A solution of the product from Example 64B (69.7 mg, 0.141 mmol), 3-furaldehyde (13.5 mg, 0.141 mmol) and sodium cyanoborohydride (8.7 mg, 0.141 mmol) in 2 ml methanol was stirred 18 hr at room temperature. The solvent was evaporated under vacuum and the resultant residue purified by HPLC with TFA to provide the title compound as a trifluoroacetic acid salt (16 mg, 14%). 1H NMR (300 MHz, DMSO-D6) δ ppm: 2.75 (s, 3 H), 3.85 (s, 1 H), 4.09 (s, 2 H), 6.47 (s, 1 H), 6.53 (d, J=8.82 Hz, 2 H), 6.62-6.75 (m, 2 H), 6.94 (d, J=8.46 Hz, 3 H), 7.21-7.32 (m, 1 H), 7.61 (s, 1 H), 7.83 (d, J=8.46 Hz, 1 H), 8.77 (s, 1 H). 8.88 (s, 1 H), 9.51 (s, 1 H), 11.68 (s, 1 H).

Example 65

4-[4-Hydroxymethyl-2-(7-isopropyl-pyrido[2,3-d]pyrimidin-4-ylamino)-phenylsulfanyl]-phenol

Example 65A 4-(4-Hydroxy-phenylsulfanyl)-3-nitro-benzoic acid methyl ester

A solution of 4-Chloro-3-nitro-benzoic acid methyl ester (4.0 g, 18.55 mmol) in anhydrous N,N-dimethylformamide (25 mL) was treated with 4-mercaptophenol (2.34 g, 18.55 mmol) and cesium carbonate (9.07 g, 27.83 mmol) at room temperature for 23 hours. The solvent was then removed by rotary evaporation under vacuum, the residue taken up in water (100 mL) and the pH adjusted to 3 with 1N aqueous HCl. The aqueous solution was extracted with ethyl acetate (2×100 mL), and the combined organic extracts washed with brine (50 mL). The organic layer was dried over magnesium sulfate, filtered, and concentrated by rotary evaporation to provide the product as an orange oil contaminated with N,N-dimethylformamide (7.28 g).

Example 65B

3-Amino-4-(4-hydroxy-phenylsulfanyl)-benzoic acid methyl ester

A suspension of the product of Example 65A (as a mono DMF adduct) (7.25 g, 19.23 mmol) ammonium chloride (1.54 g, 28.8 mmol) and iron powder (5.37 g, 96.15 mmol) in tetrahydrofuran (75 mL), water (25 mL) and ethanol (75 mL) was heated at reflux for 3 hours. The reaction was cooled to room temperature, and the mixture was filtered through a pad of celite, which was then washed with methanol, and the filtrate concentrated to a solid under vacuum. The residue was then dissolved in water (100 mL) and extracted with dichloromethane (2×50 mL). The combined organic extracts were washed with brine (25 mL), dried over magnesium sulfate, filtered, and concentrated under vacuum to provide the title compound as a white solid (4.2 g, 79%).

Example 65C 4-(2-Amino-4-hydroxymethyl-phenylsulfanyl)-phenol

To the product from Example 65B (500 mg, 1.82 mmol) in tetrahydrofuran (50 mL) was added a solution of lithium aluminum hydride (1.0M in THF, 1.8 mL, 1.82 mmol) dropwise at room temperature followed by heating the mixture to 70° C. for 4 hours. Water (25 mL) was then carefully added to the solution and the organic layer separated, dried and concentrated under vacuum to provide the title compound (295 mg, 66%).

Example 65D

4-[4-Hydroxymethyl-2-(7-isopropyl-pyrido[2,3-d]pyrimidin-4-ylamino)-phenylsulfanyl]-phenol The product from Example 65C was reacted with the product from Example 12E using the procedure from Example 12I substituting the product from Example 65C for the product from Example 12H to provide the crude residue which was purified by HPLC with TFA to provide the title compound as a trifluoroacetic acid salt (30 mg, 31%). 1H NMR (300 MHz, DMSO-D6) δ ppm: 1.36 (d, J=7.0 Hz, 6H), 3.30 (m, 1H), 4.50 (s, 2H), 6.72 (d, J=8.5 Hz, 2H), 7.05 (d, J=8.1 Hz, 1H), 7.19 (d, J=8.5 Hz, 2H), 7.27 (m, 1H), 7.35 (s, 1H), 7.87 (d, J=8.5 Hz, 1H), 8.79 (s, 1H), 8.98 (m, 1H), 9.82 (s, 1H), 11.43 (bs, 1H); MS (ESI+) m/z 419 (M+H)+.

Example 66

Acetic acid 4-(4-hydroxy-phenylsulfanyl)-3-(7-isopropyl-pyrido[2,3-d]pyrimidin-4-ylamino)-benzyl ester The product from Example 65C was reacted with the product from Example 12E using the procedure from Example 12I substituting the product from Example 65C for the product from Example 12H to provide the crude residue which was purified by HPLC with TFA to provide the title compound as a trifluoroacetic acid salt (12 mg, 11%). 1H NMR (300 MHz, DMSO-D6) δ ppm: 1.36 (d, J=6.6 Hz, 6H), 2.05 (s, 3H), 3.30 (m, 1H), 5.07 (s, 2H), 6.71 (d, J=8.5 Hz, 2H), 7.03 (d, J=8.1 Hz, 1H), 7.19 (d, J=8.5 Hz, 2H), 7.27 (m, 1H), 7.40 (m, 1H), 7.95 (d, J=8.8 Hz, 1H), 8.89 (s, 1H), 9.02 (d, J=8.8 Hz, 1H), 9.75 (bs, 1H), 11.79 (bs, 1H); MS (ESI+) m/z 461 (M+H)+.

Example 67

4-[4-Amino-2-(7-isopropyl-pyrido[2,3-d]pyrimidin-4-ylamino)-phenylsulfanyl]phenol

Example 67A

4-[2-(7-Isopropyl-pyrido[2,3-d]pyrimidin-4-ylamino)-4-nitro-phenylsulfanyl]-phenol A solution of the product from Example 10B (340 mg, 2.31 mmol), and the product of Example 63A (610 mg, 2.30 mmol) in acetic acid (10 mL) was stirred in an oil bath preheated to 130° C. for 10 minutes. The mixture was then cooled to room temperature, the acetic acid removed under vacuum providing a brown oil as the title compound (0.92 g, 92%).

Example 67B

4-[4-Amino-2-(7-isopropyl-pyrido[2,3-d]pyrimidin-4-ylamino)-phenylsulfanyl]-phenol A slurry of the compound prepared in Example 67A (0.7 g, 1.73 mmol) and 10% Pd/C (100 mg) in acetic acid (10 ml) and methanol (10 mL) was placed under a hydrogen balloon atmosphere with stirring for 20 hours at room temperature. The slurry was filtered and the solvent removed under vacuum to provide the title compound as an acetic acid salt (540 mg, 63%). 1H NMR (300 MHz, DMSO-D6) δ ppm: 1.35 (d, J=7.0 Hz, 6H), 1.91 (s, 6H), 3.27 (m, 1H), 6.55 (d, J=8.8 Hz, 2H), 6.62 (m, 1H), 6.69 (m, 1H), 6.95 (d, J=8.8 Hz, 2H), 7.20 (d, J=8.5 Hz, 1H), 7.87 (d, J=8.5 Hz, 1H), 7.95 (s, 1H), 8.75 (s, 1H), 8.99 (m, 1H), 9.52 (s, 1H), 11.57 (bs, 1H); MS (ESI+) m/z 404 (M+H)+.

Example 68

N-[4-(4-Hydroxy-phenylsulfanyl)-3-(7-isopropyl-pyrido[2,3-d]pyrimidin-4-ylamino)-phenyl]-benzenesulfonamide A solution containing the product from Example 67B (100 mg, 0.200 mmol), benzenesulfonyl chloride (43 mg, 0.250 mmol) in 1 ml pyridine was stirred 18 hr at room temperature. The solvent was evaporated under vacuum and the resultant residue purified by HPLC with TFA to provide the title compound as a trifluoroacetic acid salt (23 mg, 18%). 1H NMR (300 MHz, DMSO-D6) δ ppm: 1.35 (d, J=6.99 Hz, 6 H), 3.21-3.37 (m, 1 H), 6.57-6.77 (m, 2 H), 6.94-7.06 (m, 2 H), 7.04-7.21 (m, 2 H), 7.21 (d, J=1.47 Hz, 1 H), 7.51-7.71 (m, 3 H), 7.80 (d, J=6.99 Hz, 2 H), 7.88 (d, J=8.46 Hz, 1 H), 8.79 (s, 1 H), 8.92 (d, J=8.46 Hz, 1 H), 9.80 (s, 1 H), 10.59 (s, 1 H), 11.50 (s, 1 H).

Example 69

[4-(4-Hydroxy-phenylsulfanyl)-3-(7-isopropyl-pyrido[2,3-d]pyrimidin-4-ylamino)-phenyl]-carbamic acid methyl ester A solution containing the product from Example 67B (100 mg, 0.200 mmol), methoxycarbonyl chloride (25 mg, 0.250 mmol) in 1 ml pyridine was stirred 18 hr at room temperature. The solvent was evaporated under vacuum and the resultant residue was purified by HPLC with TFA to provide the title compound as a trifluoroacetic acid salt (15 mg, 13%). 1H NMR (300 MHz, DMSO-D6) δ ppm: 1.35 (d, J=6.99 Hz, 6 H), 3.23-3.32 (m, 1 H), 3.66 (s, 3 H), 6.54-6.74 (m, 2 H), 7.01-7.24 (m, 3 H), 7.37 (dd, J=8.82, 2.21 Hz, 1 H), 7.61 (s, 1 H), 7.86 (d, J=8.46 Hz, 1 H), 8.78 (s, 1 H), 8.95 (s, 1 H), 9.72 (s, 1 H), 9.92 (s, 1 H), 11.41 (bs, 1 H).

Example 70

[4-(4-Hydroxy-phenylsulfanyl)-3-(7-isopropyl-pyrido[2,3-d]pyrimidin-4-ylamino)-phenyl]-carbamic acid benzyl ester A solution containing the product from Example 67B and benzyloxycarbonyl chloride was reacted according to the procedure from Example 69 substituting benzyloxycarbonyl chloride for methoxycarbonyl chloride which was purified by HPLC with TFA to provide the title compound as a trifluoroacetic acid salt (27 mg, 21%). 1H NMR (300 MHz, DMSO- D6) δ ppm: 1.36 (d, J=6.62 Hz, 6 H), 3.18-3.40 (m, 1 H), 5.15 (s, 2 H), 6.47-6.74 (m, 2 H), 7.10 (d, J=8.46 Hz, 2 H), 7.18 (d, J=8.46 Hz, 1 H), 7.30-7.47 (m, 6 H), 7.65 (d, J=1.84 Hz, 1 H), 7.91 (d, J=8.46 Hz, 1 H), 8.82 (s, 1 H), 8.97 (d, J=8.46 Hz, 1 H), 9.73 (s, 1 H), 10.07 (s, 1 H), 11.68 (s, 1 H).

Example 71

4-[2-(7-Methyl-pyrido[2,3-d]pyrimidin-4-ylamino)-4-pyrrol-1-yl-phenylsulfanyl]-phenol To a solution of the product from Example 64B (50 mg, 0.101 mmol) and succinic dialdehyde (40% in water solution) (0.065 mL, 0.303 mmol) in toluene (5 mL) and methanol (3 mL) was added 4A molecular sieves (100 mg). The mixture was then heated to 60° C. for 7 hours, cooled to room temperature, the solvent removed under vacuum, a solution of 0.1 N aqueous hydrochloric acid (20 mL) added and the mixture extracted with dichloromethane (2×25 mL) and dioxane (25 mL). The combined organic extracts were dried and concentrated under vacuum then the resultant residue purified by HPLC with TFA to provide the title compound as a trifluoroacetic acid salt (14 mg, 26%). $^1$H NMR (300 MHz, DMSO-D6) δ ppm: 2.68 (s, 3H), 6.26 (m, 2H), 6.77 (d, J=8.5 Hz, 2H), 7.05 (d, J=8.5 Hz, 1H), 7.24 (d, J=8.5 Hz, 2H), 7.37 (m 2H), 7.48 (dd, J=8.6, 2.4 Hz, 1H), 7.57 (d, J=8.5 Hz, 1H), 7.73 (d, J=2.6 Hz, 1H), 8.57 (s, 1H), 8.80 (d, J=8.4 Hz, 1H), 9.81 (s, 1H), 10.11 (s, 1H); MS (ESI+) m/z 426 (M+H)+.

Example 72

4-[2,4-Bis-(7-methyl-pyrido[2,3-d]pyrimidin-4-ylamino)-phenylsulfanyl]-phenol

To a solution of the product from Example 64B (50 mg, 0.101 mmol) and the product from Example 10B (19 mg, 0.101 mmol) in acetic acid (1 mL) was heated to 120° C. for 2 hours. After cooling to room temperature, the solvent was removed under vacuum and methanol (2 mL) was added. The resultant solid was collected and triturated with methanol to provide the title compound as a light brown solid (12 mg, 23%). $^1$H NMR (300 MHz, DMSO-D6) δ ppm: 2.67 (s, 3H), 2.68 (m, 3H), 6.75 (d, J=8.8 Hz, 2H), 6.83 (m, 1H), 7.12 (m, 1H), 7.21 (d, J=8.8 Hz, 2H), 7.34 (m, 1H), 7.58 (m, J=8.8 Hz, 2H), 8.73 (s, 1H), 8.81 (m, 1H), 8.88 (m, 1H), 9.76 (s, 1H), 10.13 (s, 1H), 11.95 (bs, 1H); MS (ESI+) m/z 519 (M+H)+.

Example 73

4-[4-Methyl-2-(7-methyl-pyrido[2,3-d]pyrimidin-4-ylamino)-phenylsulfanyl]-phenol To a solution of the product from Example 10B (100 mg, 0.575 mmol) and the product from Example 9c (146 mg, 0.632 mmol) in acetic acid (1 mL) was heated at 130° C. for 1 hour. The mixture was then allowed to cool to room temperature, then methanol (5 mL) added to the solution and the resulting solid collected and washed with methanol to provide the title compound (120 mg, 56%). 1H NMR (300 MHz, DMSO-D6) δ ppm: 2.29 (s, 3H), 2.66 (s, 3H), 6.73 (d, J=8.8 Hz, 2H), 6.93 (m, 1H), 7.03 (m, 1H), 7.18 (d, J=8.5 Hz, 2H), 7.26 (s, 1H), 7.53 (d, J=8.5 Hz, 1H), 8.53 (s, 1H), 8.77 (m, 1H), 9.76 (bs, 1H), 9.96 (bs, 1H); MS (ESI)+ m/z 375 (M+H)+.

Example 74

[3-(3-Bromo-phenoxymethyl)-phenyl]-(7-methyl-pyrido[2,3-d]pyrimidin-4-yl)-amine

Example 74A

1-Nitro-3-(3-bromo-phenoxymethyl)-benzene

To a solution of 3-nitrobenzyl chloride (1.0 g, 5.83 mmol), 3-bromophenol (1.01 g, 5.83 mmol) and potassium carbonate (806 mg, 5.83 mmol) in acetone (25 mL) was heated to reflux for 23 hours. After cooling the solid was filtered off and the filtrate was concentrated under vacuum to a yellow residue which was dissolved in ethyl acetate (50 mL) and washed with 1N aqueous sodium hydroxide solution (25 mL) and water (25 mL) then dried and concentrated under vacuum to the title compound as a white solid (1.64 g, 91%).

Example 74B 3-(3-Bromo-phenoxymethyl)-phenylamine

To a solution of the product from Example 74A (1.64 g, 5.32 mmol), iron powder (1.49 g, 26.62 mmol) and ammonium chloride (430 mg, 7.98 mmol) in a mixture of tetrahydrofuran (20 mL), water (6 mL) and ethanol (20 mL) was heated to reflux for 3 hours. The mixture was cooled to room temperature, filtered through a pad of celite, which was washed with ethanol and the resultant filtrate concentrated under vacuum. The material was then dissolved in water (50 mL) and extracted with ethyl acetate (50 mL), the organic layer dried and concentrated under vacuum to provide the title compound as a yellow oil (1.43 g, 97%).

Example 74C

[3-(3-Bromo-phenoxymethyl)-phenyl]-(7-methyl-pyrido[2,3-d]pyrimidin-4-yl)-amine

To a solution of the product from Example 10C (50 mg, 0.266 mmol) and the product from Example 74B (74 mg, 0.266 mol) in acetic acid (3 mL) was heated to 130° C. for 30 minutes. After cooling to room temperature the solution was concentrated under vacuum and purified by HPLC with TFA to provide the title compound as a trifluoroacetic acid salt (62 mg, 44%). 1H NMR (300 MHz, DMSO-D6) δ ppm: 2.71 (s, 3H), 5.20 (s, 2H), 7.05 (m, 1H), 7.16 (m, 1H), 7.24 (m, 2H), 7.33 (m, 1H), 7.49 (t, J=7.7 Hz, 1H), 7.70 (d, J=8.5 Hz, 1H), 7.79 (m, 1H), 7.84 (s, 1H), 8.83 (s, 1H), 8.96 (d, J=8.4 Hz, 1H), 10.75 (bs, 1H); MS (ESI)+ m/z 421/423 (M+H)+.

Example 75

{2-2-(4-Methoxy-phenyl)-ethyl]-5-methyl-phenyl}-(7-methyl-pyrido[2,3-d]pyrimidin-4-yl)amine Example 75A 1-[2-(4-Methoxy-phenyl)-vinyl-4-methyl-2-nitro-benzene To a solution of 1-Bromo-4-methyl-2-nitro-benzene (0.76 g, 3.5 mmol), 1-methoxy-4-vinyl-benzene (0.59 g, 4.4 mmol), triethylamine (0.88 g, 8.8 mmol), tri-o-tolylphosphine (0.022 g) and palladium acetate (0.008 g) in N,N-dimethylformamide (7 mL) was placed in a high-pressure tube and purged with nitrogen for 10 mins. The tube was sealed and heated at 120° C. for 16 hours. The mixture was partitioned with water and ethyl acetate adjusting the pH to 3. The organic layer was washed with brine, dried (sodium sulfate) and filtered through a plug of silica. The filtrate was evaporated under vacuum and the residue was triturated with hexane/ethyl acetate (9:1) to provide the title compound (0.55 g, 58%).

Example 75B

2-[2-(4-Methoxy-phenyl)-ethyl]-5-methyl-phenylamine

To a solution of the product from Example 75A (164 mg, 0.6 mmol) and 10% palladium on charcoal (50 mg) in ethanol (20 ml) was hydrogenated with a hydrogen balloon for three days. The solvent was filtered through celite, washed with ethanol and evaporated under vacuum to provide the title compound (140 mg, 97%).

Example 75C

{2-2-(4-Methoxy-phenyl)-ethyl]-5-methyl-phenyl}-(7-methyl-pyrido[2,3-d]pyrimidin-4-yl)amine The product from Example 75B was reacted with the product from Example 10C using the procedure from Example 74C substituting the product from Example 75B for the product from Example 74B to provide the crude residue which was purified by chromatography on silica eluting with 99:1 dichloromethane/methanol to provide the title compound (53 mg, 69%). 1H NMR (300 MHz, DMSO-D6) δ ppm: 2.30 (s, 3 H), 2.69 (m, 7 H), 3.64 (s, 3 H), 6.69 (d, J=8.8 Hz, 2 H), 6.89 (d, J=8.8 Hz, 2 H), 7.08 (d, J=7.7 Hz, 1 H), 7.13 (s, 1 H), 7.22 (d, J=7.7 Hz, 1 H), 7.53 (d, J=8.5 Hz, 1 H), 8.50 (s, 1 H), 8.79 (d, J=8.5 Hz, 1 H), 9.83 (s, 1 H); (ESI+) m/z 385 (M+H)+.

Example 76

N-{4-[2-(7-Isopropyl-pyrido[2,3-d]pyrimidin-4-ylamino)-4-methyl-phenylsulfanyl]-phenyl}-acetamide The product from Example 22b was reacted with the product from Example 12E using the procedure from Example 12I substituting the product from Example 22b for the product from Example 12H to provide the crude residue which was purified by HPLC with TFA to provide the title compound as a trifluoroacetic acid salt. 1H NMR (300 MHz, DMSO-D6) δ ppm: 1.35 (d, J=6.99 Hz, 6 H), 2.02 (s, 3 H), 2.33 (s, 3 H), 3.28 (t, J=6.89 Hz, 1 H), 7.18 (s, 1 H), 7.20 (d, J=8.46 Hz, 2 H), 7.28 (s, 1 H), 7.46 (d, J=8.46 Hz, 2 H), 7.86 (d, J=8.46 Hz, 1 H) 8.79 (s, 1 H), 8.93 (d, J=8.82 Hz, 1 H), 9.99 (s, 1 H), 11.46 (s, 1 H); MS (ESI+) m/z 444 (M+H)+.

Example 77

(7-Cyclopropyl-pyrido[2,3-d]pyrimidin-4-yl)-(5-methyl-2-phenylsulfanyl-phenyl)-amine Example 77A N'-(3-Cyano-6-cyclopropyl-pyridin-2-yl)-N,N-dimethyl-formamidine Cyclopropyl methyl ketone was reacted according to the procedures described in Examples 12A-12E to provide the title compound.

Example 77B (7-Cyclopropyl-pyrido[2,3-d]pyrimidin-4-yl)-(5-methyl-2-phenylsulfanyl-phenyl)-amine The product from Example 7f was reacted with the product from Example 77A using the procedure from Example 73 substituting the product from Example 7f for the product from Example 9c and substituting the product from Example 77A for the product from Example 10B to provide the crude residue which was purified by trituration with methanol to provide the title compound. 1H NMR (300 MHz, DMSO-D6) δ ppm: 1.05-1.19 (m, 4 H), 2.22-2.41 (m, 1 H), 2.35 (s, 3 H), 7.05-7.31 (m, 7 H), 7.37 (s, 1 H), 7.58 (d, J=8.46 Hz, 1 H), 8.50 (s, 1 H), 8.65 (d, J=8.46 Hz, 1 H), 10.21 (s, 1 H); MS (ESI)+ m/z 385 (M+H)+.

Example 78

4-(4-Amino-phenylsulfanyl)-N-(4-bromo-phenyl)-3-(7-isopropyl-pyrido[2,3-d]pyrimidin-4-ylamino)-benzenesulfonamide Example 78A N-(4-Bromo-phenyl)-4-chloro-3-nitro-benzenesulfonamide A solution of 4-chloro-3-nitrobenzenesulfonyl chloride (2.561 g, 10 mmol) in acetic acid (20 mL) was treated with 4-bromoaniline (1.72 g, 10 mmol) and anhydrous sodium acetate (1.23 g, 15 mmol), then heated at 100° for 30 minutes. The reaction was cooled to room temperature and the acetic acid removed by rotary evaporation under vacuum. The residue was taken up in ethyl acetate (100 mL) and washed with water (2×25 mL) and brine (25 mL). The organic phase was dried over anhydrous sodium sulfate, filtered, and concentrated under vacuum, co-evaporating the oil with methylene chloride/hexanes. Purification by silica gel chromatography using methylene chloride followed by 5% ethyl acetate/methylene chloride as eluent provided the title compound as a yellow solid (2.038 g, 52%).

Example 78B 4-(4-Amino-phenylsulfanyl)-N-(4-bromo-phenyl)-3-nitro-benzenesulfonamide A mixture of the product of Example 78A (500 mg, 1.277 mmol), 4-aminothiophenol (240 mg, 1.915 mmol) and anhydrous sodium acetate (524 mg, 6.384 mmol) in anhydrous ethanol (9 mL) was heated at reflux under a nitrogen atmosphere for 1 hour. The reaction was cooled to room temperature and the ethanol removed by rotary evaporation under vacuum. The residue was taken up in ethyl acetate (100 mL) and washed with water (2×50 mL) and brine (50 mL). The organic phase was dried over anhydrous sodium sulfate, filtered, and concentrated under vacuum, co-evaporating the oil with methylene chloride/hexanes to obtain the title compound as an orange foam (613 mg, 100%).

Example 78C

{4-[4-(4-Bromo-phenylsulfamoyl)-2-nitro-phenylsulfanyl]-phenyl}-carbamic acid tert-butyl ester A solution of the product of Example 78B (613 mg, 1.277 mmol) in anhydrous 1,4-dioxane (10 mL) was treated with di-tert-butyl dicarbonate (418 mg, 1.92 mmol) at room temperature, then the reaction was heated at reflux under a nitrogen atmosphere for 3 hours. The reaction was cooled to room temperature, additional di-tert-butyl dicarbonate (500 mg) was added, and the reaction refluxed for 17 hours. The reaction was cooled to room temperature and the solvent removed by rotary evaporation under vacuum. Purification of the residue by silica gel chromatography using 3% ethyl acetate/methylene chloride as eluent provided the title compound as a yellow solid (512 mg, 69%).

Example 78D

{4-[2-Amino-4-(4-bromo-phenylsulfamoyl)-phenylsulfanyl]-phenyl}-carbamic acid tert-butyl ester The product of Example 78C (510 mg, 0.879 mmol), iron powder (302 mg, 5.40 mmol), and ammonium chloride (308 mg, 5.76 mmol) in water (4 mL) and ethanol (8 mL) were heated at 80° for 40 minutes. The reaction was cooled to room temperature, diluted with ethyl acetate (100 mL), and washed with water (2×50 mL) and brine (50 mL). The organic phase was dried over anhydrous sodium sulfate, filtered, and concentrated by rotary evaporation under vacuum to provide the title compound as a white foam (436 mg, 90%).

Example 78E

{4-[4-(4-Bromo-phenylsulfamoyl)-2-(7-isopropyl-pyrido[2,3-d]pyrimidin-4-ylamino)-phenylsulfanyl]-phenyl}-carbamic acid tert-butyl ester A solution of the product from Example 12E (59 mg, 0.2725 mmol) and the product from Example 78D (150 mg, 0.2725 mmol) in acetic acid (4 mL) was stirred in an oil bath preheated to 140° C. for 25 minutes. The reaction was cooled to room temperature, diluted with hexanes (100 mL), concentrated by rotary evaporation under vacuum, and co-evaporated with methylene chloride/hexanes (4×). The residue was dried under vacuum, then purified by silica gel chromatography using 4% methanol/methylene chloride as eluent to provide the title compound as a tan solid (67 mg, 34%).

Example 78F 4-(4-Amino-phenylsulfanyl)-N-(4-bromo-phenyl)-3-(7-isopropyl-pyrido[2,3-d]pyrimidin-4-ylamino)-benzenesulfonamide The product from Example 78E (44 mg, 0.061 mmol) was treated with trifluoroacetic acid (2 mL) in methylene chloride (2 mL) at room temperature for 30 minutes. The solvents were removed by rotary evaporation under vacuum and the residual oil dried under hi-vacuum. Purification by silica gel chromatography using 5% methanol/methylene chloride as eluent provided the title compound as a trifluoroacetic acid salt (25 mg, 48%). $^1$H NMR (300 MHz, DMSO-D6) δ ppm: 1.35 (d, J=6.62 Hz, 6H), 3.13-3.38 (m, 1 H), 6.63 (d, J=8.46 Hz, 2 H), 6.87 (d, J=7.72 Hz, 1 H), 7.01-7.09 (d, J=8.82 Hz, 2 H), 7.12 (d, J=8.46 Hz, 2 H), 7.44 (d, J=8.82 Hz, 2 H), 7.61 (dd, J=7.72, 1.47 Hz, 1 H), 7.71 (s, 1 H), 7.81 (dd, J=6.62, 1.47 Hz, 1 H), 8.66-8.80 (m, 1 H), 8.90 (d, J=6.99 Hz, 1 H), 10.55 (s, 1 H); MS (ESI+) m/z 621/623 (M+H)$^+$.

Example 79

4-[2-(7-Ethylsulfanyl-pyrimido[4,5-d]pyrimidin-4-ylamino)-4-methyl-phenylsulfanyl]-phenol

Example 79A

4-Amino-2-ethylsulfanyl-pyrimidine-5-carbonitrile

A solution of 2-Ethyl-2-thiopsuedourea hydrobromide (1.52 g, 8.19 mmol), (Ethoxymethylene)malononitrile (1.0 g, 8.19 mmol) and N,N-diisopropylethylamine (3.57 mL, 20.05 mmol) in ethanol (20 mL) was stirred at room temperature for 3.5 hours. The resultant solid was collected, washed with ethanol, and the dried under vacuum to provide the title compound as a light yellow solid (580 mg, 39%).

Example 79B

N'-(5-Cyano-2-ethylsulfanyl-pyrimidin-4-yl)-N,N-dimethyl-formamidine

A solution of the product from Example 79A (200 mg, 1.11 mmol) and N,N-dimethylformamide dimethyl acetal (0.15 mL, 1.11 mmol) in toluene (10 mL) was refluxed for 2.5 hours. After cooling to room temperature the solution was concentrated under vacuum to provide the title compound as a colorless solid (260 mg, 100%).

Example 79C

4-[2-(7-Ethylsulfanyl-pyrimido[4,5-d]pyrimidin-4-ylamino)-4-methyl-phenylsulfanyl]-phenol A solution of the product from Example 9c (54 mg, 0.234 mmol) and the product from Example 79B (50 mg, 0.213 mmol) in acetic acid (2 mL) was heated at 130° C. for 1.5 hours. The solution was then allowed to cool to room temperature, the acetic acid removed under vacuum and the resultant residue purified by HPLC with TFA to provide the title compound as a trifluoroacetic acid salt (51 mg, 45%). $^1$H NMR (300 MHz, DMSO-d$_6$) δ ppm: 1.38 (t, J=7.4 Hz, 3H), 2.30 (s, 3H), 3.23 (q, J=7.3 Hz, 2H), 6.72 (d, J=8.8 Hz, 2H), 6.98 (d, J=8.1 Hz, 1H), 7.10 (m, 1H), 7.18 (d, J=8.7 Hz, 2H), 7.21 (s, 1H), 8.62 (s, 1H), 9.70 (s, 1H), 9.78 (bs, 1H), 10.85 (s, 1H); MS (ESI)+ m/z 422 (M+H)+.

Example 80

4-[4-Methyl-2-(7-piperidin-1-yl-pyrimido[4,5-d]pyrimidin-4-ylamino)-phenylsulfanyl]-phenol To a solution of the product from Example 79C (42 mg, 0.1 mmol) in piperidine (1 ml) was microwaved (CEM Discover microwave) at 180° C. for 2 hours. The solution was concentrated under vacuum and the residue was purified by HPLC with TFA to provide the title compound as a trifluoroacetic acid salt (17 mg, 38%). 1H NMR (300 MHz, DMSO-D6) δ ppm: 1.64 (m, 6H), 2.30 (s, 3H), 3.96 (m, 4H), 6.72 (m, 2H), 7.01 (d, J=7.72 Hz, 1H), 7.17 (m, 4H), 8.59 (s, 1H), 9.53 (s, 1H), 9.83 (s, 1H), 11.43 (s, 1H); (ESI+) m/z 445 (M+H)+.

Example 81

4-[5-(3-Fluoro-benzyloxy)-2-(4-hydroxy-phenylsulfanyl)-phenylamino]-7-methyl-pyrido[2,3-d]pyrimidine-6-carbonitrile

Example 81A

N'-(3,5-Dicyano-6-methyl-pyridin-2-yl)-N,N-dimethylformamidine

A solution of 2-Amino-6-methyl-pyridine-3,5-dicarbonitrile (0.158 g, 1.0 mmol) and N,N-Dimethylformamide dimethyl acetal (0.119 g, 1.0 mmol) in toluene (10 mL) was heated at reflux for 6 hours. After cooling to room temperature, the solution was concentrated under vacuum to provide the title compound as a brown solid (0.2 g, 94%).

Example 81B

4-[5-(3-Fluoro-benzyloxy)-2-(4-hydroxy-phenylsulfanyl)-phenylamino]-7-methyl-pyrido[2,3-d]pyrimidine-6-carbonitrile The product of Example 81A was reacted with the product of Example 10B using the procedure of Example 10F substituting the product of Example 81A for the product of Example 10E to provide the crude material which was purified by HPLC with TFA to provide the title compound as a trifluoroacetic acid salt (18 mg, 29%). 1H NMR (300 MHz, DMSO-D6) δ ppm: 2.82 (s, 3H), 5.13 (s, 2H), 6.64 (d, J=8.46 Hz, 2H), 6.99 (d, J=9.56 Hz, 1H), 7.09 (d, J=8.82 Hz, 2H), 7.12-7.21 (m, 3H), 7.29 (d, J=7.72 Hz, 2H), 7.39-7.53 (m, 1H), 8.63 (s, 1H), 9.36 (s, 1H), 9.64 (s, 1H), 10.33 (s, 1H).

Example 82

[2-(2-Amino-6-chloro-pyrimidin-4-ylsulfanyl)-5-benzyloxy-phenyl]-(7-methyl-pyrido[2,3-d]pyrimidin-4-yl)-amine

Example 82A

4-Benzyloxy-2-nitro-phenylamine

A solution containing 4-amino-3-nitro phenol (1.09 g, 7.07 mmole), benzylbromide (1.28 g, 7.5 mmole and cesium carbonate (2.43 g, 7.5 mmole) were stirred for 4 days at room temperature. After the reaction was complete, the reaction mixture was poured into ice water (500 ml), stirred 1 hour, and the resultant solid was filtered and dried under vacuum to provide the title compound (1.1 g, 64%).

Example 82B 4-benzyloxy-2-nitrobenzenediazonium tetrafluoroborate

The product from Example 82A (0.5 g, 2.05 mmole) was dissolved in THF (10 ml) and added dropwise to a cold (−20° C.) solution containing boron trifluoride etherate (1.1 ml, 8.20 mmole), and tert-butyl nitrite (0.6 ml, 4.92 mmole) over a 5 min period. The resultant mixture was stirred for 10 minutes at −20° C., then 2 hr at 10° C. The reaction mixture was then poured into hexane (100 ml) and the solid was filtered, washed with ether and dried under vacuum to provide the title compound (0.61 g, 87%).

Example 82C 4-(4-Benzyloxy-2-nitro-phenylsulfanyl)-6-chloropyrimidin-2-ylamine A solution of the product from Example 82B (0.1 g, 0.290 mmol) in dimethylsulfoxide (1 ml) was added dropwise to a solution containing potassium thioacetate (0.04 g, 0.350 mmol) in dimethylsulfoxide (1 ml). The reaction mixture immediately began bubbling. The mixture was stirred 90 minutes at room temperature when the bubbling had subsided. The resultant dark green mixture was then treated with an aqueous 3M potassium hydroxide solution (0.1 ml) and stirred an additional 80 minutes, whereupon, solid 4,6 dichloro-2-aminopyrimidine was added and the mixture stirred an additional 60 minutes. The reaction mixture was diluted with ethyl acetate (50 ml), washed with water (20 ml), 10% sodium bicarbonate and 10% sodium chloride solution, dried over sodium sulfate, filtered and the solvent removed under vacuum to provide a tan solid as the title compound (0.1 g, 88%).

Example 82D 4-(2-Amino-4-benzyloxy-phenylsulfanyl)-6-chloropyrimidin-2-ylamine A solution of the product from Example 82C (0.1 g, 0.257 mmol), iron powder (0.058 g, 1.03 mmol) and ammonium chloride (0.017 g, 0.310 mmol) in a methanol (5 mL), tetrahydrofuran (5 mL), and water (2 mL) solution was heated to reflux for 1.5 hours. The resultant mixture was diluted with methanol (50 mL) and filtered through a pad of celite. The filtrate was concentrated under vacuum to a volume of 10 mL, the solution diluted with water (50 mL) and extracted with ethyl acetate (2×50 mL). The combined extracts were washed with 10% sodium chloride then dried over magnesium sulfate, filtered and concentrated under vacuum to provide the title compound (0.04 g, 43%).

Example 82E

[2-(2-Amino-6-chloro-pyrimidin-4-ylsulfanyl)-5-benzyloxy-phenyl]-(7-methyl-pyrido[2,3-d]pyrimidin-4-yl)-amine A solution of the product from Example 10B (21 mg, 0.112 mmol), and the product from Example 82D (40 mg, 0.112 mmol) in acetic acid (1 mL) was stirred in an oil bath preheated to 130° C. for 10 minutes. The mixture was then cooled to room temperature, the acetic acid removed under vacuum, and the resultant residue was treated with 50% TFA in $CH_2Cl_2$ (2 ml) for 30 minutes at room temperature. The solvent was evaporated under vacuum and the resultant residue was purified by HPLC with TFA to provide the title compound as a trifluoroacetic acid salt (5 mg, 7%). 1H NMR (300 MHz, DMSO-D6) δ ppm: 2.66 (s, J=6.25 Hz, 3H), 5.21 (s, 2H), 6.53 (s, 1H), 7.07 (s, 1H), 7.14 (dd, J=8.64, 2.76 Hz, 1H), 7.25-7.61 (m, 6H), 7.62-7.72 (m, 1H), 8.52 (S, 1H), 8.66 (d, J=8.82 Hz, 1H), 8.71 (s, 1H), 8.88 (d, J=8.46 Hz, 1H), 10.05 (s, 1H).

Example 83

{4-[4-(4-Bromo-phenylcarbamoyl)-2-(7-isopropyl-pyrido[2,3-d]pyrimidin-4-ylamino)-phenylsulfanyl]-phenyl}-carbamic acid 1-methyl-piperidin-3-ylmethyl ester The product from Example 60 (76 mg, 0.1 mmol), (1-methyl-piperidin-3-yl)-methanol (65 mg, 0.5 mmol) and 1,8- diazabicyclo[5.4.0]undec-7-ene (15 μL, 0.1 mmol) in tetrahydrofuran (5 mL) was heated at 60° C. for 1 hour. The mixture was added saturated sodium carbonate, extracted with ethyl acetate, dried with magnesium sulfate, filtered and evaporated. The residue was purified by reverse phase preparative HPLC with TFA method to give the title compound as a trifluoroacetic acid salt (36 mg, 37%). $^1$H NMR (300 MHz, DMSO-$d_6$) δ ppm; 1.20 (m, 1 H) 1.36 (d, J=6.99 Hz, 6 H) 1.78 (m, 3 H) 2.14 (m, 1 H) 2.79 (d, J=4.04 Hz, 3 H) 3.28 (m, 1 H) 3.44 (m, 4 H) 4.02 (m, 2 H) 7.07 (d, J=8.09 Hz, 1 H) 7.40 (d, J=8.82 Hz, 2 H) 7.54 (m, 4 H) 7.73 (d, J=8.82 Hz, 2 H) 7.85 (m, 2 H) 7.98 (s, 1 H) 8.79 (s, 1 H) 8.95 (d, J=8.46 Hz, 1 H) 9.46 (s, 1 H) 9.96 (s, 1 H) 10.38 (s, 1 H) 11.38 (s, 1 H); MS (ESI+) m/z 740 742 (M+H)+.

Example 84

4-(4-Amino-phenylsulfanyl)-N-(3-fluoro-phenyl)-3-(7-isopropyl-pyrido[2,3-d]pyrimidin-4-ylamino)-N-methyl-benzamide

Example 84a

3-Nitro-4-[4-(2,2,2-trichloro-ethoxycarbonylamino)-phenylsulfanyl]-benzoic acid

To a solution of 4-(4-Amino-phenylsulfanyl)-3-nitro-benzoic acid (4.0 g, 13.8 mmol) in 75 mL of $CH_2Cl_2$ was added dropwise at room temperature Bis(trimethylsilyl)acetamide (6.73 mL, 27.6 mmol) over 10 minutes. The reaction mixture was stirred at room temperature for 1 hour. Pyridine (2.23 mL, 27.6 mmol) was added to the reaction mixture followed by the dropwise addition of TROC-chloroformate (2.04 mL, 15.2 mmol). After stirring for 2 hours the reaction mixture was concentrated under vacuum, diluted with 200 mL of water and the pH adjusted to 3.0 with 1N HCl. Decant off the aqueous solution and take the residue up in $CH_2Cl_2$ and filter off the resulting yellow precipitate providing the title compound (5.14 g, 80%).

Example 84b

[4-(4-Chlorocarbonyl-2-nitro-phenylsulfanyl)-phenyl]-carbamic acid 2,2,2-trichloro-ethyl ester The product from Example 84a (2.0 g, 42.9 mmol) in thionyl chloride (10 mL) containing 1 drop of dimethylformamide and was heated to reflux for 3 hours. Cooled and concentrated under vacuum and dried under high vacuum overnight. The title compound was used without further purification.

Example 84c (4-{4-[(3-Fluoro-phenyl)-methyl-carbamoyl]-2-nitro-phenyl sulfanyl}-phenyl)-carbamic acid 2,2,2-trichloro-ethyl ester The product from Example 84b (0.25 g, 0.516 mmol) and (4-Fluoro-phenyl)-methyl-amine (71 mg, 0.568 mmol) in toluene (20 mL) was heated to reflux for 3 hours. After cooling the solution, the reaction mixture was concentrated under vacuum to afford the title compound (295 mg, 99% yield) as pale yellow solid.

Example 84d (4-{2-Amino-4-[(4-fluoro-phenyl)-methyl-carbamoyl]-phenylsulfanyl}-phenyl)-carbamic acid 2,2,2-trichloro-ethyl ester The product from Example 84c (295 mg, 0.516 mmol) was reduced with Fe and $NH_4Cl$ following the procedure from Example 10E providing the title compound was isolated as a white solid (205 mg, 73% yield).

Example 84e

{4-[4-[(4-Fluoro-phenyl)-methyl-carbamoyl]-2-(7-isopropyl-pyrido[2,3-d]pyrimidin-4-ylamino)-phenylsulfanyl]-phenyl}-carbamic acid 2,2,2-trichloro-ethyl ester The product from Example 84d (205.2 mg, 0.3780 mmol) and the product from Example 12E (81.8 mg, 0.3780 mmol) in 10 mL of acetic acid was heated at 140° C. for 1 hour. The reaction mixture was cooled to room temperature and then concentrated under vacuum giving the crude title compound that was purified by silica gel chromatography eluting with 4% methanol in dichloromethane to provide the title compound was isolated as a white solid (175 mg, 65% yield).

Example 84f 4-(4-Amino-phenylsulfanyl)-N-(4-fluoro-phenyl)-3-(7-isopropyl-pyrido[2,3-d]pyrimidin-4-ylamino)-N-methyl-benzamide The product from Example 84d (70 mg, 0.0980 mmol) in THF (10 mL) was reacted with 1N NaOH (1 mL, 1.00 mmol) and reaction mixture heated at 55° C. for 1 hour. The reaction mixture was cooled and concentrated under vacuum to remove the THF. The pH was adjusted to 6.0 with 1N HCl and the resulting precipitate was removed by vacuum filtration and dried under high vacuum providing the title compound as a pale yellow solid (45 mg, 85% yield). $^1$H NMR (300 MHz, DMSO-$d_6$) δ ppm: 1.32 (d, J=6.99 Hz, 6 H) 3.12-3.25 (m, 1 H) 3.34 (s, 3 H) 6.52-6.67 (m, 3 H) 6.94-7.11 (m, 5 H) 7.10-7.20 (m, 2 H) 7.20-7.41 (m, 2 H) 7.61 (d, J=8.46 Hz, 1 H) 8.51 (s, 1 H) 8.80 (d, J=8.09 Hz, 1 H) 10.10 (s, 1 H); MS (ESI) m/z 539 (M+H)+.

Example 85

[4-(4-Amino-phenylsulfanyl)-3-(7-isopropyl-pyrido[2,3-d]pyrimidin-4-ylamino)-phenyl]-(2,6-dimethyl-morpholin-4-yl)-methanone

Example 85A

{4-[4-(2,6-Dimethyl-morpholine-4-carbonyl)-2-(7-isopropyl-pyrido[2,3-c]pyrimidin-4-ylamino)-phenylsulfanyl]-phenyl}-carbamic acid 2,2,2-trichloro-ethyl ester The product of Example 84b (75 mg, 0.1236 mmol) was dissolved in anhydrous N,N-dimethylformamide (2 mL) under a nitrogen atmosphere, and treated with cis-2,6-dimethylmorpholine (16.1 mg, 0.1359 mmol), 3-(diethoxyphosphoryloxy)-1,2,3-benzotriazin-4(3 H)-one (74 mg, 0.2472 mmol), and triethylamine (0.052 mL, 0.3707 mmol). The reaction was stirred at room temperature for 16 hours, then diluted with ethyl acetate (50 mL) and washed with 10% aqueous sodium carbonate (2×25 mL), water (25 mL), and brine (25 mL). The organic phase was dried over anhydrous sodium sulfate, filtered, and concentrated by rotary evaporation in vacuo. Purification of the residue by silica gel chromatography eluting with 3% methanol/methylene chloride afforded the title compound as a light yellow solid (58 mg, 67%).

Example 85B

[4-(4-Amino-phenylsulfanyl)-3-(7-isopropyl-pyrido[2,3-d]pyrimidin-4-ylamino)-phenyl]-(2,6-dimethyl-morpholin-4-yl)-methanone A solution of the product of Example 85A (56 mg, 0.0795 mmol) in 1,4-dioxane (2 mL) was treated with a solution of sodium hydroxide (8 mg, 0.1988 mmol) in water (1 mL), and heated at 60° C. for 30 minutes. The reaction was then cooled to room temperature and diluted with ethyl acetate (50 mL) and water (25 mL). The aqueous pH was adjusted to 5 with 1N aqueous hydrochloric acid, the layers were separated, and the organic phase washed with water (2×25 mL) and brine (25 mL). The organic extract was dried over anhydrous sodium sulfate, filtered, and concentrated by rotary evaporation in vacuo. Purification of the residue by silica gel flash chromatography with 5% methanol/methylene chloride provided the title compound as an off-white solid (18 mg, 43%). $^1$H NMR (300 MHz, DMSO-$d_6$/TFA) δ ppm: 0.91-1.25 (m, 6 H) 1.37 (d, J=6.99 Hz, 6 H) 2.70-2.97 (m, 1 H) 3.25-3.40 (m, 1 H) 3.45-3.64 (m, 4 H) 4.20-4.52 (m, 1 H) 5.72 (s, 2 H) 7.29 (d, J=8.09 Hz, 1 H) 7.35 (d, J=8.46 Hz, 2 H) 7.48 (dd, J=7.91, 2.02 Hz, 1 H) 7.50 (d, J=8.45 Hz, 2 H) 7.60 (d, J=1.84 Hz, 1 H) 7.96 (d, J=8.82 Hz, 1 H) 8.97 (s, 1 H) 9.07 (d, J=8.82 Hz, 1 H); MS (ESI+) m/z 529 (M+H)$^+$, (ESI−) m/z 527 (M−H)$^-$.

Example 86

4-[4-(2,5-Difluoro-benzyloxy)-2-(pyrido[2,3-d]pyrimidin-4-ylamino)-phenylsulfanyl]-phenol

Example 86a

2-Bromomethyl-1,4-difluoro-benzene

To a solution of (2,5-difluoro-phenyl)-methanol (4.8 g, 33.6 mmol) in dichloromethane (40 mL) was added drop wise phosphorus tribromide (94 g, 33.6 mmol). The mixture was stirred at room temperature for 16 h. The reaction was poured onto ice/water. The aqueous phase was made basic with sodium bicarbonate. The aqueous phase was extracted with dichloromethane. The organic phase was concentrated under reduced pressure. The residue was purified by silica gel chromatography eluting with (hexanes/ethyl acetate 90:10) to give the title compound (3.5 g, 50%).

Example 86b

1-Chloro-4-(2,5-fluoro-benzyloxy)-2-nitro-benzene

To Example 86a (2.2 g, 10.4 mmol) in DMF (50 mL) was added 4-chloro-3-nitro-phenol (1.8 g, 10.4 mmol), and $K_2CO_3$ (2.87 g, 20.8 mmol). The mixture was heated at 80° C. for 16 h. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by silica gel chromatography eluting with (hexanes/ethyl acetate 90:10) to give the title compound (2.48 g, 66%).

Example 86c

4-[4-(2,5-Difluoro-benzyloxy)-2-nitro-phenylsulfanyl]-phenol

To Example 86b (2.5 g, 8.3 mmol) in DMF (50 mL) was added 4-mercaptophenol (1.0 g, 8.3 mmol), and $K_2CO_3$ (2.3 g, 16.5 mmol). The mixture was heated at 80° C. for 16 h. The reaction was cooled and poured into water. The aqueous phase was extracted with ethyl acetate (2×) and the combined phases were washed with water, brine, and dried over sodium sulfate. The organic phase was concentrated under reduced pressure. The residue was purified by flash chromatography eluting with (hexanes/ethyl acetate/methanol 75:15:5) to give the title compound (1.7 g, 52%).

Example 86d

4-[2-Amino-4-(2,5-difluoro-benzyloxy)-phenylsulfanyl]-phenol

The product from Example 86c (1.70 g, 4.2 mmol) was reacted with Fe and $NH_4Cl$ as described in Example 10E to give the title compound (1.3 g, 84%).

Example 86e

4-[4-(2,5-Difluoro-benzyloxy)-2-(pyrido[2,3-d]pyrimidin-4-ylamino)-phenylsulfanyl]-phenol The product from Example 15A (100 mg, 0.57 mmol) was reacted with Example 86d (206 mg, 0.57 mmol) in acetic acid (10 mL) at 125° C. in a sealed tube for 5 minute giving the crude title compound which was purified by HPLC with TFA providing the product as the trifluoroacetic acid (140 mg, 39%). $^1$H NMR (300 MHz, DMSO-$d_6$) δ ppm: 5.13 (s, 2 H) 6.67 (d, J=8.46 Hz, 2 H) 6.93-7.01 (m, 1 H) 7.10-7.16 (m, 3 H) 7.22-7.37 (m, 4 H) 7.41-7.52 (m, J=5.79, 5.79, 2.76 Hz, 1H) 7.64 (dd, J=8.09, 4.41 Hz, 1 H) 8.53 (s, 1 H) 8.84 (d, J=7.72 Hz, 1 H) 9.05 (s, 1 H); MS (ESI+) m/z 489 (M+H)+.

Example 87

4-(4-Amino-2-chloro-phenoxy)-N-(4-bromo-phenyl)-3-(7-isopropyl-pyrido[2,3-d]pyrimidin-4-ylamino)-benzamide The title compound was prepared following the Troc procedure from Example 60A-C and reacting with the methyl amidine from Example 10B substituting 4-amino-2-chlorophenol for 4-aminophenol. The crude product was purified by chromatography on silica gel (3% methanol in dichloromethane) to give the title compound (0.09 g, 51%). $^1$H NMR (300 MHz, DMSO-$d_6$) δ ppm: 1.32 (d, J=6.99 Hz, 6 H), 3.16-3.28 (m, 1 H), 5.37 (s, 2 H), 6.55 (dd, J=8.82, 2.57 Hz, 1 H), 6.68 (d, J=2.21 Hz, 1 H), 6.72 (d, J=8.82 Hz, 1 H), 6.94 (d, J=8.82 Hz, 1 H), 7.53 (d, J=8.82 Hz, 2 H), 7.61 (d, J=8.46 Hz, 1 H), 7.75 (d, J=9.19 Hz, 2 H), 7.85 (dd, J=8.64, 2.02 Hz, 1 H), 8.16 (d, J=1.84 Hz, 1 H), 8.63 (s, 1 H), 8.86 (d, J=8.46 Hz, 1 H), 10.03 (s, 1 H), 10.31 (s, 1 H); MS (ESI+) m/z 603 (M+H)+.

Example 88

Morpholine-4-carboxylic acid {4-[4-(4-bromo-phenylcarbamoyl)-2-(7-isopropyl-pyrido[2,3-d]pyrimidin-4-ylamino)-phenoxy]-phenyl}-amide

Example 88A 4-(4-Amino-phenoxy)-N-(4-bromo-phenyl)-3-nitro-benzamide

A mixture of the product from Example 49A (3.55 g, 10 mmol), 4-aminophenol (1.09 g, 10 mmol), and potassium hydroxide (1.12 g, 20 mmol) were dissolved in dimethyl sulfoxide (15 mL) and heated at 100° C. in a CEM Discover microwave for 25 minutes. The mixture was then cooled to room temperature, poured into water (300 mL), the pH of the solution adjusted to 6 with 1N aqueous hydrochloric acid, the resultant solution stirred for 30 minutes and the resultant solid collected and dried to provide the title compound as a yellow solid (4.2 g, 98%).

Example 88B

{4-[4-(4-Bromo-phenylcarbamoyl)-2-nitro-phenoxy]-phenyl}-carbamic acid 2,2,2-trichloro-ethyl ester To the product from Example 88A (4.2 g, 9.8 mmol) dissolved in dichloromethane (100 mL) was added pyridine (1.62 mL, 20 mmol) followed by the dropwise addition of 2,2,2-trichloroethyl chloroformate (2.29 g, 10.8 mmol). The resultant solution was stirred for 4 hours and then concentrated under vacuum. The mixture was then poured into water (200 mL), the pH of the solution adjusted to 5 with 1N aqueous hydrochloric acid, the resultant solution stirred for 30 minutes and the resultant solid collected and dried to provide the title compound (6.0 g, 100%).

Example 88C

{4-[2-Amino-4-(4-bromo-phenylcarbamoyl)-phenoxy]-phenyl}-carbamic acid 2,2,2-trichloro-ethyl ester The product from Example 88B (6.0 g, 10 mmol), iron powder (2.8 g, 50 mmol) and ammonium chloride (0.81 g, 15 mmol) in a mixture of ethanol (60 mL), tetrahydrofuran (60 mL), and water (20 mL) was heated under reflux for 5 hours and then cooled to room temperature. The reaction mixture was filtered through Celite and the filter pad was rinsed with ethanol (100 mL). The filtrate was evaporated under reduced pressure to leave a residue which was triturated with hexanes/ethyl acetate 4/1 to provide the title product (2.39 g, 42%) as a tan solid.

Example 88D

{4-[4-(4-Bromo-phenylcarbamoyl)-2-(7-isopropyl-pyrido[2,3-d]pyrimidin-4-ylamino)-phenoxy]-phenyl}-carbamic acid 2,2,2-trichloro-ethyl ester A mixture of the product from Example 88C (2.39 g, 4.2 mmol) and the product from Example 12E (0.91 g, 4.2 mmol) in glacial acetic acid (10 mL) was heated in a 130° C. oil bath for 15 min. The reaction mixture was then cooled to room temperature and the solvent evaporated under reduced pressure to provide the title product as a brown powder.

Example 88E

Morpholine-4-carboxylic acid {4-[4-(4-bromo-phenylcarbamoyl)-2-(7-isopropyl-pyrido[2,3-d]pyrimidin-4-ylamino)-phenoxy]-phenyl}-amide A mixture of the product from Example 88D (74 mg, 0.1 mmol), 1,8-diazabicyclo[5.4.0]undec-7-ene (30 mg, 0.2 mmol), and morpholine (87 mg, 1.0 mmol) in tetrahydrofuran (2 ml) was heated at 65° C. in a sealed tube for 1 hour. The mixture was then cooled to room temperature, concentrated under vacuum and the resultant residue purified by HPLC with TFA to provide the title compound as a trifluoroacetic acid salt (50 mg, 63%). 1H NMR (300 MHz, DMSO-D6) δ ppm: 1.34 (d, J=6.99 Hz, 6 H), 3.19-3.32 (m, 1 H), 3.35-3.44 (m, 4 H), 3.57-3.63 (m, 4 H), 6.95-7.03 (m, 3 H), 7.47 (d, J=9.19 Hz, 2 H), 7.54 (d, J=8.82 Hz, 2 H), 7.75 (d, J=8.82 Hz, 2 H), 7.82 (d, J=8.46 Hz, 1 H), 7.98 (dd, J=8.64, 2.02 Hz, 1 H), 8.14 (d, J=1.84 Hz, 1 H), 8.56 (s, 1 H), 8.85 (s, 1 H), 8.94 (d, J=8.46 Hz, 1 H), 10.38 (s, 1 H); MS (ESI+) m/z 682/684 (M+H)+.

Example 89

(S)-4-(4-Amino-phenylsulfanyl)-3-(7-isopropyl-pyrido[2,3-d]pyrimidin-4-ylamino)-N-(1-phenyl-ethyl)-benzamide

Example 89A 4-(4-Amino-phenylsulfanyl)-3-nitro-benzoic acid methyl ester

A mixture of 4-chloro-3-nitrobenzoic acid methyl ester (15.0 g, 68 mmol), 4-aminothiophenol (8.8 g, 68 mmol) and K2CO3 (11.8 g, 85 mmol) in DMF (150 mL) was heated at 90° C. for 1.5 hours, cooled to room temperature, and then poured into H2O (450 mL) under stirring. The aqueous mixture was extracted with AcOEt (400 mL). The extract was washed with H2O (3 times) and brine, dried over MgSO4, and evaporated to give the crude product as orange crystal. The crude product was suspended in 150 mL of i-Pr2O and stirred at room temperature for 1 hour. The crystal was collected by filtration, washed with i-Pr2O and dried at 60° C. for 3 days under reduced pressure to give purified title compound as orange crystal (18.6 g, 90%).

Example 89B 4-(4-tert-Butoxycarbonylamino-phenylsulfanyl)-3-nitro-benzoic acid methyl ester A solution of 4-(4-amino-phenylsulfanyl)-3-nitro-benzoic acid methyl ester (18.5 g, 61 mmol) and Boc2O (26.8 g, 122 mmol) in p-dioxane (280 mL) was heated at 90° C. for 3 hours. An additional Boc2O (26.8 g, 122 mmol) was added and the mixture was heated at 90° C. for 3 hours. A second additional Boc2O (13.4 g, 61 mmol) was added and the mixture was heated at 90° C. for 4 hours. The reaction mixture was cooled to room temperature, and then evaporated. The residue was diluted with i-Pr2O (250 mL) and the mixture was stirred at room temperature for 1 hour. The resulting crystal was collected by filtration, washed with i-Pr2O and dried at 60° C. overnight under reduced pressure to give the title compound as yellow crystal (22.8 g, 93%).

Example 89C

3-Amino-4-(4-tert-butoxycarbonylamino-phenylsulfanyl)-benzoic acid methyl ester

A suspension of 4-(4-tert-butoxycarbonylamino-phenylsulfanyl)-3-nitro-benzoic acid methyl ester (22.8 g, 56 mmol), Fe powder (16.4 g, 282 mmol) and NH4Cl (15.1 g, 282 mmol) in aqueous EtOH [prepared from EtOH (228 mL) and H2O (228 mL)] was gradually heated to reflux and gently refluxed for 2 hours. The reaction mixture was cooled to room temperature and filtered through celite pad. The filtrate was evaporated. The aqueous residue was portioned between AcOEt and H2O, made basic to pH 9 with K2CO3, and then filtered through celite pad. The organic layer was separated, washed with 1-120 and brine, dried over MgSO4 and evaporated. The oily residue was crystallized in the treatment with i-Pr2O (200 mL) and stirred at room temperature for 30 minutes. The resulting crystal was collected by filtration, washed with i-Pr2O and dried at 60° C. overnight under reduced pressure to give the title compound as colorless crystal (13.9 g, 66%).

Example 89D 4-(4-tert-Butoxycarbonylamino-phenylsulfanyl)-3-(7-isopropyl-pyrido[2,3-a]pyrimidin-4-ylamino)-benzoic acid methyl ester A suspension of N'-(3-cyano-6-isopropyl-pyridin-2-yl)-N,N-dimethyl-formamidine (2.00 g, 9.3 mmol) and 3-amino-4-(4-tert-butoxycarbonylamino-phenylsulfanyl)-benzoic acid methyl ester (3.46 g, 9.3 mmol) in AcOH (40 mL) was heated at 120° C. for 20 minutes under N2. After cooling to room temperature, the reaction mixture was portioned between AcOEt (150 mL) and H2O (200 mL), and then made basic to pH 9 with K2CO3 under stirring. The organic layer was separated, washed with 10% NaHCO3, H2O and brine, dried over MgSO4, and evaporated to give pale brown oil. The oily residue was separated by silica gel column chromatography (AcOEt/n-hexane=5/1) to give yellow crystal. Further purification by washing with cold AcOEt (15 mL) gave the title compound as slightly yellow crystal (3.27 g, 65%).

Example 89E 4-(4-tert-Butoxycarbonylamino-phenylsulfanyl)-3-(7-isopropyl-pyrido[2,3-d]pyrimidin-4-ylamino)-benzoic acid To a solution of 4-(4-tert-butoxycarbonylamino-phenylsulfanyl)-3-(7-isopropyl-pyrido[2,3-d]pyrimidin-4-ylamino)-benzoic acid methyl ester (3.25 g, 6.0 mmol) in THF (32.5 mL) was added aqueous LiOH [prepared from LiOH monohydrate (1.02 g, 24 mmol) and H2O (10 mL)] dropwise at room temperature. The mixture was stirred at room temperature for 26 hours, and then evaporated. The aqueous mixture was diluted with 100 mL of H2O, washed with AcOEt (50 mL), and then carefully acidified to pH 4-5 with 10% HCl at 5° C. under stirring. The resulting solid was collected by filtration, washed with H2O, and dried at 60° C. overnight under reduced pressure to give the title compound as pale yellow crystal (3.09 g, 98%). $^1$H-NMR (300 MHz, DMSO-d6) δ ppm: 1.34 (d, J=7.0 Hz, 6H), 1.48 (s, 9H), 3.22 (septet, J=7.0 Hz, 1H), 6.93 (d, J=8.5 Hz, 1H), 7.36 (d, J=8.8 Hz, 2H), 7.54 (d, J=8.8 Hz, 2H), 7.63 (d, J=8.5 Hz, 1H), 7.75 (dd, J=8.5, 1.8 Hz, 1H), 7.89 (d, J=1.8 Hz, 1H), 8.58 (s, 1H), 8.84 (d, J=8.5 Hz, 1H), 9.61 (s, 1H), 10.16 (s, 1H), 12.98 (br-s, 1H)

Example 89F (S)-{4-[2-(7-Isopropyl-pyrido[2,3-d]pyrimidin-4-ylamino)-4-(1-phenyl-ethyl carbamoyl)-phenylsulfanyl]-phenyl}-carbamic acid tert-butyl ester To a suspension of 4-(4-tert-butoxycarbonylamino-phenylsulfanyl)-3-(7-isopropyl-pyrido[2,3-d]pyrimidin-4-ylamino)-benzoic acid (100 mg, 0.19 mmol) and O-benzotriazol-1-yl-N,N,N',N'-tetramethyluronium tetrafluoroborate [TBTU] (68 mg, 0.21 mmol) in DMSO (1 mL) was added S-(−)-α-ethylbenzylamine (25 μL, 0.19 mmol) and N,N-diisopropylethylamine (67 μL, 0.38 mmol) dropwise at room temperature under N2. The mixture was stirred at room temperature for 1 hour under N2, and then poured into H2O (20 mL) under stirring. The resulting precipitate was extracted with AcOEt (20 mL). The organic layer was washed with H2O (3 times) and 10% NaHCO3, dried over MgSO4, and evaporated to give yellow amorphous. The oily residue was separated by silica gel column chromatography (AcOEt/n-hexane=10/1) to give pale yellow amorphous, which was solidified by the treatment of i-Pr2O. The resulting solid was collected by filtration, washed with i-Pr2O, and dried at 40° C. for 3 days under reduced pressure to give the title compound as pale yellow crystal (92 mg, 77%). 1H-NMR (300 MHz, DMSO-d6) δ ppm: 1.33 (d, J=7.0 Hz, 6H), 1.45 (d, J=7.3 Hz, 3H), 1.47 (s, 9H), 3.22 (septet, J=7.0 Hz, 1H), 5.16 (quintet, J=7.3 Hz, 1H), 6.97 (d, J=8.4 Hz, 1H), 7.17-7.25 (m, 1H), 7.26-7.40 (m, 4H), 7.32 (d, J=8.8 Hz, 2H), 7.51 (d, J=8.8 Hz, 2H), 7.63 (d, J=8.5 Hz, 1H), 7.74 (br-d, J=8.4 Hz, 1H), 7.93 (br-s, 1H), 8.57 (s, 1H), 8.81 (d, J=7.3 Hz, 1H), 8.84 (d, J=8.5 Hz, 1H), 9.58 (s, 1H), 10.19 (s, 1H) MS ESI+ m/z: 635 (M+H)

Example 89G (S)-4-(4-Amino-phenylsulfanyl)-3-(7-isopropyl-pyrido[2,3-d]pyrimidin-4-ylamino)-N-(1-phenyl-ethyl)-benzamide To a solution of (S)-{4-[2-(7-isopropyl-pyrido[2,3-c]pyrimidin-4-ylamino)-4-(1-phenyl-ethylcarbamoyl)-phenylsulfanyl]-phenyl}-carbamic acid tert-butyl ester (80 mg) in dichloromethane (1.6 mL) was added trifluoroacetic acid [TPA] (0.40 mL) dropwise at room temperature and the mixture was stirred at room temperature for 1 hour. The reaction mixture was portioned between AcOEt and aqueous K2CO3. The organic layer was separated, washed with H2O and brine, dried over MgSO4, and evaporated to pale yellow amorphous, which was solidified by trituration in i-Pr2O. The resulting solid was collected by filtration, washed with i-Pr2O, and dried at 40° C. overnight under reduced pressure to give the title compound as yellow crystal (57 mg, 85%). 1H-NMR (300 MHz, DMSO-d6) δ ppm: 1.34 (d, J=7.0 Hz, 6H), 1.45 (d, J=7.3 Hz, 3H), 3.23 (septet, J=7.0 Hz, 1H), 5.15 (quintet, J=7.3 Hz, 1H), 5.58 (s, 2H), 6.62 (d, J=8.4 Hz, 2H), 6.84 (d, J=8.5 Hz, 1H), 7.12 (d, J=8.4 Hz, 2H), 7.16-7.25 (m, 1H), 7.25-7.40 (m, 4H), 7.63 (d, J=8.4 Hz, 1H), 7.71 (dd, J=8.5, 1.8 Hz, 1H), 7.88 (d, J=1.8 Hz, 1H), 8.57 (s, 1H), 8.75 (d, J=7.3 Hz, 1H), 8.87 (d, J=8.5 Hz, 1H), 10.12 (s, 1H) MS ESI+ m/z: 535 (M+H)

Example 90

(S)-5-(4-aminophenylthio)-4-(7-isopropylpyrido[2,3-c]pyrimidin-4-ylamino)-N-(2-phenylpropyl)thiophene-2-carboxamide Example 90A Ethyl 5-chloro-4-nitrothiophene-2-carboxylate To fuming nitric acid (50 mL) cooled in an ice bath to 5° was added neat ethyl 5-chloro-2-thiophene-2-carboxylate (10 g, 0.0524 mol) dropwise at such a rate that the reaction temperature remained below 10°. The reaction was stirred for 30 minutes at 5-10°, then added ice (200 g) and extracted with ethyl acetate (2×100 mL). The combined organic extracts were washed with water (2×100 mL) and brine (50 mL), then dried over magnesium sulfate and filtered. The filtrate was concentrated by rotary evaporation and the residue purified by silica gel flash chromatography eluting with 10:90 ethyl acetate/hexanes to afford the title compound as a crystalline light yellow solid (7.6 g, 0.0322 mol, 62%). $^1$H NMR (300 MHz, DMSO-D6) δ ppm 1.31 (t, J=7.17 Hz, 3 H) 4.35 (q, J=7.23 Hz, 2 H) 8.17 (s, 1 H).

Example 90B

Ethyl 5-(4-aminophenylthio)-4-nitrothiophene-2-carboxylate

The product of Example 90A (1.0 g, 4.244 mmol), 4-aminothiophenol (0.797 g, 6.366 mmol), and anhydrous sodium acetate (1.74 g, 21.22 mmol) were heated in anhydrous ethanol (40 mL) under a nitrogen atmosphere at reflux for 30 minutes. The reaction was cooled to room temperature, partitioned with ethyl acetate (100 mL) and water (50 mL), separated layers, and washed organic phase with water (2×50 mL) and brine (50 mL). The organic extract was dried over sodium sulfate, filtered, and concentrated by rotary evaporation. Trituration of the resulting solid with ethyl ether (2×30 mL) afforded the title compound as a bright yellow solid (1.167 g, 3.598 mmol, 85%). $^1$H NMR (300 MHz, DMSO-D6) δ ppm 1.24 (t, J=7.17 Hz, 3 H) 4.24 (q, J=7.23 Hz, 2 H) 5.94 (s, 2 H) 6.71 (d, J=8.82 Hz, 2 H) 7.35 (d, J=8.46 Hz, 2 H) 8.08 (s, 1 H); MS (ESI+) m/z 325 (M+H)$^+$, MS (ESI−) m/z 323 (M−H)$^-$.

Example 90C

Ethyl 5-(4-(((9H-fluoren-9-yl)methoxy)carbonylamino)phenylthio)-4-nitrothiophene-2-carboxylate A suspension of the product of Example 90B (0.500 g, 1.541 mmol) and 9-fluorenylmethoxycarbonyl chloride (0.478 g, 1.849 mmol) in methylene chloride (10 mL) under a nitrogen atmosphere was treated with pyridine (0.25 mL, 3.083 mmol), and the resulting solution stirred for 18 hours at room temperature. The reaction was diluted with methylene chloride (50 mL) and washed with 1N aqueous HCl (50 mL) then water (50 mL). The organic was dried over magnesium sulfate, filtered, and concentrated by rotary evaporation. Purification by silica gel flash chromatography eluting with methylene chloride afforded the title compound as a bright yellow solid (0.842 g, quantitative). $^1$H NMR (300 MHz, DMSO-D6) δ ppm 1.23 (t, J=7.17 Hz, 3 H) 4.24 (q, J=7.23 Hz, 2 H) 4.35 (t, J=6.43 Hz, 1 H) 4.57 (d, J=6.25 Hz, 2 H) 7.29-7.50 (m, 4 H) 7.69 (s, 4 H) 7.77 (d, J=7.35 Hz, 2 H) 7.92 (d, J=7.35 Hz, 2 H) 8.11 (s, 1 H) 10.15 (s, 1 H); MS (ESI+) m/z 564 (M+NH$_4$)$^+$, 569 (M+Na)$^+$.

Example 90D

Ethyl 5-(4-(((9H-fluoren-9-yl)methoxy)carbonylamino)phenylthio)-4-aminothiophene-2-carboxylate A solution of the product of Example 90C (0.918 g, 1.679 mmol) in ethanol (14 mL) and tetrahydrofuran (14 mL) was treated with iron powder (0.577 g, 10.33 mmol) and a solution of ammonium chloride (0.588 g, 10.99 mmol) in water (7 mL), then refluxed for one hour. The reaction was cooled, diluted with ethyl acetate (100 mL), and washed with water (3×25 mL) and brine (25 mL). The organic extract was dried over sodium sulfate, filtered, and concentrated by rotary evaporation to afford the title compound as a yellow solid (0.698 g, 1.351 mmol, 80%). $^1$H NMR (300 MHz, DMSO-D6) δ ppm 1.27 (t, J=6.99 Hz, 3 H) 4.19-4.36 (m, 3 H) 4.48 (d, J=6.62 Hz, 2 H) 5.56 (s, 2 H) 7.10 (d, J=8.09 Hz, 2 H) 7.28-7.55 (m, 7 H) 7.74 (d, J=7.35 Hz, 2 H) 7.90 (d, J=7.35 Hz, 2 H) 9.73 (s, 1 H); MS (ESI+) m/z 517 (M+H)$^+$, 539 (M+Na)$^+$.

Example 90E

Ethyl 5-(4-(((9H-fluoren-9-yl)methoxy)carbonylamino)phenylthio)-4-(7-isopropylpyrido[2,3-d]pyrimidin-4-ylamino)thiophene-2-carboxylate The products of Example 12E (0.105 g, 0.484 mmol) and Example 90D (0.250 g, 0.484 mmol) in acetic acid (5 mL) were reacted under a nitrogen atmosphere in a preheated 140° oil bath for 30 minutes. The reaction was cooled and the solvent removed by rotary evaporation. The residue was co-concentrated with methylene chloride/hexanes (1:1 v/v) four times and the resulting solid dried on high vacuum. Purification by silica gel flash chromatography eluting with 3:97 methanol/methylene chloride afforded the title compound (0.247 g, 0.359 mmol, 74%). $^1$H NMR (300 MHz, DMSO-D6) δ ppm 1.27 (t, J=6.99 Hz, 3 H) 1.32 (d, J=6.99 Hz, 6 H) 3.13-3.26 (m, 1 H) 4.18-4.38 (m, 3 H) 4.50 (d, J=6.25 Hz, 2 H) 7.29-7.50 (m, 8 H) 7.62 (d, J=8.82 Hz, 1 H) 7.74 (d, J=7.35 Hz, 2 H) 7.90 (d, J=7.72 Hz, 2 H) 7.92 (d, J=2.21 Hz, 1 H) 8.65 (s, 1 H) 8.79 (d, J=8.46 Hz, 1H) 9.85 (s, 1 H) 10.07 (s, 1 H); MS (ESI+) m/z 688 (M+H)+.

Example 90F 5-(4-Aminophenylthio)-4-(7-isopropylpyrido[2,3-d]pyrimidin-4-ylamino)thiophene-2-carboxylic acid The product of Example 90E (0.245 g, 0.356 mmol) in 1,4-dioxane (3 mL), was treated with a solution of lithium hydroxide monohydrate (0.0747 g, 1.78 mmol) in water (1.5 mL) at room temperature, the resulting mixture was heated at 60° for 25 minutes. The reaction mixture was cooled, diluted with water (10 mL), adjusted the pH to 3 with 1N aqueous HCl, and the resulting precipitate was collected by vacuum filtration. Washing of the crude product with small volumes of 1,4-dioxane afforded the title compound (0.113 g, 0.258 mmol, 72%). MS (ESI+) m/z 438 (M+H)$^+$, MS (ESI−) m/z 436 (M−H)$^-$.

Example 90G (S)-5-(4-aminophenylthio)-4-(7-isopropylpyrido[2,3-d]pyrimidin-4-ylamino)-N-(2-phenylpropyl)thiophene-2-carboxamide The product of Example 90F (62 mg, 0.142 mmol) in dimethyl sulfoxide (2 mL) under a nitrogen atmosphere was reacted with (S)-(-)-☐-methylphenethylamine (23 mg, 0.170 mmol), N,N-diisopropylethylamine (0.123 mL, 0.708 mmol), and O-benzotriazol-1-yl-N,N,N',N'-tetramethyluronium tetrafluoroborate (55 mg, 0.170 mmol at room temperature for 20 hours. The reaction mixture was diluted with water (10 mL), and extracted with ethyl acetate (50 mL). The organic extract was washed sequentially with water (3×10 mL), saturated aqueous sodium hydrogencarbonate (20 mL), and brine (20 mL), dried over magnesium sulfate, filtered, and concentrated by rotary evaporation. Purification of the residue by silica gel flash chromatography eluting with 4:96 methanol/methylene chloride afforded the title compound (67 mg, 0.121 mmol, 85%). $^1$H NMR (300 MHz, DMSO-D6) δ ppm 1.19 (d, J=6.99 Hz, 3 H) 1.33 (d, J=6.99 Hz, 6 H) 2.91-3.07 (m, 1 H) 3.14-3.29 (m, 1 H) 5.50 (s, 2 H) 6.51 (d, J=8.46 Hz, 2 H) 7.12 (d, J=8.82 Hz, 2 H) 7.16-7.34 (m, 5 H) 7.63 (d, J=8.46 Hz, 1 H) 7.77 (s, 1 H) 8.50 (t, J=5.88 Hz, 1 H) 8.62 (s, 1 H) 8.82 (d, J=8.82 Hz, 1 H) 9.97 (s, 1 H); MS (ESI+) m/z 555 (M+H)$^+$, 1109 (2M+H)$^+$, MS (ESI-) m/z 553 (M-H)$^-$.

Example 91

(S)-4-(4-aminophenylthio)-3-(7-isopropylquinazoline-4-ylamino)-N-(1-phenylethyl)benzamide

Example 91A

1-Bromo-4-isopropyl-2-nitrobenzene

To fuming nitric acid (5 mL) cooled to 5° was added neat 4-bromoisopropylbenzene (1.0 g, 5.023 mmol) dropwise at such a rate that the reaction temperature remained below 10°. The reaction was stirred for 2 hours at 5-10°, quenched with ice (50 g), extracted with ethyl acetate (50 mL), and the organic extract was washed with water (2×25 mL) and brine (25 mL), then dried over magnesium sulfate.filtered and concentrated by rotary evaporation. The residue was purified by silica gel flash chromatography eluting with 5:95 ethyl acetate/hexanes to afford the title compound as a light yellow solid (1.03 g, 4.22 mmol, 84%). $^1$H NMR (300 MHz, CHLOROFORM-D) δ ppm 1.27 (d, J=6.99 Hz, 6 H) 2.75-3.23 (m, 1 H) 7.29 (dd, J=8.82, 2.21 Hz, 1 H) 7.63 (d, J=8.09 Hz, 1 H) 7.69 (d, J=2.21 Hz, 1 H); MS (DCI) m/z 261/263 (M+NH$_4$)$^+$.

Example 91B

4-Isopropyl-2-nitrobenzonitrile

The product of Example 91A (0.581 g, 2.380 mmol) and copper (I) cyanide (0.426 g, 4.760 mmol) in N,N-dimethylformamide (5 mL) under a nitrogen atmosphere were heated in 160° oil bath for 1.5 hour. The reaction was cooled, treated with a solution of iron (III) chloride hexahydrate (2.48 g) in water (3.72 mL) and concentrated hydrochloric acid (0.62 mL), and then heated at 65° for 20 minutes. The cooled reaction mixture was extracted with ethyl ether (2×50 mL). The combined ethereal extracts were washed sequentially with 1N aqueous HCl (25 mL), 3N aqueous sodium hydroxide (25 mL), water (25 mL), and brine (25 mL) then dried over magnesium sulfate, filtered, and concentrated by rotary evaporation. Purification of the residue by silica gel flash chromatography eluting with 20:80 ethyl acetate/hexanes afforded the title compound as a yellow liquid (0.351 g, 1.845 mmol, 58%). $^1$H NMR (300 MHz, CHLOROFORM-D) ☐ppm 1.33 (d, J=6.99 Hz, 6 H) 2.82-3.47 (m, 1 H) 7.66 (dd, J=7.91, 1.29 Hz, 1 H) 7.83 (d, J=7.72 Hz, 1 H) 8.18 (d, J=1.47 Hz, 1 H); MS (DCI) m/z 208 (M+NH$_4$)$^+$.

Example 91C 4-isopropyl-2-nitrobenzoic acid

The product of Example 91B (1.746 g, 9.1798 mmol) dissolved in a 2:1:1 v/v/v mixture of water/acetic acid/concentrated sulfuric acid (24 mL) was heated at reflux for 3 days. The reaction was cooled, poured onto ice water (80 mL) and adjusted to pH12 with 6N aqueous sodium hydroxide. The reaction was washed with ethyl ether (3×50 mL). The aqueous phase was acidified to pH 2 with concentrated hydrochloric acid and extracted with ethyl ether (2×75 mL). The ethereal extracts were dried over magnesium sulfate, filtered, and concentrated by rotary evaporation. The residue was co-concentrated with methylene chloride (5 mL)/hexanes (100 mL) three times and dried on high vacuum to afford the title compound as an off-white solid (1.402 g, 6.702 mmol, 73%). $^1$H NMR (300 MHz, DMSO-D6) δ ppm 1.23 (d, J=6.62 Hz, 6 H) 2.88-3.23 (m, 1 H) 7.66 (dd, J=8.09, 1.84 Hz, 1 H) 7.80 (d, J=7.72 Hz, 1 H) 7.83 (d, J=1.47 Hz, 1 H) 13.70 (br s, 1 H).

Example 91D

2-Amino-4-isopropylbenzoic acid

The product of Example 91C (0.697 g, 3.332 mmol) was hydrogenated in methanol (30 mL) with 10% palladium-on-carbon (70 mg) at 1 atmosphere hydrogen pressure (balloon) for 2 hours. The reaction was filtered through a 0.45 micron PTFE membrane and the catalyst thoroughly washed with methanol. The filtrate was concentrated by rotary evaporation to give the title compound (0.585 g, 3.264 mmol, 98%). $^1$H NMR (300 MHz, DMSO-D6) δ ppm 1.15 (d, J=6.62 Hz, 6 H) 2.61-2.92 (m, 1 H) 6.41 (dd, J=8.46, 1.47 Hz, 1 H) 6.58 (d, J=1.84 Hz, 1 H) 7.60 (d, J=8.46 Hz, 1 H) 8.46 (br s, 2 H); MS (ESI+) m/z 180 (M+H)$^+$.

Example 91E

7-Isopropylquinazolin-4(3H)-one

The product of Example 91D (0.579 g, 3.231 mmol) was reacted with formamide (1.3 mL) under a nitrogen atmosphere in a microwave (Personal Chemistry Emrys Creator, 300 W) at 150° C. for 30 minutes. The cooled reaction gave a solid mass which was recrystallized from absolute ethanol (2 mL) to afford the title compound as an off-white solid (0.208 g, 1.105 mmol, 34%). $^1$H NMR (300 MHz, DMSO-D6) δ ppm 1.26 (d, J=6.99 Hz, 6 H) 2.91-3.21 (m, 1 H) 7.44 (dd, J=8.27, 1.65 Hz, 1 H) 7.50 (d, J=1.84 Hz, 1 H) 8.02-8.07 (m, 2 H) 12.15 (s, 1 H); MS (APCI) m/z 189 (M+H)$^+$, 211 (M+Na)$^+$.

Example 91F

4-Chloro-7-isopropylquinazoline

The product of Example 91E (100 mg, 0.5313 mmol) in phosphorous oxychloride (2 mL) was heated under a nitrogen atmosphere at reflux for one hour. The reaction was cooled and concentrated by rotary evaporation. The residue was dissolved in ethyl acetate (50 mL) and washed sequentially with saturated aqueous sodium hydrogencarbonate (2×25 mL), water (25 mL), and brine (25 mL). The organic extract was dried over sodium sulfate, filtered, and concentrated by rotary evaporation to afford the title compound as a yellow oil (107 mg, 0.5177 mmol, 97%). $^1$H NMR (300 MHz, DMSO-D6) δ ppm 1.33 (d, J=6.99 Hz, 6 H) 3.14-3.29 (m, 1 H) 7.86 (dd, J=8.64, 1.65 Hz, 1 H) 7.93 (s, 1 H) 8.22 (d, J=8.46 Hz, 1 H) 9.07 (s, 1 H).

Example 91G (S)-tert-butyl 4-(2-(7-isopropylquinazoline-4-ylamino)-4-(1-phenylethylcarbamoyl)phenylthio) phenylcarbamate (S)-tert-butyl 4-(2-amino-4-(1-phenylethylcarbamoyl) phenylthio)-phenylcarbamate (50 mg, 0.1078 mmol) and the product of Example 91F (24.5 mg, 0.1186 mmol) were heated at reflux in anhydrous ethanol (2 mL) under a nitrogen atmosphere for one hour. The reaction was cooled and concentrated by rotary evaporation. The residue was purified by silica gel flash chromatography eluting with 3:97 methanol/methylene chloride to afford the title compound as an off-white solid (51 mg, 0.0805 mmol, 68%). $^1$H NMR (300 MHz, DMSO-D6) δ ppm 1.31 (d, J=6.99 Hz, 6 H) 1.45 (d, J=7.35 Hz, 3 H) 1.47 (s, 9 H) 3.03-3.21 (m, 1 H) 5.01-5.29 (m, 1 H) 6.96 (d, J=8.46 Hz, 1 H) 7.16-7.25 (m, 1 H) 7.26-7.43 (m, 3 H) 7.32 (d, J=8.09 Hz, 2 H) 7.51 (d, J=8.82 Hz, 2 H) 7.55-7.63 (m, 2 H) 7.72 (dd, J=8.46, 1.47 Hz, 1 H) 7.94 (d, J=1.47 Hz, 1 H) 8.41 (d, J=8.82 Hz, 1 H) 8.44 (s, 1 H) 8.80 (d, J=8.09 Hz, 1 H) 9.58 (s, 1 H) 9.95 (s, 1 H); MS (ESI+) m/z 634 (M+H)+; MS (ESI−) m/z 632 (M−H)+.

Example 91H (S)-4-(4-aminophenylthio)-3-(7-isopropylquinazoline-4-ylamino)-N-(1-phenylethyl)benzamide The product of Example 91G (36 mg, 0.0568 mmol) was treated with 1:1 v/v methylene chloride/trifluoroacetic acid (3 mL) at room temperature for one hour then concentrated by rotary evaporation. The residue was dissolved in ethyl acetate (50 mL), washed with saturated aqueous sodium hydrogencarbonate (25 mL), water (25 mL), and brine (25 mL) then dried over magnesium sulfate, filtered, and concentrated by rotary evaporation. Purification by silica gel flash chromatography eluting with 3:97 methanol/methylene chloride afforded the title compound as a white solid (22 mg, 0.0412 mmol, 73%). $^1$H NMR (300 MHz, DMSO-D6) δ ppm 1.31 (d, J=6.99 Hz, 6 H) 1.45 (d, J=7.35 Hz, 3 H) 3.01-3.20 (m, 1 H) 5.07-5.26 (m, 1 H) 5.57 (s, 2 H) 6.61 (d, J=8.46 Hz, 2 H) 6.83 (d, J=8.46 Hz, 1 H) 7.11 (d, J=8.82 Hz, 2 H) 7.17-7.43 (m, 5 H) 7.54-7.64 (m, 2 H) 7.69 (dd, J=8.46, 1.10 Hz, 1 H) 7.89 (d, J=1.47 Hz, 1 H) 8.43 (t, J=4.23 Hz, 2 H) 8.74 (d, J=7.72 Hz, 1 H) 9.88 (s, 1 H); MS (ESI+) m/z 534 (M+H)+, 1067 (2M+H)+; MS (ESI−) m/z 532 (M−H)−.

Example 92

(R)-4-(4-Aminophenylthio)-N-(2,3-dihydro-1H-inden-1-yl)-3-(7-isopropylquinazoline-4-ylamino)benzamide Example 92A Methyl 4-(4-aminophenylthio)-3-nitrobenzoate A solution of methyl 4-chloro-3-nitrobenzoate (1.00 g, 4.638 mmol) in anhydrous ethanol (40 mL) was treated with 4-aminothiophenol (0.813 g, 6.494 mmol) and anhydrous sodium acetate (1.90 g, 23.19 mmol) at room temperature under a nitrogen atmosphere, at reflux for 2 hours. The reaction was cooled, diluted with ethyl acetate (100 mL), and washed with water (3×50 mL) and brine (50 mL). The organic phase was dried over magnesium sulfate, filtered, and concentrated by rotary evaporation. The resulting orange solid was triturated with ethyl ether/hexanes (1:1 v/v, 3×30 mL), and dried in vacuo to afford the title compound (1.36 g, 4.469 mmol, 96%). $^1$H NMR (300 MHz, DMSO-D6) δ ppm 3.87 (s, 3 H) 5.80 (s, 2 H) 6.70 (d, J=8.46 Hz, 2 H) 7.00 (d, J=8.46 Hz, 1 H) 7.23 (d, J=8.46 Hz, 2 H) 8.05 (dd, J=8.46, 1.84 Hz, 1 H) 8.64 (d, J=1.84 Hz, 1 H). MS (ESI+) m/z 305 (M+H)+.

Example 92B

Methyl 4-(4-tert-butoxycarbonylamino)phenylthio)-3-nitrobenzoate

The product of Example 92A (1.36 g, 4.469 mmol) in 1,4-dioxane (25 mL) under a nitrogen atmosphere was treated with a solution of di-tert-butyl dicarbonate (1.46 g, 6.703 mmol) in 1,4-dioxane (5 mL) at room temperature, then refluxed for 3.5 hours. The reaction was cooled and additional di-tert-butyl dicarbonate (1.46 g) was added, and refluxed for another 3.5 hours. Recooled the reaction, treated with di-tert-butyl dicarbonate (1.46 g), and refluxed for 16 hours. The reaction was cooled to room temperature and concentrated by rotary evaporation, then dried. The residue was triturated with ethyl acetate (30 mL) and vacuum filtered to give the title compound as a yellow solid (1.56 g, (3.857 mmol, 86%). $^1$H NMR (300 MHz, DMSO-D6) δ ppm 1.50 (s, 9 H) 3.87 (s, 3 H) 6.95 (d, J=8.46 Hz, 1 H) 7.47-7.57 (d, J=8.82 Hz, 2 H) 7.67 (d, J=8.82 Hz, 2 H) 8.05 (dd, J=8.64, 2.02 Hz, 1 H) 8.66 (d, J=1.84 Hz, 1 H) 9.77 (s, 1 H). MS (ESI+) m/z 422 (M+NH$_4$)+, 427 (M+Na)+.

Example 92C

Methyl 3-amino-4-(4-tert-butoxycarbonylamino) phenylthio)benzoate

The product of Example 92B (1.56 g, 3.857 mmol) in ethanol (20 mL) and tetrahydrofuran (20 mL) was treated with iron powder (1.32 g, 23.72 mmol) and a solution of ammonium chloride (1.351 g, 25.26 mmol) in water (10 mL), then heated at 80° for three hours. The reaction was cooled, diluted with ethyl acetate (150 mL), and washed with water (3×50 mL) and brine (50 mL). The organic extract was dried over magnesium sulfate, filtered, and concentrated by rotary evaporation. Purification by silica gel flash chromatography eluting with 3:97 methanol/methylene chloride afforded the title compound as a yellow solid (0.920 g, 2.46 mmol, 64%). $^1$H NMR (300 MHz, DMSO-D6) δ ppm 1.46 (s, 9 H) 3.80 (s, 3 H) 5.53 (s, 2 H) 7.05-7.14 (m, 2 H) 7.19 (d, J=8.82 Hz, 2 H) 7.36 (d, J=1.84 Hz, 1 H) 7.44 (d, J=8.82 Hz, 2 H) 9.46 (s, 1 H). MS (ESI−) m/z 373 (M−H)−.

Example 92D methyl 4-(4-(tert-butoxycarbonylamino)phenylthio)-3-(7-isopropylquinazoline-4-ylamino)benzoate The products of Example 91F (0.572 g, 2.768 mmol) and methyl 3-amino-4-(4-(tert-butoxycarbonylamino)phenylthio)benzoate the product of Example 89C or Example 92C (0.902 g, 2.409 mmol) were reacted in anhydrous ethanol (25 mL) under a nitrogen atmosphere at reflux for 30 minutes. The reaction was cooled and concentrated by rotary evaporation. The residue was dissolved in methylene chloride (50 mL) and washed with saturated aqueous sodium hydrogencarbonate (25 mL) and water (25 mL). The organic phase was dried over magnesium sulfate, filtered, and concentrated by rotary evaporation. Purification by silica gel flash chromatography eluting with 3:97 methanol/methylene chloride afforded the title compound as a white solid (0.505 g, 0.927 mmol, 33%). $^1$H NMR (300 MHz, DMSO-D6) δ ppm 1.32 (d, J=6.99 Hz, 6 H) 1.48 (s, 9 H) 2.99-3.21 (m, 1 H) 3.83 (s, 3 H) 6.93 (d, J=8.46 Hz, 1 H) 7.37 (d, J=8.82 Hz, 2 H) 7.55 (d, J=8.82 Hz, 2 H) 7.55-7.64 (m, 2 H) 7.75 (dd, J=8.46, 1.84 Hz, 1 H) 7.91 (d, J=1.84 Hz, 1 H) 8.41 (d, J=8.46 Hz, 1 H) 8.45 (s, 1 H) 9.62 (s, 1 H) 9.92 (s, 1 H). MS (ESI+) m/z 545 (M+H)+.

Example 92E 4-(4-(tert-butoxycarbonylamino)phenylthio)-3-(7-isopropylquinazoline-4-ylamino)benzoic acid The product of Example 92D (0.505 g, 0.927 mmol) was suspended in 1,4-dioxane (6 mL), treated with a solution of lithium hydroxide monohydrate (0.078 g, 1.85 mmol) in water (3 mL) at room temperature, then heated at 50° for one hour. The reaction was diluted with water (25 mL), adjusted to pH 1 with 1N aqueous HCl, and extracted with ethyl acetate (50 mL). The organic extract was washed with water (25 mL) and brine (25 mL), dried over magnesium sulfate, filtered, and concentrated by rotary evaporation to afford the title compound as a light yellow solid (0.433 g, 0.816 mmol, 88%). $^1$H NMR (300 MHz, DMSO-D6) δ ppm 1.31 (d, J=6.99 Hz, 6 H) 1.48 (s, 9 H) 2.98-3.23 (m, 1 H) 6.92 (d, J=8.09 Hz, 1 H) 7.36 (d, J=8.46 Hz, 2 H) 7.54 (d, J=8.82 Hz, 2 H) 7.59 (d, J=11.77 Hz, 1 H) 7.73 (d, J=8.09 Hz, 1 H) 7.89 (s, 1 H) 8.34-8.49 (m, 2 H) 9.61 (s, 1 H) 9.94 (s, 1 H). MS (ESI+) m/z 531 (M+H)+.

Example 92F (R)-4-(4-Aminophenylthio)-N-(2,3-dihydro-1H-inden-1-yl)-3-(7-isopropylquinazoline-4-ylamino)benzamide The product of Example 92E (45 mg, 0.0848 mmol) was dissolved in dichloromethane (2 mL), treated with trifluoroacetic acid (2 mL), at room temperature for one hour. The reaction was concentrated by rotary evaporation and azeotroped from dichloromethane/hexanes (25 mL, 1:1 v/v) again. Drying under high vacuum afforded the deprotected compound as a yellow powder, which was dissolved in dimethyl sulfoxide (2 mL) under a nitrogen atmosphere and treated with (R)-(−)-1-aminoindane (13.6 mg, 0.102 mmol), N,N-diisopropylethylamine (0.074 mL, 0.424 mmol) and O-benzotriazol-1-yl-N,N,N',N'-tetramethyluronium tetrafluoroborate (32.7 mg, 0.102 mmol) at room temperature for 2 hours. The reaction was diluted with water (10 mL), extracted with ethyl acetate (50 mL) and the organic extract was washed with water (3×10 mL), saturated aqueous sodium hydrogencarbonate (20 mL), and brine (20 mL). The organic phase was dried over magnesium sulfate, filtered, and concentrated by rotary evaporation. Purification by silica gel flash chromatography eluting with 4:96 methanol/methylene chloride afforded the title compound as a white solid (22 mg, 0.0403 mmol, 48%). $^1$H NMR (300 MHz, DMSO-D6) δ ppm 1.31 (d, J=6.99 Hz, 6 H) 1.85-2.09 (m, 1 H) 2.35-2.47 (m, 1 H) 2.75-3.03 (m, 2 H) 3.04-3.18 (m, 1 H) 5.50-5.60 (m, 1 H) 5.57 (s, 2 H) 6.62 (d, J=8.46 Hz, 2 H) 6.82 (d, J=8.46 Hz, 1 H) 7.12 (d, J=8.46 Hz, 2 H) 7.15-7.29 (m, 4 H) 7.57 (dd, J=8.46, 1.47 Hz, 1 H) 7.60 (s, 1 H) 7.73 (dd, J=8.46, 1.84 Hz, 1 H) 7.91 (d, J=1.84 Hz, 1 H) 8.42 (t, J=4.41 Hz, 2 H) 8.72 (d, J=8.09 Hz, 1 H) 9.83 (s, 1 H). MS (ESI+) m/z 546 (M+H)+, 1091 (2M+H)+.

Example 93

4-(4-Aminophenylthio)-N-(1-(hydroxymethyl)-2,3-dihydro-1H-inden-1-yl)-3-(7-isopropylpyrido[2,3-d]pyrimidin-4-ylamino)benzamide Example 93A Ethyl 1-amino-2,3-dihydro-1H-indene-1-carboxylate Thionyl chloride (0.617 mL, 8.465 mmol) was added dropwise to anhydrous ethanol (6 mL) cooled to −30° followed by 1-amino-2,3-dihydro-1H-indene-1-carboxylic acid (0.300 g, 1.693 mmol) the reaction was then refluxed for 4 hours. The reaction was concentrated by rotary evaporation and diluted with water (5 mL) and the pH was adjusted to 9 with 6N aqueous sodium hydroxide. The solution was extracted with ethyl acetate (2×25 mL) and the organic extracts were washed with brine (25 mL), dried over sodium sulfate, filtered, and concentrated by rotary evaporation to afford the title compound as an oil (0.293 g, 1.43 mmol, 84%). $^1$H NMR (300 MHz, DMSO-D6) ☐ ppm 1.12 (t, J=7.17 Hz, 3 H) 1.85-2.07 (m, 1 H) 2.31 (s, 2 H) 2.51-2.66 (m, 1 H) 2.93 (t, J=6.99 Hz, 2 H) 3.90-4.21 (m, 2 H) 7.13-7.34 (m, 4 H). MS (DCI) m/z 206 (M+H)+, 223 (M+NH$_4$)+.

Example 93B (1-Amino-2,3-dihydro-1H-inden-1-yl)methanol

The product of Example 93A (0.292 g, 1.423 mmol) and sodium borohydride (0.275 g, 7.113 mmol) were reacted in 1:3 v/v water/ethanol (7 mL), at reflux for 4 hours. The reaction was concentrated by rotary evaporation the partitioned between water (5 mL), ethyl ether (20 mL), 1N aqueous sodium hydroxide (0.712 mL). Solid sodium chloride was added to saturate the aqueous phase and separate the phases. The aqueous phase was extracted with ethyl ether (2×25 mL). The combined ethereal extracts were washed with brine (25 mL), dried over potassium carbonate, filtered, and concentrated by rotary evaporation to afford the title compound (0.197 g, 1.209 mmol, 85%). NMR (300 MHz, DMSO-D6) δ ppm 1.64-1.80 (m, 1 H) 1.85 (s, 2 H) 2.16-2.31 (m, 1 H) 2.63-2.91 (m, 2 H) 3.30 (d, J=5.52 Hz, 2 H) 4.74 (t, J=5.52 Hz, 1 H) 6.80-7.63 (m, 4 H). MS (DCI) m/z 164 (M+H)+, 181 (M+NH$_4$)+.

Example 93C 4-(4-Aminophenylthio)-N-(1-(hydroxymethyl)-2,3-dihydro-1H-inden-1-yl)-3-(7-isopropylpyrido[2,3-c]pyrimidin-4-ylamino)benzamide The product of Example 96H (57 mg, 0.0865 mmol) was reacted with the product of Example 93B (16.9 mg, 0.104 mmol), N,N-diisopropylethylamine (0.075 mL, 0.433 mmol), and O-benzotriazol-1-yl-N,N,N',N'-tetramethyluronium tetrafluoroborate (33 mg, 0.104 mmol) in dimethyl sulfoxide (2 mL) under a nitrogen atmosphere at room temperature for 1 hour. The reaction was diluted with water (10 mL), extracted with ethyl acetate (50 mL). The organic extract was washed sequentially with water (3×10 mL), saturated aqueous sodium hydrogencarbonate (20 mL), and brine (20 mL) then dried over magnesium sulfate, filtered, and concentrated by rotary evaporation. Purification of the residue by silica gel flash chromatography eluting with 5:95 methanol/methylene chloride afforded the title compound as a light yellow solid (28 mg, 0.0486 mmol, 56%). $^1$H NMR (300 MHz, DMSO-D6) δ ppm 1.33 (d, J=6.99 Hz, 6 H) 2.19-2.38 (m, 1 H) 2.49-2.63 (m, 1 H) 2.76-2.90 (m, 1 H) 2.91-3.07 (m, 1 H) 3.16-3.28 (m, 1 H) 3.53 (dd, J=11.03, 5.88 Hz, 1 H) 3.73 (dd, J=11.03, 5.88 Hz, 1 H) 5.09 (t, J=6.07 Hz, 1 H) 5.57 (s, 2 H) 6.61 (d, J=8.46 Hz, 2 H) 6.81 (d, J=8.09 Hz, 1 H) 7.05-7.22 (m, 3 H) 7.10 (d, J=8.46 Hz, 2 H) 7.27 (d, J=7.35 Hz, 1 H) 7.55-7.71 (m, 2 H) 7.80 (d, J=1.84 Hz, 1 H) 7.94 (s, 1 H) 8.56 (s, 1 H) 8.86 (d, J=8.46 Hz, 1 H) 10.10 (s, 1 H). MS (ESI+) m/z 577 (M+H)$^+$. MS (ESI−) m/z 575 (M−H)$^-$.

Example 94

Sodium (S)-2-(4-(4-(2-(7-isopropylpyrido[2,3-d]pyrimidin-4-ylamino)-4-(1-phenylethylcarbamoyl)phenylthio)phenylthio)-2-methyl-4-oxobutan-2-yl)-3,5-dimethylphenyl phosphate

Example 94A 4,4,5,7-tetramethylchroman-2-one 3,5-Dimethylphenol (5.00 g, 0.0409 mol) and methyl 3,3-dimethylacrylate (5.14 g, 0.045 mol) were added to methanesulfonic acid (5 mL) at room temperature followed by heating at 70° for 17 hours. The reaction was cooled, diluted with water (750 mL), extracted with ethyl acetate (2×200 mL) and the combined organic extracts were washed with saturated aqueous sodium hydrogencarbonate (2×100 mL) and brine (50 mL). The organic phase was dried over magnesium sulfate, filtered, and concentrated by rotary evaporation. Purification by silica gel flash chromatography eluting with methylene chloride afforded the title compound as a beige solid (7.73 g, 0.0378 mol, 92%). $^1$H NMR (300 MHz, CHLOROFORM-D) δ ppm 1.43 (s, 6 H) 2.27 (s, 3 H) 2.46 (s, 3 H) 2.59 (s, 2 H) 6.74 (s, 2 H). MS (DCI) m/z 205 (M+H)$^+$, 222 (M+NH$_4$)$^+$.

Example 94B 2-(4-Hydroxy-2-methylbutan-2-yl)-3,5-dimethylphenol

The product of Example 94A (4.00 g, 0.0196 mol) in tetrahydrofuran (75 mL) was added dropwise to a solution of lithium aluminum hydride (1.0 M in tetrahydrofuran, 20.6 mL, 0.0206 mol) in tetrahydrofuran (105 mL) at room temperature over a period of 30 minutes then stirred an additional one hour at ambient temperature. The stirred reaction was quenched by dropwise addition of saturated aqueous ammonium chloride (5 mL) after 15 minutes, the precipitate was removed by vacuum filtration. The filtrate was concentrated by rotary evaporation and the residue purified by silica gel flash chromatography eluting with 4:96 methanol/methylene chloride to afford the title compound as a white solid (2.94 g, 0.014 mol, 72%). $^1$H NMR (300 MHz, DMSO-D6) δ ppm 1.44 (s, 6 H) 2.00-2.07 (m, 2 H) 2.08 (s, 3 H) 2.36 (s, 3 H) 3.11-3.28 (m, 2 H) 4.09 (t, J=4.78 Hz, 1 H) 6.29 (s, 1 H) 6.42 (s, 1 H) 8.95 (s, 1 H). MS (ESI+) m/z 209 (M+H)$^+$, 226 (M+NH$_4$)$^+$.

Example 94C 2-(4-tert-Butyldimethylsilyloxy)-2-methylbutan-2-yl)-3,5-dimethylphenol The product of Example 94B (2.938 g, 0.0141 mol) was treated with tert-butyldimethylsilyl chloride (2.63 g, 0.0169 mol) and imidazole (2.40 g, 0.0353 mol) in N,N-dimethylformamide (30 mL) under a nitrogen atmosphere at room temperature for 2 hours. The solvent was removed by rotary evaporation and high vacuum. The residue was purified by silica gel flash chromatography eluting with 30:70 ethyl acetate/hexanes to afford the title compound as a white solid (4.295 g, 0.0133 mol, 94%). $^1$H NMR (300 MHz, DMSO-D6) δ ppm −0.07 (s, 6 H) 0.80 (s, 9 H) 1.45 (s, 6 H) 2.00-2.17 (m, 5 H) 2.37 (s, 3 H) 3.34-3.44 (m, 2 H) 6.30 (s, 1 H) 6.43 (s, 1 H) 9.00 (s, 1 H). MS (DCI) m/z 323 (M+H)$^+$, 340 (M+NH$_4$)$^+$.

Example 94D

Dibenzyl 2-(4-(tert-butyldimethylsilyloxy)-2-methylbutan-2-yl)-3,5-dimethylphenyl phosphate The product of Example 94C (1.70 g, 5.272 mmol) was treated with solid potassium tert-butoxide (0.685 g, 5.799 mmol) in tetrahydrofuran (90 mL) at 60° for 5 minutes followed by tetrabenzyl pyrophosphate (3.123 g, 5.799 mmol) for one additional hour. Upon cooling the resulting thick white reaction mixture was diluted with hexanes (125 mL), vacuum filtered and the filtrate was concentrated by rotary evaporation. Purification of the residue by silica gel flash chromatography eluting with 20:80 ethyl acetate/hexanes afforded the title compound as a colorless oil (3.07 g, 5.27 mmol, quantitative). $^1$H NMR (300 MHz, CHLOROFORM-D) δ ppm −0.07 (s, 6 H) 0.82 (s, 9 H) 1.51 (s, 6 H) 2.07 (t, J=7.35 Hz 2 H) 2.16 (s, 3 H) 2.49 (s, 3 H) 3.47 (t, J=7.35 Hz, 2 H) 5.10 (d, J=8.09 Hz, 4 H) 6.70 (s, 1 H) 7.08 (s, 1 H) 7.27-7.38 (m, 10 H). MS (ESI+) m/z 583 (M+H)$^+$, 605 (M+Na)$^+$.

Example 94E 3-(2-Bis(benzyloxy)phosphoryloxy)-4,6-dimethylphenyl)-3-methylbutanoic acid The product of Example 94D (0.732 g, 1.256 mmol) was reacted with potassium fluoride (0.0803 g, 1.382 mmol) in acetone (10 mL) at 0° followed by dropwise addition of Jones reagent (1.04 mL, prepared according to Fieser and Fieser 1, p. 142) over 20 minutes. After 2 hours, added additional Jones reagent (0.50 mL) and then quenched after an additional 2 hours with isopropyl alcohol (1 mL) for 20 minutes. The reaction mixture was concentrated by rotary evaporation, dissolved in water (25 mL), extracted with ethyl acetate (3×50 mL), and the combined organic layers were washed with brine (25 mL) and dried over magnesium sulfate. Filtration and concentration of the filtrate by rotary evaporation afforded the title compound as an oil (0.544 g, 1.127 mmol, 90%). $^1$H NMR (300 MHz, CHLOROFORM-D) δ ppm 1.61 (s, 6 H) 2.12 (S, 3 H) 2.51 (s, 3 H) 2.84 (s, 2 H) 5.11 (d, J=8.09 Hz, 4 H) 6.73 (s, 1 H) 6.97 (s, 1 H) 7.28-7.42 (m, 10 H). MS (ESI+) m/z 483 (M+H)$^+$, 505 (M+Na)$^+$. MS (ESI−) m/z 481 (M−H)$^-$.

Example 94F (S)-Dibenzyl 2-(4-(2-(7-isopropylpyrido[2,3-c]pyrimidin-4-ylamino)-4-(1-phenylethylcarbamoyl)phenylthio)phenylamino)-2-methyl-4-oxobutan-2-yl)-3,5-dimethylphenyl phosphate The product of Example 94E (0.235 g, 0.4863 mmol) was treated with N-(3-dimethylaminopropyl)-N'-ethylcarbodiimide hydrochloride (0.129 g, 0.6733 mmol) and 4-dimethylaminopyridine (7 mg, 0.056 mmol) in N,N-dimethylformamide (3.7 mL) under a nitrogen atmosphere at 0° for 15 minutes, followed by the product of Example 89G (0.200 g, 0.374 mmol) at 0° to room temperature over 20 hours. The reaction was concentrated by rotary evaporation and under high vacuum. Purification by silica gel flash chromatography eluting with 3:97 methanol/methylene chloride afforded the title compound as a yellow solid (0.151 g, 0.151 mmol, 40%). $^1$H NMR (300 MHz, DMSO-D6) δ ppm 1.33 (d, J=6.99 Hz, 6 H) 1.45 (d, J=6.99 Hz, 3 H) 1.56 (s, 6 H) 2.10 (s, 3 H) 2.48 (s, 3 H) 2.89 (s, 2 H) 3.14-3.27 (m, 1 H) 5.14 (d, J=8.09 Hz, 4 H) 6.73 (s, 1 H) 6.92 (s, 1 H) 6.97 (d, J=8.82 Hz, 1 H) 7.15-7.43 (m, 17 H) 7.53 (d, J=8.46 Hz, 2 H) 7.62 (d, J=8.09 Hz, 1 H) 7.71 (d, J=8.46 Hz, 1 H) 7.93 (s, 1 H) 8.58 (s, 1 H) 8.81 (t, J=8.46 Hz, 2 H) 9.89 (s, 1 H) 10.23 (s, 1 H). MS (ESI+) m/z 999 (M+H)$^+$. MS (ESI-) m/z 997 (M-H)$^-$.

Example 94G

Sodium (S)-2-(4-(4-(2-(7-isopropylpyrido[2,3-c]pyrimidin-4-ylamino)-4-(1-phenylethylcarbamoyl)phenylthio)phenylthio)-2-methyl-4-oxobutan-2-yl)-3,5-dimethylphenyl phosphate A suspension of the product of Example 94F (0.149 g, 0.1491 mmol) in acetonitrile (3 mL) under a nitrogen atmosphere was treated with sodium iodide (0.0894 g, 0.5965 mmol) followed by dropwise addition of chlorotrimethylsilane (0.076 mL, 0.5965 mmol) at room temperature. After 3 hours the reaction was quenched with water (3 mL), adjusted pH to 9 with saturated aqueous sodium hydrogencarbonate, water was added until solution clouded then sufficient methanol to regain a clear solution. The solution was injected on a $C_{18}$ HPLC column (Biotage 40S cartridge) and eluted with water (5 minutes) followed by a gradient of 0% to 100% methanol over 25 minutes. The product containing fractions, which eluted at 21-26 minutes, were combined, concentrated by rotary evaporation, and co-evaporated with a mixture of methanol, methylene chloride, and hexanes. Drying on high vacuum overnight afforded the title compound as a yellow solid (0.055 g, 0.0637 mmol, 43%). $^1$H NMR (300 MHz, DMSO-D6) δ ppm 1.28 (d, J=6.99 Hz, 6 H) 1.43 (d, J=6.99 Hz, 3 H) 1.63 (s, 6 H) 2.07 (s, 3 H) 2.33 (s, 3 H) 2.80 (s, 2 H) 2.98-3.13 (m, 1 H) 5.02-5.23 (m, 1 H) 6.36 (s, 1 H) 7.09-7.47 (m, 10 H) 7.58 (d, J=8.82 Hz, 2 H) 7.93 (s, 1 H) 8.59 (br s, 2 H) 11.70 (s, 1 H). MS (ESI+) m/z 819 (M+H)$^+$, 862 (M+2Na)$^+$. MS (ESI-) m/z 817 (M-H)$^-$.

Example 95 sodium 2-(4-(4-aminophenylthio)-3-(7-isopropylpyrido[2,3-d]pyrimidin-4-ylamino)benzamido)-2-methylpropyl phosphate

Example 95A benzyl 1-hydroxy-2-methylpropan-2-ylcarbamate

A solution of 2-amino-2-methylpropan-1-ol (1.0 g, 11.2 mmol), triethylamine (1.7 mL, 12.2 mmol) and N-(benzyloxycarbonyloxy)-succinimide (3.1 g, 12.4 mmol) in THF (100 mL) at 0° C. were reacted for 0.5 hours then at room temperature for an additional hour. The reaction was concentrated and extracted with ethyl acetate (100 mL). The organic extract was washed sequentially with water, brine, dried over MgSO4, and concentrated in vacuo. The residue was purified by chromatography on silica gel, eluting with a gradient of ethyl acetate in dichloromethane (0-20%) to give the title compound as a colorless oil (2.5 g, quantitative).

Example 95B benzyl 1-(di-tert-butoxyphosphoryloxy)-2-methylpropan-2-ylcarbamate The product of Example 95A (0.80 g, 3.8 mmol), di-tert-butyl diethylphosphoramidite (1.07 mL, 3.8 mmol), and 1-H-tetrazole (0.63 g, 8.99 mmol) in THF (35 mL) were reacted at room temperature for 12 hours. The reaction was diluted with dichloromethane (35 mL) and cooled to −45° C., and treated with mCPBA (0.90 g, 4.0 mmol) for 0.5 hours then diluted with ethyl acetate (100 mL). The organics were washed with 10% Na2CO3 (2×), brine, dried over MgSO4, and concentrated. The residue was purified by chromatography on silica gel, eluting with a gradient of ethyl acetate in dichloromethane (0-25%) to give the title compound as a colorless oil (0.926 g, 62%).

Example 95C 2-amino-2-methylpropyl di-tert-butyl phosphate

The product of Example 95B (0.40 g, 0.96 mmol) and 20% palladium hydroxide on carbon (0.21 g) in a ethyl acetate (10 mL) and methanol (1 mL) was stirred under a an atmosphere of hydrogen for 0.5 hours. The reaction was filtered through a bed of celite and concentrate to give the title product (0.256 g).

Example 95D tert-butyl 4-(4-(1-(di-tert-butoxyphosphoryloxy)-2-methylpropan-2-ylcarbamoyl)-2-(7-isopropylpyrido[2,3-d]pyrimidin-4-yl amino)phenylthio)phenylcarbamate To a solution of the product of Example 89E (100 mg, 0.19 mmol), O-benzotriazol-1-yl-N,N,N',N'-tetramethyluronium tetrafluoroborate [TBTU] (72 mg, 0.22 mmol), the product of Example 95C (65 mg, 0.23 mmol) in DMSO (1 mL) was added N,N-diisopropylethylamine (0.065 mL, 0.37 mmol) dropwise at room temperature under N2. The mixture was stirred at room temperature for 12 hours under N2. The reaction was diluted with ethyl acetate and the organic layer was washed sequentially with water (3×) and brine, dried over MgSO4, and concentrated. The residue was purified by chromatography on silica gel, eluting with a gradient of ethyl acetate in dichloromethane (0-100%) to give the title compound (93 mg, 62%).

Example 95E sodium 2-(4-(4-aminophenylthio)-3-(7-isopropylpyrido[2,3-d]pyrimidin-4-ylamino)benzamido)-2-methylpropyl phosphate The product of Example 95D (90 mg, 0.11 mmol) in dichloromethane (0.5 mL) was reacted with trifluoroacetic acid [TFA] (0.5 mL) dropwise at room temperature then stirred for 1 hour. The reaction was concentrated and redissolved in a mixture of methanol and water to which was added sodium hydrogencarbonate (0.10 g, 1.19 mmol). Purification of the residue on a reverse phase C18 column eluting with a gradient of methanol in water (0-100%) gave the title compound as a yellow solid (62.5 mg, 88%). 1H NMR (300 MHz, DMSO-D6) δ ppm 1.29 (d, J=6.99 Hz, 6 H) 1.32 (s, 6 H) 3.03-3.20 (m, 1 H) 3.54 (d, J=11.40 Hz, 2 H) 5.45 (s, 2 H) 6.50-6.53 (m, 1 H) 6.62 (d, J=8.46 Hz, 2 H) 7.11 (d, J=8.46 Hz, 2 H) 7.34 (s, 1 H) 7.60 (s, 1 H) 7.87 (s, 1 H) 8.29 (s, 1 H) 8.74 (s, 1 H) 9.82 (s, 1 H).

Example 96

(RS)-4-(4-Amino-3-fluorophenylthio)-N-(1-hydroxy-2-phenylpropan-2-yl)-3-(7-isopropylpyrido[2,3-d]pyrimidin-4-ylamino)benzamide Example 96A 4-amino-3-fluorobenzenethiol hydrochloride 2-Fluoroaniline (9.8 mL, 0.1 mol) and sodium thiocyanate (24.9 g, 0.3 mol) in MeOH (55 mL) were treated with a cold solution of bromine (5.7 mL, 0.11 mol) in saturated NaBr-MeOH solution (50 mL) added dropwise at −5-0° C. over 2 hours. After the addition, the reaction mixture was poured into cold water (200 mL) with stirring, adjusted to pH 8-9 with NaHCO3 (10 g), and stirred at 5° C. for 30 minutes. The resulting crystals were collected by filtration, washed with cold water, and dried at room temperature overnight in vacuum to give crude product 2-fluoro-4-thiocyanatoaniline (14.5 g) as slightly brown crystal. A mixture of the crude 2-fluoro-4-thiocyanatoaniline (14.5 g) and concentrated hydrochloric acid (58 mL) in EtOH (15 mL) was refluxed for 8 hours. The reaction mixture was cooled and stirred at room temperature overnight. The resulting crystals were collected by filtration, washed with cold EtOH and i-Pr2O, dried at room temperature overnight in vacuum to give the title compound as its hydrochloride salt (pale yellow crystal, 10.1 g, 56%).

Example 96B

Methyl 4-(4-amino-3-fluorophenylthio)-3-nitrobenzoate

A mixture of methyl 4-chloro-3-nitrobenzoate (3.0 g, 14 mmol), the product of Example 96A (2.8 g, 16 mmol) and Cs2CO3 (8.9 g, 27 mmol) in DMF (30 mL) was heated at 90° C. for 3 hours. The reaction was cooled, poured into water (90 mL) with stirring and extracted with ethyl acetate (100 mL). The organic extract was washed with water (3×40 mL) and brine, dried over MgSO4, and concentrated to give the crude product as yellow crystal. The crystalline residue was suspended in 30 mL of i-Pr2O and stirred at room temperature for 30 minutes. Crystals were collected by filtration, washed with i-Pr2O, and dried at 40° C. in vacuum overnight to give the title compound as pale yellow crystal (3.6 g, 82%).

Example 96C

Methyl 4-(3-fluoro-4-((2,2,2-trichloroethoxy)carbonylamino)phenylthio)-3-nitrobenzoate The product of Example 96B (2.0 g, 6.2 mmol) and pyridine (0.55 mL, 6.8 mmol) in $CH_2Cl_2$ (20 mL) was reacted with 2,2,2-trichloroethyl chloroformate (0.92 mL, 6.5 mmol) dropwise at 5° C. The mixture was stirred at 5° C. for 30 minutes and concentrated. The residue was diluted with water (50 mL). The resulting crystals were collected by filtration, washed with water and i-Pr2O, and dried at room temperature in vacuum overnight to give the title compound as pale yellow crystals (2.9 g, 93%).

Example 96D

Methyl 3-amino-4-(3-fluoro-4-((2,2,2-trichloroethoxy)carbonylamino)phenylthio)benzoate The product of Example 96C (2.8 g, 5.6 mmol), Fe powder (1.6 g, 28 mmol) and NH4Cl (1.5 g, 28 mmol) in a mixture of EtOH (28 mL), THF (14 mL) and water (28 mL) was gently refluxed for 1 hour. The reaction mixture was cooled and filtered through celite pad. The filtrate was concentrated. The aqueous residue was partitioned between ethyl acetate and water, and adjusted to pH 8-9 with NaHCO3. The organic layer was separated, washed with water and brine, dried over MgSO4 and concentrated. The oily residue was separated by column chromatography (SiO2, n-hexane/ethyl acetate=3/1) to give the title compound as pale yellow crystal (1.3 g, 48%).

Example 96E

Methyl 4-(3-fluoro-4((2,2,2-trichloroethoxy)carbonylamino)phenylthio)-3-(7-isopropylpyrido[2,3-c]pyrimidin-4-ylamino)benzoate A suspension of the product of Example 12E (0.50 g, 2.3 mmol) and the product of Example 96D in AcOH (10 mL) were heated at 120° C. for 1 hour under N2. The reaction mixture was cooled to room temperature, partitioned between ethyl acetate (50 mL) and water (50 mL), and adjusted to pH 9-10 with K2CO3 under stirring. The organic layer was washed with water (1×30 mL) and brine, dried over MgSO4, and concentrated. The oily residue was separated by column chromatography (SiO2, n-hexane/ethyl acetate=1/3) product containing fractions solidified on treatment of i-Pr2O. The resulting solid was collected by filtration, washed with i-Pr2O, and dried at 40° C. in vacuum overnight to give the title compound as yellow crystals (1.26 g, 85%).

Example 96F 4-(4-Amino-3-fluorophenylthio)-3-(7-isopropylpyrido[2,3-d]pyrimidin-4-ylamino)benzoic acid The product of Example 96E (1.25 g, 2.0 mmol) in THF (12.5 mL) was reacted with aqueous LiOH solution [prepared from LiOH monohydrate (0.42 g, 10 mmol) and water (8.4 mL)] dropwise at room temperature. The mixture was stirred at 40° C. for 16 hours, and then concentrated. The aqueous mixture was diluted with 50 mL of water, washed with ethyl acetate (1×40 mL), and then carefully acidified to pH 5-6 with 1N HCl under stirring. After 30 minutes, the resulting precipitate was collected by filtration, washed with cold water, and dried at 40° C. for 3 days in vacuum to give the title compound as pale brown crystal (0.77 g, 87%). 1H-NMR (300 MHz, DMSO-d6) δ ppm: 1.34 (d, J=7.0 Hz, 6H), 3.23 (septet, J=7.0 Hz, 1H), 5.67 (s, 2H), 7.15-7.30 (m, 2H), 6.81 (dd, J=9.2, 8.4 Hz, 1H), 6.91 (d, J=8.4 Hz, 1H), 7.02 (dd, J=8.4, 1.8 Hz, 1H), 7.11 (dd, J=11.4, 1.8 Hz, 1H), 7.64 (d, J=8.5 Hz, 1H), 7.76 (dd, J=8.4, 1.9 Hz, 1H), 7.86 (d, J=1.9 Hz, 1H), 8.57 (s, 1H), 8.85 (d, J=8.5 Hz, 1H), 10.12 (s, 1H). MS ESI+ m/z: 450 (M+H), ESI− m/z: 448 (M−H).

Example 96G (RS)-Methyl 2-amino-2-phenylpropanoate

The title compound was prepared from 2-phenylglycine methyl ester hydrochloride by the procedure described in *J. Med. Chem.*, 1995, 38, 4446.

Example 96H (RS)-2-Amino-2-phenylpropan-1-ol

The product of Example 96G (0.58 g, 3.2 mmol) and sodium borohydride (0.12 g, 3.2 mmol) in 75% aqueous EtOH (7.6 mL) were refluxed for 1.5 hours. The reaction mixture was concentrated and the residue was diluted with water (15 mL) and extracted with ethyl acetate (2×25 mL). The organic layer was washed with water (2×10 mL) and brine, dried over MgSO4, concentrated to give the title compound as colorless viscous oil, which later crystallized (0.27 g, 55%). 1H-NMR (300 MHz, CDCl3) δ ppm: 1.46 (s, 3H), 1.86 (br-s, 2H), 3.59 (d, J=10.7 Hz, 1H), 3.65 (d, J=10.7 Hz, 1H), 7.22-7.30 (m, 1H), 7.31-7.41 (m, 2H), 7.41-7.49 (m, 2H). MS ESI+ m/z: 152 (M+H).

Example 96I (RS)-4-(4-Amino-3-fluorophenylthio)-N-(1-hydroxy-2-phenylpropan-2-yl)-3-(7-isopropylpyrido[2,3-d]pyrimidin-4-ylamino)benzamide To the product of Example 96F (150 mg, 0.31 mmol) and O-(7-azabenzotriazol-1-yl)-N,N,N',N'-tetramethyluronium hexafluorophosphate [HATU] (132 mg, 0.21 mmol) in DMSO (1.5 mL) was added the product of Example 96H (49 mg, 0.32 mmol) and N,N-diisopropylethylamine (0.11 mL, 0.61 mmol) added dropwise at room temperature under N2. The mixture was stirred at room temperature for 2 hours, then poured into water (30 mL) with stirring. The resulting precipitate was extracted with ethyl acetate (1×30 mL). The organic layer was washed with water (3×15 mL) and 10% NaHCO3 (1×15 mL), dried over MgSO4, and concentrated. The residue was purified by column chromatography (SiO2, gradient elution of ethyl acetate/MeOH=98/2 to 95/5) to give a yellow solid. Trituration of product containing fractions with ethyl acetate gave the title compound as pale yellow crystal (86 mg, 48%). 1H-NMR (300 MHz, DMSO-d6) δ ppm: 1.34 (d, J=7.0 Hz, 6H), 1.69 (s, 3H), 3.23 (septet, J=7.0 Hz, 1H), 3.52 (dd, J=11.0, 6.3 Hz, 1H), 3.74 (dd, J=11.0, 5.9 Hz, 1H), 5.09 (dd, J=6.3, 5.9 Hz, 1H), 5.61 (s, 2H), 6.79 (dd, J=9.2, 8.4 Hz, 1H), 6.95 (d, J=8.5 Hz, 1H), 6.99 (dd, J=8.4, 1.8 Hz, 1H), 7.08 (dd, J=11.4, 1.8 Hz, 1H), 7.17 (br-t, J=7.0 Hz, 1H), 7.27 (t, J=7.0 Hz, 2H), 7.33 (br-d, J=7.0 Hz, 2H), 7.64 (d, J=8.4 Hz, 1H), 7.69 (dd, J=8.5, 1.8 Hz, 1H), 7.87 (d, J=1.8 Hz, 1H), 8.07 (s, 1H), 8.58 (s, 1H), 8.86 (d, J=8.4 Hz, 1H), 10.17 (s, 1H). MS ESI+ m/z: 583 (M+H), ESI− m/z: 581 (M−H).

Biological Evaluation

Representative compounds of the invention were analyzed according to the assays described below.

The following acronyms are used herein:

| | |
|---|---|
| $IC_{50}$ | 50% inhibitory concentration |
| $TC_{50}$ | 50% toxicity concentration |
| DMEM | Dulbecco's Modified Essential Medium ™ |
| RNA | ribonucleic acid |
| RT-PCR | reverse transcriptase polymerase chain reaction |
| SEAP | secreted alkaline phosphatase |

The hepatitis C virus genome encodes a large polyprotein, which after processing produces the necessary functional components to synthesize progeny RNA. Selectable cell lines that produce high and sustained levels of subgenomic HCV RNA (replicons) have been derived from human hepatoma cells (Huh7) as described in Ikeda et al., *J. Virology*, 76(6): 2997-3006 (2002), and Blight et al., *Science*, 290:1972-1974 (2000). The mechanism of RNA replication in these cell lines is considered to be identical to the replication of full length HCV RNA in infected hepatocytes. The compounds of this invention are inhibitors of HCV RNA replication in the replicon assay systems described below.

RNA Assay and SEAP Assay

The purpose of these assays was to evaluate the efficacy of the compounds in inhibiting the replication of HCV genotype 1a and 1b replicons in vitro.

Genotype 1a and/or 1b replicon cells were plated at 3-5× $10^3$ cells per well in 96-well plate in DMEM medium containing 5% fetal calf serum. The next day, the culture medium was removed and replaced with fresh medium containing eight serial dilutions of compound. The untreated control culture was treated in an identical manner except no inhibitor was added to the medium. Plates were incubated in a $CO_2$ incubator at 37° C. On day 4, 100 μl lysis buffer (RTL) (Qiagen) was added to each well after removal of culture medium. RNA was purified according to manufacturer's recommendations (Qiagen RNAeasy) and eluted in 200 μl of water. The HCV RNA level was quantified from a portion (5 μl out of 200 μl) of the purified RNA by real-time RT-PCR method. The primers and probe were derived from specific sequence in the 5'-Untranslated Region (5'UTR). RT-PCR reaction was performed at 48° C. for 30 min, followed by 40 cycles set to 95° C., 15 s; 54° C., 30 s; and 72° C., 40 s. Alternatively, the activity of SEAP was measured in each culture supernatant after four days incubation with compound according to the manufacturer's instructions. The percentage reduction of HCV RNA or SEAP in the presence of compound was calculated and the 50% inhibitory concentration ($IC_{50}$) was calculated by non-linear regression analysis using the Prism program (version 4.0, GraphPad software, San Diego, Calif.).

When tested using the above method, representative compounds of the present invention inhibited HCV replicon replication with $IC_{50}$ values in the range of from about 0.5 μM to about 100 μM.

Pharmaceutical Compositions and Uses

The present invention features pharmaceutical compositions comprising the compounds of the invention. As a non-limiting example, a pharmaceutical composition of the present invention comprises one or more compounds of this invention, wherein each compound is independently selected from Formulae I, I(a) or I(b).

The present invention also features pharmaceutical compositions comprising pharmaceutically acceptable salts, solvates, or prodrugs of the compounds of this invention. Pharmaceutically acceptable salts can be zwitterions or derived from pharmaceutically acceptable inorganic or organic acids or bases. Preferably, a pharmaceutically acceptable salt of a compound of the invention retains the biological effectiveness of the free acid or base of the compound without undue toxicity, irritation, or allergic response, has a reasonable benefit/risk ratio, and is effective for their intended use and not biologically or otherwise undesirable. Non-limiting examples of pharmaceutically acceptable salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. The basic nitrogen-containing groups can also be quaternized with such agents as loweralkyl halides (e.g., methyl, ethyl, propyl or butyl chlorides, bromides or iodides), dialkyl sulfates (e.g., dimethyl, diethyl, dibutyl or diamyl sulfates), long chain halides (e.g., decyl, lauryl, myristyl or stearyl chlorides, bromides or iodides), aralkyl halides (e.g., benzyl or phenethyl bromides). Other salts that can be used in the present invention include salts with alkali or alkaline earth metals, such as sodium, potassium, calcium or magnesium, or with organic bases. Examples of acids which can be used to form pharmaceutically acceptable acid addition salts include, but are not limited to, hydrochloric acid, sulphuric acid, phosphoric acid, oxalic acid, maleic acid, succinic acid, citric acid, or other suitable inorganic or organic acids.

The present invention further features pharmaceutical compositions comprising a compound of the invention (or a salt, solvate or prodrug thereof) and another therapeutic agent. In a non-limiting example, a pharmaceutical composition of the present invention includes 1, 2, 3 or more compounds of the invention (or salts, solvates or prodrugs thereof), and 1, 2, 3 or more other therapeutic agents. By way of illustration not limitation, these other therapeutic agents can be selected from antiviral agents (e.g., anti-1-NV agents or other anti-HCV agents), immunomodulators, anti-cancer or chemotherapeutic agents, or anti-inflammation agents. Specific examples of these other therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals);

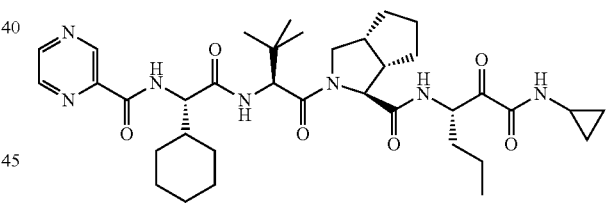

(hereinafter compound VX-950, Vertex Pharmaceuticals Inc.);

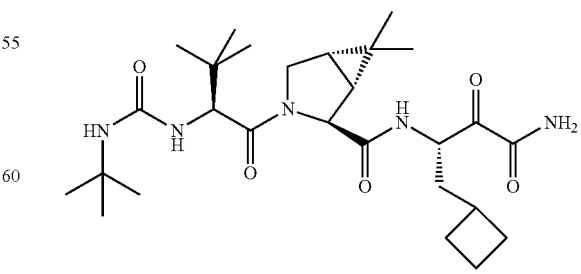

(hereinafter compound SCH503034, Schering-Plough Co.); and

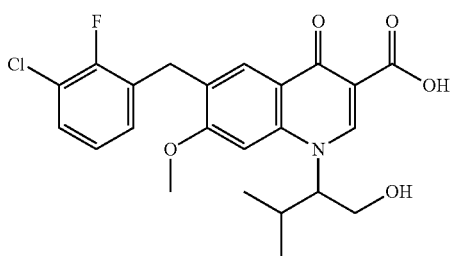

(hereinafter compound GS9137, Gilead Sciences, Inc., Foster City, Calif.). Any other desirable therapeutic agent(s) can also be included in a pharmaceutical composition of the present invention.

In one embodiment, a pharmaceutical composition of the present invention comprises one or more compounds of the present invention (or salts, solvates or prodrugs thereof), and one or more other antiviral agents.

In another embodiment, a pharmaceutical composition of the present invention comprises one or more compounds of the present invention (or salts, solvates or prodrugs thereof), and one or more other anti-HCV agents. In one example, each of the compounds of the present invention is independently selected from Formulae I, I(a) or I(b), and each of the other anti-HCV agents is independently selected from HCV RNA dependent RNA polymerase inhibitors (e.g., nucleoside or non-nucleoside type polymerase inhibitors), HCV protease inhibitors, or HCV helicase inhibitors.

In a further embodiment, a pharmaceutical composition of the present invention comprises one or more compounds of the present invention (or salts, solvates or prodrugs thereof), and two or more other anti-HCV inhibitors. Preferably, each compound of the present invention is independently selected from Formulae I, I(a) or I(b). The other anti-HCV inhibitors can be selected from the same inhibitor class (e.g., all of them are selected from HCV RNA dependent RNA polymerase inhibitors, or from HCV protease inhibitors), or selected from different inhibitor classes (e.g., one or more are selected from HCV RNA dependent RNA polymerase inhibitor and the other or others are selected from HCV protease inhibitors).

In still another embodiment, a pharmaceutical composition of the present invention comprises at least one compound of the present invention (or a salt, solvate or prodrug thereof), and at least one HCV RNA dependent RNA polymerase inhibitor. Preferably, each compound of the present invention is independently selected from Formulae I, I(a) or I(b).

In another embodiment, a pharmaceutical composition of the present invention comprises at least one compound of the present invention (or a salt, solvate or prodrug thereof), and at least one HCV protease inhibitor. Preferably, the compound of the present invention is selected from Formulae I, I(a) or I(b).

In yet another embodiment, a pharmaceutical composition of the present invention comprises at least one compound of the present invention (or a salt, solvate or prodrug thereof), at least one HCV RNA dependent RNA polymerase inhibitor, and at least one HCV protease inhibitor. Preferably, the compound of the present invention is selected from Formulae I, I(a) or I(b).

In still yet another embodiment, a pharmaceutical composition of the present invention comprises at least one compound of the present invention (or a salt, solvate or prodrug thereof), and two or more anti-HCV agents each of which is independently selected from HCV RNA dependent RNA polymerase inhibitors or HCV protease inhibitors. Preferably, the compound of the present invention is selected from Formulae I, I(a) or I(b).

In still another embodiment, a pharmaceutical composition of the present invention comprises at least one compound of the present invention (or a salt, solvate or prodrug thereof), and three or more other anti-HCV agents each of which is independently selected from HCV RNA dependent RNA polymerase inhibitors or HCV protease inhibitors. Preferably, the compound of the present invention is selected from Formulae I, I(a) or I(b).

Non-limiting examples of HCV RNA dependent RNA polymerase inhibitors include those described in WO0190121(A2), U.S. Pat. No. 6,348,587B1, WO0160315, WO0132153, EP1162196A1 and WO0204425. Non-limiting examples of HCV protease inhibitors include BILN-2061, VX-950, and SCH503034.

In another embodiment, a pharmaceutical composition of the present invention comprises at least one compound of the present invention (or a salt, solvate or prodrug thereof), and one or more other antiviral agents, such as anti-HBV or anti-HIV agents. Non-limiting examples of anti-HBV agents include adefovir, lamivudine, and tenofovir. Non-limiting examples of anti-HIV drugs include ritonavir, lopinavir, indinavir, nelfinavir, saquinavir, amprenavir, atazanavir, tipranavir, TMC-114, fosamprenavir, zidovudine, lamivudine, didanosine, stavudine, tenofovir, zalcitabine, abacavir, efavirenz, nevirapine, delavirdine, TMC-125, L-870812, S-1360, enfuvirtide, T-1249, and other HIV protease, reverse transcriptase, integrase or fusion inhibitors. Other desirable antiviral agents can also be included in a pharmaceutical composition of the present invention, as appreciated by those skilled in the art.

In one embodiment, a pharmaceutical composition of the present invention comprises at least one compound of the present invention selected from Formulae I, I(a) or I(b) (or a salt, solvate or prodrug thereof), and at least one anti-HBV agent. In another embodiment, a pharmaceutical composition of the present invention comprises at least one compound of the present invention selected from Formulae I, I(a) or I(b) (or a salt, solvate or prodrug thereof), and at least one anti-HIV agent. In yet another embodiment, a pharmaceutical composition of the present invention comprises at least one compound of the present invention selected from Formulae I, I(a) or I(b) (or a salt, solvate or prodrug thereof), and at least one anti-hepatitis A, anti-hepatitis D, anti-hepatitis E or anti-hepatitis G agent.

In still yet another embodiment, a pharmaceutical composition of the present invention comprises at least one compound of the present invention selected from Formulae I, I(a) or I(b) (or a salt, solvate or prodrug thereof), and at least one agent suitable for treating liver inflammation.

A pharmaceutical composition of the present invention typically includes a pharmaceutically acceptable carrier or excipient. Non-limiting examples of suitable pharmaceutically acceptable carriers/excipients include sugars (e.g., lactose, glucose or sucrose), starches (e.g., corn starch or potato starch), cellulose or its derivatives (e.g., sodium carboxymethyl cellulose, ethyl cellulose or cellulose acetate), oils (e.g., peanut oil, cottonseed oil, safflower oil, sesame oil, olive oil, corn oil or soybean oil), glycols (e.g., propylene glycol), buffering agents (e.g., magnesium hydroxide or aluminum hydroxide), agar, alginic acid, powdered tragacanth, malt, gelatin, talc, cocoa butter, pyrogen-free water, isotonic saline, Ringer's solution, ethanol, or phosphate buffer solutions. Lubricants, coloring agents, releasing agents, coating agents, sweetening, flavoring or perfuming agents, preservatives, or antioxidants can also be included in a pharmaceutical composition of the present invention, as appreciated by those of ordinary skill in the art.

A pharmaceutical composition of the present invention can be administered to a patient in need thereof via a variety of routes, such as orally, parenterally, sublingually, rectally, topically or by inhalation spray. Topical administration may involve the use of transdermal administration such as transdermal patches or iontophoresis devices. Parenteral administration includes, but is not limited to, subcutaneous, intravenous, intramuscular or intrasternal injections, and infusion techniques.

The pharmaceutical compositions of the present invention can be formulated based on their routes of administration using methods well known in the art. For example, a sterile injectable preparation can be prepared as a sterile injectable aqueous or oleagenous suspension using suitable dispersing or wetting agents and suspending agents. Suppositories for rectal administration can be prepared by mixing drugs with a suitable nonirritating excipient such as cocoa butter or polyethylene glycols which are solid at ordinary temperatures but liquid at the rectal temperature and will therefore melt in the rectum and release the drugs. Solid dosage forms for oral administration can be capsules, tablets, pills, powders or granules. In such solid dosage forms, the active compounds can be admixed with at least one inert diluent such as sucrose lactose or starch. Solid dosage forms may also comprise other substances in addition to inert diluents, such as lubricating agents. In the case of capsules, tablets and pills, the dosage forms may also comprise buffering agents. Tablets and pills can additionally be prepared with enteric coatings. Liquid dosage forms for oral administration can include pharmaceutically acceptable emulsions, solutions, suspensions, syrups or elixirs containing inert diluents commonly used in the art. Liquid dosage forms may also comprise wetting, emulsifying, suspending, sweetening, flavoring, or perfuming agents. The pharmaceutical compositions of the present invention can also be administered in the form of liposomes, as described in U.S. Pat. No. 6,703,403. Formulation of drugs that are applicable to the present invention is generally discussed in, for example, Hoover, John E., REMINGTON'S PHARMACEUTICAL SCIENCES (Mack Publishing Co., Easton, Pa.: 1975), and Lachman, L., eds., PHARMACEUTICAL DOSAGE FORMS (Marcel Decker, New York, N.Y., 1980).

The present invention further features methods of using the compounds of the present invention (or salts, solvates or prodrugs thereof) to inhibit HCV replication. In one embodiment, the methods comprise contacting HCV virus with an effective amount of a compound of the present invention (or a salt, solvate or prodrug thereof), thereby inhibiting the replication of the HCV virus. In another embodiment, the methods comprise contacting cells infected with HCV virus with an effective amount of a compound of the present invention (or a salt, solvate or prodrug thereof), thereby inhibiting the replication of the HCV virus in the cells. In still another embodiment, the methods comprise contacting HCV virus or infected cells with an effective amount of two or more compounds of the present invention (or salts, solvates or prodrugs thereof), thereby inhibiting the replication of the HCV virus. As used herein, "inhibiting" means significantly reducing, or abolishing, the activity being inhibited (e.g., viral replication). In many cases, representative compounds of the present invention can reduce the replication of HCV virus (e.g., in HCV replicon assays as described above) by at least 10%, 20%, 30%, 40%, 50%, 60%, 70%, 80%, 90%, 95% or more.

The compounds of the present invention may inhibit all HCV subtypes. Examples of HCV subtypes that are amenable to the present invention include, but are not limited to, HCV genotypes 1, 2, 3, 4, 5 and 6, including HCV genotypes 1a, 1b, 2a, 2b, 2c or 3a. In one embodiment, a compound or compounds of the present invention (or salts, solvates or prodrugs thereof) are used to inhibit the replication of HCV genotype 1a. In another embodiment, a compound or compounds of the present invention (or salts, solvates or prodrugs thereof) are used to inhibit the replication of HCV genotype 1b. In still another embodiment, a compound or compounds of the present invention (or salts, solvates or prodrugs thereof) are used to inhibit the replication of both HCV genotypes 1a and 1b.

The present invention also features methods of using the compounds of the present invention (or salts, solvates or prodrugs thereof) to treat HCV infection. These methods typically comprise administering a therapeutic effective amount of a compound of the present invention (or a salt, solvate or prodrug thereof) to an HCV patient, thereby reducing the HCV viral level in the blood or liver of the patient. As used herein, the term "treating" refers to reversing, alleviating, inhibiting the progress of, or preventing the disorder or condition, or one or more symptoms of such disorder or condition to which such term applies. The term "treatment" refers to the act of treating. In one embodiment, the methods comprise administering a therapeutic effective amount of two or more compounds of the present invention (or salts, solvates or prodrugs thereof) to an HCV patient, thereby reducing the HCV viral level in the blood or liver of the patient. Preferably, the compound(s) employed in these methods have Formulae I(a) or I(b).

In another aspect, the present invention features methods of using a pharmaceutical composition of the present invention to treat HCV infection. Any pharmaceutical composition described herein can be used for this purpose. These methods typically comprise administering a therapeutic effective amount of a pharmaceutical composition of the present invention to an HCV patient, thereby reducing the HCV viral level in the blood or liver of the patient. Where the pharmaceutical composition includes other therapeutic agent(s), it may also treat other diseases, disorders or conditions in the patient.

In one embodiment, the pharmaceutical composition being administered comprises at least one compound of the present invention selected from Formulae I(a) or I(b) (or a salt, solvate or prodrug thereof), and at least another anti-HCV agent selected from HCV RNA dependent RNA polymerase inhibitors, HCV protease inhibitors or HCV helicase inhibitors. In another embodiment, the pharmaceutical composition being administered comprises at least one compound of the present invention selected from Formulae I(a) or I(b) (or a salt, solvate or prodrug thereof), and at least two other anti-HCV agents each of which is independently selected from HCV RNA dependent RNA polymerase inhibitors, HCV protease inhibitors or HCV helicase inhibitors. In still another embodiment, the pharmaceutical composition being administered comprises at least one compound of the present invention selected from Formulae I(a) or I(b) (or a salt, solvate or prodrug thereof), and 1, 2 or more HCV RNA dependent RNA polymerase inhibitors (e.g., those described in WO0190121(A2), U.S. Pat. No. 6,348,587B1, WO0160315, WO0132153, EP1162196A1 and WO0204425). In yet another embodiment, the pharmaceutical composition being administered comprises at least one compound of the present invention selected from Formulae I(a) or I(b) (or a salt, solvate or prodrug thereof), and 1, 2 or more HCV protease inhibitors (e.g., BILN-2061, VX-950, and SCH503034).

In a further embodiment, the pharmaceutical composition being administered comprises at least one compound of the present invention selected from Formulae I(a) or I(b) (or a salt, solvate or prodrug thereof), and at least one antiviral agent selected from anti-HIV agents, anti-HBV agents, anti-hepatitis A agents, anti-hepatitis D agents, anti-hepatitis E agents, or anti-hepatitis G agents.

In yet another aspect, the present invention provides methods of using a compound(s) of the present invention and another therapeutic agent(s) to treat HCV infection. The methods comprise administering a therapeutic effective amount of a compound(s) of the present invention and another therapeutic agent(s) to an HCV patient, thereby reducing the HCV viral level in the blood or liver of the patient. Each compound of the present invention (or a salt, solvate or prodrug thereof) and the other therapeutic agent(s) can be combined in a single formulation and administered simultaneously to the patient. They can also be administered simultaneously but in different formulations. In addition, they can be administered sequentially.

In one embodiment, the compound(s) of the present invention being administered includes one or more compounds selected from Formulae I(a) or I(b), and the other therapeutic agent(s) being administered includes one or more agents selected from HCV RNA dependent RNA polymerase inhibitors, HCV protease inhibitors or HCV helicase inhibitors. In another embodiment, the compound(s) of the present invention being administered includes one or more compounds selected from Formulae I(a) or I(b), and the other therapeutic agent(s) being administered includes two or more agents selected from HCV RNA dependent RNA polymerase inhibitors, HCV protease inhibitors or HCV helicase inhibitors. In yet another embodiment, the compound(s) of the present invention being administered includes one or more compounds selected from Formulae I(a) or I(b), and the other therapeutic agent(s) being administered includes one, two or more HCV RNA dependent RNA polymerase inhibitors (e.g., those described in WO0190121(A2), U.S. Pat. No. 6,348, 587B1, WO0160315, WO0132153, EP1162196A1 and WO0204425). In still yet another embodiment, the compound(s) of the present invention being administered includes one or more compounds selected from Formulae I(a) or I(b), and the other therapeutic agent(s) being administered includes one, two or more HCV protease inhibitors (e.g., BILN-2061, VX-950, and SCH503034).

A compound of the present invention (or a salt, solvate or prodrug thereof) can also be coadministered with other desired drugs, such as anti-HIV agents, anti-HBV agents, anti-hepatitis A agents, anti-hepatitis D agents, anti-hepatitis E agents, anti-hepatitis G agents, or other antiviral drugs.

A compound of the present invention (or a salt, solvent or prodrug thereof) can be administered to a patient in a single dose or divided doses. A typical daily dosage can range, without limitation, from 0.1 to 200 mg/kg body weight, such as from 0.25 to 100 mg/kg body weight. Single dose compositions can contain these amounts or submultiples thereof to make up the daily dose. Preferably, each dosage contains a sufficient amount of a compound of the present invention that is effective in reducing the HCV viral load in the blood or liver of the patient. The amount of the active ingredient, or the active ingredients that are combined, to produce a single dosage form may vary depending upon the host treated and the particular mode of administration. It will be understood that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

In still another aspect, the compounds of Formulae I, I(a) or I(b), or their pharmaceutically acceptable salts, stereoisomers or tautomers, can be administered as the sole active pharmaceutical agent, or used in combination with one or more other agents, to treat infections or symptoms associated with other RNA-containing viruses.

Treatment or prevention of infection caused by RNA-containing viruses can be provided by a combination therapy comprising a therapeutically effective amount of a first antiviral agent provided by one or more compounds, or salts thereof, of Formulae I, I(a) or I(b), along with a therapeutically-effective amount of a second agent provided by one or more compounds selected from the group consisting of another anti-viral agent; a host immune modulator; interferon derivative, such as interferon-alpha, pegylated-interferon-alpha, interferon-beta, and interferon-gamma; a cytokine; a vaccine; a nucleoside analog; inhibitors of key enzymes which result in HCV dysfunction, examples of such enzymes being HCV metalloprotease, HCV serine protease, inosine monophosphate dehydrogenase (IMPDH), and HCV helicase; inhibitors of viral particle proteins such as HCV NS4B protein, and HCV NS5a protein; and agents which inhibit HCV function, such as HCV entry, HCV assembly, and HCV egress. Also included are vaccines comprising HCV antigens or antigen adjuvant combinations directed against HCV. Further included are agents that interact with host cellular components to block viral protein synthesis by inhibiting the internal ribosome entry site (IRES) initiated translation step of HCV viral replication or to block viral particle maturation and release with agents targeted toward the viroporin family of membrane proteins such as, for example, HCV P7.

In one embodiment, the present invention is directed to a method of treating or preventing infection caused by an RNA-containing virus comprising administering to a patient in need of such treatment a therapeutically effective amount of a compound of Formulae I, I(a) or I(b), or a pharmaceutically acceptable salt thereof.

In another embodiment, the present invention is directed to a method of treating or preventing infection caused by an RNA-containing virus comprising co-administering to a patient in need of such treatment one or more agents selected from the group consisting of a host immune modulator and a second antiviral agent, or a combination thereof, with a therapeutically effective amount of a compound of Formulae I, I(a) or I(b), or a pharmaceutically acceptable salt thereof.

In yet another embodiment, the present invention is directed to a method of treating or preventing infection caused by an RNA-containing virus comprising co-administering to a patient in need of such treatment one or more agents selected from the group consisting of interferon-alpha, pegylated-interferon-alpha, interferon-beta, interferon-gamma, a cytokine, a vaccine, and a vaccine comprising an antigen and an adjuvant, and a second antiviral agent, or a combination thereof, with a therapeutically effective amount of a compound of Formulae I, I(a) or I(b), or a pharmaceutically acceptable salt thereof.

In still another embodiment, the present invention provides a method of treating or preventing infection caused by an RNA-containing virus comprising co-administering to a patient in need of such treatment one or more agents selected from the group consisting of a host immune modulator and a second antiviral agent which inhibits replication of HCV by inhibiting host cellular functions associated with viral replication, or a combination thereof, with a therapeutically effective amount of a compound of Formulae I, I(a) or I(b), or a pharmaceutically acceptable salt thereof.

In a further embodiment, the present invention provides a method of treating or preventing infection caused by an RNA-containing virus comprising co-administering to a patient in need of such treatment an agent or combination of agents that treat or alleviate symptoms of HCV infection including cirrhosis and inflammation of the liver, with a therapeutically effective amount of a compound of Formulae I, I(a) or I(b), or a pharmaceutically acceptable salt thereof.

In another embodiment, the present invention provides a method of treating or preventing infection caused by an RNA-containing virus comprising co-administering to a patient in need of such treatment one or more agents that treat patients for disease caused by hepatitis B (HBV) infection, with a therapeutically effective amount of a compound of Formulae I, I(a) or I(b), or a pharmaceutically acceptable salt thereof.

In yet another embodiment, the present invention provides a method of treating or preventing infection caused by an RNA-containing virus comprising co-administering to a patient in need of such treatment one or more agents that treat patients for disease caused by human immunodeficiency virus (HIV) infection, with a therapeutically effective amount of a compound of Formulae I, I(a) or I(b), or a pharmaceutically acceptable salt thereof.

The phrase "combination therapy" (or "co-therapy"), is intended to embrace administration of each agent in a sequential manner in a regimen that will provide beneficial effects of the drug combination, and is intended as well to embrace co-administration of these agents in a substantially simultaneous manner, such as by oral ingestion or a single capsule having a fixed ratio of these active agents or ingestion of multiple, separate capsules for each agent. "Combination therapy" will also include simultaneous or sequential administration by oral, intravenous, intramuscular or other parenteral routes into the body, including direct absorption through mucous membrane tissues, as found in the sinus passages. Sequential administration also includes drug combinations where the individual agents may be administered at different times and/or by different routes but which act in combination to provide a beneficial effect, for example, by co-action of pharmacokinetic or pharmacodynamic effects of each agent.

The present invention also features use of the compounds of the invention, or pharmaceutically acceptable salts, solvates or prodrugs thereof, for the manufacture of medicaments for the treatment of HCV or other viral infections. In one embodiment, the present invention features the use of a compound of the present invention selected from Formulae I, I(a) or I(b), or a salt, solvate or prodrug thereof, for the manufacture of a medicament for the treatment of HCV infection. In another embodiment, the present invention features the use of two or more compounds of the present invention (or salts, solvates or prodrugs thereof) for the manufacture of a medicament for the treatment of HCV infection, wherein each of the two or more compounds is independently selected from Formulae I, I(a) or I(b).

In still another embodiment, the present invention features the use of at least one compound of the present invention (or a salt, solvate or prodrug thereof) and at least one additional therapeutic agent for the manufacture of a medicament for the treatment of HCV infection. Preferably, the compound(s) of the present invention is selected from Formulae I, I(a) or I(b), and the additional therapeutic agent(s) can be selected, by way of illustration not limitation, from antiviral agents (e.g., anti-HIV agents or other anti-HCV agents), immunomodulators, anti-cancer or chemotherapeutic agents, and anti-inflammation agents. Specific examples of additional therapeutic agents include, but are not limited to, ribavirin; interferons (e.g., IFN alpha 2a or 2b); protease inhibitors; immunosuppressants; antibodies (e.g., therapeutic monoclonal or chimeric antibodies); antisense or siRNA; HIV inhibitors; hepatitis B (HBV) inhibitors; agents for treating cirrhosis and inflammation of the liver; Omega IFN (BioMedicines Inc., Emeryville, Calif.); BILN-2061 serine protease inhibitor (Boehringer Ingelheim Pharma KG, Ingelheim, Germany); Summetrel antiviral (Endo Pharmaceuticals Holdings Inc., Chadds Ford, Pa.); Roferon A IFN-alpha 2a (F. Hoffmann-La Roche LTD, Basel, Switzerland); Pegasys PEGylated IFN-alpha 2a (F. Hoffmann-La Roche LTD, Basel, Switzerland); Pegasys and Ribavirin PEGylated IFN-alpha 2a/ribavirin (F. Hoffmann-La Roche LTD, Basel, Switzerland); CellCept HCV IgG immunosuppressant (F. Hoffmann-La Roche LTD, Basel, Switzerland); Wellferon lymphoblastoid IFN-alpha n1 (GlaxoSmithKline plc, Uxbridge, UK); Albuferon-alpha albumin IFN-alpha 2b (Human Genome Sciences Inc., Rockville, Md.); Levovirin ribavirin (ICN Pharmaceuticals, Costa Mesa, Calif.); IDN-6556 caspase inhibitor (Idun Pharmaceuticals Inc., San Diego, Calif.); IP-501 antifibrotic (Indevus Pharmaceuticals Inc., Lexington, Mass.); Actimmune INF-gamma (InterMune Inc., Brisbane, Calif.); Infergen A IFN alfacon-1 (InterMune Pharmaceuticals Inc., Brisbane, Calif.); ISIS 14803 antisense (ISIS Pharmaceuticals Inc., Carlsbad, Calif./Elan Pharmaceuticals Inc., New York, N.Y.); JTK-003 RdRp inhibitor (Japan Tobacco Inc., Tokyo, Japan); Pegasys and Ceplene PEGylated IFN-alpha 2a/immune modulator (Maxim Pharmaceuticals inc., San Diego, Calif.); Ceplene immune modulator (Maxim Pharmaceuticals Inc., San Diego, Calif.); Civacir HCV IgG immunosuppressant (Nabi Biopharmaceuticals Inc., Boca Raton, Fla.); Intron A and Zadaxin IFN-alpha 2b/alpha 1-thymosin (RegeneRx Biopharmiceuticals Inc., Bethesda, Md./SciClone Pharmaceuticals Inc., San Mateo, Calif.); Levovirin IMPDH inhibitor (Ribapharm Inc., Costa Mesa, Calif.); Viramidine IMPDH inhibitor (Ribapharm Inc., Costa Mesa, Calif.); Heptazyme ribozyme (Ribozyme Pharmaceuticals Inc., Boulder, Colo.); Intron A IFN-alpha 2b (Schering-Plough Corporation, Kenilworth, N.J.); PEG-Intron PEGylated IFN-alpha 2b (Schering-Plough Corporation, Kenilworth, N.J.); Rebetron IFN-alpha 2b/ribavirin (Schering-Plough Corporation, Kenilworth, N.J.); Ribavirin (Schering-Plough Corporation, Kenilworth, N.J.); PEG-Intron/Ribavirin PEGylated IFN-alpha 2b/ribavirin (Schering-Plough Corporation, Kenilworth, N.J.); Zadazim immune modulator (SciClone Pharmaceuticals Inc., San Mateo, Calif.); Rebif IFN-beta 1a (Serono, Geneva, Switzerland); IFN-beta and EMZ701 IFN-beta and EMZ701 (Transition Therapeutics Inc., Ontario, Canada); T67 beta-tubulin inhibitor (Tularik Inc., South San Francisco, Calif.); VX-497 IMPDH inhibitor (Vertex Pharmaceuticals Inc., Cambridge, Mass.); VX-950/LY-570310 serine protease inhibitor (Vertex Pharmaceuticals Inc., Cambridge, Mass./Eli Lilly and Co., Inc., Indianapolis, Ind.); Omniferon natural IFN-alpha (Viragen Inc., Plantation, Fla.); XTL-002 monoclonal antibody (XTL Biopharmaceuticals); compound VX-950 (Vertex Pharmaceuticals Inc.); compound SCH503034 (Schering-Plough Co.); and compound GS9137 (Gilead Sciences, Inc., Foster City, Calif.).

In yet another embodiment, the present invention features the use of at least one compound of the present invention (or a salt, solvate or prodrug thereof) and at least one additional anti-viral agent for the manufacture of a medicament for the treatment of viral infection. Preferably, the compound(s) of the present invention is selected from Formulae I, I(a) or I(b), and the additional anti-viral agent(s) can be selected, without limitation, from anti-HCV or anti-HIV agents. In one example, the present invention features the use of at least one compound of the present invention selected from Formulae I, I(a) or I(b) (or a salt, solvate or prodrug thereof), and at least one additional anti-HCV agent for the manufacture of a medicament for the treatment of HCV infection. Non-limiting examples of anti-HCV agents include HCV RNA dependent RNA polymerase inhibitors (e.g., nucleoside or non-nucleoside type polymerase inhibitors) or HCV protease inhibitors. In another example, the present invention features the use of at least one compound of the present invention selected from Formulae I, I(a) or I(b) (or a salt, solvate or prodrug thereof), and at least two or more additional anti-HCV agents for the manufacture of a medicament for the treatment of HCV infection. Each of the additional anti-HCV agents can be independently selected from HCV RNA dependent RNA polymerase inhibitors or HCV protease inhibitors.

In still another embodiment, the present invention features the use of at least one compound of the present invention selected from Formulae I, I(a) or I(b) (or a salt, solvate or prodrug thereof), and at least one anti-HIV agent for the manufacture of a medicament for the treatment of HIV or HCV infection. In still yet another embodiment, the present invention features the use of at least one compound of the present invention selected from Formulae I, I(a) or I(b) (or a salt, solvate or prodrug thereof), and at least one anti-hepatitis A, anti-hepatitis B, anti-hepatitis D, anti-hepatitis E or anti-hepatitis G agent for the manufacture of a medicament for the treatment of viral hepatitis. In a further embodiment, the present invention features the use of at least one compound of the present invention selected from Formulae I, I(a) or I(b) (or a salt, solvate or prodrug thereof), and at least one agent for treating liver inflammation, for the manufacture of a medicament for the treatment of Hepatitis C.

The foregoing description of the present invention provides illustration and description, but is not intended to be exhaustive or to limit the invention to the precise one disclosed. Modifications and variations are possible in light of the above teachings or may be acquired from practice of the invention. Thus, it is noted that the scope of the invention is defined by the claims and their equivalents.

What is claimed is:

1. A compound, a tautomer of the compound, or a pharmaceutically acceptable salt of the compound or tautomer, wherein said compound has Formula I,

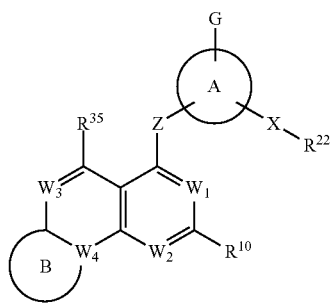

wherein:
A is carbocyclyl and B is heterocyclyl, and wherein A and B are each independently optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, carbocyclyl, heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$,-$L_S$-N($R_S R_{S'}$), -$L_S$-C(=N$R_S$)$R_{S''}$, -$L_S$-S(O)$R_S$, -$L_S$-SO$_2$$R_S$, -$L_S$-C(O)N($R_S R_{S'}$), -$L_S$-N($R_S$)C(O)$R_{S''}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N($R_S$)SO$_2$$R_{S''}$, -$L_S$-SO$_2$N($R_S R_{S'}$), and -$L_S$-N($R_S$)SO$_2$N($R_S R_{S''}$);

Z is a bond, —$CR^{41}R^{41'}$— or —$NR^{41}$—, wherein $R^{41}$ and $R^{41'}$ are each independently selected from the group consisting of hydrogen, alkyl, alkenyl and alkynyl;

$R^{10}$ and $R^{35}$ are each independently selected at each occurrence from the group consisting of hydrogen, halogen, oxo, thioxo, hydroxy, mercapto, nitro, cyano, amino, carboxy, formyl, phosphate, azido, alkyl, alkenyl, alkynyl, carbocyclyl, heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S''}$, -$L_S$-S(O)$R_S$, -$L_S$-SO$_2$$R_S$, -$L_S$-C(O)N($R_S R_{S'}$), -$L_S$-N($R_S$)C(O)$R_{S''}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N($R_S$)SO$_2$$R_{S''}$, -$L_S$-SO$_2$N($R_S R_{S'}$), and -$L_S$-N($R_S$)SO$_2$N($R_S R_{S''}$);

X is selected from the group consisting of a bond, alkylene, alkenylene, alkynylene, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is carbocyclyl or heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S''}$, -$L_S$-S(O)$R_S$, -$L_S$-SO$_2$$R_S$, -$L_S$-C(O)N($R_S R_{S'}$), -$L_S$-N($R_S$)C(O)$R_{S''}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N=C(N$R_S R_{S'}$)(N$R_S R_{S'}$), -$L_S$-N($R_S$)SO$_2$$R_{S''}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl); or $R^{22}$ is alkyl, alkenyl or alkynyl, and is optionally substituted with one or more $R^{26}$; or $R^{22}$ is hydrogen;

G is selected from the group consisting of hydrogen, halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S''}$, -$L_S$-S(O)$R_S$, -$L_S$-SO$_2$$R_S$, -$L_S$-C(O)N($R_S R_{S'}$), -$L_S$-N($R_S$)C(O)$R_{S''}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N($R_S$)SO$_2$$R_{S''}$, -$L_S$-SO$_2$N($R_S R_{S'}$), -$L_S$-N($R_S$)SO$_2$N($R_S R_{S''}$), and —Y—$R^{50}$, wherein G is optionally substituted with one or more $R^{18}$;

Y is selected from the group consisting of a bond, —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)—, —N($R^{15}$)S(O)—, —N($R^{15}$)S(O)$_2$—, —S(O)N($R^{15}$)—, —S(O)$_2$N($R^{15}$)—, —C(S)N($R^{15}$)O—, —N($R^{15}$)C(S)O—, —OC(S)N($R^{15}$)—, —N($R^{15}$)C(S)N($R^{15'}$)—, and —C(S)N($R^{15}$)N($R^{15'}$)—, wherein $R^{15}$ and $R^{15'}$ are each independently selected at each occurrence from the group consisting of hydrogen, alkyl, alkenyl and alkynyl;

$R^{50}$ is -$L^1$-$A^1$, wherein $A^1$ is selected from the group consisting of carbocyclyl, heterocyclyl, alkyl, alkenyl and alkynyl, and $L^1$ is selected from the group consisting of a bond, alkylene, alkenylene and alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, alkyl, alkenyl, alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, alkoxy, thioalkoxy, alkylcarbonyl, alkoxycarbonyl, alkylcarbonyloxy, alkylamino, alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), carbocyclyl, heterocyclyl, carbocyclylalkyl, heterocyclylalkyl, -$L_E$-Q-$L_{E'}$-(C$_3$-C$_{18}$carbocyclyl) and -$L_E$-Q-$L_{E'}$-(M$_3$-M$_{18}$heterocyclyl);

$L_S$ is independently selected at each occurrence from the group consisting of a bond, alkylene, alkenylene and alkynylene;

$R_S$, $R_{S'}$ and $R_{S''}$ are each independently selected at each occurrence from the group consisting of hydrogen, alkyl, alkenyl, alkynyl, alkoxy, thioalkoxy, alkoxyalkyl, alkoxyalkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl;

$L_E$ and $L_{E'}$ are each independently selected at each occurrence from the group consisting of a bond, alkylene, alkenylene and alkynylene;

Q is independently selected at each occurrence from the group consisting of a bond, alkylene, alkenylene, alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$-O—, —O—S(O)—, —S(O)—O—, —C(O)O— and —OC(O)—;

$R^{10}$, $R^{15}$, $R^{15'}$, $R^{18}$, $R^{26}$, $R^{30}$, $R^{35}$, $R^{38}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate and azido; and each C$_3$-C$_{18}$carbocyclyl and M$_3$-M$_{18}$heterocyclyl moiety in -$L_E$-Q-$L_{E'}$-(C$_3$-C$_{18}$carbocyclyl) and -$L_E$-Q-$L_{E'}$-(M$_3$-M$_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, alkyl, alkenyl, alkynyl, alkoxy, thioalkoxy, alkoxyalkyl, thioalkoxyalkyl, alkylcarbonyl, alkylcarbonylalkyl, alkoxycarbonyl, alkoxycarbonylalkyl, alkylcarbonyloxy, alkylcarbonyloxyalkyl, alkylamino, alkylaminoalkyl, alkoxycarbonylamino, and alkoxycarbonylaminoalkyl.

2. The compound, tautomer or salt of claim 1, wherein:

A is C$_3$-C$_{18}$carbocyclyl and B is M$_3$-M$_{18}$heterocyclyl, and are each independently optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, C$_3$-C$_6$carbocyclyl, M$_3$-M$_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

Z is a bond, —CR$^{41}$R$^{41'}$— or —NR$^{41}$—, wherein $R^{41}$ and $R^{41'}$ are each independently selected from the group consisting of hydrogen, C$_1$-C$_6$alkyl, C$_2$-C$_6$alkenyl and C$_2$-C$_6$alkynyl;

$R^{10}$ and $R^{35}$ are each independently selected at each occurrence from the group consisting of hydrogen, halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, C$_3$-C$_6$carbocyclyl, M$_3$-M$_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

X is selected from the group consisting of a bond, C$_1$-C$_6$alkylene, C$_2$-C$_6$alkenylene, C$_2$-C$_6$alkynylene, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_{S'}$)C(=N$R_S$)—, -$L_S$-S(O)—, -$L_S$-SO$_2$—, -$L_S$-C(O)O— and -$L_S$-OC(O)—;

$R^{22}$ is C$_3$-C$_{18}$carbocyclyl or M$_3$-M$_{18}$heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N=C(N$R_S R_{S'}$)(N$R_S R_{S'}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-(C$_3$-C$_{18}$carbocyclyl) and -$L_E$-Q-$L_{E'}$-(M$_3$-M$_{18}$heterocyclyl); or $R^{22}$ is C$_1$-C$_6$alkyl, C$_2$-C$_6$alkenyl or C$_2$-C$_6$alkynyl, and is optionally substituted with one or more $R^{26}$; or $R^{22}$ is hydrogen;

G is selected from the group consisting of hydrogen, halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), and —Y—$R^{50}$, wherein G is optionally substituted with one or more $R^{18}$;

Y is selected from the group consisting of a bond, —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)—, —N($R^{15}$)S(O)—, —N($R^{15}$)S(O)$_2$—, —S(O)N($R^{15}$)—, —S(O)$_2$N($R^{15}$)—, —C(S)N($R^{15}$)O—, —N($R^{15}$)C(S)O—, —OC(S)N($R^{15}$)—, —N($R^{15}$)C(S)N($R^{15'}$)—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl, and $C_2$-$C_6$alkynyl;

$R^{50}$ is -$L^1$-$A^1$, wherein $A^1$ is selected from the group consisting of $C_3$-$C_{18}$carbocyclyl, $M_3$-$M_{18}$heterocyclyl, $C_1$-$C_6$alkyl, $C_2$-$C_6$alkenyl and $C_2$-$C_6$alkynyl, and $L^1$ is selected from the group consisting of a bond, $C_1$-$C_6$alkylene, $C_2$-$C_6$alkenylene and $C_2$-$C_6$alkynylene, wherein $A^1$ is optionally substituted with one or more $R^{30}$, and $R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl), and wherein $L^1$ is optionally substituted with one or more $R^{38}$, and $R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2$$R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S'''}$, -$L_S$-N($R_S$)C(O)N($R_S R_{S''}$), -$L_S$-N($R_S$)SO$_2$$R_{S'}$, -$L_S$-SO$_2$N($R_S R_{S'}$), -$L_S$-N($R_S$)SO$_2$N($R_S R_{S''}$), $C_3$-$C_{18}$carbocyclyl, $M_3$-$M_{18}$heterocyclyl, $C_3$-$C_{18}$carbocyclyl$C_1$-$C_6$alkyl, $M_3$-$M_{18}$heterocyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkyl, $C_1$-$C_6$alkenyl and $C_1$-$C_6$alkynyl;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{18}$, $R^{26}$, $R^{30}$, $R^{35}$, $R^{38}$, $R^{41}$, and $R^{41'}$ are each independently optionally substituted at each occurrence with at least one substituent selected from the group consisting of halogen, oxo, thioxo, hydroxy, mercapto, nitro, cyano, amino, carboxy, formyl, phosphate and azido; and each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl.

3. The compound, tautomer or salt of claim 2, wherein A is $C_5$-$C_6$carbocyclyl and is optionally substituted with one or more $R^{18}$, and B is $M_5$-$M_6$heterocyclyl optionally substituted with one or more $R^{18}$.

4. The compound, tautomer or salt of claim 2, wherein G is —Y—$R^{50}$, $R^{50}$ is -$L^1$-$A^1$- and $A^1$ is $C_5$-$C_{12}$carbocyclyl or $M_5$-$M_{10}$heterocyclyl and is optionally substituted with one or more $R^{30}$.

5. The compound, tautomer or salt of claim 4, wherein Y is —O—, —S—, —C(O)N($R^{15}$)— or —N($R^{15}$)C(O)—, $R^{15}$ is hydrogen, $C_1$-$C_6$alkyl, $C_2$-$C_6$alkenyl or $C_2$-$C_6$alkynyl, $L^1$ is $C_1$-$C_6$alkylene optionally substituted with one or more $R^{38}$, and $A^1$ is a $C_4$-$C_7$carbocyclyl or $M_4$-$M_7$heterocyclyl and is optionally substituted with one or more $R^{30}$.

6. The compound, tautomer or salt of claim 4, wherein Y is —O—, —S—, —C(O)N($R^{15}$)— or —N($R^{15}$C(O)—, $R^{15}$ is hydrogen, $C_1$-$C_6$alkyl, $C_2$-$C_6$alkenyl or $C_2$-$C_6$alkynyl, $L^1$ is a bond or $C_1$-$C_6$alkylene optionally substituted with one or more $R^{38}$, and $A^1$ is a bicyclic ring which has from 6 to 11 ring atoms and is optionally substituted with one or more $R^{30}$.

7. The compound, tautomer or salt of claim 4, wherein X is —O— or —S—, and $R^{22}$ is $C_5$-$C_6$carbocyclyl or $M_5$-$M_6$heterocyclyl and is optionally substituted with one or more $R^{26}$.

8. The compound, tautomer or salt of claim 4, wherein $R^{10}$, $R^{35}$, $R^{41}$ and $R^{41'}$ are each independently selected at each occurrence from hydrogen, halogen or $C_1$-$C_6$alkyl.

9. The compound, tautomer or salt of claim 2, wherein:

Z is —N$R^{41}$—;

$R^{35}$ is selected from hydrogen, halogen or $C_1$-$C_5$alkyl;

$R^{41}$ is selected from hydrogen or $C_1$-$C_6$alkyl;

$R^{10}$ is hydrogen;

A is a $C_5$-$C_6$carbocyclyl and is optionally substituted with one or more $R^{18}$;

B is $M_5$-$M_6$heterocyclyl optionally substituted with one or more $R^{18}$

X is —S— or —O—;

$R^{22}$ is

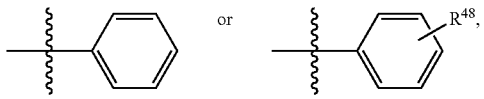

wherein $R^{48}$ is hydroxy, amino, $C_1$-$C_6$alkylamino, $C_1$-$C_6$alkoxy, $C_1$-$C_6$alkoxycarbonylamino or $C_1$-$C_6$alkylcarbonyloxy, and $R^{22}$ is optionally substituted with one or more $R^{26}$;

G is —Y—$R^{50}$;

Y is —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)—, —N($R^{15}$)S(O)—, —N($R^{15}$)S(O)$_2$—, —S(O)N($R^{15}$)—, —S(O)$_2$N($R^{15}$)—, —C(S)N($R^{15}$)O—, —N($R^{15}$)C(S)O—, —OC(S)N($R^{15}$)—, —N($R^{15}$)C(S)N($R^{15'}$)—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl and $C_2$-$C_6$alkynyl;

$R^{50}$ is -$L^1$-$A^1$, wherein:

$L^1$ is $C_1$-$C_6$alkylene and is optionally substituted with one or more $R^{38}$, and $A^1$ is a $C_4$-$C_{12}$carbocyclyl or $M_4$-$M_{12}$heterocyclyl and is optionally substituted with one or more $R^{30}$; or $L^1$ is a bond, and $A^1$ is a $C_4$-$C_6$carbocyclyl or $M_4$-$M_{12}$heterocyclyl and is optionally substituted with one or more $R^{30}$; or $L^1$ is a bond, and $A^1$ is a bicyclic ring having from 6 to 12 ring atoms and is optionally substituted with one or more $R^{30}$.

10. The compound, tautomer or salt of claim 1, wherein said compound has Formula I(a),

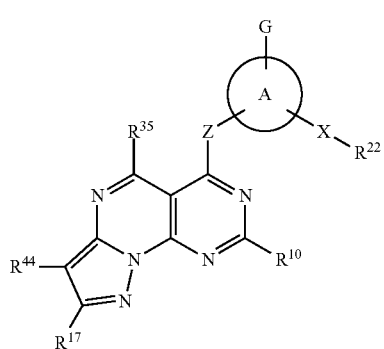

I(a)

wherein:

A is a carbocyclyl or heterocyclyl, and is optionally substituted with one or more $R^{18}$, wherein $R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

$R^{10}$, $R^{17}$, $R^{35}$ and $R^{44}$ are each independently selected at each occurrence from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_3$-$C_6$carbocyclyl, $M_3$-$M_6$heterocyclyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

Z is a bond, —C$R^{41}R^{41'}$— or —N$R^{41}$—, wherein $R^{41}$ and $R^{41'}$ are each independently selected from the group consisting of hydrogen, $C_1$-$C_6$alkyl, $C_2$-$C_6$alkenyl and $C_2$-$C_6$alkynyl;

X is selected from the group consisting of a bond, $C_1$-$C_6$alkylene, $C_2$-$C_6$alkenylene, $C_2$-$C_6$alkynylene, -$L_S$-O—, -$L_S$-S—, -$L_S$-C(O)—, -$L_S$-N($R_S$)—, -$L_S$-N($R_S$)C(O)—, -$L_S$-C(O)N($R_S$)—, -$L_S$-N($R_S$)C(O)O—, -$L_S$-OC(O)N($R_S$)—, -$L_S$-N($R_S$)C(O)N($R_{S'}$)—, -$L_S$-C(=N$R_S$)N($R_{S'}$)—, -$L_S$-N($R_S$)C(=N$R_{S'}$)—, -$L_S$-S(O)—, -$L_S$-SO$_2$—, -$L_S$-C(O)O— and -$L_S$-OC(O)—;

$R^{22}$ is $C_3$-$C_{18}$carbocyclyl or $M_3$-$M_{18}$heterocyclyl, and is optionally substituted with one or more $R^{26}$, wherein $R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N=C(N$R_S R_{S'}$)(N$R_S R_{S'}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl); or $R^{22}$ is $C_1$-$C_6$alkyl, $C_2$-$C_6$alkenyl or $C_2$-$C_6$alkynyl, and is optionally substituted with one or more $R^{26}$; or $R^{22}$ is hydrogen;

G is selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), and —Y—$R^{50}$, wherein G is optionally substituted with one or more $R^{18}$;

Y is selected from the group consisting of a bond, —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)—, —N($R^{15}$)S(O)—, —N(R$^{15}$)S(O)$_2$—, —S(O)N(R$^{15}$)—, —S(O)$_2$N(R$^{15}$)—, —C(S)N(R$^{15}$)O—, —N(R$^{15}$)C(S)O—, —OC(S)N(R$^{15}$)—, —N(R$^{15}$)C(S)N(R$^{15'}$)—, and —C(S)N(R$^{15}$)N(R$^{15'}$)—, wherein R$^{15}$ and R$^{15'}$ are each independently selected at each occurrence from the group consisting of hydrogen, C$_1$-C$_6$alkyl, C$_2$-C$_6$alkenyl, C$_2$-C$_6$alkynyl;

R$^{50}$ is -L$^1$-A$^1$, wherein A$^1$ is selected from the group consisting of C$_3$-C$_{18}$carbocyclyl, M$_3$-M$_{18}$heterocyclyl, C$_1$-C$_6$alkyl, C$_2$-C$_6$alkenyl and C$_2$-C$_6$alkynyl, and L$^1$ is selected from the group consisting of a bond, C$_1$-C$_6$alkylene, C$_2$-C$_6$alkenylene and C$_2$-C$_6$alkynylene, wherein A$^1$ is optionally substituted with one or more R$^{30}$, and R$^{30}$ is independently selected at each occurrence from the group consisting of halogen, oxo, thioxo, hydroxy, mercapto, nitro, cyano, amino, carboxy, formyl, phosphate, azido, C$_1$-C$_6$alkyl, C$_2$-C$_6$alkenyl, C$_2$-C$_6$alkynyl, -L$_S$-O—R$_S$, -L$_S$-S—R$_S$, -L$_S$-C(O)R$_S$, -L$_S$-OC(O)R$_S$, -L$_S$-C(O)OR$_S$, -L$_S$-N(R$_S$R$_{S'}$), -L$_S$-C(=NR$_S$)R$_{S'}$, -L$_S$-S(O)R$_S$, -L$_S$-SO$_2$R$_S$, -L$_S$-C(O)N(R$_S$R$_{S'}$), -L$_S$-N(R$_S$)C(O)R$_{S'}$, -L$_S$-C(=NR$_S$)N(R$_S$R$_{S''}$), -L$_S$-N(R$_{S'}$)C(=NR$_S$)R$_{S''}$, -L$_S$-N(R$_S$)C(O)N(R$_S$R$_{S''}$), -L$_S$-N(R$_S$)SO$_2$R$_{S'}$, -L$_S$-SO$_2$N(R$_S$R$_{S'}$), -L$_S$-N(R$_S$)SO$_2$N(R$_S$R$_{S''}$), -L$_E$-Q-L$_{E'}$-(C$_3$-C$_{18}$carbocyclyl) and -L$_E$-Q-L$_{E'}$-(M$_3$-M$_{18}$heterocyclyl), and wherein L$^1$ is optionally substituted with one or more R$^{38}$, and R$^{38}$ is independently selected at each occurrence from the group consisting of halogen, oxo, thioxo, hydroxy, mercapto, nitro, cyano, amino, carboxy, formyl, phosphate, azido, C$_1$-C$_6$alkoxy, C$_1$-C$_6$thioalkoxy, C$_1$-C$_6$alkylcarbonyl, C$_1$-C$_6$alkoxycarbonyl, C$_1$-C$_6$alkylcarbonyloxy, C$_1$-C$_6$alkylamino, C$_1$-C$_6$alkoxycarbonylamino, -L$_S$-O—R$_S$, -L$_S$-S—R$_S$, -L$_S$-C(O)R$_S$, -L$_S$-OC(O)R$_S$, -L$_S$-C(O)OR$_S$, -L$_S$-N(R$_S$R$_{S'}$), -L$_S$C(=NR$_S$)R$_{S'}$, -L$_S$-S(O)R$_S$, -L$_S$-SO$_2$R$_S$, -L$_S$-C(O)N(R$_S$R$_{S'}$), -L$_S$-N(R$_S$)C(O)R$_{S'}$, -L$_S$-C(=NR$_S$)N(R$_S$R$_{S''}$), -L$_S$-N(R$_{S'}$)C(=NR$_S$)R$_{S''}$, -L$_S$-N(R$_S$)C(O)N(R$_S$R$_{S''}$), -L$_S$-N(R$_S$)SO$_2$R$_{S'}$, -L$_S$-SO$_2$N(R$_S$R$_{S'}$), -L$_S$-N(R$_S$)SO$_2$N(R$_S$R$_{S''}$), C$_3$-C$_{18}$carbocyclyl, M$_3$-M$_{18}$heterocyclyl, C$_3$-C$_{18}$carbocyclylC$_1$-C$_6$alkyl, M$_3$-M$_{18}$heterocyclylC$_1$-C$_6$alkyl, -L$_E$-Q-L$_{E'}$-(C$_3$-C$_{18}$carbocyclyl) and -L$_E$-Q-L$_{E'}$-(M$_3$-M$_{18}$heterocyclyl);

L$_S$ is independently selected at each occurrence from the group consisting of a bond, C$_1$-C$_6$alkylene, C$_2$-C$_6$alkenylene and C$_2$-C$_6$alkynylene;

R$_S$, R$_{S'}$ and R$_{S''}$ are each independently selected at each occurrence from the group consisting of hydrogen, C$_1$-C$_6$alkyl, C$_2$-C$_6$alkenyl, C$_2$-C$_6$alkynyl, C$_1$-C$_6$alkoxy, C$_1$-C$_6$thioalkoxy, C$_1$-C$_6$alkoxyC$_1$-C$_6$alkyl, C$_1$-C$_6$alkoxyC$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonylC$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino, and C$_1$-C$_6$alkoxycarbonylaminoC$_1$-C$_6$alkyl;

L$_E$ and L$_{E'}$ are each independently selected at each occurrence from the group consisting of a bond, C$_1$-C$_6$alkyl, C$_2$-C$_6$alkenyl and C$_2$-C$_6$alkynyl;

Q is independently selected at each occurrence from the group consisting of a bond, C$_1$-C$_6$alkylene, C$_2$-C$_6$alkenylene, C$_2$-C$_6$alkynylene, —S—, —O—, —C(O)—, —N(R$_S$)—, —N(R$_S$)C(O)—, —C(O)N(R$_S$)—, —N(R$_S$)C(O)O—, —OC(O)N(R$_S$)—, —N(R$_S$)C(O)N(R$_{S'}$)—, —C(=NR$_S$)N(R$_{S'}$)—, —N(R$_{S'}$)C(=NR$_S$)—, —S(O)—, —SO$_2$—, —O—SO$_2$—, —SO$_2$—O—, —O—S(O)—, —S(O)—O—, —C(O)O— and —OC(O)—;

R$^{10}$, R$^{15}$, R$^{15'}$, R$^{17}$, R$^{18}$, R$^{26}$, R$^{30}$, R$^{33}$, R$^{35}$, R$^{38}$, R$^{41}$, R$^{41'}$ and R$^{44}$ are each independently optionally substituted at each occurrence with at least one substituent selected from the group consisting of halogen, oxo, thioxo, hydroxy, mercapto, nitro, cyano, amino, carboxy, formyl, phosphate and azido; and each C$_3$-C$_{18}$carbocyclyl and M$_3$-M$_{18}$heterocyclyl moiety in -L$_E$-Q-L$_{E'}$-(C$_3$-C$_{18}$carbocyclyl) and -L$_E$-Q-L$_{E'}$-(M$_3$-M$_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, C$_1$-C$_6$alkyl, C$_1$-C$_6$alkenyl, C$_2$-C$_6$alkynyl, C$_1$-C$_6$alkoxy, C$_1$-C$_6$thioalkoxy, C$_1$-C$_6$alkoxyC$_1$-C$_6$alkyl, C$_1$-C$_6$thioalkoxyC$_1$-C$_6$alkyl, C$_1$-C$_6$alkylcarbonyl, C$_1$-C$_6$alkylcarbonyl C$_1$-C$_6$alkyl, C$_1$-C$_6$alkoxycarbonyl, C$_1$-C$_6$alkoxycarbonylC$_1$-C$_6$alkyl, C$_1$-C$_6$alkylcarbonyloxy, C$_1$-C$_6$alkylcarbonyloxyC$_1$-C$_6$alkyl, C$_1$-C$_6$alkylamino, C$_1$-C$_6$alkylaminoC$_1$-C$_6$alkyl, C$_1$-C$_6$alkoxycarbonylamino, and C$_1$-C$_6$alkoxycarbonylaminoC$_1$-C$_6$alkyl.

11. The compound, tautomer or salt of claim 10, wherein Z is —NR$^{41}$—.

12. The compound, tautomer or salt of claim 11, wherein A is C$_5$-C$_6$carbocyclyl and is optionally substituted with one or more R$^{18}$, G is —Y—R$^{50}$, and A$^1$ is C$_5$-C$_6$carbocyclyl or M$_5$-M$_6$heterocyclyl and is optionally substituted with one or more R$^{30}$.

13. The compound, tautomer or salt of claim 12, wherein X is —O— or —S—, R$^{22}$ is C$_5$-C$_6$carbocyclyl or M$_5$-M$_6$heterocyclyl and is optionally substituted with one or more R$^{26}$.

14. The compound, tautomer or salt of claim 13, wherein Y is —O—, —S—, —C(O)N(R$^{15}$)— or —N(R$^{15}$)C(O)—.

15. The compound, tautomer or salt of claim 1, wherein said compound has Formula I(b),

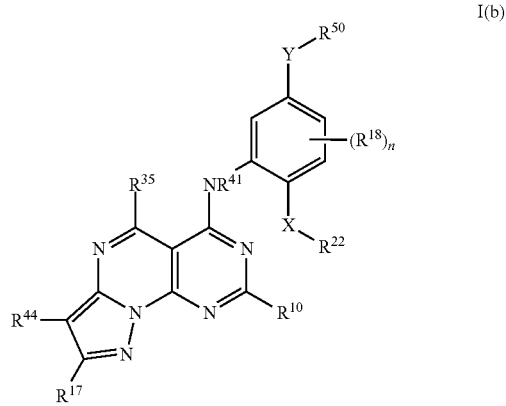

I(b)

wherein:
R$^{10}$, R$^{17}$, R$^{35}$, R$^{41}$ and R$^{44}$ are each independently selected from hydrogen, halogen, C$_1$-C$_6$alkyl or C$_3$-C$_6$cycloalkyl;

X is —S— or —O—;

$R^{22}$ is

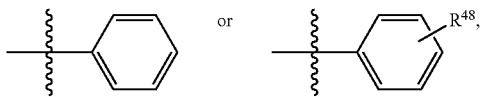

wherein $R^{48}$ is hydroxy, amino, $C_1$-$C_6$alkylamino or $C_1$-$C_6$alkoxy, and $R^{22}$ is optionally substituted with one or more $R^{26}$;

Y is selected from the group consisting of —O—, —C(O)—, —S(O)—, —S(O)$_2$—, —N($R^{15}$)—, —C(O)O—, —OC(O)—, —C(O)N($R^{15}$)—, —N($R^{15}$)C(O)—, —C(O)N($R^{15}$)O—, —N($R^{15}$)C(O)O—, —OC(O)N($R^{15}$)—, —N($R^{15}$)C(O)N($R^{15'}$)—, —C(O)N($R^{15}$)N($R^{15'}$)—, —S—, —C(S)—, —C(S)O—, —OC(S)—, —C(S)N($R^{15}$)—, —N($R^{15}$)C(S)—, —OS(O)$_2$—, —OS(O)—, —OC(O)O—, —N($R^{15}$)—, —N($R^{15}$)S(O)—, —N($R^{15}$)S(O)$_2$—, —S(O)N($R^{15}$)—, —S(O)$_2$N($R^{15}$)—, —C(S)N($R^{15}$)O—, —N($R^{15}$)C(S)O—, —OC(S)N($R^{15}$)—, —N($R^{15}$)C(S)N($R^{15'}$)—, and —C(S)N($R^{15}$)N($R^{15'}$)—, wherein $R^{15}$ and $R^{15'}$ are each independently selected at each occurrence from the group consisting of hydrogen, $C_1$-$C_6$alkyl, $C_2$-$C_6$alkenyl, $C_2$-$C_6$alkynyl;

$R^{50}$ is -$L^1$-$A^1$, wherein $L^1$ a bond or $C_1$-$C_6$alkylene optionally substituted with one or more $R^{38}$, and $A^1$ is $C_5$-$C_{10}$carbocyclyl or $M_5$-$M_{10}$heterocyclyl and is optionally substituted with one or more $R^{30}$;

$R^{18}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), and -$L_S$-N($R_S$)SO$_2$N($R_S R_{S''}$);

$R^{26}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N=C(N$R_S R_{S'}$)(N$R_S R_{S'}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

$R^{30}$ is independently selected at each occurrence from the group consisting of halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), -$L_E$-Q-$L_{E'}$-($C_3$-$C_{18}$carbocyclyl) and -$L_E$-Q-$L_{E'}$-($M_3$-$M_{18}$heterocyclyl);

$R^{38}$ is independently selected at each occurrence from the group consisting of halogen, oxo, thioxo, hydroxy, mercapto, nitro, cyano, amino, carboxy, formyl, phosphate, azido, $C_1$-$C_6$alkoxy, $C_1$-$C_6$thioalkoxy, $C_1$-$C_6$ alkylcarbonyl, $C_1$-$C_6$alkoxycarbonyl, $C_1$-$C_6$alkylcarbonyloxy, $C_1$-$C_6$alkylamino, $C_1$-$C_6$alkoxycarbonylamino, -$L_S$-O—$R_S$, -$L_S$-S—$R_S$, -$L_S$-C(O)$R_S$, -$L_S$-OC(O)$R_S$, -$L_S$-C(O)O$R_S$, -$L_S$-N($R_S R_{S'}$), -$L_S$-C(=N$R_S$)$R_{S'}$, -$L_S$-S(O)$R_S$, -$L_S$-SO$_2 R_S$, -$L_S$-C(O)N($R_S R_{S'}$), -$L_S$-N($R_S$)C(O)$R_{S'}$, -$L_S$-C(=N$R_S$)N($R_S R_{S''}$), -$L_S$-N($R_{S'}$)C(=N$R_S$)$R_{S''}$, -$L_S$-N($R_S$)C(O)N($R_S R_{S''}$), -$L_S$-N($R_S$)SO$_2 R_{S'}$, -$L_S$-SO$_2$N($R_S R_{S'}$), -$L_S$-N($R_S$)SO$_2$N($R_S R_{S''}$), $C_3$-$C_{18}$carbocyclyl, $M_3$-$M_{18}$heterocyclyl, $C_3$-$C_{18}$carbocyclyl$C_1$-$C_6$alkyl, $M_3$-$M_{18}$heterocyclyl$C_1$-$C_6$alkyl, -$L_E$-Q-$L_{E'}$-($C_3$-$C_{18}$carbocyclyl) and -$L_E$-Q-$L_{E'}$-($M_3$-$M_{18}$heterocyclyl);

$L_S$ is independently selected at each occurrence from the group consisting of a bond, $C_1$-$C_6$alkylene, $C_2$-$C_6$alkenylene and $C_2$-$C_6$alkynylene;

$R_S$, $R_{S'}$ and $R_{S''}$ are each independently selected at each occurrence from the group consisting of hydrogen, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$alkoxy$C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl;

$L_E$ and $L_{E'}$ are each independently selected at each occurrence from the group consisting of a bond, $C_1$-$C_6$alkyl, $C_2$-$C_6$alkenyl and $C_2$-$C_6$alkynyl;

Q is independently selected at each occurrence from the group consisting of a bond, $C_1$-$C_6$alkylene, $C_2$-$C_6$alkenylene, $C_2$-$C_6$alkynylene, —S—, —O—, —C(O)—, —N($R_S$)—, —N($R_S$)C(O)—, —C(O)N($R_S$)—, —N($R_S$)C(O)O—, —OC(O)N($R_S$)—, —N($R_S$)C(O)N($R_{S'}$)—, —C(=N$R_S$)N($R_{S'}$)—, —N($R_{S'}$)C(=N$R_S$)—, —S(O)—, —SO$_2$—, —O—SO$_2$—, —SO$_2$—O—, —O—S(O)—, —S(O)—O—, —C(O)O— and —OC(O)—;

$R^{10}$, $R^{15}$, $R^{15'}$, $R^{17}$, $R^{18}$, $R^{26}$, $R^{30}$, $R^{35}$, $R^{38}$, $R^{41}$, and $R^{44}$ are each independently optionally substituted at each occurrence with at least one substituent selected from the group consisting of halogen, oxo, thioxo, hydroxy, mercapto, nitro, cyano, amino, carboxy, formyl, phosphate and azido;

each $C_3$-$C_{18}$carbocyclyl and $M_3$-$M_{18}$heterocyclyl moiety in -$L_E$-Q-$L_{E'}$-($C_3$-$C_{18}$carbocyclyl) and -$L_E$-Q-$L_{E'}$-($M_3$-$M_{18}$heterocyclyl) is independently optionally substituted at each occurrence with at least one substituent selected from the group consisting of hydrogen, halogen, oxo, thioxo, hydroxy, mercapto, nitro, cyano, amino, carboxy, formyl, phosphate, azido, $C_1$-$C_6$alkyl, $C_2$-$C_6$alkenyl, $C_2$-$C_6$alkynyl, $C_1$-$C_6$alkoxy, $C_1$-$C_6$thioalkoxy, $C_1$-$C_6$alkoxy$C_1$-$C_6$alkyl, $C_1$-$C_6$thioalkoxy$C_1$-$C_6$alkyl, $C_1$-$C_6$alkylcarbonyl, $C_1$-$C_6$alkylcarbonyl$C_1$-$C_6$alkyl, $C_1$-$C_6$alkoxycarbonyl, $C_1$-$C_6$alkoxycarbonyl$C_1$-$C_6$alkyl, $C_1$-$C_6$alkylcarbonyloxy, $C_1$-$C_6$alkylcarbonyloxy$C_1$-$C_6$alkyl, $C_1$-$C_6$alkylamino, $C_1$-$C_6$alkylamino$C_1$-$C_6$alkyl, $C_1$-$C_6$alkoxycarbonylamino, and $C_1$-$C_6$alkoxycarbonylamino$C_1$-$C_6$alkyl; and n is 0, 1, 2, or 3.

16. A pharmaceutical composition comprising a compound, tautomer or salt according to claim 1.

17. A method of inhibiting HCV virus replication, comprising contacting HCV virus with an effective amount of a compound, tautomer or salt of claim 1, thereby inhibiting replication of said virus.

18. A method of treating HCV infection, comprising administering an effective amount of a compound, tautomer or salt of claim 1 to an HCV patient in need thereof, thereby reducing HCV viral level in the blood or liver of the patient.

19. The compound, tautomer or salt of claim 15, wherein the compound is selected from the group consisting of 4-[4-Methyl-2-(1,4,7,9,9b-pentaaza-cyclopenta[a]naphthalen-6-ylamino)-phenylsulfanyl]-phenol;

4-[4-(3-Bromo-benzyloxy)-2-(1,4,7,9,9b-pentaaza-cyclopenta[a]naphthalen-6-ylamino)-phenylsulfanyl]-phenol;

4-[4-Methyl-2-(2-methyl-1,4,7,9,9b-pentaaza-cyclopenta[a]naphthalen-6-ylamino)-phenylsulfanyl]-phenol;

4-[4-(3-Fluoro-benzyloxy)-2-(2-methyl-1,4,7,9,9b-pentaaza-cyclopenta[a]naphthalen-6-ylamino)-phenylsulfanyl]-phenol; and 4-[2-(2-Methyl-1,4,7,9,9b-pentaaza-cyclopenta[a]naphthalen-6-ylamino)-4-(3-trifluoromethyl-benzyloxy)-phenylsulfanyl]-phenol.

* * * * *